(12) United States Patent
Bayly et al.

(10) Patent No.: US 7,375,134 B2
(45) Date of Patent: May 20, 2008

(54) CATHEPSIN CYSTEINE PROTEASE INHIBITORS

(75) Inventors: Christopher I. Bayly, Beaconsfield (CA); Cameron Black, Baie d'Urfe (CA); Serge Leger, Notre-Dame-de l'Ile-Perrot (CA); Chun Sing Li, Dollard-Des-Ormeaux (CA); Dan McKay, Ottawa (CA); Christophe Mellon, L'ile-Bizard (CA); Jacques Yves Gauthier, Laval (CA); Vouy-Linh Truong, Pierrefonds (CA); Cheuk Lau, Ile Bizard (CA); Michel Therien, Laval (CA)

(73) Assignees: Axys Pharmaceuticals, Inc., South San Francisco, CA (US); Merck Frosst Canada & Co., Quebec (CA)

( * ) Notice: Subject to any disclaimer, the term of this patent is extended or adjusted under 35 U.S.C. 154(b) by 631 days.

(21) Appl. No.: 10/505,796

(22) PCT Filed: Feb. 28, 2003

(86) PCT No.: PCT/US03/06147

§ 371 (c)(1),
(2), (4) Date: Aug. 25, 2004

(87) PCT Pub. No.: WO03/075836

PCT Pub. Date: Sep. 18, 2003

(65) Prior Publication Data

US 2005/0240023 A1 Oct. 27, 2005

Related U.S. Application Data

(60) Provisional application No. 60/408,704, filed on Sep. 6, 2002, provisional application No. 60/361,818, filed on Mar. 5, 2002.

(51) Int. Cl.
*A01N 37/34* (2006.01)

(52) U.S. Cl. .......... 514/521; 514/252.01; 514/357; 514/365; 544/393; 544/400; 546/330; 548/204; 558/404; 558/414; 558/431; 558/434

(58) Field of Classification Search .......... 514/252.1, 514/357, 365, 396, 521; 544/393, 400; 546/330; 548/204, 205, 3; 558/404, 414, 431, 434
See application file for complete search history.

(56) References Cited

U.S. PATENT DOCUMENTS

| 2005/0014941 A1* | 1/2005 | Black et al. ............... 544/163 |
| 2005/0182096 A1* | 8/2005 | Link et al. ................. 514/317 |
| 2006/0111440 A1* | 5/2006 | Gauthier et al. ........... 514/519 |

FOREIGN PATENT DOCUMENTS

| WO | WO 00/55126 | 9/2000 |
| WO | WO 00/49007 | 8/2003 |

OTHER PUBLICATIONS

Alessandro Volonterio, et al. "Synthesis of Partially Modified Retro and Retroinverso Ψ[NHCH(CF3)]-Peptides," Organic Letters 2000, vol. 2, No. 13, 1827-1830.
Alessandro Volonterio, et al. "Solution/solid-phase synthesis of partially modified retro-ψ [NHCH(CF3)]-peptidyl hydroxamates," Tetrahedron Letters 42 (2001), 3141-3144.
Alessandro Volonterio, et al. "Solid-phase synthesis of partially-modified retro and retro-inverso Ψ[NHCH(CF3)]-peptides," Tetrahedron Letters 41 (2000), 6517-6521.
Ishii, et al. "Asymmetric Addition Reactions of Grignard Reagents to Chiral Fluoral Hemiacetal: Asymmetric Synthesis of 1-Substituted-2,2,2,-Trifluoroethylamines," Synlett, Dec. 1997, 1381-1382.
Ishii, et al. "Stereospecific Reduction with Retention of Chiral Fluoral-derived 1,3-Oxazolidines with LiAlH4: Asymmetric Synthesis of 1-Substituted 2,2,2-Trifluoroethylamines," Chem. Letters 1998, 119-120.

* cited by examiner

*Primary Examiner*—James O. Wilson
*Assistant Examiner*—Ebenezer Sackey
(74) *Attorney, Agent, or Firm*—Nicole M. Beeler; David A. Muthard

(57) ABSTRACT

This invention relates to a novel class of compounds which are cysteine protease inhibitors, including but not limited to, inhibitors of cathepsins K, L, S and B. These compounds are useful for treating diseases in which inhibition of bone resorption is indicated, such as osteoporosis.

10 Claims, No Drawings

CATHEPSIN CYSTEINE PROTEASE INHIBITORS

PRIORITY CLAIM

This application is a §371 National Stage Application of PCT/US03/06147, filed on Feb. 28, 2003, which claims priority from U.S. Provisional Application Ser. Nos. 60/361,818 filed on Mar. 5, 2002, and 60/408,704 filed on Sep. 6, 2002.

BACKGROUND OF THE INVENTION

A variety of disorders in humans and other mammals involve or are associated with abnormal bone resorption. Such disorders include, but are not limited to, osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, metastatic bone disease, hypercalcemia of malignancy, and multiple myeloma. One of the most common of these disorders is osteoporosis, which in its most frequent manifestation occurs in postmenopausal women. Osteoporosis is a systemic skeletal disease characterized by a low bone mass and microarchitectural deterioration of bone tissue, with a consequent increase in bone fragility and susceptibility to fracture. Osteoporotic fractures are a major cause of morbidity and mortality in the elderly population. As many as 50% of women and a third of men will experience an osteoporotic fracture. A large segment of the older population already has low bone density and a high risk of fractures. There is a significant need to both prevent and treat osteoporosis and other conditions associated with bone resorption. Because osteoporosis, as well as other disorders associated with bone loss, are generally chronic conditions, it is believed that appropriate therapy will typically require chronic treatment.

Osteoporosis is characterized by progressive loss of bone architecture and mineralization leading to the loss in bone strength and an increased fracture rate. The skeleton is constantly being remodeled by a balance between osteoblasts that lay down new bone and osteoclasts that breakdown, or resorb, bone. In some disease conditions and advancing age the balance between bone formation and resorption is disrupted; bone is removed at a faster rate. Such a prolonged imbalance of resorption over formation leads to weaker bone structure and a higher risk of fractures.

Bone resorption is primarily performed by osteoclasts, which are multinuclear giant cells. Osteoclasts resorb bone by forming an initial cellular attachment to bone tissue, followed by the formation of an extracellular compartment or lacunae. The lacunae are maintained at a low pH by a proton-ATP pump. The acidified environment in the lacunae allows for initial demineralization of bone followed by the degradation of bone proteins or collagen by proteases such as cysteine proteases. See Delaisse, J. M. et al., 1980, *Biochem J* 192:365-368; Delaisse, J. et al., 1984, *Biochem Biophys Res Commun:* 441-447; Delaisse, J. M. et al.,1987, *Bone* 8:305-313, which are hereby incorporated by reference in their entirety. Collagen constitutes 95% of the organic matrix of bone. Therefore, proteases involved in collagen degradation are an essential component of bone turnover, and as a consequence, the development and progression of osteoporosis.

Cathepsins belong to the papain superfamily of cysteine proteases. These proteases function in the normal physiological as well as pathological degradation of connective tissue. Cathepsins play a major role in intracellular protein degradation and turnover and remodeling. To date, a number of cathepsin have been identified and sequenced from a number of sources. These cathepsins are naturally found in a wide variety of tissues. For example, cathepsin B, F, H, L, K, S, W, and Z have been cloned. Cathepsin K (which is also known by the abbreviation cat K) is also known as cathepsin O and cathepsin $O_2$. See PCT Application WO 96/13523, Khepri Pharmaceuticals, Inc., published May 9, 1996, which is hereby incorporated by reference in its entirety. Cathepsin L is implicated in normal lysosomal proteolysis as well as several diseases states, including, but not limited to, metastasis of melanomas. Cathepsin S is implicated in Alzheimer's disease and certain autoimmune disorders, including, but not limited to juvenile onset diabetes, multiple sclerosis, pemphigus vulgaris, Graves' disease, myasthenia gravis, systemic lupus erythemotasus, rheumatoid arthritis, and Hashimoto's thyroiditis; allergic disorders, including, but not limited to asthma; and allogenic immunbe responses, including, but not limited to, rejection of organ transplants or tissue grafts. Increased Cathepsin B levels and redistribution of the enzyme are found in tumors, suggesting a role in tumor invasion and matastasis. In addition, aberrant Cathpsin B activity is implicated in such disease states as rheumatoid arthritis, osteoarthritis, pneumocystisis carinii, acute pancreatitis, inflammatory airway disease and bone and joint disorders.

Cysteine protease inhibitors such as E-64 (trans-epoxysuccinyl-L-leucylamide-(4-guanidino) butane) are known to be effective in inhibiting bone resorption. See Delaisse, J. M. et al., 1987, *Bone* 8:305-313, which is hereby incorporated by reference in its entirety. Recently, cathepsin K was cloned and found specifically expressed in osteoclasts See Tezuka, K. et al., 1994, *J Biol Chem* 269:1106-1109; Shi, G. P. et al., 1995, *FEBS Lett* 357:129-134; Bromme, D. and Okamoto, K., 1995, *Biol Chem Hoppe Seyler* 376:379-384; Bromme, D. et al., 1996, *J Biol Chem* 271:2126-2132; Drake, F. H. et al., 1996, *J Biol Chem* 271:12511-12516, which are hereby incorporated by reference in their entirety. Concurrent to the cloning, the autosomal recessive disorder, pycnodysostosis, characterized by an osteopetrotic phenotype with a decrease in bone resorption, was mapped to mutations present in the cathepsin K gene. To date, all mutations identified in the cathepsin K gene are known to result in inactive protein. See Gelb, B. D. et al., 1996, *Science* 273:1236-1238; Johnson, M. R. et al., 1996, *Genome Res* 6:1050-1055, which are hereby incorporated by reference in their entirety. Therefore, it appears that cathepsin K is involved in osteoclast mediated bone resorption.

Cathepsin K is synthesized as a 37 kDa pre-pro enzyme, which is localized to the lysosomal compartment and where it is presumably autoactivated to the mature 27 kDa enzyme at low pH. See McQueney, M. S. et al., 1997, *J Biol Chem* 272:13955-13960; Littlewood-Evans, A. et al., 1997, *Bone* 20:81-86, which are hereby incorporated by reference in their entirety. Cathepsin K is most closely related to cathepsin S having 56% sequence identity at the amino acid level. The $S_2P_2$ substrate specificity of cathepsin K is similar to that of cathepsin S with a preference in the P1 and P2 positions for a positively charged residue such as arginine, and a hydrophobic residue such as phenylalanine or leucine, respectively. See Bromme, D. et al., 1996, *J Biol Chem* 271: 2126-2132; Bossard, M. J. et al., 1996, *J Biol Chem* 271: 12517-12524, which are hereby incorporated by reference in their entirety. Cathepsin K is active at a broad pH range with significant activity between pH 4-8, thus allowing for good catalytic activity in the resorption lacunae of osteoclasts where the pH is about 4-5.

Human type I collagen, the major collagen in bone is a good substrate for cathepsin K. See Kafienah, W., et al., 1998, *Biochem J* 331:727-732, which is hereby incorporated by reference in its entirety. In vitro experiments using antisense oligonucleotides to cathepsin K, have shown diminished bone resorption in vitro, which is probably due to a reduction in translation of cathepsin K mRNA. See Inui, T., et al., 1997, *J Biol Chem* 272:8109-8112, which is hereby incorporated by reference in its entirety. The crystal structure of cathepsin K has been resolved. See McGrath, M. E., et al., 1997, *Nat Struct Biol* 4:105-109; Zhao, B., et al., 1997, *Nat Struct Biol* 4: 109-11, which are hereby incorporated by reference in their entirety. Also, selective peptide based inhibitors of cathepsin K have been developed See Bromie, D., et al., 1996, *Biochem J* 315:85-89; Thompson, S. K., et al., 1997, *Proc Natl Acad Sci USA* 94:14249-14254, which are hereby incorporated by reference in their entirety. Accordingly, inhibitors of Cathepsin K can reduce bone resorption. Such inhibitors would be useful in treating disordersinvolving bone resorption, such as osteoporosis.

SUMMARY OF THE INVENTION

The present invention relates to compounds that are capable of treating and/or preventing cathepsin dependent conditions or disease states in a mammal in need thereof. One embodiment of the present invention is illustrated by a compound of Formula I, and the pharmaceutically acceptable salts, stereoisomers and N-oxide derivatives thereof:

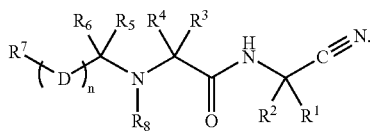

I

DETAILED DESCRIPTION OF THE INVENTION

The present invention relates to compounds of the following chemical formula:

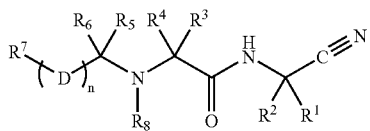

wherein $R^1$ is hydrogen, $C_{1-6}$ alkyl or $C_{2-6}$ alkenyl wherein said alkyl and alkenyl groups are optionally substituted with one to six halo, $C_{3-6}$ cycloalkyl, —$SR^9$, —$SR^{12}$, —$SOR^9$, —$SOR^{12}$, —$SO_2R^9$, —$SO_2R^{12}$, —$SO_2CH(R^{12})(R^{11})$, —$OR^{12}$, —$OR^9$, —$N(R^{12})_2$, aryl, heteroaryl or heterocyclyl wherein said aryl, heteroaryl and heterocyclyl groups are optionally substituted with one or two substitutents independently selected from $C_{1-6}$ alkyl, halo, hydroxyalkyl, hydroxy, alkoxy or keto;

$R^2$ is hydrogen, $C_{1-6}$ alkyl or $C_{2-6}$ alkenyl wherein said alkyl and alkenyl groups are optionally substituted with one to six halo, $C_{3-6}$ cycloalkyl, —$SR^9$, —$SR^{12}$, —$SOR^9$, —$SOR^{12}$, —$SO_2R^9$, —$SO_2R^{12}$, —$SO_2CH(R^{12})(R^{11})$, —$OR^{12}$, —$OR^9$, —$N(R^{12})_2$, aryl, heteroaryl or heterocyclyl wherein said aryl, heteroaryl and heterocyclyl groups are optionally substituted with one or two substituents independently selected from $C_{1-6}$ alkyl, halo, hydroxyalkyl, hydroxy, alkoxy or keto;

or $R^1$ and $R^2$ can be taken together with the carbon atom to which they are attached to form a $C_{3-8}$ cycloalkyl or heterocyclyl ring wherein said ring system is optionally substituted with one or two substituents independently selected from $C_{1-6}$ alkyl, hydroxyalkyl, haloalkyl, or halo;

$R^3$ is hydrogen, $C_{1-6}$ alkyl or $C_{2-6}$ alkenyl wherein said alkyl and alkenyl groups are optionally substituted with $C_{3-6}$ cycloalkyl or one to six halo;

$R^4$ is hydrogen, $C_{1-6}$ alkyl or $C_{2-6}$ alkenyl wherein said alkyl and alkenyl groups are optionally substituted with $C_{3-6}$ cycloalkyl or one to six halo;

or $R^3$ and $R^4$ can be taken together with the carbon atom to which they are attached to form a $C_{3-8}$ cycloalkyl ring, $C_{5-8}$ cycloalkenyl ring, or five to seven membered heterocyclyl wherein said cycloalkyl, cycloalkenyl and heterocyclyl groups are optionally substituted with one or two substitutents independently selected from $C_{1-6}$ alkyl, halo, hydroxyalkyl, hydroxy, alkoxy or keto;

$R^5$ is selected from hydrogen or $C_{1-6}$ alkyl substituted with 1-6 halo;

$R^6$ is aryl, heteroaryl, $C_{1-6}$ haloalkyl, arylalkyl or heteroarylalkyl, wherein said aryl, heteroaryl, arylalkyl and heteroarylalkyl groups are optionally substituted with one, two, or three substituents independently selected from halo, $C_{1-6}$ alkyl, $C_{1-6}$ haloalkyl, $C_{3-6}$ cycloalkyl, haloalkoxy, —$SR^9$, —$SR^{12}$, —$SOR^9$, —$SOR^{12}$, —$SO_2R^9$, —$SO_2R^{12}$, —$SO_2CH(R^{12})(R^{11})$, —$OR^{12}$, —$N(R^{10})(R^{11})$, cyano, oraryl which is optionally substituted with —$SO_2R^{12}$;

each D is independently $C_{1-3}$ alkyl, $C_{2-3}$ alkenyl, $C_{2-3}$ alkynyl, aryl, heteroaryl, $C_{3-8}$ cycloalkyl or heterocyclyl wherein each said aryl, heteroaryl, cycloalkyl and heterocyclyl groups, which may be monocyclic or bicyclic, is optionally substituted on either the carbon or the heteroatom with one to five substituents independently selected from $C_{1-6}$ alkyl, haloalkyl, halo, keto, alkoxy, —$SR^9$, —$SR^{12}$, —$OR^9$, —$OR^{12}$, $N(R^{12})_2$, —$SO_2R^9$, or —$SO_2R^{10}$;

$R^7$ is hydrogen, $C_{1-6}$ alkyl, $C_{2-6}$ alkenyl, $C_{2-6}$ alkynyl, $C_{1-6}$ alkyloxy, halo, nitro, cyano, aryl, heteroaryl, $C_{3-8}$ cycloalkyl, heterocyclyl, —$C(O)OR^{10}$, —$C(O)OSi[CH(CH_3)_2]_3$, —$OR^9$, —$OR^{10}$, —$C(O)R^{10}$, —$R^{10}C(O)R^9$, —$C(O)R^9$, —$C(O)N(R^a)(R^b)$, —$C(O)N(R^{12})(R^{12})$, —$C(O)N(R^{10})(R^{11})$, —$C(R^{10})(R^{11})OH$, —$SR^{12}$, —$SR^9$, —$R^{10}SR^9$, —$R^9$, —$C(R^9)_3$, —$C(R^{10})(R^{11})N(R^9)_2$, —$NR^{10}C(O)NR^{10}S(O)_2R^9$, —$SO_2R^{12}$, —$SO(R^{12})$, —$SO_2R^9$, —$SO_mN(R^c)(R^d)$, —$SO_mCH(R^{10})(R^{11})$, —$SO_2N(R^{10})C(O)(R^{12})$, —$SO_2(R^{10})C(O)N(R^{12})_2$, —$OSO_2R^{10}$, —$N(R^{10})(R^{11})$, —$N(R^{10})C(O)N(R^{10})(R^9)$, —$N(R^{10})C(O)R^9$, —$N(R^{10})C(O)R^{10}$, —$N(R^{10})C(O)OR^{10}$, —$N(R^{10})SO_2(R^{10})$, —$C(R^{10})(R^{11})NR^{10}C(R^{10})(R^{11})R^9$, —$C(R^{10})(R^{11})N(R^{10})R^9$, —$C(R^{10})(R^{11})N(R^{10})(R^{11})$, —$C(R^{10})(R^{11})SC(R^{10})(R^{11})(R^9)$, $R^{10}S—$, —$C(R^a)(R^b)NR^aC(R^a)(R^b)(R^9)$, —$C(R^a)(R^b)N(R^a)(R^b)$, —$C(R^a)(R^b)C(R^a)(R^b)N(R^a)(R^b)$, —$C(O)C(R^a)(R^b)N(R^a)(R^b)$, —$C(R^a)(R^b)N(R^a)C(O)$ $R^9$, —$C(O)C(R^a)(R^b)S(R^a)$, $C(R^a)(R^b)C(O)N(R^a)(R^b)$, —$B(OH)_2$, —$OCH_2O—$ or 4,4,5,5-tetramethyl-1,3,2-dioxaborolan-2-yl; wherein said groups are optionally substituted on either the carbon or the heteroatom with one to five substituents independently selected from $C_{1-6}$ alkyl, halo, keto, cyano, haloalkyl, hydroxyalkyl, —$OR^9$, —$NO_2$, —$NH_2$, —NHS$(O)_2R^8$, —$R^9SO_2R^{12}$, —$SO_2R^{12}$, —$SO(R^{12})$, —$SR^{12}$, —$SR^9$, —$SO_mN(R^c)(R^d)$, —$SO_mN(R^{10})C(O)(R^{12})$, —$C(R^{10})(R^{11})N(R^{10})(R^{11})$, —$C(R^{10})(R^{11})OH$, —COOH, —$C(R^a)(R^b)C(O)N(R^a)(R^b)$, —$C(O)(R^a)(R^b)$, —$N(R^{10})C(R^{10})(R^{11})(R^9)$, —$N(R^{10})CO(R^9)$, —NH$(CH_2)_2OH$, —$NHC(O)OR^{10}$, —$Si(CH_3)_3$, heterocycyl, aryl, or heteroaryl;

$R^8$ is hydrogen or $C_{1-6}$ alkyl;

or $R^4$ and $R^8$ or can be taken together with any of the atoms to which they may be attached or are between them to form a 4-10 membered heterocyclyl ring system wherein said ring system, which may be monocyclic or bicyclic, is optionally substituted with one or two substituents independently selected from $C_{1-6}$ alkyl, halo, hydroxyalkyl, hydroxy, keto, —$OR^{10}$, —$SR^{10}$ or —$N(R^{10})_2$;

$R^9$ is selected from the group consisting of hydrogen, aryl, aryl($C_{1-4}$)alkyl, heteroaryl, heteroaryl($C_{1-4}$)alkyl, $C_{3-8}$cycloalkyl, $C_{3-8}$cycloalkyl($C_{1-4}$)alkyl, and heterocyclyl($C_{1-4}$)alkyl wherein said groups can be optionally substituted with one, two, or three substituents independently selected from halo, alkoxy or —$SO_2R^{12}$;

$R^{10}$ is hydrogen or $C_{1-6}$ alkyl $R^{11}$ is hydrogen or $C_{1-6}$ alkyl;

$R^{12}$ is hydrogen or $C_{1-6}$ alkyl which is optionally substituted with one, two, or three substituents independently selected from halo, alkoxy, cyano, —$NR^{10}$or —$SR^{10}$;

$R^a$ is hydrogen, $C_{1-6}$ alkyl, ($C_{1-6}$ alkyl)aryl, ($C_{1-6}$ alkyl)hydroxyl, —$O(C_{1-6}$ alkyl), hydroxyl, halo, aryl, heteroaryl, $C_{3-8}$ cycloalkyl, heterocyclyl, wherein said alkyl, aryl, heteroaryl, $C_{3-8}$ cycloalkyl and heterocyclyl can be optionally substituted on either the carbon or the heteroatom with one, two, or three substituents independently selected from $C_{1-6}$ alkyl or halo;

$R^b$ is hydrogen, $C_{1-6}$ alkyl, ($C_{1-6}$ alkyl)aryl, ($C_{1-6}$ alkyl)hydroxyl, alkoxyl, hydroxyl, halo, aryl, heteroaryl, $C_{3-8}$ cycloalkyl, heterocyclyl,wherein said alkyl, aryl, heteroaryl, $C_{3-8}$ cycloalkyl and heterocyclyl can be optionally substituted on either the carbon or the heteroatom with one, two, or three substituents independently selected from $C_{1-6}$ alkyl or halo;

or $R^a$ and $R^b$ can be taken together with the carbon atom to which they are attached or are between them to form a $C_{3-8}$ cycloalkyl ring or $C_{3-8}$ heterocyclyl ring wherein said 3-8 membered ring system may be optionally substituted with one or two substituents independently selected from $C_{1-6}$ alkyl and halo;

$R^c$ is hydrogen or $C_{1-6}$ alkyl which is optionally substituted with one, two, or three substituents independently selected from halo or —$OR^9$;

$R^d$ is hydrogen or $C_{1-6}$ alkyl which is optionally substituted with one, two, or three substituents independently selected from halo or —$OR^9$;

or $R^c$ and $R^d$ can be taken together with the nitrogen atom to which they are attached or are between them to form a $C_{3-8}$ heterocyclyl ring which is optionally substituted with one or two substituents independently selected from $C_{1-6}$ alkyl, halo hydroxyalkyl, hydroxy, alkoxy or keto;

n is independently selected from an integer from zero to three;

each m is independently selected from an integer from zero to two;

and the pharmaceutically acceptable salts, stereoisomers and N-oxide derivatives thereof.

Preferably, the present invention relates to compounds of the following chemical formula:

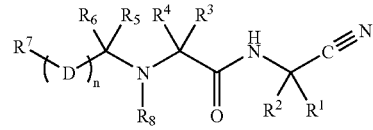

wherein $R^1$ is hydrogen, $C_{1-6}$ alkyl or $C_{2-6}$ alkenyl wherein said alkyl and alkenyl groups are optionally substituted with one to six halo, $C_{3-6}$ cycloalkyl, —$SR^9$, —$SR^{12}$, —$SOR^9$, —$SOR^{12}$, —$SO_2R^9$, —$SO_2R^{12}$, —$SO_2CH(R^{12})(R^{11})$, —$OR^{12}$, —$OR^9$, —$N(R^{12})_2$, aryl, heteroaryl or heterocyclyl wherein said aryl, heteroaryl and heterocyclyl groups are optionally substituted with one or two substitutents independently selected from $C_{1-6}$ alkyl, halo, hydroxyalkyl, hydroxy, alkoxy or keto;

$R^2$ is hydrogen, $C_{1-6}$ alkyl or $C_{2-6}$ alkenyl wherein said alkyl and alkenyl groups are optionally substituted with one to six halo, $C_{3-6}$ cycloalkyl, —$SR^9$, —$SR^{12}$, —$SOR^9$, —$SOR^{12}$, —$SO_2R^9$, —$SO_2R^{12}$, —$SO_2CH(R^{12})(R^{11})$, —$OR^{12}$, —$OR^9$, —$N(R^{12})_2$, aryl, heteroaryl or heterocyclyl wherein said aryl, heteroaryl and heterocyclyl groups are optionally substituted with one or two substitutents independently selected from $C_{1-6}$ alkyl, halo, hydroxyalkyl, hydroxy, alkoxy or keto;

or $R^1$ and $R^2$ can be taken together with the carbon atom to which they are attached to form a $C_{3-8}$ cycloalkyl or heterocyclyl ring wherein said ring system is optionally substituted with one or two substituents independently selected from $C_{1-6}$ alkyl, hydroxyalkyl, haloalkyl, or halo;

$R^3$ is hydrogen, $C_{1-6}$ alkyl or $C_{2-6}$ alkenyl wherein said alkyl and alkenyl groups are optionally substituted with $C_{3-6}$ cycloalkyl or one to six halo;

$R^4$ is hydrogen, $C_{1-6}$ alkyl or $C_{2-6}$ alkenyl wherein said alkyl and alkenyl groups are optionally substituted with $C_{3-6}$ cycloalkyl or one to six halo;

or $R^3$ and $R^4$ can be taken together with the carbon atom to which they are attached to form a $C_{3-8}$ cycloalkyl ring, $C_{5-8}$ cycloalkenyl ring, or five to seven membered heterocyclyl wherein said cycloalkyl, cycloalkenyl and heterocyclyl groups are optionally substituted with one or two substitutents independently selected from $C_{1-6}$ alkyl, halo, hydroxyalkyl, hydroxy, alkoxy or keto;

$R^5$ is selected from hydrogen or $C_{1-6}$ alkyl substituted with 1-6 halo;

$R^6$ is aryl, heteroaryl, $C_{1-6}$ haloalkyl, arylalkyl or heteroarylalkyl, wherein said aryl, heteroaryl, arylalkyl and heteroarylalkyl groups are optionally substituted with one, two, or three substituents independently selected from halo, $C_{1-6}$ alkyl, $C_{1-6}$ haloalkyl, $C_{3-6}$ cycloalkyl, haloalkoxy, —$SR^9$, —$SR^{12}$, —$SOR^9$, —$SOR^{12}$, —$SO_2R^9$, —$SO_2R^{12}$, —$SO_2CH(R^{12})(R^{11})$, —$OR^{12}$, —$N(R^{10})(R^{11})$, cyano, or aryl which is optionally substituted with —$SO_2R^{12}$;

each D is independently $C_{1-3}$ alkyl, $C_{2-3}$ alkenyl, $C_{2-3}$ alkynyl, aryl, heteroaryl, $C_{3-8}$ cycloalkyl or heterocyclyl wherein each said aryl, heteroaryl, cycloalkyl and heterocyclyl groups, which may be monocyclic or bicyclic, is optionally substituted on either the carbon or the heteroatom with one to five substituents independently selected from $C_{1-6}$ alkyl, haloalkyl, halo, keto, alkoxy, —$SR^9$, —$SR^{12}$, —$OR^9$, —$OR^{12}$, $N(R^{12})_2$, —$SO_2R^9$, or —$SO_2R^{10}$;

$R^7$ is hydrogen, $C_{1-6}$ alkyl, $C_{2-6}$ alkenyl, $C_{2-6}$ alkynyl, $C_{1-6}$ alkyloxy, halo, nitro, cyano, aryl, heteroaryl, $C_{3-8}$ cycloalkyl, heterocyclyl, —$C(O)OR^{10}$, —$C(O)OSi[CH(CH_3)_2]_3$, —$OR^9$, —$OR^{10}$, —$C(O)R^{10}$, —$R^{10}C(O)R^9$, —$C(O)R^9$, —$C(O)N(R^a)(R^b)$, —$C(O)N(R^{12})(R^{12})$, —$C(O)N(R^{10})(R^{11})$, —$C(R^{10})(R^{11})OH$, —$SR^{12}$, —$SR^9$, —$R^{10}SR^9$, —$R^9$, —$C(R^9)_3$, —$C(R^{10})(R^{11})N(R^9)_2$, —$NR^{10}C(O)NR^{10}S(O)_2R^9$, —$SO_2R^{12}$, —$SO(R^{12})$, —$SO_2R^9$, —$SO_mN(R^c)(R^d)$, —$SO^mCH(R^{10})(R^{11})$, —$SO_2N(R^{10})C(O)(R^{12})$, —$SO_2(R^{10})C(O)N(R^{12})_2$, —$OSO_2R^{10}$, —$N(R^{10})(R^{11})$, —$N(R^{10})C(O)N(R^{10})(R^9)$, —$N(R^{10})C(O)R^9$, —$N(R^{10})C(O)R^{10}$, —$N(R^{10})C(O)OR^{10}$, —$N(R^{10})SO_2(R^{10})$, —$C(R^{10})(R^{11})NR^{10}C(R^{10})(R^{11})R^9$, —$C(R^{10})(R^{11})N(R^{10})R^9$, —$C(R^{10})(R^{11})N(R^{10})(R^{11})$, —$C(R^{10})(R^{11})SC(R^{10})(R^{11})(R^9)$, $R^{10}S$—, —$C(R^a)(R^b)NR^aC(R^a)(R^b)(R^9)$, —$C(R^a)(R^b)N(R^a)(R^b)$, —$C(R^a)(R^b)C(R^a)(R^b)N(R^a)(R^b)$, —$C(O)C(R^a)(R^b)N(R^a)(R^b)$, —$C(R^a)(R^b)N(R^a)C(O)R^9$, —$C(O)C(R^a)(R^b)S(R^a)$, $C(R^a)(R^b)C(O)N(R^a)(R^b)$, —$B(OH)_2$, —$OCH_2O$— or 4,4,5,5-tetramethyl-1,3,2-dioxaborolan-2-yl; wherein said groups are optionally substituted on either the carbon or the heteroatom with one to five substituents independently selected from $C_{1-6}$ alkyl, halo, keto, cyano, haloalkyl, hydroxyalkyl, —$OR^9$, —$NO_2$, —$NH_2$, —$NHS(O)_2R^8$, —$R^9SO_2R^{12}$, —$SO_2R^{12}$, —$SO(R^{12})$, —$SR^{12}$, —$SR^9$, —$SO_mN(R^c)(R^d)$, —$SO_mN(R^{10})C(O)(R^{12})$, —$C(R^{10})(R^{11})N(R^{10})(R_{11})$, —$C(R^{10})(R^{11})OH$, —$COOH$, —$C(R^a)(R^b)C(O)N(R^a)(R^b)$, —$C(O)(R^a)(R^b)$, —$N(R^{10})C(R^{10})(R^{11})(R^9)$, —$N(R^{10})CO(R^9)$, —$NH(CH_2)_2OH$, —$NHC(O)OR^{10}$, —$Si(CH_3)_3$, heterocycyl, aryl, or heteroaryl;

$R^8$ is hydrogen or $C_{1-6}$ alkyl;

or $R^4$ and $R^8$ or can be taken together with any of the atoms to which they may be attached or are between them to form a 4-10 membered heterocyclyl ring system wherein said ring system, which may be monocyclic or bicyclic, is optionally substituted with one or two substituents independently selected from $C_{1-6}$ alkyl, halo, hydroxyalkyl, hydroxy, keto, —$OR^{10}$, —$SR^{10}$ or —$N(R^{10})_2$;

$R^9$ is selected from the group consisting of hydrogen, aryl, aryl($C_{1-4}$)alkyl, heteroaryl, heteroaryl($C_{1-4}$)alkyl, $C_{3-8}$cycloalkyl, $C_{3-8}$cycloalkyl($C_{1-4}$)alkyl, and heterocyclyl($C_{1-4}$)alkyl wherein said groups can be optionally substituted with one, two, or three substituents independently selected from halo, alkoxy or —$SO_2R^{12}$;

$R^{10}$ is hydrogen or $C_{1-6}$ alkyl $R^{11}$ is hydrogen or $C_{1-6}$ alkyl;

$R^{12}$ is hydrogen or $C_{1-6}$ alkyl which is optionally substituted with one, two, or three substituents independently selected from halo, alkoxy, cyano, —$NR^{10}$or —$SR^{10}$;

$R^a$ is hydrogen, $C_{1-6}$ alkyl, ($C_{1-6}$ alkyl)aryl, ($C_{1-6}$ alkyl)hydroxyl, —$O(C_{1-6}$ alkyl), hydroxyl, halo, aryl, heteroaryl, $C_{3-8}$ cycloalkyl, heterocyclyl, wherein said alkyl, aryl, heteroaryl, $C_{3-8}$ cycloalkyl and heterocyclyl can be optionally substituted on either the carbon or the heteroatom with one, two, or three substituents independently selected from $C_{1-6}$ alkyl or halo;

$R^b$ is hydrogen, $C_{1-6}$ alkyl, ($C_{1-6}$ alkyl)aryl, ($C_{1-6}$ alkyl)hydroxyl, alkoxyl, hydroxyl, halo, aryl, heteroaryl, $C_{3-8}$ cycloalkyl, heterocyclyl,wherein said alkyl, aryl, heteroaryl, $C_{3-8}$ cycloalkyl and heterocyclyl can be optionally substituted on either the carbon or the heteroatom with one, two, or three substituents independently selected from $C_{1-6}$ alkyl or halo;

or $R^a$ and $R^b$ can be taken together with the carbon atom to which they are attached or are between them to form a $C_{3-8}$ cycloalkyl ring or $C_{3-8}$ heterocyclyl ring wherein said 3-8 membered ring system may be optionally substituted with one or two substituents independently selected from $C_{1-6}$ alkyl and halo;

$R^c$ is hydrogen or $C_{1-6}$ alkyl which is optionally substituted with one, two, or three substituents independently selected from halo or —$OR^9$;

$R^d$ is hydrogen or $C_{1-6}$ alkyl which is optionally substituted with one, two, or three substituents independently selected from halo or —$OR^9$;

or $R^c$ and $R^d$ can be taken together with the nitrogen atom to which they are attached or are between them to form a $C_{3-8}$ heterocyclyl ring which is optionally substituted with one or two substituents independently selected from $C_{1-6}$ alkyl, halo hydroxyalkyl, hydroxy, alkoxy or keto;

n is independently selected from an integer from one to three;

each m is independently selected from an integer from zero to two;

and the pharmaceutically acceptable salts, stereoisomers and N-oxide derivatives thereof.

In an embodiment of the invention, $R^1$ and $R^2$ are each hydrogen. In another embodiment of the invention, $R^1$ and $R^2$, when on the same carbon atom, can be taken together with the carbon atom to which they are attached to form a 3-8 membered cycloalkyl ring system wherein said ring system is optionally substituted with $C_{1-6}$ alkyl, hydroxyalkyl and halo. Examples of ring systems that can be formed include cyclopropyl, cyclobutyl, cyclopentyl, cyclohexyl and cycloheptyl. A preferred embodiment is when cyclopropyl is formed.

In another embodiment of the invention, $R^1$ and $R^2$ together with the carbon atom to which they are attached to form a 3-8 membered heterocyclyl ring system wherein said ring system is optionally substituted with $C_{1-6}$ alkyl, hydroxyalkyl or haloalkyl. Examples of ring systems that can be formed include piperidinyl, pyrrolidinyl, or tetrahydropyranyl.

In an embodiment of the invention, $R^3$ and $R^4$ are each independently $C_{1-4}$ alkyl or H. In a further embodiment of the invention $R^3$ is isobutyl or n-propyl and $R^4$ is H, more preferably $R^3$ is n-propyl.

In a further embodiment, $R^3$ is $C_{1-6}$ alkyl wherein said alkyl is substituted with $C_{3-6}$ cycloalkyl or halo. Preferably, $R^3$ is 2-fluoro-2-methylpropyl, 2-trifluoromethylpropyl, 3-fluoro-2-(2-fluoromethyl)propyl, 2,2-difluoroethyl, 2,2-difluoropropyl, 3,3,3-trifluoropropyl, or 2,2-dichloroethyl and $R^4$is hydrogen. More preferably $R^3$ is 2-fluoro-2-methylpropyl.

In another embodiment of the invention, $R^3$ and $R^4$ taken together with the carbon atom to which they are attached to form $C_{3-8}$ cycloalkyl ring, $C_{5-8}$ cycloalkenyl ring, or five to seven membered heterocyclyl wherein said cycloalkyl, cycloalkenyl and heterocyclyl groups are optionally substituted with $C_{1-6}$ alkyl, halo, hydroxyalkyl, hydroxy, alkoxy or keto. Examples of ring systems that can be formed include, but are not limited to the following, keeping in mind that the heterocycle is optionally substituted with one or more substituents as described above: cyclopropyl, cyclobutyl, cyclopentyl, cyclohexyl and cycloheptyl. In a class of the embodiment cyclohexyl is formed.

In an embodiment of the invention, $R^5$ is $C_{1-6}$ alkyl substituted with 1-6 halo and $R^6$ is $C_{1-6}$ alkyl substituted with 1-6 halo. In another embodiment of the invention, $R^5$ is hydrogen and $R^6$ is $C_{1-6}$ alkyl substituted with 1-6 halo. In a further embodiment, $R^5$ is hydrogen and $R^6$ is $C_{1-6}$ alkyl substituted with 1-6 fluoro. In a further embodiment, $R^5$ is hydrogen and $R^6$ is $C_{1-3}$ alkyl substituted with 3 fluoro. In another embodiment, $R^5$ is hydrogen and $R^6$ is trifluoromethyl or 3,3,3,2,2-pentafluoroethyl, more preferably $R^6$ is trifluoromethyl.

In another embodiment of the invention, $R^5$ is hydrogen and $R^6$ is aryl or heteoaryl, wherein said aryl and heteroaryl are optionally substituted with halo or —$SO_2R^{12}$.

In another embodiment of this invention, $R^1$ and $R^2$ taken together with the carbon atom to which they are attached to form cyclopropyl, cyclobutyl, cyclopentyl, cyclohexyl and cycloheptyl, more preferably cyclopropyl; $R^3$ is n-propyl, isobutyl, 2-fluoro-2-methylpropyl, 2-trifluoromethylpropyl, 3-fluoro-2-(2-fluoromethyl)propyl, 2,2-difluoroethyl, 2,2-difluoropropyl, 3,3,3-trifluoropropyl, or 2,2-dichloroethyl; $R^4$ and $R^5$ are hydrogen; and $R^6$ is $C_{1-6}$ alkyl substituted with 1-6 halo; preferably $R^6$ is $C_{1-3}$ alkyl substituted with 3 fluoro; more preferably, $R^6$ is trifluoromethyl or 3,3,3,2,2-pentafluoroethyl, most preferably trifluoromethyl. Within this embodiment, a particularly preferred embodiment is that wherein n is 1. Another particularly preferred embodiment is that wherein n is 2. Yet another particularly preferred embodiments is that wherein n is 3. Preferably n is 1 where D is heteroaryl which is optionally substituted with halo or phenyl which is substituted with hydroxyalkyl, —$COR^{10}$ (where $R^{10}$ is $C_{1-6}$ alkyl) or —$SO_2R^{12}$ or D is phenyl which is optionally substituted with halo, —$CONR^aR^b$ (where $R^a$ is hydrogen or $C_{1-6}$ alkyl, and $R^b$ is hydrogen, $C_{1-6}$ alkyl, cycloalkyl or $C_{1-6}$ alkoxy or $R^a$ and $R^b$ together with the nitrogen atom to which they are attached form heterocylyl wherein said heterocyclyl is optionally substituted with alkyl, hydroxyalkyl, or haloalkyl), —$SO_2R^{12}$ (where $R^{12}$ is $C_{1-6}$ alkyl), —$COOR^{10}$, alkynyl optionally substituted with hydroxy or cycloalkyl, alkenyl substituted with hydroxy, alkyl optionally substituted with hydroxy, —$OR^9$ (where $R^9$ is aryl), —$OR^{10}$, —$CR^{10}R^{11}SC^{10}R^{11}R^9$ (where $R^9$ is aryl), —$CH_2S(aryl)$, cyano, —$COR^9$ or heteroaryl.

Preferably, n is 2 and each D is phenyl wherein the second phenyl is attached at the 4-position of the first phenyl ring (phenyl attached to carbon carrying the $R^5$ and $R^6$ groups) and further wherein each phenyl is optionally substituted with one or two substituents independently selected from $C_{1-6}$ alkyl, halo, hydroxy, alkoxy, haloalkyl, haloalkoxy or —$SO_2R^{12}$ (where $R^{12}$ is $C_{1-6}$ alkyl) and the second phenyl is additionally substituted with $R^7$. More preferably, each D is phenyl wherein the second phenyl is attached at the 4-position of the first phenyl ring and the second phenyl is optionally substituted with $R^7$ which is located at the 4-position of the phenyl ring and is —$SO_2R^{12}$ (where $R^{12}$ is $C_{1-6}$ alkyl which is optionally substituted with hydroxy or halo), —$SO_2NR^cR^d$ (where $R^c$ and $R^d$ are independently hydrogen or $C_{1-6}$ alkyl or $R^c$ and $R^d$ together with the nitrogen atom to which they are attached form a heterocyclyl ring), —$SR^{12}$ (where $R^{12}$ is $C_{1-6}$ alkyl), —$SOR^{12}$ (where $R^{12}$ is $C_{1-6}$ alkyl), —$NHCOR^{10}$ (where $R^{10}$ is $C_{1-6}$ alkyl), —$NR^{10}R^{11}$ (where $R^{10}$ and $R^{11}$ are $C_{1-6}$ alkyl), —$SO_2NHCOR^{10}$, heteroaryl, halo, —$COOR^{10}$ (where $R^{10}$ is hydrogen or $C_{1-6}$ alkyl l), —$OR^9$ (where $R^9$ is hydrogen or aryl), —$OR^{10}$ (where $R^{10}$ is $C_{1-6}$ alkyl), aryl substituted with —$SO_2R^{12}$ (where $R^{12}$ is $C_{1-6}$ alkyl), cyano, haloalkyl, —$C(R^{10})(R^{11})OH$, $C_{1-6}$ alkyl optionally substituted with —$OR^{10}$ and halo, $COR^9$ (where $R^9$ is aryl), —$COR^{10}$, or —$NHSO_2R^{10}$ (where $R^{10}$ is $C_{1-6}$ alkyl) and additionally the second phenyl ring is optionally substituted with a second substitutent selected from $C_{1-6}$ alkyl, —CHO, —$COOR^{10}$, —$COR^{10}$, —$NHCOR^{10}$, halo, haloalkyl, —$OR^{10}$ (where $R^{10}$ is hydrogen or $C_{1-6}$ alkyl wherein said alkyl is optionally substituted with halo), —$SO_2NH_2$, —$NHCOR^{10}$ (where $R^{10}$ is $C_{1-6}$ alkyl), or —$SO_2R^{12}$ (where $R^{12}$ is $C_{1-6}$alkyl). More preferably,the second phenyl is substituted with with $R^7$ at the 4-position wherein $R^7$ is —$SOR^{12}$, $SO_2R^{12}$ where $R^{12}$ is $C_{1-6}$alkyl (preferably methyl) or —$SO_mNR^cR^d$ where $R^c$ and $R^d$ are independently hydrogen or alkyl or $R^c$ and $R^d$ together form heterocyclyl, and m is an integer from zero to two. Preferably $R^7$ is methylsulfonyl, N-methylaminosulfonyl, aminosulfonyl, or morpholin-4-ylsulfonyl.

Preferably, n is 2 where the first D (D attached to carbon carrying the $R^5$ and $R^6$ groups) is phenyl and the second D is heterocyclyl (preferably morpholin-4-yl, piperazin-1-yl or piperidin-4-yl) which is optionally substituted with cycloalkyl, heteroaryl, $C_{1-6}$ alkyl or hydroxyalkyl, more preferably cyclopropyl, methyl, ethyl, or hydroxyethyl and said heterocyclyl ring is attached at the 4-position of the phenyl ring.

Preferably, n is 2 where the first D (D attached to carbon carrying the $R^5$ and $R^6$ groups) is phenyl and the second D is heteroaryl which is substituted with one or two substituents independently selected from hydroxyalkyl, —$SO_2R^{12}$ (where $R^{12}$ is $C_{1-6}$ alkyl), $C_{1-6}$ alkyl, halo, haloalkyl, amino, or —$OR^{10}$.

Preferably n is 3 wherein the first and the second Ds are phenyl and the third D is heterocyclyl and are optionally substituted as defined above. More preferably first and the second Ds are phenyl wherein the second phenyl is attached at the 4-position of the first phenyl and the heterocyclyl is morpholin-4-yl, pyrrolidin-1-yl, piperidin-1-yl, piperidin-4-yl or piperazin-1-yl which are substituted with $R^7$. Preferably $R^7$ is hydrogen, alkyl, hydroxyalkyl, haloalkyl, cycloalkyl, $COOR^{10}$ or —$SO_2R^{12}$ (where $R^{12}$ is $C_{1-6}$ alkyl).

In another embodiment of this invention, $R^1$ and $R^2$ taken together with the carbon atom to which they are attached to form cyclopropyl, cyclobutyl, cyclopentyl, cyclohexyl and cycloheptyl, more preferably cyclopropyl; $R^3$ and $R^4$ taken together with the carbon atom to which they are attached form $C_{3-8}$ cycloalkyl ring, $C_{5-8}$ cycloalkenyl ring, or five to seven membered heterocyclyl wherein said cycloalkyl, cycloalkenyl and heterocyclyl groups are optionally substituted with $C_{1-6}$ alkyl, halo, hydroxyalkyl, hydroxy, alkoxy or keto. Examples of ring systems that can be formed include, but are not limited to the following, keeping in mind that the heterocycle is optionally substituted with one or more substituents as described above: cyclopropyl, cyclobutyl, cyclopentyl, cyclohexyl, cycloheptyl, tetrahydrofuran-4-yl, piperidin-4-yl. Preferably $R^3$ and $R^4$ taken together with the carbon atom to which they are attached form cyclopropyl, cyclobutyl, cyclopentyl, cyclohexyl, or cycloheptyl. A more preferred embodiment is when $R^3$ and $R^4$ taken together with the carbon atom to which they are attached form cyclohexyl is formed. Within this embodiment, a particularly preferred embodiment is that wherein $R^5$ are hydrogen; and $R^6$ is $C_{1-6}$ alkyl substituted with 1-6 halo; preferably $R^6$ is $C_{1-3}$ alkyl substituted with 3 fluoro; more preferably, $R^6$ is trifluoromethyl or 3,3,3,2,2-pentafluoroethyl, most preferably trifluoromethyl. Within this embodiment, a particularly preferred embodiment is that wherein n is 1. Another particularly preferred embodiment is that wherein n is 2. Yet another particularly preferred embodiments is that wherein n is 3. Preferably n is 1 where D is heteroaryl which is optionally substituted with halo or phenyl with is substituted with hydroxyalkyl, —COR$^{10}$ (where R$^{10}$ is C$_{1-6}$ alkyl) or —SO$^2$R$^{12}$ or D is phenyl which is optionally substituted with halo, —CONR$^a$R$^b$ (where R$^a$ is hydrogen or C$_{1-6}$ alkyl, and R$^b$ is hydrogen, C$_{1-6}$ alkyl, cycloalkyl or C$_{1-6}$ alkoxy or R$^a$ and R$^b$ together with the nitrogen atom to which they are attached form heterocylyl wherein said heterocyclyl is optionally substituted with alkyl or haloalkyl), —SO$_2$R$^{12}$ (where R$^{12}$ is C$_{1-6}$ alkyl), —COOR$^{10}$, alkynyl substituted with hydroxy, alkenyl substituted with hydroxy, alkyl optionally substituted with hydroxy, —OR$^{10}$, —CR$^{10}$R$^{11}$SC$^{10}$R$^{11}$R$^9$ (where R$^9$ is aryl), —CH$^2$S(aryl)-COR$^9$ or heteroaryl.

Preferably, n is 2 and each D is phenyl wherein the second phenyl is attached at the 4-position of the first phenyl ring (phenyl attached to carbon carrying the R$^5$ and R$^6$ groups) and further wherein each phenyl is optionally substituted with one or two substituents independently selected from C$_{1-6}$ alkyl, halo, hydroxy, alkoxy, haloalkyl, haloalkoxy and the second phenyl is additionally substituted with R$^7$. More preferably, each D is phenyl wherein the second phenyl is attached at the 4-position of the first phenyl ring and the second phenyl is optionally substituted with R$^7$ which is located at the 4-position of the phenyl ring and is —SO$_2$R$_{12}$ (where R$_{12}$ is C$_{1-6}$ alkyl which is optionally substituted with halo), —SO$_2$NR$^c$R$^d$ (where R$^c$ and R$^d$ are independently hydrogen or C$_{1-6}$ alkyl or R$^c$ and R$^d$ together with the nitrogen atom to which they are attached form a heterocyclyl ring), —SR$^{12}$ (where R$^{12}$ is C$_{1-6}$ alkyl), —NHCOR$^9$ (where R$^9$ is C$_{1-6}$ alkyl), —NR$^{10}$R$^{11}$ (where R$^{10}$ and R$^{11}$ are C$_{1-6}$ alkyl), heteroaryl, halo, —COOR$^{10}$ (where R$^{10}$ is hydrogen or C$_{1-6}$ alkyl l), —OR$^9$ (where R$^9$ is hydrogen or aryl), aryl substituted with —SO$_2$R$^{12}$ (where R$^{12}$ is C$_{1-6}$ alkyl), cyano, haloalkyl, —CHO, —C(R$^{10}$)(R$^{11}$)OH, C$_{1-6}$ alkyl optionally substituted with —OR$^{10}$ and halo, —COR$^{10}$, or —NHSO$^2$R$^{10}$ (where R$^{10}$ is C$_{1-6}$ alkyl) and additionally the second phenyl ring is optionally substituted with a second substitutent selected from halo, haloalkyl, —OR$^{10}$ (where R$^{10}$ is hydrogen or C1-6alkyl wherein said alkyl is optionally substituted with halo) or —SO$_2$R$^{12}$ (where R$^{12}$ is C$_{1-6}$alkyl). More preferably,the second phenyl is substituted with with R$^7$ at the 4-position wherein R$^7$ is —SO$_2$R$^{12}$ where R$^{12}$ is C$_{1-6}$alkyl (preferably methyl) or —SO$^m$NR$^c$R$^d$ where R$^c$ and R$^d$ are independently hydrogen or alkyl or R$^c$ and R$^d$ together form heterocyclyl, and m is an integer from zero to two. Preferably R$^7$ is methylsulfonyl, N-methylaminosulfonyl, aminosulfonyl, or morpholin-4-ylsulfonyl.

Preferably, n is 2 where the first D (D attached to carbon carrying the R$^5$ and R$^6$ groups) is phenyl and the second D is heterocyclyl (preferably piperazin-1-yl or piperidin-4-yl) substituted with cycloalkyl, C$_{1-6}$ alkyl or hydroxyalkyl, more preferably cyclopropyl, methyl, ethyl, or hydroxyethyl and said heterocyclyl ring is attached at the 4-position of the phenyl ring.

Preferably, n is 2 where the first D (I attached to carbon carrying the R$^5$ and R$^6$ groups) is phenyl and the second D is heteroaryl which is substituted with one or two substituents independently selected from hydroxyalkyl, —SO$_2$R$^{12}$ (where R$^{12}$ is C$_{1-6}$ alkyl), C$_{1-6}$ alkyl, halo, or —OR$^{10}$.

Preferably n is 3 wherein the first and the second Ds are phenyl and the third D is heterocyclyl and are optionally substituted as defined above. More preferably first and the second Ds are phenyl wherein the second phenyl is attached at the 4-position of the first phenyl and the heterocyclyl is morpholin-4-yl, pyrrolidin-1-yl, piperidin-1-yl, piperidin-4-yl or piperazin-1-yl which are substituted with R$^7$. Preferably R$^7$ is hydrogen, alkyl, hydroxyalkyl, haloalkyl or cycloalkyl.

In another embodiment of the invention, R$^5$ is hydrogen and R$^6$ is aryl optionally substituted with one, two, or three substituents independently selected from halo, C$_{1-6}$ alkyl, C$_{1-6}$ haloalkyl, C$_{3-6}$ cycloalkyl, haloalkoxy, —SR$^9$, —SR$^{12}$, —SOR$^9$, —SOR$^{12}$, —SO$_2$R$^9$, —SO$_2$R$^{12}$, —SO$_2$CH(R$^{12}$)(R$^{11}$), —OR$^{12}$, —N(R$^{10}$)(R$^{11}$), cyano, or aryl which is optionally substituted with —SO$_2$R$^{12}$. More preferably phenyl substituted with C$_{1-6}$alkyl, halo, haloalkyl, or haloalkoxy. Within this embodiment, a preferred embodiment is that wherein R$^1$ and R$^2$ are each hydrogen. Within this embodiment, another preferred embodiment is that wherein R$^1$ and R$^2$ taken together with the carbon atom to which they are attached to form a 3-8 membered cycloalkyl or heterocyclyl ring system wherein said ring system is optionally substituted with C$_{1-6}$ alkyl, hydroxyalkyl and halo. Preferable ring systems that can be formed include cyclopropyl, cyclobutyl, cyclopentyl, cyclohexyl and cycloheptyl, more preferably cyclopropyl. Within these preferred and more preferred embodiments, an even more preferred embodiment is that wherein R$^3$ is C$_{1-4}$ alkyl and R$^4$ is H. Preferably, R$^3$ is n-propyl or isobutyl and R$^4$ is H. Within these preferred and more preferred embodiments, another even more preferred embodiment is that wherein R$^3$ is 2-fluoro-2-methylpropyl, 2-trifluoromethylpropyl, 3-fluoro-2-(2-fluoromethyl)propyl, 2,2-difluoroethyl, 2,2-difluoropropyl, 3,3,3-trifluoropropyl, or 2,2-dichloroethyl; and R$^4$ is hydrogen. Within these preferred and more preferred embodiments, another even more preferred embodiment is that wherein R$^3$ and R$^4$can be taken together with the carbon atom to which they are attached to form C$_{3-8}$ cycloalkyl ring, C$_{5-8}$ cycloalkenyl ring, or five to seven membered heterocyclyl wherein said cycloalkyl, cycloalkenyl and heterocyclyl groups are optionally substituted with C$_{1-6}$ alkyl, halo, hydroxyalkyl, hydroxy, alkoxy or keto. Examples of ring systems that can be formed include, but are not limited to the following, keeping in mind that the heterocycle is optionally substituted with one or more substituents as described above: cyclopropyl, cyclobutyl, cyclopentyl, cyclohexyl and cycloheptyl. A preferred embodiment is when cyclohexyl is formed.

Within this embodiment, a particularly preferred embodiment is that wherein n is 1. Another particularly preferred embodiment is that wherein n is 2. Yet another particularly preferred embodiments is that wherein n is 3. Preferably n is 1 where D is heteroaryl which is optionally substituted with halo or phenyl with is substituted with hydroxyalkyl, —COR$^{10}$ (where R$^{10}$ is C$_{1-6}$ alkyl) or —SO$_2$R$^{12}$ or D is phenyl which is optionally substituted with halo, —CONR$^a$R$^b$ (where R$^a$ is hydrogen or C$_{1-6}$ alkyl, and R$^b$ is hydrogen, C$_{1-6}$ alkyl, cycloalkyl or C$_{1-6}$ alkoxy or R$^a$ and R$^b$ together with the nitrogen atom to which they are attached form heterocylyl wherein said heterocyclyl is optionally substituted with alkyl or haloalkyl), —SO$_2$R$^{12}$ (where R$^{12}$ is C$_{1-6}$ alkyl), —COOR$^{10}$, alkynyl substituted with hydroxy, alkenyl substituted with hydroxy, alkyl optionally substituted with hydroxy, —OR$^{10}$, —CR$^{10}$R$^{11}$SC$^{10}$R$^{11}$R$^9$ (where R$^9$ is aryl), —CH$_2$S(aryl)-COR$^9$ or heteroaryl.

Preferably, n is 2 and each D is phenyl wherein the second phenyl is attached at the 4-position of the first phenyl ring (phenyl attached to carbon carrying the R$^5$ and R$^6$ groups) and further wherein each phenyl is optionally substituted with one or two substituents independently selected from C$_{1-6}$ alkyl, halo, hydroxy, alkoxy, haloalkyl, haloalkoxy and the second phenyl is additionally substituted with R$^7$. More preferably, each D is phenyl wherein the second phenyl is attached at the 4-position of the first phenyl ring and the second phenyl is optionally substituted with R$^7$ which is located at the 4-position of the phenyl ring and is —SO$_2$R$_{12}$ (where R$_{12}$ is C$_{1-6}$ alkyl which is optionally substituted with halo), —SO$_2$NR$^c$R$^d$ (where R$^c$ and R$^d$ are independently hydrogen or C$_{1-6}$ alkyl or R$^c$ and R$^d$ together with the nitrogen atom to which they are attached form a heterocyclyl ring), —SR$^{12}$ (where R$^{12}$ is C$_{1-6}$ alkyl), —NHCOR$^9$ (where R$^9$ is C$_{1-6}$ alkyl), —NR$^{10}$OR$^{11}$ (where R$^{10}$ and R$^{11}$ are C$_{1-6}$ alkyl), heteroaryl, halo, —COOR$^{10}$ (where R$^{10}$ is hydrogen or C$_{1-6}$ alkyl l), —OR$^9$ (where R$^9$ is hydrogen or aryl), aryl substituted with —SO$_2$R$^{12}$ (where R$^{12}$ is C$_{1-6}$ alkyl), cyano, haloalkyl, —CHO, —C(R$^{10}$)(R$^{11}$)OH, C$_{1-6}$ alkyl optionally substituted with —OR$^{10}$ and halo, —COR$^{10}$, or —NHSO$_2$R$^{10}$ (where R$^{10}$ is C$_{1-6}$ alkyl) and additionally the second phenyl ring is optionally substituted with a second substitutent selected from halo, haloalkyl, —OR$^{10}$ (where R$^{10}$ is hydrogen or C1-6alkyl wherein said alkyl is optionally substituted with halo) or —SO$_2$R$^{12}$ (where R$^{12}$ is C$_{1-6}$alkyl). More preferably, the second phenyl is substituted with with R$^7$ at the 4-position wherein R$^7$ is —SO$_2$R$^{12}$ where R$^{12}$ is C$_{1-6}$alkyl (preferably methyl) or —SO$_m$NR$^c$R$^d$ where R$^c$ and R$^d$ are independently hydrogen or alkyl or R$^c$ and R$^d$ together form heterocyclyl, and m is an integer from zero to two. Preferably R$^7$ is methylsulfonyl, N-methylaminosulfonyl, aminosulfonyl, or morpholin-4-ylsulfonyl.

Preferably, n is 2 where the first D (D attached to carbon carrying the R$^5$ and R$^6$ groups) is phenyl and the second D is heterocyclyl (preferably piperazin-1-yl or piperidin-4-yl) substituted with cycloalkyl, C$_{1-6}$ alkyl or hydroxyalkyl, more preferably cyclopropyl, methyl, ethyl, or hydroxyethyl and said heterocyclyl ring is attached at the 4-position of the phenyl ring.

Preferably, n is 2 where the first D (D attached to carbon carrying the R$^5$ and R$^6$ groups) is phenyl and the second D is heteroaryl which is substituted with one or two substituents independently selected from hydroxyalkyl, —SO$_2$R$^{12}$ (where R$^{12}$ is C$_{1-6}$ alkyl), C$_{1-6}$ alkyl, halo, or —OR$^{10}$.

Preferably n is 3 wherein the first and the second Ds are phenyl and the third D is heterocyclyl and are optionally substituted as defined above. More preferably first and the second Ds are phenyl wherein the second phenyl is attached at the 4-position of the first phenyl and the heterocyclyl is morpholin-4-yl, pyrrolidin-1-yl, piperidin-1-yl, piperidin-4-yl or piperazin-1-yl which are substituted with R$^7$. Preferably R$^7$ is hydrogen, alkyl, hydroxyalkyl, haloalkyl or cycloalkyl.

In an embodiment of the invention, R$^5$ is hydrogen and R$^6$ is heteroaryl optionally substituted with C1-6alkyl, halo, haloalkyl, or haloalkoxy. Preferably, R$^6$ is thiazolyl, pyridinyl, tetrazolyl, thienyl, or furanyl, optionally substituted with C$_{1-4}$ alkyl or halo. Within this embodiment, a preferred embodiment is that wherein R$^1$ and R$^2$ are each hydrogen. Within this embodiment, another preferred embodiment is that wherein R$^1$ and R$^2$ taken together with the carbon atom to which they are attached to form a 3-8 membered cycloalkyl or heterocyclyl ring system wherein said ring system is optionally substituted with C$_{1-6}$ alkyl, hydroxyalkyl and halo. Preferable ring systems that can be formed include cyclopropyl, cyclobutyl, cyclopentyl, cyclohexyl and cycloheptyl, more preferably cyclopropyl. Within these preferred and more preferred embodiments, an even more preferred embodiment is that wherein R$^3$ is C$_{1-4}$ alkyl and R$^4$ is H. Preferably, R$^3$ is n-propyl or isobutyl and R$^4$ is H. Within these preferred and more preferred embodiments, another even more preferred embodiment is that wherein R$^3$ is 2-fluoro-2-methylpropyl, 2-trifluoromethylpropyl, 3-fluoro-2-(2-fluoromethyl)propyl, 2,2-difluoroethyl, 2,2-difluoropropyl, 3,3,3-trifluoropropyl, or 2,2-dichloroethyl; and R$^4$ is hydrogen. Within these preferred and more preferred embodiments, another even more preferred embodiment is that wherein R$^3$ and R$^4$ can be taken together with the carbon atom to which they are attached to form C$_{3-8}$ cycloalkyl ring, C$_{5-8}$ cycloalkenyl ring, or five to seven membered heterocyclyl wherein said cycloalkyl, cycloalkenyl and heterocyclyl groups are optionally substituted with C$_{1-6}$ alkyl, halo, hydroxyalkyl, hydroxy, alkoxy or keto. Examples of ring systems that can be formed include, but are not limited to the following, keeping in mind that the heterocycle is optionally substituted with one or more substituents as described above: cyclopropyl, cyclobutyl, cyclopentyl, cyclohexyl and cycloheptyl. A preferred embodiment is when cyclohexyl is formed.

Within this embodiment, a particularly preferred embodiment is that wherein n is 1. Another particularly preferred embodiment is that wherein n is 2. Yet another particularly preferred embodiments is that wherein n is 3. Preferably n is 1 where D is heteroaryl which is optionally substituted with halo or phenyl with is substituted with hydroxyalkyl, —COR$^{10}$ (where R$^{10}$ is C$_{1-6}$ alkyl) or —SO$_2$R$^{12}$ or D is phenyl which is optionally substituted with halo, —CONR$^a$R$^b$ (where R$^a$ is hydrogen or C$_{1-6}$ alkyl, and R$^b$ is hydrogen, C$_{1-6}$ alkyl, cycloalkyl or C$_{1-6}$ alkoxy or R$^a$ and R$^b$ together with the nitrogen atom to which they are attached form heterocylyl wherein said heterocyclyl is optionally substituted with alkyl or haloalkyl), —SO$_2$R$^{12}$ (where R$^{12}$ is C$_{1-6}$ alkyl), —COOR$^{10}$, alkynyl substituted with hydroxy, alkenyl substituted with hydroxy, alkyl optionally substituted with hydroxy, —OR$^{10}$, —CR$^{10}$R$^{11}$SC$^{10}$R$^{11}$R$^9$ (where R$^9$ is aryl), —CH$_2$S(aryl)-COR$^9$ or heteroaryl.

Preferably, n is 2 and each D is phenyl wherein the second phenyl is attached at the 4-position of the first phenyl ring (phenyl attached to carbon carrying the R$^5$ and R$^6$ groups) and further wherein each phenyl is optionally substituted with one or two substituents independently selected from C$_{1-6}$ alkyl, halo, hydroxy, alkoxy, haloalkyl, haloalkoxy and the second phenyl is additionally substituted with R$^7$. More preferably, each D is phenyl wherein the second phenyl is attached at the 4-position of the first phenyl ring and the second phenyl is optionally substituted with R$^7$ which is located at the 4-position of the phenyl ring and is —SO$_2$R$_{12}$ (where R$_{12}$ is C$_{1-6}$ alkyl which is optionally substituted with halo), —SO$_2$NR$^c$R$^d$ (where R$^c$ and R$^d$ are independently hydrogen or C$_{1-6}$ alkyl or R$^c$ and R$^d$ together with the nitrogen atom to which they are attached form a heterocyclyl ring), —SR$^{12}$ (where R$^{12}$ is C$_{1-6}$ alkyl), —NHCOR$^9$ (where R$^9$ is C$_{1-6}$ alkyl), —NR$^{10}$R$^{11}$ (where R$^{10}$ and R$^{11}$ are C$_{1-6}$ alkyl), heteroaryl, halo, —COOR$^{10}$ (where R$^{10}$ is hydrogen or C$_{1-6}$ alkyl l), —OR$^9$ (where R$^9$ is hydrogen or aryl), aryl substituted with —SO$_2$R$^{12}$ (where R$^{12}$ is C$_{1-6}$ alkyl), cyano, haloalkyl, —CHO, —C(R$^{10}$)(R$^{11}$)OH, C$_{1-6}$ alkyl optionally substituted with —OR$^{10}$ and halo, —COR$^{10}$, or —NHSO$_2$R$^{10}$ (where R$^{10}$ is C$_{1-6}$ alkyl) and additionally the second phenyl ring is optionally substituted with a second substitutent selected from halo, haloalkyl, —OR$^{10}$ (where R$^{10}$ is hydrogen or C1-6alkyl wherein said alkyl is optionally substituted with halo) or —SO$_2$R$^{12}$ (where R$^{12}$ is C$_{1-6}$alkyl). More preferably,the second phenyl is substituted with with R$^7$ at the 4-position wherein R$^7$ is —SO$_2$R$^{12}$ where R$^{12}$ is C$_{1-6}$alkyl (preferably methyl) or —SO$_m$NR$^c$R$^d$ where R$^c$ and R$^d$ are independently hydrogen or alkyl or R$^c$ and R$^d$ together form heterocyclyl, and m is an integer from zero to two. Preferably R$^7$ is methylsulfonyl, N-methylaminosulfonyl, aminosulfonyl, or morpholin-4-ylsulfonyl.

Preferably, n is 2 where the first D (D attached to carbon carrying the $R^5$ and $R^6$ groups) is phenyl and the second D is heterocyclyl (preferably piperazin-1-yl or piperidin-4-yl) substituted with cycloalkyl, $C_{1-6}$ alkyl or hydroxyalkyl, more preferably cyclopropyl, methyl, ethyl, or hydroxyethyl and said heterocyclyl ring is attached at the 4-position of the phenyl ring.

Preferably, n is 2 where the first D (D attached to carbon carrying the $R^5$ and $R^6$ groups) is phenyl and the second D is heteroaryl which is substituted with one or two substituents independently selected from hydroxyalkyl, $—SO_2R^{12}$ (where $R^{12}$ is $C_{1-6}$ alkyl), $C_{1-6}$ alkyl, halo, or $—OR^{10}$.

Preferably n is 3 wherein the first and the second Ds are phenyl and the third D is heterocyclyl and are optionally substituted as defined above. More preferably first and the second Ds are phenyl wherein the second phenyl is attached at the 4-position of the first phenyl and the heterocyclyl is morpholin-4-yl, pyrrolidin-1-yl, piperidin-1-yl, piperidin-4-yl or piperazin-1-yl which are substituted with $R^7$. Preferably $R^7$ is hydrogen, alkyl, hydroxyalkyl, haloalkyl or cycloalkyl.

In an embodiment of the invention, $R^4$ and $R^8$ or can be taken together with any of the atoms to which they may be attached or are between them to form a 4-10 membered heterocyclyl ring system wherein said ring system, which may be monocyclic or bicyclic, is optionally substituted with $C_{1-6}$ alkyl, halo, hydroxyalkyl, hydroxy, keto, $—OR^{10}$, $—SR^{10}$ or $—N(R^{10})_2$. In a further embodiment of the invention, $R^4$ and $R^8$ are defined such that they can be taken together with the nitrogen to which they are attached to form a monocyclic or bicyclic heterocyclyl with 5-7 members in each ring and optionally containing, in addition to the nitrogen, 1 or 2 additional heteroatoms selected from N, O and S, said heterocycle optionally substituted with one or more substituents selected from $C_{1-6}$ alkyl, halo, hydroxyalkyl, hydroxy, keto, $—OR^{10}$, $—SR^{10}$ or $—N(R^{10})_2$. In a further example, $R^4$ and $R^8$ are defined such that they can be taken together with the nitrogen to which they are attached to form a 5 or 6 membered heterocyclyl ring system. Examples of the heterocycles that can thus be formed include, but are not limited five or six membered rings containing at least one nitrogen, which is optionally substituted with one or more substituents as described above. A preferred embodiment is when optionally substituted pyrolidinyl is formed.

In an embodiment of the invention, $R^a$ and $R^b$ are defined such that they can be taken together with the carbon or nitrogen to which they are attached to form a monocyclic or bicyclic carbocycle or heterocycle with 5-7 members in each ring. The heterocycle can optionally contain, in addition to the nitrogen, 1 or 2 additional heteroatoms selected from N, O and S. Said carbocycle and heterocycle can be optionally substituted with one or more substituents selected from $C_{1-6}$ alkyl and halo.

Reference to the preferred embodiments set forth above is meant to include all combinations of particular and preferred groups unless stated otherwise.

Another embodiment of the present invention encompasses a process for preparing compounds of the present invention, comprising:

(i) reacting a compound of formula (a):

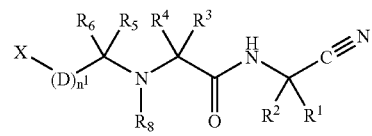

(a)

where $R^1$-$R^6$ and D are as defined as above, $n^1$ is an integer from 1-3, and X is halo, with a compound of formula (b):

(b)

where $R^7$ is as defined as above, n2 is an integer from 0 to 2 provided that $n^1$ and n2 together are an integer from 1-3, and Y is boronic acid or 4,4,5,5-tetramethyl-1,3,2-dioxaborolan-2-yl; or (ii) reacting a compound of formula (c):

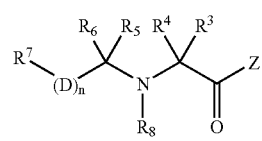

(c)

where $R^3$-$R^7$, n, and D are as defined as above and Z is hydroxy, halo, or succinimido ester with a compound of formula (d):

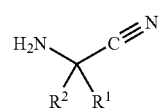

or a salt thereof where $R^1$ and $R^2$ are as defined as above;

(iii) optionally modifying any of the $R^1$-$R^7$ and D groups;

(iv) optionally treating a compound of formula (I), prepared in Steps (i)-(iii) above, with an acid to provide a corresponding acid addition salt;

(v) optionally treating a compound of formula (I), prepared in Steps (i)-(iii) above, with a base to provide a corresponding free base; and (vi) optionally separating a mixture of stereoisomers of a compound of formula (I) prepared in Steps (i), (ii), (iii), (iv), or (v) above, to provide a single stereoisomer.

Embodied by the present invention are methods for treating disorders related to abnormal bone resorption. Such disorders include, but are not limited to, osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, metastatic bone disease, hypercalcemia of malignancy, and multiple myeloma. A preferred embodiment includes methods for treating osteoporosis and metastatic bone disease. A more preferred embodiment includes methods for treating osteoporosis.

Representative compounds of the present invention are disclosed in Tables I-IV below:

Compound of Formula I where $R^1$, $R^2$, $R^4$, $R^5$, and $R^8$ are hydrogen are shown in Table I below:

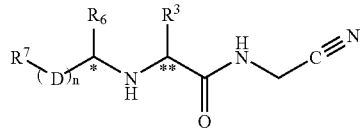

| Stereochem at (*C, **C) | $R^3$ | $R^6$ | —(D)$_n$—$R^7$ |
|---|---|---|---|
| RS,S | 2-methylpropyl | CF$_3$ | phenyl |
| RS,S | 2-methylpropyl | CF$_3$ | 4'-(4-tert-butoxycarbonylpiperazin-1-yl)-biphen-4-yl |
| RS,S | 2-methylpropyl | CF$_3$ | 4'-(piperazin-1-yl)biphen-4-yl |
| RS,S | 2-methylpropyl | CF$_3$ | 4'-[4-(2-hydroxyethyl)piperazin-1-yl]-biphen-4-yl |
| RS,S | 2-methylpropyl | CF$_3$ | 4'-[4-(2-hydroxy-2-methy)propyl)-piperazin-1-yl]-biphen-4-yl |
| RS,R | 2-methylpropyl | CF$_3$ | 4-bromophenyl |
| RS,R | 2-methylpropyl | CF$_3$ | 4'-methylsulfonylbiphen-4-yl |
| RS,R | 2-methylpropyl | CF$_3$ | 4'-morpholin-4-ylsulfonylbiphen-4-yl |
| RS,R | 2-methylpropyl | CF$_3$ | 4'-N-methylaminosulfonylbiphen-4-yl |
| R,S | 2-methylpropyl | CF$_3$ | 4-pyridin-4-ylphenyl |
| RS,S | 2-methylpropyl | CF$_3$ | 4-N,N-dimethylaminocarbonylphenyl |
| R,S | 2-methylpropyl | CF$_3$ | 4-(pyridin-4-yl-1-N-oxide)phenyl |
| RS,S | 2-methylpropyl | CF$_3$ | 4-[6-(1-hydroxy-1-methylethyl)pyridin-3-yl-1-N-oxide]phenyl |
| RS,S | 2-methylpropyl | CF$_3$ | 4-(6-methylsulfonylpyridin-3-yl)-phenyl |
| RS,S | 2-methylpropyl | CF$_3$ | 4'-(methylsulfinyl)biphen-4-yl |
| RS,S | 2-methylpropyl | CF$_3$ | 4-morpholin-4-ylphenyl |
| RS,S | 2-methylpropyl | CF$_3$ | 4-piperazin-1-ylphenyl |
| RS,S | 2-methylpropyl | 2,4,6-trifluorophenyl | 4-bromophenyl |
| RS,S | 2-methylpropyl | CF$_3$ | 4-cyclopropylaminocarbonylphenyl |
| RS,S | 2-methylpropyl | CF$_3$ | 4'-methylthiobiphen-4-yl |
| RS,S | 2-methylpropyl | CF$_3$ | 4-(2-methylquinolin-7-yl)phenyl |
| RS,S | 2-methylpropyl | CF$_3$ | 4-(1H-indol-5-yl)phenyl |
| RS,S | 2-methylpropyl | CF$_3$ | 4-carboxyphenyl |
| RS,S | 2-methylpropyl | CF$_3$ | 3'-acetylaminobiphen-4-yl |
| RS,S | 2-methylpropyl | CF$_3$ | 4-piperidin-4-ylphenyl |
| RS,S | 2-methylpropyl | CF$_3$ | 4-(4-pyridin-2-ylpiperazin-1-yl)phenyl |
| RS,S | 2-methylpropyl | 2,4,6-trifluorophenyl | 4-pyridin-4-ylphenyl |
| RS,S | 2-methylpropyl | CF$_3$ | 4-[2-(4-methylpiperazin-1-yl)-1,3-thiazol-4-yl]-phenyl |
| RS,S | 2-methylpropyl | CF$_3$ | 4-(4-ethylpiperazin-1-yl)phenyl |
| RS,S | 2-methylpropyl | CF$_3$ | 4'-(4-(2-fluoroethyl)piperazin-1-yl)-biphen-4-yl |
| RS,S | 2-methylpropyl | CF$_3$ | 4-(4-methylpiperazin-1-yl-carbonyl)phenyl |
| RS,S | 2-methylpropyl | CF$_3$ | 4'-dimethylaminobiphen-4-yl |
| RS,S | 2-methylpropyl | CF$_3$ | 4-(piperazin-1-ylcarbonyl)phenyl |
| RS,S | 2-methylpropyl | CF$_3$ | 4-[4-(2-hydroxyethyl)piperazin-1-yl-carbonyl]phenyl |
| R,S | 2-methylpropyl | CF$_3$ | 4-[4-(2-fluoroethyl)piperazin-1-yl-carbonyl]phenyl |
| RS,S | 2-methylpropyl | CF$_3$ | 4-[4-(2-hydroxy-2-methylpropyl)-piperazin-1-ylcarbonyl]phenyl |
| R,S | 2-methylpropyl | CF$_3$ | 4-cyanomethylaminocarbonylphenyl |
| RS,RS | cyclopropylmethyl | CF$_3$ | 4-bromophenyl |
| RS,RS | cyclopropylmethyl | CF$_3$ | 4-pyridin-4-ylphenyl |
| S,S | 2-methylpropyl | CF$_3$ | 4-morpholin-4-ylcarbonylphenyl |
| RS,S | 2-methylpropyl | CF$_3$ | 4'-(pyridin4-yl)biphen-4-yl |
| S,S | 2-methylpropyl | CF$_3$ | 4-(2-methylpyridin-5-yl)phenyl |
| RS,S | 2-methylpropyl | CF$_3$ | 5-phenylthien-2-yl |
| RS,S | 2-methylpropyl | CF$_3$ | 4-quinolin-8-ylphenyl |
| RS,S | 2-methylpropyl | CF$_3$ | biphen-4-yl |
| S,S | 2-methylpropyl | CF$_3$ | 4-pyridin-2-ylphenyl |
| S,S | 2-methylpropyl | CF$_3$ | 4-[3-(3-trifluoromethylphenyl)-oxadiazol-5-yl]-phenyl |
| RS,S | 2-methylpropyl | CF$_3$ | 4'-(aminosulfonyl)biphen-4-yl |

-continued

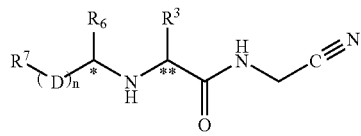

| Stereochem at (*C, **C) | R³ | R⁶ | —(D)ₙ—R⁷ |
|---|---|---|---|
| S,S | 2-methylpropyl | CF₃ | 4'-(N-methyl-N-methoxyaminocarbonyl)-phenyl |
| RS,S | 2-methylpropyl | CF₃ | 4-(3-hydroxy-3-methylbut-1-ynyl)-phenyl |
| S,S | 2-methylpropyl | CF₃ | 4-(trans-3-hydroxy-3-methylbut-1-enyl)phenyl |
| R,S | 2-methylpropyl | CF₃ | 4-(3-hydroxy-3-methylbutyl)phenyl |
| S,S | 2-methylpropyl | CF₂CF₃ | 4-bromophenyl |
| S,S | 2-methylpropyl | CF₂CF₃ | 4-pyridin-4-ylphenyl |
| S,S | 2-methylpropyl | CF₃ | 4-(2-methyl-1,3-thiazol-4-yl)phenyl |
| RS,S | 2-methylpropyl | CF₃ | 4-(3-tert-butyl-1,2,4-triazin-5-yl)-phenyl |
| S,S | 2-methylpropyl | CF₃ | 4'-fluorobiphen-4-yl |
| S,S | 2-methylpropyl | CF₃ | 4-methoxycarbonylphenyl |
| S,S | 2-methylpropyl | CF₃ | 4-(E-2-quinolin-2-ylethenyl)phenyl |
| RS,S | 2-methylpropyl | CF₃ | 3'-methylsulfonylbiphen-4-yl |
| RS,S | 2-methylpropyl | CF₃ | 4'-carboxylbiphen-4-yl |
| S,S | 2-methylpropyl | CF₂CF₃ | 4'-methylthiobiphen-4-yl |
| R,S | 2-methylpropyl | CF₃ | 1,3-thiazol-2-yl |
| S,S | 2-methylpropyl | CF₃ | 4'-methoxybiphen-4-yl |
| RS,S | 2-methylpropyl | CF₃ | 4'-(N-methyl-N-methoxyamino)-biphen-4-yl |
| S,S | 2-methylpropyl | CF₃ | 4-methoxyphenyl |
| S,S | 2-methylpropyl | CF₂CF₃ | 4'-methylsulfonylbiphen-4-yl |
| RS,S | 2-methylpropyl | CF₃ | 4-[2-(3-methylsulfonylphenyl)-1,3-thiazol-4-yl]phenyl |
| S,S | 2-methylpropyl | CF₃ | 4-[2-(1H-pyrazol-4-yl)-1,3-thiazol-4-yl]phenyl |
| S,S | 2-methylpropyl | CF₃ | 4-(4-methylsulfonylbenzyl-thiomethyl)phenyl |
| S,S | 2-methylpropyl | CF₃ | 4-(3-methyl-[1,2,4]oxadiazol-5-yl)-phenyl |
| S,S | 2-methylpropyl | CF₃ | 4-(3-chloropyridin-6-yl)-phenyl |
| S,S | 2-methylpropyl | CF₃ | 3'-aminosulfonyl-4'-bromobiphen-4-yl |
| S,S | 2-methylpropyl | CF₃ | 3'-methylsulfonyl-4'-bromobiphen-4-yl |
| S,S | 2-methylpropyl | CF₃ | 4-phenoxyphenyl |
| S,S | 2-methylpropyl | CF₃ | 4-[3-(5-bromopyridin-3-yl)-[1,2,4]oxadiazol-5-yl]-phenyl |
| S,S | 2-methylpropyl | CF₃ | 4-(phenylthiomethyl)-phenyl |
| S,S | 2-methylpropyl | CF₃ | 4-(benzoyl)phenyl |
| S,S | 2-methylpropyl | CF₃ | 4'-bromobiphen-4-yl |
| RS,S | 2-methylpropyl | CF₃ | 4'-[4-methylsulfonylpiperazin-1-yl]-biphen-4-yl |
| S,S | 2-methylpropyl | CF₃ | 4-(4-chloropyridin-3-yl)-phenyl |
| S,S | 2-methylpropyl | CF₃ | 4'-acetylamino-2'-methylbiphen-4-yl |
| S,S | 2-methylpropyl | CF₃ | 4'-trifluoromethylsulfonylbiphen-4-yl |
| S,S | 2-methylpropyl | CF₃ | 4-(4-fluorobenzoylaminomethyl)-phenyl |
| S,S | 2-methylpropyl | CF₃ | 4-(thien-2-ylcarbonyl)-phenyl |
| S,S | 2-methylpropyl | CF₃ | 4-methylsulfonylphenyl |
| S,S | 2-methylpropyl | CF₃ | 4-(1,3-thiazol-2-ylcarbonyl)-phenyl |
| S,S | 2-methylpropyl | CF₃ | 4-(6-methoxypyridin-3-yl)-phenyl |
| S,S | 2-methylpropyl | CF₃ | 4-(6-methoxypyridin-2-yl)-phenyl |
| S,S | 2-methylpropyl | CF₃ | 4-ethylsulfonylbiphen-4-yl |
| S,S | 2-methylpropyl | CF₃ | 4-(3-(2-chloro-6-fluorophenyl)-5-methyl-isoxazol-4-ylcarbonyl-aminomethyl)phenyl |
| S,S | 2-methylpropyl | CF₃ | 4-(cis-2-(4-methylsulfonylphenyl)-ethenyl)-phenyl |
| S,S | 2-methylpropyl | CF₃ | 4-(9-chloro-3-methyl-4-oxo-isoxazolo[4,3-c]-quinolin-5(H)ylmethyl)phenyl |
| S,S | 2-methylpropyl | CF₃ | 4'-methoxy-3'-methylsulfonyl-biphen-4-yl |
| RS,S | 2-methylpropyl | CF₃ | 3-bromophenyl |
| S,S | 2-methylpropyl | CF₃ | 4'-(4-methylsulfonylphenyl)biphen-4-yl |
| S,S | 2-methylpropyl | CF₃ | 4'-(4-isopropylsulfonylphenyl)biphen-4-yl |
| S,S | 2-methylpropyl | CF₃ | 4'-methylsulfonyl-2'-(4-chloro-phenyl)-biphen-4-yl |
| S,S | 2-methylpropyl | CF₃ | 4'-methylsulfonyl-2'-methoxy-biphen-4-yl |
| S,S | 2-methylpropyl | CF₃ | 4-(4-bromo-1,3-thiazol-2-yl)-phenyl |
| S,S | 2-methylpropyl | CF₃ | 2'-chloro-4'-methylsulfonyl-biphen-4-yl |
| S,S | 1-methyl-cyclopropyl-methyl | CF₃ | 4-bromophenyl |

-continued

[Structure: R7—(D)n—*C(R6)(H)—NH—**C(R3)(H)—C(=O)—NH—CH2—C≡N]

| Stereochem at (*C, **C) | R³ | R⁶ | —(D)n—R⁷ |
|---|---|---|---|
| S,S | 1-methyl-cyclopropyl-methyl | CF₃ | 4'-methylsulfonylbiphen-4-yl |
| RS,S | 2-methylpropyl | CF₃ | 2-bromothien-5-yl |
| S,S | 2-methylpropyl | CF₃ | 4-thien-3-ylphenyl |
| S,S | 2-methylpropyl | CF₃ | 4-pyridin-2-ylphenyl |
| S,S | 2-methylpropyl | CF₃ | 4-(4-methylpyridin-2-yl)phenyl |
| S,S | 2-methylpropyl | CF₃ | 2'-fluorobiphen-4-yl |
| S,S | 2-methylpropyl | CF₃ | 4-(3,5-dimethylisoxazol-4-yl)phenyl |
| S,S | 2-methylpropyl | CF₃ | 4'-hydroxymethylbiphen-4-yl |
| S,S | 2-methylpropyl | CF₃ | 4'-cyanobiphen-4-yl |
| S,S | 2-methylpropyl | CF₃ | 3',4'-difluorobiphen-4-yl |
| S,S | 2-methylpropyl | CF₃ | 2'-methoxycarbonylbiphen-4-yl |
| S,S | 2-methylpropyl | CF₃ | 3'-methoxycarbonylbiphen-4-yl |
| S,S | 2-methylpropyl | CF₃ | 3',4'-dimethoxybiphen-4-yl |
| S,S | 2-methylpropyl | CF₃ | 2'-trifluoromethylbiphen-4-yl |
| S,S | 2-methylpropyl | CF₃ | 3',4'-dichlorobiphen-4-yl |
| S,S | 2-methylpropyl | CF₃ | 3'-formylbiphen-4-yl |
| S,S | 2-methylpropyl | CF₃ | 4-(2-oxo-2,3-dihydrobenzothiazol-6-yl)-phenyl |
| S,S | 2-methylpropyl | CF₃ | 4-(5-bromopyridin-3-yl)phenyl |
| S,S | 2-methylpropyl | CF₃ | 4'-trifluoromethoxybiphen-4-yl |
| S,S | 2-methylpropyl | CF₃ | 4-(1H-indol-4-yl)phenyl |
| S,S | 2-methylpropyl | CF₃ | 4-(pyrimidin-5-yl)phenyl |
| S,S | 2-methylpropyl | CF₃ | 4-(quinolin-3-yl)phenyl |
| S,S | 2-methylpropyl | CF₃ | 4-(1,3-thiazol-2-yl)phenyl |
| S,S | 2-methylpropyl | CF₃ | 4'-methoxycarbonylbiphen-4-yl |
| S,S | 2-methylpropyl | CF₃ | 4-(pyrimidin-2-yl)phenyl |
| S,S | 2-methylpropyl | CF₃ | 4-(3-methylpyridin-2-yl)phenyl |
| S,S | 2-methylpropyl | CF₃ | 4-(furan-3-yl)phenyl |
| S,S | 2-methylpropyl | CF₃ | 4-(pyridin-3-yl)phenyl |
| S,S | 2-methylpropyl | CF₃ | 4'-(morpholin-4-ylsulfonyl)biphen-4-yl |
| S,S | 2-methylpropyl | CF₃ | 4-(trans-2-methylsulfonylphenyl-ethenyl)-phenyl |
| S,S | 2-methylpropyl | CF₃ | biphen-4-yl |
| R,S | 2-methylpropyl | CF₃ | 4'-methylsulfonylbiphen-4-yl |
| S,S | 2-methylpropyl | CF₃ | 4-bromobiphen-4-yl |
| S,S | 2-methylpropyl | CF₃ | 4-pyridin-4-ylphenyl |
| S,S | 2-methylpropyl | CF₃ | 4'-(pyridin4-yl)biphen-4-yl |
| S,S | 2-methylpropyl | CF₃ | 4'-methylthiobiphen-4-yl |
| S,S | 2-methylpropyl | CF₃ | 4'-methylsulfonylbiphen-4-yl |
| S,S | 2-methylpropyl | CF₃ | 4-(3-hydroxy-3-methylbutenyl)phenyl |
| S,S | 2-methylpropyl | CF₃ | 4-(3-hydroxy-3-methylbutyl)phenyl |
| S,S | 2-methylpropyl | CF₃ | 4'-aminosulfonylbiphen-4-yl |
| RS,S | 2-methylpropyl | CF₃ | 4'-piperazin-1-ylbiphen-4-yl |
| R,S | 2-methylpropyl | CF₃ | 4-cyanomethylaminocarbonylphenyl |
| RS,S | 2-methylpropyl | CF₃ | 4-(4-(2-fluoroethyl)piperazin-1-yl-carbonyl)phenyl |
| RS,S | 2-methylpropyl | CF₃ | 4-(4-methylpiperazin-1-ylcarbonyl)-phenyl |
| S,S | 2-methylpropyl | CF₃ | 4-(pyridin-3-yl-N-oxide)phenyl |
| RS,S | 2-methylpropyl | CF₃ | 4'-(piperazin-1-yl)biphen-4-yl |
| S,S | 2-methylpropyl | thien-2-yl | 4-bromophenyl |
| R,S | 2-methylpropyl | 4-trifluoro-methoxy-phenyl | 4-bromophenyl |
| S,S | 2-methylpropyl | 4-trfluoro-methoxy-phenyl | 4'-methylsulfonylbiphen-4-yl |
| S,S | 2-methylpropyl | thien-2-yl | 4'-methylsulfonylbiphen-4-yl |
| S,S | 2-methylpropyl | thien-2-yl | 4'-(tert-butoxycarbonylpiperazin-1-yl)biphen-4-yl |
| S,S | 2-methylpropyl | thien-2-yl | 4'-piperazin-1-ylbiphen-4-yl |
| S,S | 2-methylpropyl | 4-fluoro-phenyl | 4'-methylsulfonylbiphen-4-yl |
| S,S | 2-methylpropyl | furan-2-yl | 4-bromophenyl |
| S,S | 2-methylpropyl | furan-2-yl | 4'-methylsulfonylbiphen-4-yl |
| RS,S | n-propyl | CF₃ | 4-bromophenyl |
| RS,S | n-propyl | CF₃ | 4'-methylsulfonylbiphen-4-yl |

-continued

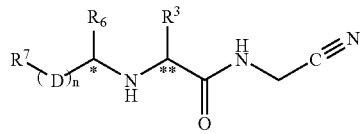

| Stereochem at (*C, **C) | R³ | R⁶ | —(D)ₙ—R⁷ |
|---|---|---|---|
| R,S | 2-methylpropyl | 4-CF₃-phenyl | 4-bromophenyl |
| S,S | 2-methylpropyl | 4-CF₃-phenyl | 4'-methylsulfonylbiphen-4-yl |
| S,S | n-propyl | CF₃ | 4'-methylsulfonylbiphen-4-yl |
| RS,S | n-propyl | CF₃ | 4'-(4-cyclopropylpiperazin-1-yl)-biphen-4-yl |
| R,S | 2-methylpropyl | 4-chlorophenyl | 4-bromophenyl |
| S,S | 2-methylpropyl | 4-chlorophenyl | 4'-methylsulfonylbiphen-4-yl |
| S,S | 2-methylpropyl | 3-methylthien-2-yl | 4-bromophenyl |
| S,S | 2-methylpropyl | thien-3-yl | 4-bromophenyl |
| RS,RS | 2-methylpropyl | 2,4-difluorophenyl | 4-bromophenyl |
| S,S | 2-methylpropyl | 2,4-difluorophenyl | 4'-methylsulfonylbiphen-4-yl |
| S,S | 2-methylpropyl | thien-3-yl | 4'-methylsulfonylbiphen-4-yl |
| S,S | 2-methylpropyl | 3-methylthien-2-yl | 4'-methylsulfonylbiphen-4-yl |
| S,S | 2-methylpropyl | 3-methylthien-2-yl | 4'-(4-cyclopropylpiperazin-1-yl)-biphen-4-yl |
| S,S | 2-methylpropyl | thien-3-yl | 4'-(4-cyclopropylpiperazin-1-yl)-biphen-4-yl |
| RS,S | 3,3,3-trifluoropropyl | CF₃ | 4-bromophenyl |
| S,S | 3,3,3-trifluoropropyl | CF₃ | 4'-methylsulfonylbiphen-4-yl |
| S,S | 2-methylpropyl | furan-3-yl | 4'-methylsulfonylbiphen-4-yl |
| S,S | 2-methylpropyl | 4-bromo-thien-2-yl | 4-bromophenyl |
| S,S | 2-methylpropyl | 4-(4-methylsulfonylphenyl)-thien-2-yl | 4'-methylsulfonylbiphen-4-yl |
| S,S | 2-methylpropyl | thien-3-yl | 4'-aminosulfonylbiphen-4-yl |
| S,S | n-propyl | CF₃ | 4'-methylsulfonylbiphen-4-yl |
| RS,S | n-propyl | pyridin-4-yl | 4-bromophenyl |
| RS,S | n-propyl | thiazol-2-yl | 4-bromophenyl |
| S,S | 2-methylpropyl | thiazol-2-yl | 4-bromophenyl |
| S,S | 2-methylpropyl | thiazol-2-yl | 4'-methylsulfonylbiphen4-yl |
| RS,S | 2-methylpropyl | 1H-tetrazol-5-yl | 4-bromophenyl |
| S,S | 2-fluoro-2-methylpropyl | CF₃ | 4'-methylsulfonylbiphen-4-yl |
| S,S | 2S-trifluoromethylpropyl | CF₃ | 4'-methylsulfonylbiphen-4-yl |
| S,S | 2S-trifluoromethylpropyl | CF₃ | 4'-methylthiobiphen-4-yl |
| S,S | 2-methylpropyl | CF₂CF₃ | 4-(6-methylpyridin-3-yl)phenyl |
| S,S | 2-methylpropyl | CF₃ | 4'-(1-hydroxyethyl)biphen-4-yl |
| S,S | 2-methylpropyl | CF₃ | 4'-(2,2,2-trifluoro-1-hydroxyethyl)biphen-4-yl |
| S,S | 2R-trifluoromethylpropyl | CF3 | 4'-(methylsulfonyl)biphen-4-yl |
| S,S | 2-methylpropyl | CF₂CF₃ | 4-(1,3-thiazol-2-yl)phenyl |
| S,S | 2-methylpropyl | CF₃ | 4-(5-methyl-1,3-thiazol-2-yl)phenyl |
| S,S | 2-methylpropyl | CF₃ | 4-(4-methyl-1,3-thiazol-2-yl)phenyl |
| S,S | 2-methylpropyl | CF₃ | 4-(4,5-dimethyl-1,3-thiazol-2-yl)phenyl |
| S,S | 2-methylpropyl | CF₂CF₃ | 4-(2-hydroxy-2-methylpropylsulfonyl)biphen-4-yl |

Compounds of Formula I where $R^1$ and $R^2$ together with the carbon atom to which they are attached from cyclopropyl, $R^4$, $R^5$, and $R^8$ are hydrogen are shown in Table II below:

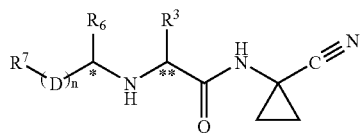

| Stereochem at (*C, **C) | $R^3$ | $R^6$ | —(D)$_n$—$R^7$ |
|---|---|---|---|
| RS,S | 2-methylpropyl | CF$_3$ | 4-bromophenyl |
| S,S | 2-methylpropyl | CF$_3$ | 4'-methylsulfonylbiphen-4-yl |
| S,S | 2-methylpropyl | 3-methyl-thien-2-yl | 4-bromophenyl |
| S,S | 2-methylpropyl | 3-methyl-thien-2-yl | 4'-methylsulfonylbiphen-4-yl |
| S,S | n-propyl | CF$_3$ | 4'-methylsulfonylbiphen-4-yl |
| S,S | n-propyl | CF$_3$ | 4-bromophenyl |
| S,S | 2-methylpropyl | thien-3-yl | 4-bromophenyl |
| S,S | 2-methylpropyl | thien-3-yl | 4'-methylsulfonylbiphen-4-yl |
| S,S | n-propyl | CF$_3$ | 4'-aminosulfonylbiphen-4-yl |
| S,S | 2-methylpropyl | thien-3-yl | 4'-aminosulfonylbiphen-4-yl |
| S,S | n-propyl | CF$_3$ | 4'-methoxy-3'-methylsulfonyl-biphen-4-yl |
| S,S | n-propyl | CF$_3$ | 4-(2-methylpyridin-4-yl)phenyl |
| S,S | 3,3,3-trifluoropropyl | CF$_3$ | 4'-methylsulfonylbiphen-4-yl |
| S,S | n-propyl | CF$_3$ | 4-(1H-pyrazol-3-yl)phenyl |
| S,S | n-propyl | CF$_3$ | 4'-(1-hydroxy-1-methylethyl)-biphen-4-yl |
| S,S | n-propyl | CF$_3$ | 4-(5-methylpyridin-2-yl)phenyl |
| S,S | n-propyl | CF$_3$ | 4'-acetylbiphen-4-yl |
| S,S | n-propyl | CF$_3$ | 2',4'-difluorobiphen-4-yl |
| S,S | n-propyl | CF$_3$ | 3',4'-difluorobiphen-4-yl |
| S,S | n-propyl | CF$_3$ | 3'-chloro-4'-fluorobiphen-4-yl |
| S,S | n-propyl | CF$_3$ | 4'-methylsulfonylamino-biphen-4-yl |
| S,S | n-propyl | CF$_3$ | 4'-chlorobiphen-4-yl |
| S,S | n-propyl | CF$_3$ | 4'-chloro-3'-methylbiphen-4-yl |
| S,S | n-propyl | CF$_3$ | 4'-chloro-2'-methylbiphen-4-yl |
| S,S | n-propyl | CF$_3$ | 4'-indol-5-ylphenyl |
| S,S | n-propyl | CF$_3$ | 3'-methylsulfonylamino-biphen-4-yl |
| S,S | n-propyl | CF$_3$ | 4'-fluorobiphen-4-yl |
| S,S | n-propyl | CF$_3$ | 4'-fluoro-3'-methylbiphen-4-yl |
| S,S | n-propyl | CF$_3$ | 3'-fluoro-4'-methylbiphen-4-yl |
| S,S | n-propyl | CF$_3$ | 4'-trifluoromethoxybiphen-4-yl |
| S,S | n-propyl | CF$_3$ | 4'-methylbiphen-4-yl |
| S,S | n-propyl | CF$_3$ | 4'-cyanobiphen-4-yl |
| S,S | n-propyl | CF$_3$ | 4'-methoxybiphen-4-yl |
| S,S | n-propyl | CF$_3$ | 4-(3,4-methylenedioxy-phenyl)phenyl |
| S,S | n-propyl | CF$_3$ | 4'-methoxycarbonylbiphen-4-yl |
| S,S | 2-methylpropyl | thiazol-2-yl | 4-bromophenyl |
| S,S | n-propyl | CF$_3$ | 4'-trifluoromethylbiphen-4-yl |
| S,S | n-propyl | CF$_3$ | 2'-trifluoromethylbiphen-4-yl |
| RS,S | 2-methylpropyl | thiazol-2-yl | 2',4'-difluorobiphen-4-yl |
| RS,S | 2-methylpropyl | thiazol-2-yl | 4'-methylsulfonylbiphen-4-yl |
| 5,S | 2-methylpropyl | 4-bromo-thien-2-yl | 4-bromophenyl |
| S,S | 2-methylpropyl | CF$_3$ | 4-methylphenyl |
| S,S | 2-methylpropyl | CF$_3$ | 4-(1H-pyrazol-3-yl)phenyl |
| S,S | 2-methylpropyl | CF$_3$ | 4-(2-methyl-1,3-oxazol-4-yl)phenyl |
| S,S | 2-methylpropyl | CF$_3$ | 4-(2-methylpyridin-4-yl)phenyl |
| S,S | 2-methylpropyl | CF$_3$ | 4-(4-methylpyridin-3-yl)phenyl |
| S,S | 2-methylpropyl | CF$_3$ | 3'-acetylbiphen-4-yl |
| S,S | 2-methylpropyl | CF$_3$ | 5-[4-(1-hydroxy-1-methylethyl)-phenyl]pyridin-2-yl |
| S,S | 2-methylpropyl | CF$_3$ | 4'-methoxy-3'-methylsulfonyl-biphen-4-yl |
| S,S | 2-methylpropyl | CF$_3$ | 3'-aminosulfonyl-4'-methoxy-biphen-4-yl |
| S,S | 2-methylpropyl | CF$_3$ | 4-(6-methoxypyridin-3-yl)phenyl |
| S,S | 2-methylpropyl | CF$_2$CF$_3$ | 4-(5-methylpyridin-2-yl)phenyl |
| S,S | 2-methylpropyl | CF$_3$ | 4-(5-methylsulfonylpyridin-2-yl)phenyl |
| S,S | 2-methylpropyl | CF$_3$ | 4-(5-methylpyridin-2-yl)phenyl |
| S,S | 2-fluoro-2-methylpropyl | CF$_3$ | 4'-methylsulfonylbiphen-4-yl |

-continued

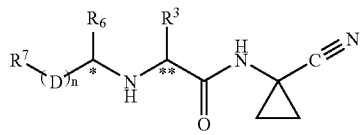

| Stereochem at (*C, **C) | R³ | R⁶ | —(D)ₙ—R⁷ |
|---|---|---|---|
| S,S | 2-fluoro-2-methylpropyl | CF₃ | 2'-methyl-4'-methylsulfonyl-biphen-4-yl |
| S,S | 2-niethylpropyl | CF₃ | 5-(quinolin-6-yl)pyridin-2-yl |
| S,S | 2-methylpropyl | CHF₂ | 4'-methylsulfonylbiphen-4-yl |
| S,S | 2-methylpropyl | CF₂CF₃ | 4'-acetylbiphen-4-yl |
| S,S | 2-methylpropyl | CF₃ | 6-chloropyridin-3-yl |
| S,S | 2-methylpropyl | CF₃ | 5-(4-acetylphenyl)pyridin-2-yl |
| S,S | 2-methylpropyl | CF₃ | 6-(4-acetylphenyl)pyridin-3-yl |
| S,S | 2-methylpropyl | CF₃ | 5-(3-acetylphenyl)pyridin-2-yl |
| S,S | 2-methylpropyl | CF₃ | 5-[4-(1-hydroxyethyl)phenyl]-pyridin-2-yl |
| S,S | 2-methylpropyl | CF₃ | 4-[2-(1H-pyrazol-4-yl)-1,3-thiazol-4-yl]phenyl |
| S,S | 2-methylpropyl | CF₃ | 4-(2-methyl-1,3-thiazol-4-yl)-phenyl |
| S,S | 2-methylpropyl | CF₃ | 4-(2-methylpyridin-4-yl)phenyl |
| S,S | 2-methylpropyl | CF₃ | 4-(2-methylpyridin-3-yl)phenyl |
| S,S | 2-fluoro-2-methylpropyl | CF₃ | 3'-acetylbiphen-4-yl |
| S,S | 2-fluoro-2-methylpropyl | CF₃ | 4-(1H-pyrazol-3-yl)phenyl |
| S,S | 2-methylpropyl | CF₃ | 5-(4-methylsulfonylphenyl)-pyridin-2-yl |
| S,S | 2-methylpropyl | CF₃ | 4'-(1-hydroxy-1-methylethyl)-biphen-4-yl |
| S,S | 2S-trifluoro-methylpropyl | CF₃ | 4'-methylsulfonylbiphen-4-yl |
| S,S | 2S-trifluoro-methylpropyl | CF₃ | 4'-methylthiobiphen-4-yl |
| S,S | 2-methylpropyl | CF₂CF₃ | 4-(6-methylpyridin-3-yl)phenyl |
| S,S | 2-methylpropyl | CF₃ | 4-(6-methylpyridin-3-yl)phenyl |
| S,S | 2-methylpropyl | CF₂CF₃ | 4'-(1-hydroxy-1-methylethyl)-biphen-4-yl |
| S,S | 2-methylpropyl | CF₂CF₃ | 4'-methylsulfonylbiphen-4-yl |
| S,S | 2-methylpropyl | CF₂CF₃ | 4-(6-methoxypyridin-2-yl)phenyl |
| S,S | 2R-trifluoro-methylpropyl | CF₃ | 4'-methylsulfonylbiphen-4-yl |
| S,S | 2-methylpropyl | CF₃ | 4-(1,3-thiazol-2-yl)phenyl |
| S,S | 2-methylpropyl | CF₃ | 4-(5-methyl-1,3-thiazol-2-yl)-phenyl |
| S,S | 2-methylpropyl | CF₃ | 4-(4-methyl-1,3-thiazol-2-yl)-phenyl |
| S,S | 2-fluoro-2-methylpropyl | CF₃ | 4'-ethylsulfonylbiphen-4-yl |
| S,S | 2-fluoro-2-methylpropyl | CF₃ | 4-pyridin-3-ylphenyl |
| S,S | 2-fluoro-2-methylpropyl | CF₃ | 4'-methoxy-3'-methylsulfonyl-biphen-4-yl |
| S,S | 2-methylpropyl | CF₃ | 4'-(2-hydroxy-2-methyl-propylsulfonyl)biphen-4-yl |
| S,S | 2-methylpropyl | CF₃ | 2'-methyl-4'-methylsulfonyl-biphen-4-yl |
| S,S | 2-methylpropyl | CF₃ | 4'-ethylsulfonylbiphen-4-yl |
| S,S | 2-fluoro-2-methylpropyl | CF₃ | 4'-aminosulfonylbiphen-4-yl |

Compounds of Formula I where $R^3$ and $R^4$ together with the carbon atom to which they are attached form cyclohexyl, $R^1$, $R^5$, and $R^8$ are hydrogen are shown in Table III below:

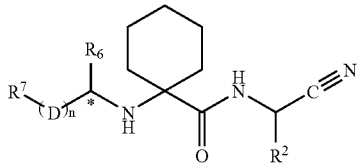

| Stereochem. AT (*C) | $R^2$ | $R^6$ | —(D)$_n$—$R^7$ |
|---|---|---|---|
| RS | H | $CF_3$ | phenyl |
| RS | H | $CF_3$ | 4-bromophenyl |
| RS | H | $CF_3$ | 4'-piperazin-1-yl)biphen-4-yl |

Compounds of Formula I where $R^1$, $R^4$, $R^5$, and $R^8$ are hydrogen are shown in Table IV below:

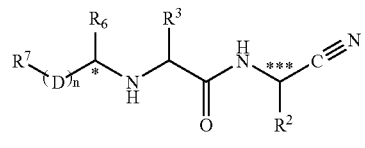

| Stereochem. at (*C, C, *C) | $R^2$ | $R^3$ | $R^6$ | —(D)$_n$—$R^7$ |
|---|---|---|---|---|
| S,S,S | methyl | 2-methyl-propyl | $CF_3$ | 4'-methylsulfonylbiphen-4-yl |
| S,S,S | 2-methylthioethyl | 2-methyl-propyl | $CF_3$ | 4'-methylsulfonylbiphen-4-yl |
| S,S,S | 2-methylsulfonyl-ethyl | 2-methyl-propyl | $CF_3$ | 4'-methylsulfonylbiphen-4-yl |

Specific embodiments of the present invention include, but are not limited to:

$N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide;

$N^1$-(cyanomethyl)-$N^2$-(2,2,2-trifluoro-1-phenylethyl)-L-leucinamide;

$N^1$-(cyanomethyl)-$N^2$-[2,2,2-trifluoro-1-(4-fluoro-3-methylphenyl)ethyl]-L-leucinamide;

$N^1$-(cyanomethyl)-$N^2$-[(1R)-2,2,2-trifluoro-1-(4-pyridin-3-ylphenyl)ethyl]-L-leucinamide;

$N^1$-(cyanomethyl)-$N^2$-[(1S)-2,2,2-trifluoro-1-(4-pyridin-3-ylphenyl)ethyl]-L-leucinamide;

$N^1$-(cyanomethyl)-$N^2$-[(1R)-2,2,2-trifluoro-1-(4-pyridin-4-ylphenyl)ethyl]-L-leucinamide;

$N^1$-(cyanomethyl)-$N^2$-[(1S)-2,2,2-trifluoro-1-(4-pyridin-4-ylphenyl)ethyl]-L-leucinamide;

$N^1$-(cyanomethyl)-$N^2$-[(1R)-2,2,2-trifluoro-1-(4-{[4-(2-fluoroethyl)piperazin-1-yl]carbonyl}phenyl)ethyl]-L-leucinamide;

$N^1$-(cyanomethyl)-$N^2$-[2,2,2-trifluoro-1-(4-{[4-(2-fluoroethyl)piperazin-1-yl]carbonyl}phenyl)ethyl]-L-leucinamide;

$N^2$-[1-(1,1'-biphenyl-4-yl)-2,2,2-trifluoroethyl]-$N^1$-(cyanomethyl)-L-leucinamide;

$N^1$-(cyanomethyl)-$N^2$-{2,2,2-trifluoro-1-[4-(3-hydroxy-3-methylbut-1-ynyl)phenyl]ethyl}-L-leucinamide;

$N^1$-(cyanomethyl)-$N^2$-{(1S)-2,2,2-trifluoro-1-[4-(3-hydroxy-3-methylbutyl)phenyl]ethyl}-L-leucinamide;

$N^2$-[(1S)-1-(4-bromophenyl)-2,2,3,3,3-pentafluoropropyl]-$N^1$-(cyanomethyl)-L-leucinamide;

$N^1$-(cyanomethyl)-$N^2$-[(1S)-2,2,3,3,3-pentafluoro-1-(4-pyridin-4-ylphenyl)propyl]-L-leucinamide;

$N^1$-(cyanomethyl)-$N^2$-[(1S)-2,2,2-trifluoro-1-(4'-fluoro-1,1'-biphenyl-4-yl)ethyl]-L-leucinamide;

$N^1$-(cyanomethyl)-$N^2$-((1S)-2,2,2-trifluoro-1-{4-[(1E)-3-hydroxy-3-methylbut-1-enyl]phenyl}ethyl)-L-leucinamide;

$N^1$-(cyanomethyl)-$N^2$-{(1S)-2,2,3,3,3-pentafluoro-1-[4'-(methylthio)-1,1'-biphenyl-4-yl]propyl}-L-leucinamide;

$N^1$-(cyanomethyl)-$N^2$-{(1S)-2,2,3,3,3-pentafluoro-1-[4'-(methylsulfonyl)-1,1'-biphenyl-4-yl]propyl}-L-leucinamide;

$N^1$-(cyanomethyl)-$N^2$-{(1S)-2,2,2-trifluoro-1-[4-(1-oxidopyridin-3-yl)phenyl-]ethyl}-L-leucinamide;

$N^1$-(cyanomethyl)-$N^2$-{(1S)-2,2,2-trifluoro-1-[4-(morpholin-4-ylcarbonyl)phenyl-]ethyl}-L-leucinamide;

$N^1$-(cyanomethyl)-$N^2$-[(1S)-2,2,2-trifluoro-1-(4-{[methoxy(methyl)amino]carbonyl}phenyl)ethyl]-L-leucinamide;

$N^1$-(cyanomethyl)-$N^2$-[(1S)-2,2,2-trifluoro-1-(4-thien-3-ylphenyl)ethyl]-L-leucinamide;

$N^1$-(cyanomethyl)-$N^2$-{(1S)-2,2,2-trifluoro-1-[4-(4-methylpyridin-2-yl)phenyl]ethyl}-L-leucinamide;

$N^1$-(cyanomethyl)-$N^2$-{(1S)-2,2,2-trifluoro-1-[4-(5-methylpyridin-2-yl)phenyl]ethyl}-L-leucinamide;

$N^1$-(cyanomethyl)-$N^2$-[(1S)-2,2,2-trifluoro-1-(2'-fluoro-1,1'-biphenyl-4-yl)ethyl]-L-leucinamide;

$N^1$-(cyanomethyl)-$N^2$-{(1S)-1-[4-(3,5-dimethylisoxazol-4-yl)phenyl]-2,2,2-trifluoroethyl}-L-leucinamide;

$N^1$-(cyanomethyl)-$N^2$-{(1S)-2,2,2-trifluoro-1-[4'-(hydroxymethyl)-1,1'-biphenyl-4-yl]ethyl}-L-leucinamide;

$N^2$-[(1S)-1-(4'-cyano-1,1'-biphenyl-4-yl)-2,2,2-trifluoroethyl]-$N^1$-(cyanomethyl)-L-leucinamide;

$N^1$-(cyanomethyl)-$N^2$-[(1S)-1-(3',4'-difluoro-1,1'-biphenyl-4-yl)-2,2,2-trifluoroethyl]-L-leucinamide;

4'-{1-[-(Cyanomethyl-carbamoyl)-3-methyl-butylamino]-2,2,2-trifluoro-ethyl}-biphenyl-2-carboxylic acid methyl ester;

4'-{1-[1-(Cyanomethyl-carbamoyl)-3-methyl-butylamino]-2,2,2-trifluoro-ethyl}-biphenyl-3-carboxylic acid methyl ester;

$N^1$-(cyanomethyl)-$N^2$-[(1S)-1-(3,4-dimethoxy-1,1'-biphenyl-4yl)-2,2,2-trifluoroethyl]-L-leucinamide;

$N^1$-(cyanomethyl)-$N^2$-{(1S)-2,2,2-uifluoro-1-[2'-(trifluoromethyl)-1,1'-biphenyl-4-yl]ethyl}-L-leucinamide;

$N^1$-(cyanomethyl)-$N^2$-[(1S)-1-(3',4'-dichloro-1,1'-biphenyl-4-yl)-2,2,2-trifluoroethyl]-L-leucinamide;

$N^1$-(cyanomethyl)-$N^2$-[(1S)-2,2,2-trifluoro-1-(3'-formyl-1,1'-biphenyl-4-yl)ethyl]-L-leucinamide;

$N^1$-(cyanomethyl)-$N^2$-{(1S)-2,2,2-trifluoro-1-[4-(2-oxo-2,3-dihydro-1,3-benzothiazol-6-yl)phenyl]ethyl}-L-leucinamide;

$N^2$-{(1S)-1-[4-(5-bromopyridin-3-yl)phenyl]-2,2,2-trifluoroethyl}-$N^1$-(cyanomethyl)-L-leucinamide;

$N^1$-(cyanomethyl)-$N^2$-{(1S)-2,2,2-trifluoro-1-[4'-(trifluoromethoxy)-1,1'-biphenyl-4-yl]ethyl}-L-leucinamide;

$N^1$-(cyanomethyl)-$N^2$-{(1S)-2,2,2-trifluoro-1-[4-(1H-indol-4-yl)phenyl]ethyl}-L-leucinamide;

$N^1$-(cyanomethyl)-$N^2$-[(1S)-2,2,2-trifluoro-1-(4-pyrimidin-5-ylphenyl)ethyl]-L-leucinamide;

$N^1$-(cyanomethyl)-$N^2$-[(1S)-2,2,2-trifluoro-1-(4-quinolin-3-ylphenyl)ethyl]-L-leucinamide;

$N^1$-(cyanomethyl)-$N^2$-{(1S)-2,2,2-trifluoro-1-[4-(1,3-thiazol-2-yl)phenyl]ethyl}-L-leucinamide;

4'-{1-[1-(Cyanomethyl-carbamoyl)-3-methyl-butylamino]-2,2,2-trifluoro-ethyl}-biphenyl-4-carboxylic acid methyl ester;

$N^1$-(cyanomethyl)-$N^2$-[(1S)-2,2,2-trifluoro-1-(4-pyrimidin-2-ylphenyl)ethyl]-L-leucinamide;

$N^1$-(cyanomethyl)-$N^2$-{(1S)-2,2,2-trifluoro-1-[4-(3-methylpyridin-2-yl)phenyl]ethyl}-L-leucinamide;

$N^1$-(cyanomethyl)-$N^2$-{(1S)-2,2,2-trifluoro-1-[4-(3-furyl)phenyl]ethyl}-L-leucinamide;

$N^1$-(cyanomethyl)-$N^2$-((1S)-2,2,2-trifluoro-1-{4-[3-(trifluoromethyl)pyridin-2-yl]phenyl}ethyl)-L-leucinamide;

$N^1$-(cyanomethyl)-$N^2$-((1S)-2,2,2-trifluoro-1-{4-[4-(trifluoromethyl)pyridin-2-yl]phenyl}ethyl)-L-leucinamide;

$N^1$-(cyanomethyl)-$N^2$-((1S)-2,2,2-trifluoro-1-{4-[5-(trifluoromethyl)pyridin-2-yl]phenyl}ethyl)-L-leucinamide;

$N^1$-(cyanomethyl)-$N^2$-[(1S)-2,2,2-trifluoro-1-(3'-methoxy-1,1'-biphenyl-4-yl)ethyl]-L-leucinamide;

$N^1$-(cyanomethyl)-$N^2$-[(1S)-2,2,2-trifluoro-1-(3'-methoxy-1,1'-biphenyl-4-yl)ethyl]-L-leucinamide;

$N^2$-{(1S)-1-[4'-(acetylamino)-3'-fluoro-1,1'-biphenyl-4-yl]-2,2,2-trifluoroethyl}-$N^1$-(cyanomethyl)-L-leucinamide;

$N^1$-(cyanomethyl)-$N^2$-{(1S)-2,2,2-trifluoro-1-[4-(3-methylthien-2-yl)phenyl]ethyl}-L-leucinamide;

$N^1$-(cyanomethyl)-$N^2$-[(1S)-2,2,2-trifluoro-1-(3'-fluoro-1,1'-biphenyl-4-yl)ethyl]-L-leucinamide;

$N^2$-{(1S)-1-[4-(5-acetylthien-2-yl)phenyl]-2,2,2-trifluoroethyl}-$N^1$-(cyanomethyl)-L-leucinamide;

$N^2$-[(1S)-1-(3'-acetyl-1,1'-biphenyl-4-yl)-2,2,2-trifluoroethyl]-$N^1$-(cyanomethyl)-L-leucinamide;

$N^1$-(cyanomethyl)-$N^2$-{(1S)-2,2,2-trifluoro-1-[3'-(trifluoromethyl)-1,1'-biphenyl-4-yl]ethyl}-L-leucinamide;

$N^1$-(cyanomethyl)-$N^2$-[(1S)-2,2,2-trifluoro-1-(5'-fluoro-2'-methoxy-1,1'-biphenyl-4-yl)ethyl]-L-leucinamide;

$N^1$-(cyanomethyl)-$N^2$-[(1S)-1-(3',5'-difluoro-1,1'-biphenyl-4-yl)-2,2,2-trifluoroethyl]-L-leucinamide;

$N^1$-(cyanomethyl)-$N^2$-[(1S)-2,2,2-trifluoro-1-(2',3',5'-trifluoro-1,1'-biphenyl-4-yl)ethyl]-L-leucinamide;

3-(4'-{1-[1-(Cyanomethyl-carbamoyl)-3-methyl-butylamino]-2,2,2-trifluoro-ethyl}-biphenyl-3-yl)-acrylic acid;

$N^2$-{(1S)-1-[4-(9-anthryl)phenyl]-2,2,2-trifluoroethyl}-$N^1$-(cyanomethyl)-L-leucinamide;

$N^2$-[(1S)-1-(4'-benzoyl-1,1'-biphenyl-4-yl)-2,2,2-trifluoroethyl]-$N^1$-(cyanomethyl)-L-leucinamide;

$N^2$-[(1S)-1-(3'-acetyl-4'-hydroxy-1,1'-biphenyl-4-yl)-2,2,2-trifluoroethyl]-$N^1$-(cyanomethyl)-L-leucinamide;

$N^1$-(cyanomethyl)-$N^2$-{(1S)-1-[2'-(cyanomethyl)-1,1'-biphenyl-4-yl]-2,2,2-trifluoroethyl}-L-leucinamide;

$N^1$-(cyanomethyl)-$N^2$-{2,2,2-trifluoro-1-[4'-(methylsulfonyl)-1,1'-biphenyl-4-yl]ethyl}-L-leucinamide;

$N^1$-(cyanomethyl)-$N^2$-{2,2,2-trifluoro-1-[4'-(methylsulfinyl)-1,1'-biphenyl-4-yl]ethyl}-L-leucinamide;

$N^1$-(cyanomethyl)-$N^2$-[2,2,2-trifluoro-1-(4-morpholin-4-ylphenyl)ethyl]-L-leucinamide;

$N^1$-(cyanomethyl)-$N^2$-{(1R)-2,2,2-trifluoro-1-[4-(6-methylpyridin-3-yl)phenyl]ethyl}-L-leucinamide;

$N^1$-(cyanomethyl)-$N^2$-{(1S)-2,2,2-trifluoro-1-[4-(6-methylpyridin-3-yl)phenyl]ethyl}-L-leucinamide;

$N^1$-(cyanomethyl)-$N^2$-[2,2,2-trifluoro-1-(5-phenylthien-2-yl)ethyl]-L-leucinamide;

$N^1$-(cyanomethyl)-$N^2$-[2,2,2-trifluoro-1-(4-quinolin-8-ylphenyl)ethyl]-L-leucinamide;

$N^1$-(cyanomethyl)-$N^2$-[(1S)-2,2,2-trifluoro-1-(4-pyridin-2-ylphenyl)ethyl]-L-leucinamide;

$N^2$-{1-[4'-(aminosulfonyl)-1,1'-biphenyl-4-yl]-2,2,2-trifluoroethyl}-$N^1$-(cyanomethyl)-L-leucinamide;

$N^2$-{(1S)-1-[4'-(aminosulfonyl)-1,1'-biphenyl-4-yl]-2,2,2-trifluoroethyl}-$N^1$-(cyanomethyl)-L-leucinamide;

$N^1$-(cyanomethyl)-$N^2$-{(1S)-2,2,2-trifluoro-1-[4'-(methylsulfonyl)-1,1'-biphenyl-4-yl]ethyl}-L-leucinamide;

$N^1$-(cyanomethyl)-$N^2$-{(1S)-2,2,2-trifluoro-1-[4'-(methylthio)-1,1'-biphenyl-4-yl]ethyl}-L-leucinamide;

$N^2$-[(1S)-1-(4-bromophenyl)-2,2,2-trifluoroethyl]-$N^1$-(cyanomethyl)-L-leucinamide;

$N^1$-(cyanomethyl)-$N^2$-{(1R)-2,2,2-trifluoro-1-[4'-(methylsulfonyl)-1,1'-biphenyl-4-yl]ethyl}-L-leucinamide;

$N^1$-(cyanomethyl)-$N^2$-{(1S)-2,2,2-trifluoro-1-[4'-(morpholin-4-ylsulfonyl)-1,1'-biphenyl-4-yl]ethyl}-L-leucinamide;

$N^1$-(cyanomethyl)-$N^2$-{(1S)-2,2,2-trifluoro-1-[4'-(isopropylsulfonyl)-1,1'-biphenyl-4-yl]ethyl}-L-leucinamide;

$N^2$-{(1S)-1-[4'-(aminosulfonyl)-1,1'-biphenyl-4-yl]-2,2,2-trifluoroethyl}-$N^1$-(cyanomethyl)-L-leucinamide;

$N^2$-((1S)-1-{4'-[(acetylamino)sulfonyl]-1,1'-biphenyl-4-yl}-2,2,2-trifluoroethyl)-$N^1$-(cyanomethyl)-L-leucinamide;

$N^1$-(cyanomethyl)-$N^2$-{(1S)-2,2,2-trifluoro-1-[2'-methyl-4'-(methylsulfonyl)-1,1'-biphenyl-4-yl]ethyl}-L-leucinamide;

$N^2$-[1-(5-bromothien-2-yl)-2,2,2-trifluoroethyl]-$N^1$-(cyanomethyl)-L-leucinamide;

$N^2$-[1-(4-bromophenyl)-2,2,2-trifluoroethyl]-$N^1$-(cyanomethyl)-L-leucinamide;

4-(4'-{1-[1-(Cyanomethyl-carbamoyl)-3-methyl-butylamino]-2,2,2-trifluoro-ethyl}-biphenyl-4-yl)-piperazine-1-carboxylic acid tert-butyl ester;

$N^1$-(cyanomethyl)-$N^2$-[2,2,2-trifluoro-1-(4'-piperazin-1-yl-1,1'-biphenyl-4-yl)ethyl]-L-leucinamide;

$N^1$-(cyanomethyl)-$N^2$-(2,2,2-trifluoro-1-{4'-[4-(2-hydroxyethyl)piperazin-1-yl]-1,1'-biphenyl-4-yl}ethyl)-L-leucinamide;

$N^1$-(cyanomethyl)-$N^2$-(2,2,2-trifluoro-1-}4'-[4-(2-hydroxy-2-methylpropyl)piperazin-1-yl]-1,1'-biphenyl-4-yl}ethyl)-L-leucinamide;

$N^1$-(cyanomethyl)-$N^2$-(1-{4-[(dimethylamino)carbonyl]phenyl}-2,2,2-trifluoroethyl)-L-leucinamide;

$N^1$-(cyanomethyl)-$N^2$-[2,2,2-trifluoro-1-(4'-piperazin-1-yl-1,1'-biphenyl-4-yl)ethyl]-L-leucinamide;

$N^1$-(cyanomethyl)-$N^2$-(1-{4-[(cyclopropylamino)carbonyl]phenyl}-2,2,2-trifluoroethyl)-L-leucinamide;

4-{1-[1-(Cyanomethyl-carbamoyl)-3-methyl-butylamino]-2,2,2-trifluoro-ethyl}-benzoic acid;

$N^1$-(cyanomethyl)-$N^2$-(2,2,2-trifluoro-1-{4'-[4-(2-fluoroethyl)piperazin-1-yl]-1,1'-biphenyl-4-yl}ethyl)-L-leucinamide;

N¹-(cyanomethyl)-N²-(2,2,2-trifluoro-1-{4-[(4-methylpiperazin-1-yl)carbonyl]phenyl}ethyl)-L-leucinamide;
N¹-(cyanomethyl)-N²-[2,2,2-trifluoro-1-(4-{[4-(2-hydroxy-2-methylpropyl)piperazin-1-yl]carbonyl}phenyl)ethyl]-L-leucinamide;
N¹-(cyanomethyl)-N²-{(1S)-2,2,2-trifluoro-1-[4-(2-methyl-1,3-thiazol-4-yl)phenyl]ethyl}-L-leucinamide;
N²-{1-[4-(3-tert-butyl-1,2,4-triazin-5-yl)phenyl]-2,2,2-trifluoroethyl}-N¹-(cyanomethyl)-L-leucinamide;
N¹-(cyanomethyl)-N²-[2,2,2-trifluoro-1-(4-{2-[3-(methylsulfonyl)phenyl]-1,3-thiazol-4-yl}phenyl)ethyl]-L-leucinamide;
N¹-(cyanomethyl)-N²-((1S)-2,2,2-trifluoro-1-{4-[2-(1H-pyrazol-4-yl)-1,3-thiazol-4-yl]phenyl}ethyl)-L-leucinamide;
N¹-(cyanomethyl)-N²-(2,2,2-trifluoro-1-{4'-[4-(methylsulfonyl)piperazin-1-yl]-1,1'-biphenyl-4-yl}ethyl)-L-leucinamide;
N²-[1-(3-bromophenyl)-2,2,2-trifluoroethyl]-N¹-(cyanomethyl)-L-leucinamide;
N¹-(cyanomethyl)-N²-{2,2,2-trifluoro-1-[4'-(methylthio)-1,1'-biphenyl-3-yl]ethyl}-L-leucinamide;
N¹-(cyanomethyl)-N²-[2,2,2-trifluoro-1-(3-pyridin-4-ylphenyl)ethyl]-L-leucinamide;
N¹-(cyanomethyl)-N²-[2,2,2-trifluoro-1-(4'-piperazin-1-yl-1,1'-biphenyl-3-yl)ethyl]-L-leucinamide;
N¹-(cyanomethyl)-N²-{2,2,2-trifluoro-1-[4'-(methylsulfonyl)-1,1'-biphenyl-3-yl]ethyl}-L-leucinamide;
N-(cyanomethyl)-1-[(2,2,2-trifluoro-1-phenylethyl)amino]cyclohexanecarboxamide;
1-{[1-(4-bromophenyl)-2,2,2-trifluoroethyl]amino}-N-(cyanomethyl)cyclohexanecarboxamide;
N-(cyanomethyl)-1-{[2,2,2-trifluoro-1-(4'-piperazin-1-yl-1,1'-biphenyl-4-yl)ethyl]amino}cyclohexanecarboxamide;
N¹-(cyanomethyl)-N²-[2,2,2-trifluoro-1-(4-piperidin-4-ylphenyl)ethyl]-L-leucinamide;
N¹-(cyanomethyl)-N²-{2,2,2-trifluoro-1-[4-(4-pyridin-2-ylpiperazin-1-yl)phenyl]ethyl}-L-leucinamide;
N²-[1-(4bromophenyl)-2,2,2-trifluoroethyl]-N¹-(cyanomethyl)-3-cyclopropylalaninamide;
N¹-(cyanomethyl)-3-cyclopropyl-N²-[2,2,2-trifluoro-1-(4-pyridin-4-ylphenyl)ethyl]alaninamide;
N¹-(cyanomethyl)-N²-[2,2,2-trifluoro-1-(4'-pyridin-4-yl-1,1'-biphenyl-4-yl)ethyl]-L-leucinamide;
N¹-(cyanomethyl)-N²-[(1R)-2,2,2-trifluoro-1-(1,3-thiazol-2-yl)ethyl]-L-leucinamide;
N¹-(cyanomethyl)-N²-[(1S)-2,2,2-trifluoro-1-(4'-methoxy-1,1'-biphenyl-4-yl)ethyl]-L-leucinamide;
N¹-(cyanomethyl)-N²-[(1S)-2,2,2-trifluoro-1-(4-methoxyphenyl)ethyl]-L-leucinamide;
N¹-(cyanomethyl)-N²-[(1S)-2,2,2-trifluoro-1-(4'-pyridin-4-yl-1,1'-biphenyl-4-yl)ethyl]-L-leucinamide;
N¹-(cyanomethyl)-N²-[(1S)-2,2,2-trifluoro-1-(4-phenoxyphenyl)ethyl]-L-leucinamide;
N²-[(1S)-1-(4'-bromo-1,1'-biphenyl-4-yl)-2,2,2-trifluoroethyl]-N¹-(cyanomethyl)-L-leucinamide;
N²-{(1S)-1-[4-(4-chloropyridin-3-yl)phenyl]-2,2,2-trifluoroethyl}-N¹-(cyanomethyl)-L-leucinamide;
N²-{(1S)-1-[4'-(acetylamino)-2'-methyl-1,1'-biphenyl-4-yl]-2,2,2-trifluoroethyl}-N¹-(cyanomethyl)-L-leucinamide;
N²-[(1S)-1-(1,1'-biphenyl-4-yl)-2,2,2-trifluoroethyl]-N¹-(cyanomethyl)-L-leucinamide;
N¹-(cyanomethyl)-N²-{(1S)-2,2,2-trifluoro-1-[4-(6-methoxypyridin-3-yl)phenyl]ethyl}-L-leucinamide;
N¹-(cyanomethyl)-N²-{(1S)-2,2,2-trifluoro-1-[4-(6-methoxypyridin-2-yl)phenyl]ethyl}-L-leucinamide;
N¹-(cyanomethyl)-N²-{(1S)-2,2,2-trifluoro-1-[4''-(methylsulfonyl)-1,1':4',1''-terphenyl-4-yl]ethyl}-L-leucinamide;
N²-[(1S)-1-(4-bromophenyl)-2,2,2-trifluoroethyl]-N¹-(cyanomethyl)-3-(1-methylcyclopropyl)-L-alaninamide;
N¹-(cyanomethyl)-3-(1-methylcyclopropyl)-N²-{(1S)-2,2,2-trifluoro-1-[4'-(methylsulfonyl)-1,1'-biphenyl-4-yl]ethyl}-L-alaninamide;
N¹-(cyanomethyl)-3-(1-methylcyclopropyl)-N²-{(1S)-2,2,2-trifluoro-1-[4'-(methylthio)-1,1'-biphenyl-4-yl]ethyl}-L-alaninamide;
N¹-(cyanomethyl)-N²-[(1S)-2,2,2-trifluoro-1-(4'-methyl-1,1'-biphenyl-4-yl)ethyl]-L-leucinamide;
N²-[(1S)-1-(4'-acetyl-1,1'-biphenyl-4-yl)-2,2,2-trifluoroethyl]-N¹-(cyanomethyl)-L-leucinamide;
N¹-(cyanomethyl)-N²-{(1S)-2,2,2-trifluoro-1-[4'-(hydroxymethyl)-1,1'-biphenyl-4-yl]ethyl}-L-leucinamide;
N²-[1-(4-bromophenyl)-2,2,2-trifluoroethyl]-N¹-(cyanomethyl)-D-leucinamide;
N¹-(cyanomethyl)-N²-{2,2,2-trifluoro-1-[4'-(methylsulfonyl)-1,1'-biphenyl-4-yl]ethyl}-D-leucinamide;
N¹-(cyanomethyl)-N²-{2,2,2-trifluoro-1-[4'-(morpholin-4-ylsulfonyl)-1,1'-biphenyl-4-yl]ethyl}-D-leucinamide;
N¹-(cyanomethyl)-N²-(2,2,2-trifluoro-1-{4'-[(methylamino)sulfonyl]-1,1'-biphenyl-4-yl}ethyl)-D-leucinamide;
N¹-(cyanomethyl)-N²-{(1R)-2,2,2-trifluoro-1-[4-(1-oxidopyridin-4-yl)phenyl]ethyl}-L-leucinamide;
N¹-(cyanomethyl)-N²-{2,2,2-trifluoro-1-[4-(1-oxidopyridin-4-yl)phenyl]ethyl}-L-leucinamide;
N¹-(cyanomethyl)-N²-(2,2,2-trifluoro-1-{4-[6-(1-hydroxy-1-methylethyl)-1-oxidopyridin-3-yl]phenyl}ethyl)-L-leucinamide;
N¹-(cyanomethyl)-N²-(2,2,2-trifluoro-1-{4-[6-(methylsulfonyl)pyridin-3-yl]phenyl}ethyl)-L-leucinamide;
N¹-(cyanomethyl)-N²-(2,2,2-trifluoro-1-{4-[2-(4-methylpiperazin-1-yl)-1,3-thiazol-4-yl]phenyl}ethyl)-L-leucinamide;
N²-[1-(4-bromophenyl)-2,2,2-trifluoroethyl]-N¹-(1-cyanocyclopropyl)-L-leucinamide;
N¹-(cyanomethyl)-N²-[2,2,2-trifluoro-1-(4-piperazin-1-ylphenyl)ethyl]-L-leucinamide;
N²-{1-[3'-(acetylamino)-1,1'-biphenyl-4-yl]-2,2,2-trifluoroethyl}-N¹-(cyanomethyl)-L-leucinamide;
N¹-(cyanomethyl)-N²-{2,2,2-trifluoro-1-[4-(4-propylpiperazin-1-yl)phenyl]ethyl}-L-leucinamide;
N¹-(cyanomethyl)-N²-{2,2,2-trifluoro-1-[4-(piperazin-1-ylcarbonyl)phenyl]ethyl}-L-leucinamide;
N¹-(cyanomethyl)-N²-[2,2,2-trifluoro-1-(4-{[4-(2-hydroxyethyl)piperazin-1-yl]carbonyl}phenyl)ethyl]-L-leucinamide;
N¹-(cyanomethyl)-N²-[(1S)-2,2,2-trifluoro-1-(4-{3-[3-(trifluoromethyl)phenyl]-1,2,4-oxadiazol-5-yl}phenyl)ethyl]-L-leucinamide;
4-{1-[1-(Cyanomethyl-carbamoyl)-3-methyl-butylamino]-2,2,2-trifluoro-ethyl}-benzoic acid methyl ester;
N¹-(cyanomethyl)-N²-((1S)-2,2,2-trifluoro-1-{4-[(E)-2-quinolin-2-ylethenyl]phenyl}ethyl)-L-leucinamide;
N¹-(cyanomethyl)-N²-{(1S)-2,2,2-trifluoro-1-[4-(3-methyl-1,2,4-oxadiazol-5-yl)phenyl]ethyl}-L-leucinamide;
N²-((1S)-1-{4-[3-(5-bromopyridin-3-yl)-1,2,4-oxadiazol-5-yl]phenyl}-2,2,2-trifluoroethyl)-N¹-(cyanomethyl)-L-leucinamide;
N²-[(1S)-1-(4-benzoylphenyl)-2,2,2-trifluoroethyl]-N¹-(cyanomethyl)-L-leucinamide;
N¹-(cyanomethyl)-N²-{(1S)-2,2,2-trifluoro-1-[4-(thien-2-ylcarbonyl)phenyl]ethyl}-L-leucinamide;
N¹-(cyanomethyl)-N²-{(1S)-2,2,2-trifluoro-1-[4-(1,3-thiazol-2-ylcarbonyl)phenyl]ethyl}-L-leucinamide;

N$^1$-(cyanomethyl)-N$^2$-[(1S)-2,2,2-trifluoro-1-(4-{(Z)-2-[4-(methylsulfonyl)phenyl]ethenyl}phenyl)ethyl]-L-leucinamide;

N$^1$-(cyanomethyl)-N$^2$-[(1S)-2,2,2-trifluoro-1-(4-{(E)-2-[4-(methylsulfonyl)phenyl]ethenyl}phenyl)ethyl]-L-leucinamide;

N$^1$-(cyanomethyl)-N$^2$-[(1S)-2,2,2-trifluoro-1-(4-isobutyrylphenyl)ethyl]-L-leucinamide;

N$^2$-{(1S)-1-[4-(4-bromo-1,3-thiazol-2-yl)phenyl]-2,2,2-trifluoroethyl}-N$^1$-(cyanomethyl)-L-leucinamide;

N$^1$-(cyanomethyl)-N$^2$-[(1S)-1-(4-cyanophenyl)-2,2,2-trifluoroethyl]-L-leucinamide;

N$^1$-(cyanomethyl)-N$^2$-[(1S)-1-(4-ethynylphenyl)-2,2,2-trifluoroethyl]-L-leucinamide;

N$^1$-(cyanomethyl)-N$^2$-[(1S)-2,2,2-trifluoro-1-(2'-fluoro-1,1'-biphenyl-4-yl)ethyl]-L-leucinamide;

N$^1$-(cyanomethyl)-N$^2$-{(1S)-2,2,2-trifluoro-1-[4-(1,3-thiazol-2-yl)phenyl]ethyl}-L-leucinamide;

N$^1$-(cyanomethyl)-N$^2$-{2,2,2-trifluoro-1-[4'-(methylthio)-1,1'-biphenyl-4-yl]ethyl}-L-leucinamide;

N$^1$-(cyanomethyl)-N$^2$-{2,2,2-trifluoro-1-[4-(2-methylquinolin-7-yl)phenyl]ethyl}-L-leucinamide;

N$^1$-(cyanomethyl)-N$^2$-{2,2,2-trifluoro-1-[4-(1H-indol-5-yl)phenyl]ethyl}-L-leucinamide;

N$^1$-(cyanomethyl)-N$^2$-{1-[4'-(dimethylamino)-1,1'-biphenyl-4-yl]-2,2,2-trifluoroethyl}-L-leucinamide;

N$^1$-(cyanomethyl)-N$^2$-[(1S)-1-(4-{[(cyanomethyl)amino]carbonyl}phenyl)-2,2,2-trifluoroethyl]-L-leucinamide;

N$^1$-(cyanomethyl)-N$^2$-[(1R)-1-(4-{[(cyanomethyl)amino]carbonyl}phenyl)-2,2,2-trifluoroethyl]-L-leucinamide;

N$^1$-(cyanomethyl)-N$^2$-{2,2,2-trifluoro-1-[3'-(methylsulfonyl)-1,1'-biphenyl-4-yl]ethyl}-L-leucinamide;

4'-{1-[1-(Cyanomethyl-carbamoyl)-3-methyl-butylamino]-2,2,2-trifluoro-ethyl}-biphenyl-4-carboxylic acid;

4'-{1-[1-(Cyanomethyl-carbamoyl)-3-methyl-butylamino]-2,2,2-trifluoro-ethyl}-biphenyl-4-carboxylic acid methoxy-methyl-amide;

N$^1$-(cyanomethyl)-N$^2$-{(1S)-2,2,2-trifluoro-1-[4-({[4-(methylsulfonyl)benzyl]thio}methyl)phenyl]ethyl}-L-leucinamide;

N$^2$-{(1S)-1-[4-(5-chloropyridin-2-yl)phenyl]-2,2,2-trifluoroethyl}-N$^1$-(cyanomethyl)-L-leucinamide;

N$^2$-{(1S)-1-[3'-(aminosulfonyl)-4'-bromo-1,1'-biphenyl-4-yl]-2,2,2-trifluoroethyl}-N$^1$-(cyanomethyl)-L-leucinamide;

N$^2$-{(1S)-1-[4'-bromo-3'-(methylsulfonyl)-1,1'-biphenyl-4-yl]-2,2,2-trifluoroethyl}-N$^1$-(cyanomethyl)-L-leucinamide;

N$^1$-(cyanomethyl)-N$^2$-((1S)-2,2,2-trifluoro-1-{4-[5-methyl-6-(methylsulfonyl)pyridin-3-yl]phenyl}ethyl)-L-leucinamide;

N$^2$-[(1S)-1-(4-{5-chloro-3-[4-(methylsulfonyl)phenyl]pyridin-2-yl}phenyl)-2,2,2-trifluoroethyl]-N$^1$-(cyanomethyl)-L-leucinamide;

N$^1$-(cyanomethyl)-N$^2$-((1S)-2,2,2-trifluoro-1-{4-[(phenylthio)methyl]phenyl}ethyl)-L-leucinamide;

N$^1$-(cyanomethyl)-N$^2$-((1S)-2,2,2-trifluoro-1-{4'-[(trifluoromethyl)sulfonyl]-1,1'-biphenyl-4-yl}ethyl)-L-leucinamide;

N$^1$-(cyanomethyl)-N$^2$-[(1S)-2,2,2-trifluoro-1-(4-{[(4-fluorobenzoyl)amino]methyl}phenyl)ethyl]-L-leucinamide;

N$^1$-(cyanomethyl)-N$^2$-{(1S)-2,2,2-trifluoro-1-[4-(methylsulfonyl)phenyl]ethyl}-L-leucinamide;

N$^1$-(1-cyanocyclopropyl)-N$^2$-{(1S)-2,2,2-trifluoro-1-[4'-(methylsulfonyl)-1,1'-biphenyl-4-yl]ethyl}-L-leucinamide;

N$^1$-(cyanomethyl)-N$^2$-{(1S)-1-[4'-(ethylsulfonyl)-1,1'-biphenyl-4-yl]-2,2,2-trifluoroethyl}-L-leucinamide;

N$^2$-((1S)-1-{4-[({[3-(2-chloro-6-fluorophenyl)-5-methylisoxazol-4-yl]carbonyl}amino)methyl]phenyl}-2,2,2-trifluoroethyl)-N$^1$-(cyanomethyl)-L-leucinamide;

N$^2$-((1S)-1-{4-[(9-chloro-3-methyl-4-oxoisoxazolo[4,3-c]quinolin-5(4H)-yl)methyl]phenyl}-2,2,2-trifluoroethyl)-N$^1$-(cyanomethyl)-L-leucinamide;

N$^1$-(cyanomethyl)-N$^2$-{(1S)-2,2,2-trifluoro-1-[4'-methoxy-3'-(methylsulfonyl)-1,1'-biphenyl-4-yl]ethyl}-L-leucinamide;

N$^2$-{(1S)-1-[4''-chloro-4'-(methylsulfonyl)-1,1':2',1''-terphenyl-4-yl]-2,2,2-trifluoroethyl}-N$^1$-(cyanomethyl)-L-leucinamide;

N$^1$-(cyanomethyl)-N$^2$-{(1S)-2,2,2-trifluoro-1-[2'-methoxy-4'-(methylsulfonyl)-1,1'-biphenyl-4-yl]ethyl}-L-leucinamide;

N$^2$-{(1S)-1-[2'-chloro-4'-(methylsulfonyl)-1,1'-biphenyl-4-yl]-2,2,2-trifluoroethyl}-N$^1$-(cyanomethyl)-L-leucinamide;

N$^1$-(cyanomethyl)-N$^2$-((1S)-2,2,2-trifluoro-1-{4'-[(2-hydroxyethyl)thio]-1,1'-biphenyl-4-yl}ethyl)-L-leucinamide;e N$^1$-(cyanomethyl)-N$^2$-{(1S)-2,2,2-trifluoro-1-[3'-fluoro-4'-(methylsulfonyl)-1,1'-biphenyl-4-yl]ethyl}-L-leucinamide;

N$^1$-(cyanomethyl)-N$^2$-((1S)-2,2,2-trifluoro-1-{4'-[(2-hydroxyethyl)sulfonyl]-1,1'-biphenyl-4-yl}ethyl)-L-leucinamide;

N$^1$-(cyanomethyl)-N$^2$-{(1S)-2,2,2-trifluoro-1-[3'-(methylsulfonyl)-1,1'-biphenyl-4-yl]ethyl}-L-leucinamide;

N$^1$-(cyanomethyl)-N$^2$-{(1S)-2,2,2-trifluoro-1-[4'-({2-[methoxy(methyl)amino]-2-oxoethyl}sulfonyl)-1,1'-biphenyl-4-yl]ethyl}-L-leucinamide;

N$^1$-(cyanomethyl)-N$^2$-((1S)-2,2,2-trifluoro-1-{4'-[(2-hydroxy-2-methylpropyl)sulfonyl]-1,1'-biphenyl-4-yl}ethyl)-L-leucinamide;

N$^2$-{(1S)-1-[4'-(aminosulfonyl)-1,1'-biphenyl-4-yl]-2,2,2-trifluoroethyl}-N$^1$-(1-cyanocyclopropyl)-L-leucinamide;

N$^2$-[(4-bromophenyl)(2,4,6-trifluorophenyl)methyl]-N$^1$-(cyanomethyl)-L-leucinamide;

N$^1$-(cyanomethyl)-N$^2$-[(4-pyridin-4-ylphenyl)(2,4,6-trifluorophenyl)methyl]-L-leucinamide;

N$^1$-(cyanomethyl)-N$^2$-[[4-(4-fluorobenzyl)phenyl](phenyl)methyl]-L-leucinamide;

N$^1$-(cyanomethyl)-N$^2$-{phenyl-[4-(pyridin-3-ylmethyl)phenyl]methyl}-L-leucinamide;

N$^2$-{(4-bromophenyl)[4-(methylsulfonyl)phenyl]methyl}-N$^1$-(cyanomethyl)-L-leucinamide;

N$^1$-(cyanomethyl)-N$^2$-{[4-(methylsulfonyl)phenyl-][4'-(methylthio)-1,1'-biphenyl-4-yl]methyl}-L-leucinamide;

N$^1$-(cyanomethyl)-N$^2$-{[4'-(methylsulfonyl)-1,1'-biphenyl-4-yl][4-(methylsulfonyl)phenyl]methyl}-L-leucinamide;

N$^1$-(cyanomethyl)-N$^2$-[2,2,2-trichloro-1-(4-glycoloylphenyl)ethyl]-L-leucinamide;

N$^1$-(cyanomethyl)-N$^2$-[2-fluoro-1-(fluoromethyl)-1-phenylethyl]-L-leucinamide;

N$^1$-(cyanomethyl)-N$^2$-{2,2,2-trifluoro-1-[4-(pyrrolidin-1-ylacetyl)phenyl]ethyl}-L-leucinamide;

N$^1$-(cyanomethyl)-N$^2$-{2,2,2-trifluoro-1-[4-(piperazin-1-ylcarbonyl)phenyl]ethyl}-L-leucinamide;

N$^1$-(cyanomethyl)-N$^2$-(2,2,2-trifluoro-1-{4-[2-(4-methylpiperazin-1-yl)-1,3-thiazol-4-yl]phenyl}ethyl)-L-leucinamide;

N$^1$-(1-cyanocyclopropyl)-3-(1-methylcyclopropyl)-N$^2$-(2,2,2-trifluoro-1-{4-[1-(2-hydroxyethyl)prolyl]phenyl}ethyl)-L-alaninamide;

N²-[[4-(4-tert-butylpiperazin-1-yl)phenyl](pentafluorophenyl)methyl]-N¹-(cyanomethyl)-L-leucinamide;

N-(cyanomethyl)-1-{1-[4-(4-methylpiperazin-1-yl)phenyl]ethyl}piperidine-2-carboxamide;

N²-[[4-(4-tert-butylpiperazin-1-yl)phenyl](pyridin-2-yl)methyl]-N¹-(cyanomethyl)-L-leucinamide;

N²-{[4-(4-tert-butylpiperazin-1-yl)phenyl-][5-(trifluoromethyl)pyridin-2-yl]methyl}-N¹-(cyanomethyl)-L-leucinamide;

(4S)-N-(cyanomethyl)-4-methyl-1-[(1S)-1-(4-piperazin-1-ylphenyl)ethyl]-L-prolinamide;

(4S)-N-(cyanomethyl)-4-methyl-1-[(1R)-1-(4-piperazin-1-ylphenyl)ethyl]-L-prolinamide;

N-(cyanomethyl)-1-[(1S)-1-(4-piperazin-1-ylphenyl)ethyl]-L-prolinamide;

N-(cyanomethyl)-1-[(1R)-1-(4-piperazin-1-ylphenyl)ethyl]-L-prolinamide;

N-(cyanomethyl)-4,4-difluoro-1-[(1S)-1-(4-piperazin-1-ylphenyl)ethyl]-L-prolinamide;

N¹-(1-cyanocyclopropyl)-N²-[(1S)-2,2,2-trifluoro-1-(4-methylphenyl)ethyl]-L-leucinamide;

N¹-(1-cyanocyclopropyl)-N²-{(1S)-2,2,2-trifluoro-1-[4-(1H-pyrazol-3-yl)phenyl]ethyl}-L-leucinamide;

N¹-(1-cyanocyclopropyl)-N²-{(1S)-2,2,2-trifluoro-1-[4-(2-methyl-1,3-oxazol-4-yl)phenyl]ethyl}-L-leucinamide;

N¹-(cyanomethyl)-N²-[(1S)-2,2,2-trifluoro-1-(4-pyrazin-2-ylphenyl)ethyl]-L-leucinamide;

N¹-(cyanomethyl)-N²-{(1S)-2,2,2-trifluoro-1-[4-(2-methylpyridin-4-yl)phenyl]ethyl}-L-leucinamide;

N¹-(cyanomethyl)-N²-{(1S)-2,2,2-trifluoro-1-[4-(4-methylpyridin-3-yl)phenyl]ethyl}-L-leucinamide;

N¹-(1-cyanocyclopropyl)-N²-{(1S)-2,2,2-trifluoro-1-[4-(1H-pyrazol-4-yl)phenyl]ethyl}-L-leucinamide;

N¹-(1-cyanocyclopropyl)-N²-[(1S)-2,2,2-trifluoro-1-(4-pyridin-4-ylphenyl)ethyl]-L-leucinamide;

N²-[(1S)-1-(3'-acetyl-1,1'-biphenyl-4-yl)-2,2,2-trifluoroethyl]-N¹-(1-cyanocyclopropyl)-L-leucinamide;

N¹-(1-cyanocyclopropyl)-N²-[(1S)-2,2,2-trifluoro-1-(3'-fluoro-4'-methyl-1,1'-biphenyl-4-yl)ethyl]-L-leucinamide;

N¹-(1-cyanocyclopropyl)-N²-((1S)-2,2,2-trifluoro-1-{5-[4-(1-hydroxy-1-methylethyl)phenyl]pyridin-2-yl}ethyl)-L-leucinamide;

N¹-(cyanomethyl)-N²-{(1S)-2,2,3,3,3-pentafluoro-1-[4'-(1-hydroxy-1-methylethyl)-1,1'-biphenyl-4-yl]propyl}-L-leucinamide;

N¹-(1-cyanocyclopropyl)-N²-[(1S)-2,2,3,3,3-pentafluoro-1-(4'-methyl-1,1'-biphenyl-4-yl)propyl]-L-leucinamide;

N¹-(cyanomethyl)-N²-{(1S)-2,2,3,3,3-pentafluoro-1-[4-(6-methoxypyridin-3-yl)phenyl]propyl}-L-leucinamide;

N¹-(cyanomethyl)-N²-[(1S)-2,2,3,3,3-pentafluoro-1-(2'-fluoro-1,1'-biphenyl-4-yl)propyl]-L-leucinamide;

N¹-(1-cyanocyclopropyl)-N²-{(1S)-2,2,2-trifluoro-1-[4'-methoxy-3'-(methylsulfonyl)-1,1'-biphenyl-4-yl]ethyl}-L-leucinamide;

N²-{(1S)-1-[3'-(aminosulfonyl)-4'-methoxy-1,1'-biphenyl-4-yl]-2,2,2-trifluoroethyl}-N¹-(1-cyanocyclopropyl)-L-leucinamide;

N¹-(1-cyanocyclopropyl)-N²-{(1S)-2,2,2-trifluoro-1-[4-(6-methoxypyridin-3-yl)phenyl]ethyl}-L-leucinamide;

N¹-(cyanomethyl)-N²-{(1S)-2,2,3,3,3-pentafluoro-1-[4-(5-methylpyridin-2-yl)phenyl]propyl}-L-leucinamide;

N¹-(1-cyanocyclopropyl)-N²-((1S)-2,2,2-trifluoro-1-{4-[5-(methylsulfonyl)pyridin-2-yl]phenyl}ethyl)-L-leucinamide;

N¹-(1-cyanocyclopropyl)-N²-{(1S)-2,2,2-trifluoro-1-[4-(5-methylpyridin-2-yl)phenyl]ethyl}-L-leucinamide;

N¹-(cyanomethyl)-4-fluoro-N²-{(1S)-2,2,2-trifluoro-1-[4'-(methylsulfonyl)-1,1'-biphenyl-4-yl]ethyl}-L-leucinamide;

N¹-(1-cyanocyclopropyl)-4-fluoro-N²-{(1S)-2,2,2-trifluoro-1-[4'-(methylsulfonyl)-1,1'-biphenyl-4-yl]ethyl}-L-leucinamide;

N¹-(1-cyanocyclopropyl)-4-fluoro-N²-{(1S)-2,2,2-trifluoro-1-[2'-methyl-4'-(methylsulfonyl)-1,1'-biphenyl-4-yl]ethyl}-L-leucinamide;

N¹-(1-cyanocyclopropyl)-N²-{(1S)-2,2,2-trifluoro-1-[5-(1H-pyrazol-3-yl)pyridin-2-yl]ethyl}-L-leucinamide;

N¹-(1-cyanocyclopropyl)-N²-[(1S)-2,2,2-trifluoro-1-(5-quinolin-5-ylpyridin-2-yl)ethyl]-L-leucinamide;

N¹-(1-cyanocyclopropyl)-N²-[(1S)-2,2,2-trifluoro-1-(5-quinolin-6-ylpyridin-2-yl)ethyl]-L-leucinamide;

N¹-(1-cyanocyclopropyl)-N²-{(1S)-2,2-difluoro-1-[4'-(methylsulfonyl)-1,1'-biphenyl-4-yl]ethyl}-L-leucinamide;

N²-[(1S)-1-(4'-acetyl-1,1'-biphenyl-4-yl)-2,2,3,3,3-pentafluoropropyl]-N¹-(1-cyanocyclopropyl)-L-leucinamide;

N²-[(1S)-1-(1,1'-biphenyl-4-yl)-2,2,2-trifluoroethyl]-N¹-(1-cyanocyclopropyl)-L-leucinamide;

N²-{(1S)-1-[4'-(aminosulfonyl)-1,1'-biphenyl-4-yl]-2,2,3,3,3-pentafluoropropyl}-N¹-(1-cyanocyclopropyl)-L-leucinamide;

N¹-(1-cyanocyclopropyl)-N²-{(1S)-1-[4-(1-ethoxyvinyl)phenyl]-2,2,2-trifluoroethyl}-L-leucinamide;

N²-[(1S)-1-(4-acetylphenyl)-2,2,2-trifluoroethyl]-N¹-(1-cyanocyclopropyl)-L-leucinamide;

N¹-(1-cyanocyclopropyl)-N²-[(1S)-2,2,2-trifluoro-1-(4-isopropylphenyl)ethyl]-L-leucinamide;

N¹-(1-cyanocyclopropyl)-N²-[(1S)-2,2,2-trifluoro-1-phenylethyl]-L-leucinamide;

N¹-(1-cyanocyclopropyl)-N²-{(1S)-2,2,2-trifluoro-1-[4-(1-hydroxy-1-methylethyl)phenyl]ethyl}-L-leucinamide;

N¹-(1-cyanocyclopropyl)-N²-{(1S)-2,2,2-trifluoro-1-[4-(1-methylcyclopropyl)phenyl]ethyl}-L-leucinamide;

N¹-(1-cyanocyclopropyl)-N²-[(1S)-2,2,2-trifluoro-1-(2',4',6'-trimethyl-1,1'-biphenyl-4-yl)ethyl]-L-leucinamide;

N²-[(1S)-1-(6-chloropyridin-3-yl)-2,2,2-trifluoroethyl]-N¹-(1-cyanocyclopropyl)-L-leucinamide;

N²-{(1S)-1-[5-(4-acetylphenyl)pyridin-2-yl]-2,2,2-trifluoroethyl}-N¹-(1-cyanocyclopropyl)-L-leucinamide;

N²-{(1S)-1-[6-(4-acetylphenyl)pyridin-3-yl]-2,2,2-trifluoroethyl}-N¹-(1-cyanocyclopropyl)-L-leucinamide;

N²-{(1S)-1-[5-(3-acetylphenyl)pyridin-2-yl]-2,2,2-trifluoroethyl}-N¹-(1-cyanocyclopropyl)-L-leucinamide;

N¹-(1-cyanocyclopropyl)-N²-((1S)-2,2,2-trifluoro-1-{5-[4-(1-hydroxyethyl)phenyl]pyridin-2-yl}ethyl)-L-leucinamide;

N²-[(1S)-1-(1,1'-biphenyl-4-yl)-2,2,3,3,3-pentafluoropropyl]-N¹-(cyanomethyl)-L-leucinamide;

N²-[(1S)-1-(4'-acetyl-1,1'-biphenyl-4-yl)-2,2,3,3,3-pentafluoropropyl]-N¹-(cyanomethyl)-L-leucinamide;

N²-[(1S)-1-(1,1'-biphenyl-4-yl)-2,2,3,3,3-pentafluoropropyl]-N¹-(1-cyanocyclopropyl)-L-leucinamide;

N²-(1-benzyl-2,2,2-trifluoroethyl)-N¹-(1-cyanocyclopropyl)-L-leucinamide;

N²-[(1S)-1-(4-tert-butylphenyl)-2,2,2-trifluoroethyl]-N¹-(1-cyanocyclopropyl)-L-leucinamide;

N²-[(1S)-1-(4-bromophenyl)-2,2,2-trifluoroethyl]-N¹-(cyanomethyl)-4-methyl-L-leucinamide;

N²-[(1S)-1-(4-bromophenyl)-2,2,2-trifluoroethyl]-N¹-(1-cyanocyclopropyl)-4-methyl-L-leucinamide;

N¹-(1-cyanocyclopropyl)-N²-((1S)-2,2,2-trifluoro-1-{[2-(1H-pyrazol-4-yl)-1,3-thiazol-4-yl]phenyl}ethyl)-L-leucinamide;

N$^1$-(1-cyanocyclopropyl)-N$^2$-{(1S)-2,2,2-trifluoro-1-[4-(2-methyl-1,3-thiazol-4-yl)phenyl]ethyl}-L-leucinamide;
N$^1$-(1-cyanocyclopropyl)-N$^2$-{(1S)-2,2,2-trifluoro-1-[4-(2-methylpyridin-4-yl)phenyl]ethyl}-L-leucinamide;
N$^1$-(1-cyanocyclopropyl)-N$^2$-{(1S)-2,2,2-trifluoro-1-[4-(2-methylpyridin-3-yl)phenyl]ethyl}-L-leucinamide;
N$^1$-(1-cyanocyclopropyl)-N$^2$-{(1S)-2,2,2-trifluoro-1-[4-(6-methylpyridin-2-yl)phenyl]ethyl}-L-leucinamide;
N$^2$-[(1S)-1-(3'-acetyl-1,1'-biphenyl-4-yl)-2,2,2-trifluoroethyl]-N$^1$-(1-cyanocyclopropyl)-4-fluoro-L-leucinamide;
N$^1$-(1-cyanocyclopropyl)-4-fluoro-N$^2$-{(1S)-2,2,2-trifluoro-1-[4-(1H-pyrazol-3-yl)phenyl]ethy}-L-leucinamide;
N$^1$-[(1S)-1-cyanoethyl]-N$^2$-{(1S)-2,2,2-trifluoro-1-[4'-(methylsulfonyl)-1,1'-biphenyl-4-yl]ethyl}-L-leucinamide;
N$^1$-[(1S)-1-cyano-3-(methylthio)propyl]-N$^2$-{(1S)-2,2,2-trifluoro-1-[4'-(methylsulfonyl)-1,1'-biphenyl-4-yl]ethyl}-L-leucinamide;
N$^1$-[(1S)-1-cyano-3-(methylsulfonyl)propyl]-N$^2$-{(1S)-2,2,2-trifluoro-1-[4'-(methylsulfonyl)-1,1'-biphenyl-4-yl]ethyl}-L-leucinamide;
N$^2$-[(1S)-1-(4-bromophenyl)-2,2,3,3,3-pentafluoropropyl]-N$^1$-(1-cyanocyclopropyl)-L-leucinamide;
N$^1$-(cyanomethyl)-N$^2$-{(1S)-2,2,3,3,3-pentafluoro-1-[4-(6-methoxypyridin-2-yl)phenyl]propyl}-L-leucinamide;
N$^2$-[(1S)-1-(5-bromopyridin-2-yl)-2,2,2-trifluoroethyl]-N$^1$-(cyanomethyl)-L-leucinamide;
N$^1$-(cyanomethyl)-N$^2$-((1S)-2,2,2-trifluoro-1-{5-[4-(methylsulfonyl)phenyl]pyridin-2-yl}ethyl)-L-leucinamide;
N$^1$-(1-cyanocyclopropyl)-N$^2$-{(1S)-2,2,2-trifluoro-1-[4'-(1-hydroxy-1-methylethyl)-1,1'-biphenyl-4-yl]ethyl}-L-leucinamide;
N$^1$-(cyanomethyl)-N$^2$-[(1S)-2,2,2-trifluoro-1-(6'-methyl-3,3'-bipyridin-6-yl)ethyl]-L-leucinamide;
N$^1$-(1-cyanocyclopropyl)-N$^2$-{(1S)-2,2,2-trifluoro-1-[4-(6-methoxypyridin-2-yl)phenyl]ethyl}-L-leucinamide;
N$^1$-(cyanomethyl)-N$^2$-{(1S)-2,2,2-trifluoro-1-[4-(6-oxo-1,6-dihydropyridin-2-yl)phenyl]ethyl}-L-leucinamide;
(4S)-N$^1$-(cyanomethyl)-5,5,5-trifluoro-N$^2$-{(1S)-2,2,2-trifluoro-1-[4'-(methylsulfonyl)-1,1'-biphenyl-4-yl]ethyl}-L-leucinamide;
(4S)-N$^1$-(1-cyanocyclopropyl)-5,5,5-trifluoro-N$^2$-{(1S)-2,2,2-trifluoro-1-[4'-(methylsulfonyl)-1,1'-biphenyl-4-yl]ethyl}-L-leucinamide;
(4S)-N$^1$-(cyanomethyl)-5,5,5-trifluoro-N$^2$-{(1S)-2,2,2-trifluoro-1-[4'-(methylthio)-1,1'-biphenyl-4-yl]ethyl}-L-leucinamide;
(4S)-N$^1$-(1-cyanocyclopropyl)-5,5,5-trifluoro-N$^2$-{(1S)-2,2,2-trifluoro-1-[4'-(methylthio)-1,1'-biphenyl-4-yl]ethyl}-L-leucinamide;
(4S)-N$^2$-[(1S)-1-(4-bromophenyl)-2,2,2-trifluoroethyl]-N$^1$-(cyanomethyl)-5,5,5-trifluoro-L-leucinamide;
(4S)-N$^2$-[(1S)-1-(4-bromophenyl)-2,2,2-trifluoroethyl]-N$^1$-(1-cyanocyclopropyl)-5,5,5-trifluoro-L-leucinamide;
N$^2$-{(1S)-1-[4-(6-aminopyridin-3-yl)phenyl]-2,2,2-trifluoroethyl}-N$^1$-(cyanomethyl)-L-leucinamide;
N$^2$-[(1S)-1-(4-bromophenyl)-2,2,2-trifluoroethyl]-N$^1$-(1-cyanocyclopropyl)-4-fluoro-L-leucinamide;
N$^1$-(cyanomethyl)-N$^2$-{(1S)-2,2,3,3,3-pentafluoro-1-[4-(6-methylpyridin-3-yl)phenyl]propyl}-L-leucinamide;
N$^1$-(1-cyanocyclopropyl)-N$^2$-{(1S)-2,2,3,3,3-pentafluoro-1-[4-(6-methylpyridin-3-yl)phenyl]propyl}-L-leucinamide;
N$^1$-(1-cyanocyclopropyl)-N$^2$-{(1S)-2,2,2-trifluoro-1-[4-(6-methylpyridin-3-yl)phenyl]ethyl}-L-leucinamide;
N$^1$-(cyanomethyl)-N$^2$-{(1S)-2,2,2-trifluoro-1-[4'-(1-hydroxyethyl)-1,1'-biphenyl-4-yl]ethyl}-L-leucinamide;
N$^1$-(cyanomethyl)-N$^2$-{(1S)-2,2,2-trifluoro-1-[4'-(2,2,2-trifluoro-1-hydroxyethyl)-1,1'-biphenyl-4-yl]ethyl}-L-leucinamide;
N$^1$-(1-cyanocyclopropyl)-N$^2$-{(1S)-2,2,3,3,3-pentafluoro-1-[4'-(methylthio)-1,1'-biphenyl-4-yl]propyl}-L-leucinamide;
N$^1$-(1-cyanocyclopropyl)-N$^2$-{(1S)-2,2,3,3,3-pentafluoro-1-[4'-(1-hydroxy-1-methylethyl)-1,1'-biphenyl-4-yl]propyl}-L-leucinamide;
N$^1$-(1-cyanocyclopropyl)-N$^2$-{(1S)-2,2,3,3,3-pentafluoro-1-[4'-(methylsulfonyl)-1,1'-biphenyl-4-yl]propyl}-L-leucinamide;
N$^1$-(1-cyanocyclopropyl)-N$^2$-{(1S)-2,2,3,3,3-pentafluoro-1-[4-(6-methoxypyridin-2-yl)phenyl]propyl}-L-leucinamide;
(4R)-N$^1$-(cyanomethyl)-5,5,5-trifluoro-N$^2$-{(1S)-2,2,2-trifluoro-1-[4'-(methylsulfonyl)-1,1'-biphenyl-4-yl]ethyl}-L-leucinamide;
(4R)-N$^1$-(1-cyanocyclopropyl)-5,5,5-trifluoro-N$^2$-{(1S)-2,2,2-trifluoro-1-[4'-(methylsulfonyl)-1,1'-biphenyl-4-yl]ethyl}-L-leucinamide;
N$^1$-(cyanomethyl)-N$^2$-[(1S)-2,2,3,3,3-pentafluoro-1-(4'-methyl-1,1'-biphenyl-4-yl)propyl]-L-leucinamide;
N$^1$-(cyanomethyl)-N$^2$-{(1S)-2,2,3,3,3-pentafluoro-1-[4-(1,3-thiazol-2-yl)phenyl]propyl}-L-leucinamide;
N$^1$-(1-cyanocyclopropyl)-N$^2$-[(1S)-1-(4-ethynylphenyl)-2,2,3,3,3-pentafluoropropyl]-L-leucinamide;
N$^1$-(cyanomethyl)-N$^2$-{(1S)-1-[4-(cyclopropylethynyl)phenyl]-2,2,2-trifluoroethyl}-L-leucinamide;
N$^1$-(1-cyanocyclopropyl)-N$^2$-{(1S)-1-[4-(cyclopropylethynyl)phenyl]-2,2,2-trifluoroethyl}-L-leucinamide;
N$^1$-(cyanomethyl)-N$^2$-{(1S)-2,2,2-trifluoro-1-[4-(5-methyl-1,3-thiazol-2-yl)phenyl]ethyl}-L-leucinamide;
N$^1$-(1-cyanocyclopropyl)-N$^2$-{(1S)-2,2,2-trifluoro-1-[4-(1,3-thiazol-2-yl)phenyl]ethyl}-L-leucinamide;
N$^1$-(1-cyanocyclopropyl)-N$^2$-{(1S)-2,2,2-trifluoro-1-[4-(5-methyl-1,3-thiazol-2-yl)phenyl]ethyl}-L-leucinamide;
N$^1$-(1-cyanocyclopropyl)-N$^2$-{(1S)-1-[4-(cyclopropylethynyl)phenyl]-2,2,3,3,3-pentafluoropropyl}-L-leucinamide;
N$^1$-(1-cyanocyclopropyl)-N$^2$-{(1S)-2,2,2-trifluoro-1-[4-(4-methyl-1,3-thiazol-2-yl)phenyl]ethyl}-L-leucinamide;
N$^1$-(cyanomethyl)-N$^2$-{(1S)-2,2,2-trifluoro-1-[4-(4-methyl-1,3-thiazol-2-yl)phenyl]ethyl}-L-leucinamide;
N$^1$-(cyanomethyl)-N$^2$-{(1S)-1-[4-(4,5-dimethyl-1,3-thiazol-2-yl)phenyl]-2,2,2-trifluoroethyl}-L-leucinamide;
N$^1$-(1-cyanocyclopropyl)-N$^2$-{(1S)-1-[4'-(ethylsulfonyl)-1,1'-biphenyl-4-yl]-2,2,2-trifluoroethyl}-4-fluoro-L-leucinamide;
N$^1$-(1-cyanocyclopropyl)-4-fluoro-N$^2$-[(1S)-2,2,2-trifluoro-1-(4-pyridin-3-ylphenyl)ethyl]-L-leucinamide;
N$^1$-(1-cyanocyclopropyl)-4-fluoro-N$^2$-{(1S)-2,2,2-trifluoro-1-[4'-methoxy-3'-(methylsulfonyl)-1,1'-biphenyl-4-yl]ethyl}-L-leucinamide;
N$^2$-[(1S)-1-(4-bromophenyl)-2,2,2-trifluoroethyl]-N$^1$-(cyanomethyl)-L-alaninamide;
N$^2$-{(1S)-1-[4'-(aminosulfonyl)-1,1'-biphenyl-4-yl]-2,2,3,3,3-pentafluoropropyl}-N$^1$-(cyanomethyl)-L-leucinamide;
N$^1$-(cyanomethyl)-N$^2$-((1S)-2,2,3,3,3-pentafluoro-1-{4'-[(2-hydroxy-2-methylpropyl)sulfonyl]-1,1'-biphenyl-4-yl}propyl)-L-leucinamide;
N$^1$-(cyanomethyl)-N$^2$-{(1S)-2,2,2-trifluoro-1-[4'-(methylsulfonyl)-1,1'-biphenyl-4-yl]ethyl}-L-alaninamide;
N$^1$-(cyanomethyl)-N$^2$-{(1S)-2,2,3,3,3-pentafluoro-1-[4'-(isopropylsulfonyl)-1,1'-biphenyl-4-yl]propyl}-L-leucinamide;

N¹-(1-cyano-1-methylethyl)-N²-{(1S)-2,2,2-trifluoro-1-[4'-(methylsulfonyl)-1,1'-biphenyl-4-yl]ethyl}-L-leucinamide;

N¹-(1-cyanocyclopropyl)-N²-((1S)-2,2,2-trifluoro-1-{4'-[(2-hydroxy-2-methylpropyl)sulfonyl]-1,1'-biphenyl-4-yl}ethyl)-L-leucinamide;

N¹-(1-cyanocyclopropyl)-N²-{(1S)-2,2,2-trifluoro-1-[2'-methyl-4'-(methylsulfonyl)-1,1'-biphenyl-4-yl]ethyl}-L-leucinamide;

N¹-(1-cyanocyclopropyl)-N²-{(1S)-1-[4'-(ethylsulfonyl)-1,1'-biphenyl-4-yl]-2,2,2-trifluoroethyl}-L-leucinamide;

N²-{(S)-1-[4'-(aminosulfonyl)-1,1'-biphenyl-4-yl]-2,2,2-trifluoroethyl}-N¹-(1-cyanocyclopropyl)-4-fluoro-L-leucinamide;

N¹-(cyanomethyl)-N²-{(S)-[4'-(methylsulfonyl)-1,1'-biphenyl-4-yl][4-(trifluoromethoxy)phenyl]methyl}-L-leucinamide;

N¹-(cyanomethyl)-N²-[(S)-[4'-(methylsulfonyl)-1,1'-biphenyl-4-yl](thien-2-yl)methyl]-L-leucinamide;

N¹-(cyanomethyl)-N²[(S)-(4'-piperazin-4-ium-1-yl-1,1'-biphenyl-4-yl)(thien-2-yl)methyl]-L-leucinamide methanesulfonate;

N¹-(cyanomethyl)-N²-{(S)-(4-fluorophenyl)[4'-(methylsulfonyl)-1,1'-biphenyl-4-yl]methyl}-L-leucinamide;

N¹-(cyanomethyl)-N²-{(S)-[4'-(methylsulfonyl)-1,1'-biphenyl-4-yl][4-(trifluoromethyl)phenyl]methyl}-L-leucinamide;

N²-{(S)-(4-chlorophenyl)[4'-(methylsulfonyl)-1,1'-biphenyl-4-yl]methyl}-N¹-(cyanomethyl)-L-leucinamide;

N¹-(cyanomethyl)-N²-{(1S)-2,2,2-trifluoro-1-[4'-(methylsulfonyl)-1,1'-biphenyl-4-yl]ethyl}-L-norvalinamide;

N²-[(S)-(4-bromophenyl)(thien-2-yl)methyl]-N¹-(cyanomethyl)-L-leucinamide;

N¹-(cyanomethyl)-N²-[(S)-[4-(4,4,5,5-tetramethyl-1,3,2-dioxaborolan-2-yl)phenyl](thien-2-yl)methyl]-L-leucinamide;

N²-{(R)-(4-bromophenyl)[4-(trifluoromethoxy)phenyl]methyl}-N¹-(cyanomethyl)-L-leucinamide;

N¹-(cyanomethyl)-N²-{(S)-[4-(4,4,5,5-tetramethyl-1,3,2-dioxaborolan-2-yl)phenyl-][4-(trifluoromethoxy)phenyl]methyl}-L-leucinamide;

N²-[(S)-(4-bromophenyl)(2-furyl)methyl]-N¹-(cyanomethyl)-L-leucinamide;

N¹-(cyanomethyl)-N²-{(S)-2-furyl[4'-(methylsulfonyl)-1,1'-biphenyl-4-yl]methyl}-L-leucinamide;

N²-[1-(4-bromophenyl)-2,2,2-trifluoroethyl]-N¹-(cyanomethyl)-L-norvalinamide;

N²-{(R)-(4-bromophenyl)[4-(trifluoromethyl)phenyl]methyl}-N¹-(cyanomethyl)-L-leucinamide;

N¹-(cyanomethyl)-N²-{1-[4'-(4-cyclopropylpiperazin-1-yl)-1,1'-biphenyl-4yl]-2,2,2-trifluoroethyl}-L-norvalinamide;

N²-[(R)-(4-bromophenyl)(4-chlorophenyl)methyl]-N¹-(cyanomethyl)-L-leucinamide;

N¹-(cyanomethyl)-N²-{2,2,2-trifluoro-1-[4'-(methylsulfonyl)-1,1'-biphenyl-4-yl]ethyl}-L-norvalinamide;

N²-[(S)-(4-bromophenyl)(3-methylthien-2-yl)methyl]-N¹-(cyanomethyl)-L-leucinamide;

N²-[(S)-(4-bromophenyl)(thien-3-yl)methyl]-N¹-(cyanomethyl)-L-leucinamide;

N¹-(cyanomethyl)-N²-{(S)-(2,4-difluorophenyl)[4'-(methylsulfonyl)-1,1'-biphenyl-4-yl]methyl}-L-leucinamide;

N¹-(cyanomethyl)-N²-[(S)-[4'-(methylsulfonyl)-1,1'-biphenyl-4-yl](thien-3-yl)methyl]-L-leucinamide;

N¹-(cyanomethyl)-N²-[(S)-[4'-(methylsulfonyl)-1,1'-biphenyl-4-yl](3-methylthien-2-yl)methyl]-L-leucinamide;

N¹-(cyanomethyl)-N²-[(S)-[4'-(4-cyclopropylpiperazin-1-yl)-1,1'-biphenyl-4-yl](3-methylthien-2-yl)methyl]-L-leucinamide;

N¹-(cyanomethyl)-N²-[(S)-[4'-(4-cyclopropylpiperazin-1-yl)-1,1'-biphenyl-4-yl](thien-3-yl)methyl]-L-leucinamide;

N²-[1-(4-bromophenyl)-2,2,2-trifluoroethyl]-N¹-(cyanomethyl)-5,5,5-trifluoro-L-norvalinamide;

N¹-(cyanomethyl)-5,5,5-trifluoro-N²-{(1S)-2,2,2-trifluoro-1-[4'-(methylsulfonyl)-1,1'-biphenyl-4-yl]ethyl}-L-norvalinamide;

N²-[(S)-(4-bromophenyl)(3-methylthien-2-yl)methyl]-N¹-(1-cyanocyclopropyl)-L-leucinamide;

N¹-(1-cyanocyclopropyl)-N²-[(S)-[4'-(methylsulfonyl)-1,1'-biphenyl-4-yl](3-methylthien-2-yl)methyl]-L-leucinamide;

N¹-(cyanomethyl)-N²-{(S)-3-furyl[4'-(methylsulfonyl)-1,1'-biphenyl-4-yl]methyl}-L-leucinamide;

N¹-(1-cyanocyclopropyl)-N²-{(1S)-2,2,2-trifluoro-1-[4'-(methylsulfonyl)-1,1'-biphenyl-4-yl]ethyl}-L-norvalinamide;

N²-[(1S)-1-(4-bromophenyl)-2,2,2-trifluoroethyl]-N¹-(1-cyanocyclopropyl)-L-norvalinamide N²-[(S)-(4-bromophenyl)(4-bromothien-2-yl)methyl]-N¹-(cyanomethyl)-L-leucinamide;

N²-[(S)-(4-bromophenyl)(thien-3-yl)methyl]-N¹-(1-cyanocyclopropyl)-L-leucinamide;

N¹-(cyanomethyl)-N²-((S)-[4'-(methylsulfonyl)-1,1'-biphenyl-4-yl]{4-[4-(methylsulfonyl)phenyl]thien-2-yl}methyl)-L-leucinamide;

N¹-(1-cyanocyclopropyl)-N²-[(S)-[4'-(methylsulfonyl)-1,1'-biphenyl-4-yl](thien-3-yl)methyl]-L-leucinamide;

N²-{(1S)-1-[4'-(aminosulfonyl)-1,1'-biphenyl-4-yl]-2,2,2-trifluoroethyl}-N¹-(1-cyanocyclopropyl)-L-norvalinamide;

N²-[(S)-(4-bromophenyl)(4-bromothien-2-yl)methyl]-N¹-(1-cyanocyclopropyl)-L-leucinamide;

N²-[(S)-[4'-(aminosulfonyl)-1,1'-biphenyl-4-yl](thien-3-yl)methyl]-N-(1-cyanocyclopropyl)-L-leucinamide;

N²-[(S)-[4'-(aminosulfonyl)-1,1'-biphenyl-4-yl](thien-3-yl)methyl]-N¹-(cyanomethyl)-L-leucinamide;

N¹-(1-cyanocyclopropyl)-N²-{(1S)-2,2,2-trifluoro-1-[4'-methoxy-3'-(methylsulfonyl)-1,1'-biphenyl-4-yl]ethyl}-L-norvalinamide;

N¹-(1-cyanocyclopropyl)-N²-{(1S)-2,2,2-trifluoro-1-[4-(2-methylpyridin-4-yl)phenyl]ethyl}-L-norvalinamide;

N¹-(1-cyanocyclopropyl)-5,5,5-trifluoro-N²-{(1S)-2,2,2-trifluoro-1-[4'-(methylsulfonyl)-1,1'-biphenyl-4-yl]ethyl}-L-norvalinamide;

N¹-(1-cyanocyclopropyl)-N²-{(1S)-2,2,2-trifluoro-1-[4-(1H-pyrazol-3-yl)phenyl]ethyl}-L-norvalinamide;

N¹-(1-cyanocyclopropyl)-N²-{(1S)-2,2,2-trifluoro-1-[4'-(1-hydroxy-1-methylethyl)-1,1'-biphenyl-4-yl]ethyl}-L-norvalinamide;

N¹-(1-cyanocyclopropyl)-N²-{(1S)-2,2,2-trifluoro-1-[4-(5-methylpyridin-2-yl)phenyl]ethyl}-L-norvalinamide;

2-{[(4-Bromo-phenyl)-pyridin-4-yl-methyl]-amino}-pentanoic acid cyanomethyl-amide;

2-{[(4-Bromo-phenyl)-thiazol-2-yl-methyl]-amino+}-pentanoic acid cyanomethyl-amide;

(2S)-2-[(S)-1-(4'-Acetylbiphenyl-4-yl)-2,2,2-trifluoroethylamino]-pentanoic acid (1-cyanocyclopropyl)-amide;

(2S)-2-[(S)-1-(2',4'-Difluorobiphenyl-4-yl)-2,2,2-trifluoroethylamino]-pentanoic acid (1-cyanocyclopropyl)-amide;

(2S)-2-[(S)-1-(3',4'-Difluorobiphenyl-4-yl)-2,2,2-trifuoroethylamino]-pentanoic acid (1-cyanocyclopropyl)-amide;

(2S)-2-[(S)-1-(3'-Chloro-4'-fluorobiphenyl-4-yl)-2,2,2-trifluoroethylamino]-pentanoic acid (1-cyano-cyclopropyl)-amide;

(2S)-2-[(S)-2,2,2-Trifluoro-1-(4'-methanesulfonylamino-biphenyl-4-yl)-ethylamino]-pentanoic acid (1-cyano-cyclopropyl)-amide;

(2S)-2-(S)-[(4-Bromo-phenyl)-thiazol-2-yl-methyl]-amino)-4-methylpentanoic acid cyanomethyl-amide;

$N^1$-(1-cyanocyclopropyl)-$N^2$-{(1S)-2,2,2-trifluoro-1-[4'-chloro-1,1'-biphenyl-4-yl]ethyl}-L-norvalinamide;

$N^1$-(1-cyanocyclopropyl)-$N^2$-{(1S)-2,2,2-trifluoro-1-[4'-chloro-3'-methyl-1,1'-biphenyl-4-yl]ethyl}-L-norvalinamide;

$N^1$-(1-cyanocyclopropyl)-$N^2$-{(1S)-2,2,2-trifluoro-1-[4¹-chloro-2'-methyl-1,1'-biphenyl-4-yl]ethyl}-L-norvalinamide;

(2S)-2-{(S)-2,2,2-Trifluoro-1-[4-(1H-indol-5-yl)-phenyl]-ethylamino}-pentanoic acid (1-cyano-cyclopropyl)-amide;

(2S)-2-[(S)-2,2,2-Trifluoro-1-(3'-methanesulfonylamino-biphenyl-4-yl)-ethylamino]-pentanoic acid (1-cyano-cyclopropyl)-amide;

$N^1$-(1-cyanocyclopropyl)-$N^2$-{(1S)-2,2,2-trifluoro-1-[4'-fluoro-1,1'-biphenyl-4-yl]ethyl}-L-norvalinamide;

$N^1$-(1-cyanocyclopropyl)-$N^2$-{(1S)-2,2,2-trifluoro-1-[4'-fluoro-3'-methyl-1,1'-biphenyl-4-yl]ethyl}-L-norvalinamide;

$N^1$-(1-cyanocyclopropyl)-$N^2$-{(1S)-2,2,2-trifluoro-1-[3'-fluoro-4'-methyl-1,1'-biphenyl-4-yl]ethyl}-L-norvalinamide;

$N^1$-(1-cyanocyclopropyl)-$N^2$-{(1S)-2,2,2-trifluoro-1-[4'-trifluoromethoxy-1,1'-biphenyl-4-yl]ethyl}-L-norvalinamide;

(2S)-2-[(S)-2,2,2-Trifluoro-1-(4'-methylbiphenyl-4-yl)-ethylamino]-pentanoic acid (1-cyanocyclopropyl)-amide;

(2S)-2-[(S)-1-(4'-Cyanobiphenyl-4-yl)-2,2,2-trifluoroethylamino]-pentanoic acid (1-cyanocyclopropyl)-amide;

$N^1$-(1-cyanocyclopropyl)-$N^2$-{(1S)-2,2,2-trifluoro-1-[4'-methoxy-1,1'-biphenyl-4-yl]ethyl}-L-norvalinamide;

$N^1$-(1-cyanocyclopropyl)-$N^2$-{(1S)-2,2,2-trifluoro-1-[4-(benzo[1,3]dioxol-5-yl)phenyl]ethyl}-L-norvalinamide;

$N^1$-(1-cyanocyclopropyl)-$N^2$-{(1S)-2,2,2-trifluoro-1-[4'-(methoxycarbonyl)-1,1'-biphenyl-4-yl]ethyl}-L-norvalinamide;

(2S)-2-{(S)-[(4-Bromophenyl)-thiazol-2-yl-methyl]-amino}-4-methylpentanoic acid (1-cyanocyclopropyl)-amide;

(2S)-2-{(S)-[(4'-Methanesulfonyl-biphenyl-4-yl)-thiazol-2-yl-methyl]-amino}-4-methyl-pentanoic acid cyanomethyl-amide;

(2S)-2-[(S)-2,2,2-Trifluoro-1-(4'-fluoromethyl-biphenyl-4-yl)-ethylamino]-pentanoic acid (1-cyano-cyclopropyl)-amide;

(2S)-2-[(S)-2,2,2-Trifluoro-1-(2'-trifluoromethyl-biphenyl-4-yl)-ethylamino]-pentanoic acid (1-cyano-cyclopropyl)-amide;

(2S)-2-{(S)-[(2',4'-Difluorobiphenyl-4-yl)-thiazol-2-yl-methyl]-amino}-4-methylpentanoic acid (1-cyanocyclopropyl)-amide;

(2S)-2-{(S)-[(4'-Methanesulfonylbiphenyl-4-yl)-thiazol-2-yl-methyl]-amino}-4-methylpentanoic acid (1-cyanocyclopropyl)-amide;

$N^1$-(1-cyanocyclopropyl)-4-fluoro-$N^2$-{(1S)-2,2,2-trifluoro-1-[4-(1-oxido-2,3-dihydro-1-benzothien-5-yl)phenyl]ethyl}-L-leucinamide;

$N^1$-(1-cyanocyclopropyl)-$N^2$-{(1S)-1-[4-(1,1-dioxido-2,3-dihydro-1-benzothien-5-yl)phenyl]-2,2,2-trifluoroethyl}-4-fluoro-L-leucinamide;

$N^1$-(1-cyanocyclopropyl)-$N^2$-{(1S)-1-[4-(1,1-dioxido-2,3-dihydro-1,2-benzisothiazol-5-yl)phenyl]-2,2,2-trifluoroethyl}-4-fluoro-L-leucinamide;

$N^1$-(1-cyanocyclopropyl)-4-fluoro-$N^2$-{(1S)-2,2,2-trifluoro-1-[4'-(methylsulfinyl)-1,1'-biphenyl-4-yl]ethyl}-L-leucinamide;

$N^1$-(1-cyanocyclopropyl)-$N^2$-{(1S)-1-[4-(1,1-dioxido-3-oxo-2,3-dihydro-1,2-benzisothiazol-5-yl)phenyl]-2,2,2-trifluoroethyl}-4-fluoro-L-leucinamide;

$N^1$-(1-cyanocyclopropyl)-4-fluoro-$N^2$-{(1S)-2,2,2-trifluoro-1-[2'-(1-hydroxy-1-methylethyl)-1,1'-biphenyl-4-yl]ethyl}-L-leucinamide;

$N^1$-(1-cyanocyclopropyl)-4,4-difluoro-$N^2$-{(1S)-2,2,2-trifluoro-1-[4'-(methylsulfonyl)-1,1'-biphenyl-4-yl]ethyl}-L-norvalinamide;

$N^1$-(cyanomethyl)-4,4-difluoro-$N^2$-{(1S)-2,2,2-trifluoro-1-[4'-(methylsulfonyl)-1,1'-biphenyl-4-yl]ethyl}-L-norvalinamide;

$N^1$-(cyanomethyl)-4-fluoro-$N^2$-{(1S)-2,2,2-trichloro-1-[4'-(methylsulfonyl)-1,1'-biphenyl-4-yl]ethyl}-L-leucinamide;

$N^1$-(1-cyanocyclopropyl)-4-fluoro-$N^2$-{(1S)-2,2,2-trichloro-1-[4'-(methylsulfonyl)-1,1'-biphenyl-4-yl]ethyl}-L-leucinamide;

$N^1$-(1-cyanocyclopropyl)-4,4-difluoro-$N^2$-{(1S)-2,2,2-trichloro-1-[4'-(methylsulfonyl)-1,1'-biphenyl-4-yl]ethyl}-L-norvalinamide;

$N^1$-(cyanomethyl)-4,4-difluoro-$N^2$-{(1S)-2,2,2-trichloro-1-[4'-(methylsulfonyl)-1,1'-biphenyl-4-yl]ethyl}-L-norvalinamide;

(2S)-N-(cyanomethyl)-4,4-difluoro-2-({(1S)-2,2,2-trifluoro-1-[4'-(methylsulfonyl)-1,1'-biphenyl-4-yl]ethyl}amino)butanamide;

(2S)-N-(1-cyanocyclopropyl)-4,4-difluoro-2-({(1S)-2,2,2-trifluoro-1-[4'-(methylsulfonyl)-1,1'-biphenyl-4-yl]ethyl}amino)butanamide;

(2S)-N-(1-cyanocyclopropyl)-4,4-difluoro-2-({(1S)-2,2,2-trichloro-1-[4'-(methylsulfonyl)-1,1'-biphenyl-4-yl]ethyl}amino)butanamide;

(2S)-N-(cyanomethyl)-4,4-difluoro-2-({(1S)-2,2,2-trichloro-1-[4'-(methylsulfonyl)-1,1'-biphenyl-4-yl]ethyl}amino)butanamide;

(2S)-4,4-dichloro-N-(cyanomethyl)-2-({(1S)-2,2,2-trifluoro-1-[4'-(methylsulfonyl)-1,1'-biphenyl-4-yl]ethyl}amino)butanamide;

(2S)-4,4-dichloro-N-(1-cyanocyclopropyl)-2-({(1S)-2,2,2-trifluoro-1-[4'-(methylsulfonyl)-1,1'-biphenyl-4-yl]ethyl}amino)butanamide;

(2S)-4,4-dichloro-N-(1-cyanocyclopropyl)-2-({(1S)-2,2,2-trichloro-1-[4'-(methylsulfonyl)-1,1'-biphenyl-4-yl]ethyl}amino)butanamide;

(2S)-4,4-dichloro-N-(cyanomethyl)-2-({(1S)-2,2,2-trichloro-1-[4'-(methylsulfonyl)-1,1'-biphenyl-4-yl]ethyl}amino)butanamide;

$N^2$-[(1S)-1-(1,1'-biphenyl-4-yl)-2,2,2-trifluoroethyl]-$N^1$-(1-cyanocyclopropyl)-4-fluoro-L-leucinamide;

$N^1$-(1-cyanocyclopropyl)-4-fluoro-$N^2${(1S)-2,2,2-trifluoro-1-[3'-(1-hydroxyethyl)-1,1'-biphenyl-4-yl]ethyl}-L-leucinamide;

$N^1$-(1-cyanocyclopropyl)-4-fluoro-$N^2$-[(1S)-2,2,2-trifuoro-1-(4'-methyl-1,1'-biphenyl-4-yl)ethyl]-L-leucinamide;

$N^1$-(1-cyanocyclopropyl)-4-fluoro-$N^2$-{(1S)-2,2,2-trifluoro-1-[3'-(1-hydroxy-1-methylethyl)-1,1'-biphenyl-4-yl]ethyl}-L-leucinamide;

N²-[(1S)-1-(4'-acetyl-1,1'-biphenyl-4-yl)-2,2,2-trifluoroethyl]-N¹-(1-cyanocyclopropyl)-4-fluoro-L-leucinamide;

N²-[(1S)-1-(2'-acetyl-1,1'-biphenyl-4-yl)-2,2,2-trifluoroethyl]-N¹-(1-cyanocyclopropyl)-4-fluoro-L-leucinamide;

N¹-(1-cyanocyclopropyl)-4-fluoro-N²-{(1S)-2,2,2-trifluoro-1-[4'-(1-hydroxyethyl-1,1'-biphenyl-4-yl]ethyl}-L-leucinamide;

N¹-(1-cyanocyclopropyl)-4-fluoro-N²-{(1S)-2,2,2-trifluoro-1-[2'-(1-hydroxyethyl)-1,1'-biphenyl-4-yl]ethyl}-L-leucinamide;

N¹-(1-cyanocyclopropyl)-4-fluoro-N²-{(1S)-2,2,2-trifluoro-1-[4'-(1-hydroxy-1-methylethyl)-1,1'-biphenyl-4yl]ethyl}-L-leucinamide;

N¹-(1-cyanocyclopropyl)-4-fluoro-N²-{(1S)-2,2,2-trifluoro-1-[2'-(1-hydroxy-1-methylethyl)-1,1'-biphenyl-4yl]ethyl}-L-leucinamide;

N¹-(1-cyanocyclopropyl)-4-fluoro-N²-((1S)-2,2,2-trifluoro-1-{5-[4-(methylsulfonyl)phenyl]pyridin-2-yl}ethyl)-L-leucinamide;

N¹-(1-cyanocyclopropyl)-4-fluoro-N²-((1S)-2,2,2-trifluoro-1-{6-[4-(methylsulfonyl)phenyl]pyridin-3-yl}ethyl)-L-leucinamide;

N¹-(1-cyanocyclopropyl)-4-fluoro-N²-[(1S)-2,2,2-trifluoro-1-(4-{6-[(methylsulfonyl)amino]pyridin-3-yl}phenyl)ethyl]-L-leucinamide;

N¹-(cyanomethyl)-4-fluoro-N²-[(1S)-2,2,2-trifluoro-1-(4-{6-[(methylsulfonyl)amino]pyridin-3-yl}phenyl)ethyl]-L-leucinamide;

N¹-(1-cyanobutyl)-4-fluoro-N²-{(1S)-2,2,2-trifluoro-1-[4'-(methylsulfonyl)-1,1'-biphenyl-4-yl]ethyl}-L-leucinamide;

N¹-(1-cyano-2-cyclopropylethyl)-4-fluoro-N²-{(1S)-2,2,2-trifluoro-1-[4'-(methylsulfonyl)-1,1'-biphenyl-4-yl]ethyl}-L-leucinamide;

N¹-(1-cyano-2-pyridin-3-ylethyl)-4-fluoro-N²{(1S)-2,2,2-trifluoro-1-[4'-(methylsulfonyl)-1,1'-biphenyl-4-yl]ethyl}-L-leucinamide;

N¹-(1-cyano-3-hydroxy-3-methylbutyl)-4-fluoro-N²-{(1S)-2,2,2-trifluoro-1-[4'-(methylsulfonyl)-1,1'-biphenyl-4-yl]ethyl}-L-leucinamide;

N¹-(1-cyanocyclopropyl)-fluoro-N²-{(1S)-2,2,2-trifluoro-1-[4-(1-oxo-1,3-dihydro-2-benzofuran-5-yl)phenyl]ethyl}-L-leucinamide;

N¹-(1-cyanocyclopropyl)-N²-{(1S)-1-[4-(3,3-dimethyl-1-oxo-1,3-dihydro-2-benzofuran-5-yl)phenyl]-2,2,2-trifluoroethyl}-4-fluoro-L-leucinamide;

N¹-(1-cyanocyclopropyl)-N²-{(1S)-1-[4-(3,3-diethyl-1-oxo-1,3-dihydro-2-benzofuran-5-yl)phenyl]-2,2,2-trifluoroethyl}-4-fluoro-L-leucinamide;

N¹-(1-cyanocyclopropyl)-4-fluoro-N²-{(1S)-2,2,2-trifluoro-1-[4-(3-oxo-1,3-dihydro-2-benzofuran-5-yl)phenyl]ethyl}-L-leucinamide;

N¹-(1-cyanocyclopropyl)-N²-{(1S)-1-[4-(1,1-dimethyl-3-oxo-1,3-dihydro-2-benzofuran-5-yl)phenyl]-2,2,2-trifluoroethyl}-4-fluoro-L-leucinamide;

N¹-(1-cyanocyclopropyl)-N²-{(1S)-1-[4-(1,1-diethyl-3-oxo-1,3-dihydro-2-benzofuran-5-yl)phenyl]-2,2,2-trifluoroethyl}-4-fluoro-L-leucinamide;

N¹-(1-cyanocyclopropyl)-4-fluoro-N²-{(1S)-2,2,2-trifluoro-1-[4'-(3-oxo-1,3-dihydro-2-benzofuran-5-yl)-1,1'-biphenyl-4-yl]ethyl}-L-leucinamide;

N¹-(1-cyanocyclopropyl)-N²-{(1S)-1-[4'-(1,1-dimethyl-3-oxo-1,3-dihydro-2-benzofuran-5-yl)-1,1'-biphenyl-4-yl]-2,2,2-trifluoroethyl}-4-fluoro-L-leucinamide;

N¹-(1-cyanocyclopropyl)-N²-{(1S)-1-[4'-(1,1-diethyl-3-oxo-1,3-dihydro-2-benzofuran-5-yl)-1,1'-biphenyl-4-yl]-2,2,2-trifluoroethyl}-4-fluoro-L-leucinamide;

N¹-(1-cyanocyclopropyl)-4-fluoro-N²-{(1S)-2,2,2-trifluoro-1-[4'-(1-oxo-1,3-2-benzofuran-5-yl)-1,1'-biphenyl-4-yl]ethyl}-L-leucinamide;

N¹-(1-cyanocyclopropyl)-N²-{(1S)-1-[4'-(3,3-dimethyl-1-oxo-1,3-dihydro-2-benzofuran-5-yl)-1,1'-biphenyl-4-yl]-2,2,2-trifluoroethyl}-4-fluoro-L-leucinamide;

N¹-(1-cyanocyclopropyl)-N²-{(1S)-1-[4'-(3,3-diethyl-1-oxo-1,3-dihydro-2-benzofuran-5-yl)-1,1'-biphenyl-4-yl]-2,2,2-trifluoroethyl}-4-fluoro-L-leucinamide;

N¹-(1-cyanocyclopropyl)-4-fluoro-N²-{(1S)-2,2,2-trifluoro-1-[4-(5-oxo-2,5-dihydrofuran-3-yl)phenyl]ethyl}-L-leucinamide;

N¹-(1-cyanocyclopropyl)-N²-{(1S)-1-[4-(2,2-dimethyl-5-oxo-2,5-dihydrofuran-3-yl)phenyl]-2,2,2-trifluoroethyl}-4-fluoro-L-leucinamide;

N¹-(1-cyanocyclopropyl)-N²-{(1S)-1-[4-(2,2-diethyl-5-oxo-2,5-dihydrofuran-3-yl)phenyl]-2,2,2-trifluoroethyl}-4-fluoro-L-leucinamide;

N¹-(1-cyanocyclopropyl)-4-fluoro-N²-{(1S)-2,2,2-trifluoro-1-[4-(2-oxo-2,5-dihydrofuran-3-yl)phenyl]ethyl}-L-leucinamide;

N¹-(1-cyanocyclopropyl)-N²-{(1S)-1-[4-(5,5-dimethyl-2-oxo-2,5-dihydrofuran-3-yl)phenyl]-2,2,2-trifluoroethyl}-4-fluoro-L-leucinamide;

N¹-(1-cyanocyclopropyl)-N²-{(1S)-1-[4-(5,5-diethyl-2-oxo-2,5-dihydrofuran-3-yl)phenyl]-2,2,2-trifluoroethyl}-4-fluoro-L-leucinamide;

N¹-(1-cyanocyclopropyl-4-fluoro-N²-{(1S)-2,2,2-trifluoro-1-[4-(5-oxo-4-oxaspiro[2.4]hept-6-en-7-yl)phenyl]ethyl}-L-leucinamide;

N¹-(1-cyanocyclopropyl)-4-fluoro-N²{(1S)-2,2,2-trifluoro-1-[4-(6-oxo-5-oxaspiro[3.4]oct-7-en-8-yl)phenyl]ethyl}-L-leucinamide;

N¹-(1-cyanocyclopropyl)-4-fluoro-N²-{(1S)-2,2,2-trifluoro-1-[4-(5-oxo-4-oxaspiro[2.4]hept-6-en-6-yl)phenyl]ethyl}-L-leucinamide;

N¹-(1-cyanocyclopropyl)-4-fluoro-N²-{(1S)-2,2,2-trifluoro-1-[4-(6-oxo-5-oxaspiro[3.4]oct-7-en-7-yl)phenyl]ethyl}-L-leucinamide;

N¹-(1-cyanocyclopropyl)-4-fluoro-N²-[(1S)-2,2,2-trifluoro-1-(4-quinolin-6-ylphenyl)ethyl]-L-leucinamide;

N¹-(1-cyanocyclopropyl)-4-fluoro-N²-{(1S)-2,2,2-trifluoro-1-[4'-(methylsulfinyl)-1,1'-biphenyl-4-yl]ethyl}-L-leucinamide;

N²-[(1S)-1-(4'-acetyl-1,1'-biphenyl-4-yl)-2,2,2-trifluoroethyl]-N¹-(1-cyanocyclopropyl)-L-leucinamide;

N¹-(1-cyanocyclopropyl)-N²-[(1S)-2,2,2-trifluoro-1-(4-quinolin-6-ylphenyl)ethyl]-L-leucinamide;

N²-[(1S)-1-(4-bromophenyl)-2,2,2-trifluoroethyl]-N¹-(1-cyanocyclopropyl)-4,4-difluoro-L-norvalinamide;

N¹-(1-cyanocyclopropyl)-4,4-difluoro-N²-{(1S)-2,2,2-trifluoro-1-[4'-(methylthio)-1,1'-biphenyl-4-yl]ethyl}-L-norvalinamide;

N¹-(1-cyanocyclopropyl)-4,4-difluoro-N²-{(1S)-2,2,2-trifluoro-1-[4'-(methylsulfonyl)-1,1'-biphenyl-4-yl]ethyl}-L-norvalinamide;

N¹-[(1S)-1-cyano-3-(methylsulfonyl)propyl]-N²-{(1S)-2,2,2-trifluoro-1-[4'-(methylsulfonyl)-1,1'-biphenyl-4-yl]ethyl}-L-leucinamide;

N¹-(1-cyanocyclopropyl)-4-fluoro-N²-[(1S)-2,2,2-trifluoro-1-(4-quinolin-6-ylphenyl)ethyl]-L-leucinamide;

N¹-(1-cyanocyclopropyl)-4-fluoro-N²-{(1S)-2,2,2-trifluoro-1-[4'-(methylsulfinyl)-1,1'-biphenyl-4-yl]ethyl}-L-leucinamide;

N¹-(1-cyanocyclopropyl)-N²-{(1S)-2,2,2-trifluoro-1-[4'-(1-hydroxyethyl)-1,1'-biphenyl-4-yl]ethyl}-L-leucinamide;

N²-[(1S)-1-(4'-acetyl-1,1'-biphenyl-4-yl)-2,2,2-trifluoroethyl]-N¹-(1-cyanocyclopropyl)-L-leucinamide;
N¹-(1-cyanocyclopropyl)-N²-[(1S)-2,2,2-trifluoro-1-(4-quinolin-6-ylphenyl)ethyl]-L-leucinamide;
N²-[(1S)-1-(4-bromophenyl)-2,2,2-trifluoroethyl]-N¹-(1-cyanocyclopropyl)-4,4-difluoro-L-norvalinamide;
N¹-(1-cyanocyclopropyl)-4,4-difluoro-N²-{(1S)-2,2,2-trifluoro-1-[4'-(methylthio)-1,1'-biphenyl-4-yl]ethyl}-L-norvalinamide;
N¹-(1-cyanocyclopropyl)-4,4-difluoro-N²-{(1S)-2,2,2-trifluoro-1-[4'-(methylsulfonyl)-1,1'-biphenyl-4-yl]ethyl}-L-norvalinamide;
N¹-(1-cyanocyclopropyl)-4-fluoro-N²-((1S)-2,2,2-trifluoro-1-{4-[5-methyl-6-(methylsulfonyl)pyridin-3-yl]phenyl}ethyl)-L-leucinamide;
N¹-(1-cyanocyclopropyl)-4-fluoro-N²-((1S)-2,2,2-trifluoro-1-{4-[6-(1-hydroxy-1-methylethyl)-5-methylpyridin-3-yl]phenyl}ethyl)-L-leucinamide;
N¹-(1-cyanocyclopropyl)-4-fluoro-N²-[(1S)-2,2,2-trifluoro-1-(4'-fluoro-1,1'-biphenyl-4-yl)ethyl]-L-leucinamide;
N¹-(1-cyanocyclopropyl)-4-fluoro-N²-{(1S)-2,2,2-trifluoro-1-[3'-methyl-4'-(methylsulfonyl)-1,1'-biphenyl-4-yl]ethyl}-L-leucinamide;
N¹-(1-cyanocyclopropyl)-4-fluoro-N²-{(1S)-2,2,2-trifluoro-1-[4-(6-methylpyridin-3-yl)phenyl]ethyl}-L-leucinamide;
N¹-(1-cyanocyclopropyl)-4-fluoro-N²-{(1S)-2,2,2-trifluoro-1-[4'-(methylthio)-1,1'-biphenyl-4-yl]ethyl}-L-leucinamide;
N¹-(1-cyanocyclopropyl)-4-fluoro-N²-{(1S)-2,2,2-trifluoro-1-[4'-(1-hydroxy-1-methylethyl)-1,1'-biphenyl-4-yl]ethyl}-L-leucinamide;
N¹-(1-cyanocyclopropyl)-4-fluoro-N²-{(1S)-2,2,2-trifluoro-1-[4-(2-methylquinolin-7-yl)phenyl]ethyl}-L-leucinamide;
N²-[(1S)-1-(4-bromophenyl)-2,2,2-trifluoroethyl]-N¹-(cyanomethyl)-4,4-difluoro-L-norvalinamide;
N¹-(1-cyanocyclopropyl)-4-fluoro-N²-((1S)-2,2,2-trifluoro-1-{4'-[(1S)-1-hydroxyethyl]-1,1'-biphenyl-4-yl}ethyl)-L-leucinamide;
N¹-(1-cyanocyclopropyl)-4-fluoro-N²-((1S)-2,2,2-trifluoro-{4'-[(1R)-1-hydroxyethyl]-1,1'-biphenyl-4-yl}ethyl)-L-leucinamide;
N¹-(1-cyanocyclopropyl)-N²-{(1S)-2,2,2-trifluoro-1-[4'-(trifluoroacetyl)-1,1'-biphenyl-4-yl]ethyl}-L-leucinamide;
N¹-(1-cyanocyclopropyl)-N²-{(1S)-2,2,2-trifluoro-1-[5-(2-naphthyl)pyridin-2-yl]ethyl}-L-leucinamide;
N¹-(cyanomethyl)-4,4-difluoro-N²-{(1S)-2,2,2-trifluoro-1-[4'-(methylthio)-1,1'-biphenyl-4-yl]ethyl}-L-norvalinamide;
N¹-(cyanomethyl)-4,4-difluoro-N²-{(1S)-2,2,2-trifluoro-1-[4'-(methylsulfonyl)-1,1'-biphenyl-4-yl]ethyl}-L-norvalinamide;
N¹-(1-cyanocyclopropyl)-4-fluoro-N²-{(1S)-2,2,2-trifluoro-1-[4-(5-methyl-1,3-thiazol-2-yl)phenyl]ethyl}-L-leucinamide;
N¹-(1-cyanocyclopropyl)-N²-{(1S)-1-[4-(1,1-dioxido-3-oxo-2,3-dihydro-1,2-benzisothiazol-5-yl)phenyl]-2,2,2-trifluoroethyl}-4-fluoro-L-leucinamide;
N²-[(4-bromophenyl)(phenyl)methyl]-N¹-(1-cyanocyclopropyl)-L-leucinamide;
N¹-(1-cyanocyclopropyl)-4-fluoro-N²-[(1S)-2,2,2-trifluoro-1-(4'-methyl-1,1'-biphenyl-4-yl)ethyl]-L-leucinamide;
N²-[(1S)-1-(1,1'-biphenyl-4-yl)-2,2,2-trifluoroethyl]-N¹-(1-cyanocyclopropyl)-4-fluoro-L-leucinamide;

N²-{(1S)-1-[4-(5-chloropyridin-2-yl)phenyl]-2,2,2-trifluoroethyl}-N¹-(1-cyanocyclopropyl)-4-fluoro-L-leucinamide;
N¹-(1-cyanocyclopropyl)-4-fluoro-N²-[(1S)-2,2,2-trifluoro-1-(4-pyridin-4-ylphenyl)ethyl]-L-leucinamide;
N¹-(1-cyanocyclopropyl)-4-fluoro-N²-((1S)-2,2,2-trifluoro-1-{4'-[(methylsulfonyl)amino]-1,1'-biphenyl-4-yl}ethyl)-L-leucinamide;
N²-[(1S)-1-(4-bromophenyl)-2,2-difluoroethyl]-N¹-(1-cyanocyclopropyl)-L-leucinamide;
N¹-(1-cyanocyclopropyl)-N²-{(1S)-2,2-difluoro-1-[4'-(methylthio)-1,1'-biphenyl-4-yl]ethyl}-L-leucinamide;
N¹-(1-cyanocyclopropyl)-4-fluoro-N²-[(1S)-2,2,2-trifluoro-1-(4-pyrimidin-5-ylphenyl)ethyl]-L-leucinamide;
N²-[(1S)-1-(4'-acetyl-1,1'-biphenyl-4-yl)-2,2,2-trifluoroethyl]-N¹-(1-cyanocyclopropyl)-4-fluoro-L-leucinamide;
N¹-(1-cyanocyclopropyl)-4-fluoro-N²-{(1S)-2,2,2-trifluoro-1-[3'-(1-hydroxyethyl)-1,1'-biphenyl-4-yl]ethyl}-L-leucinamide;
N²-[(1S)-1-(4'-acetyl-1,1'-biphenyl-4-yl)-2,2-difluoroethyl]-N¹-(1-cyanocyclopropyl)-L-leucinamide;
N¹-(1-cyanocyclopropyl)-N²-{(1S)-1-[4-(3,5-dimethylisoxazol-4-yl)phenyl]-2,2,2-trifluoroethyl}-4-fluoro-L-leucinamide;
N¹-[(1S)-1-cyano-3-(methylsulfonyl)propyl]-N²-{(1S)-2,2,2-trifluoro-1-[4'-(methylsulfonyl)-1,1'-biphenyl-4-yl]ethyl}-L-leucinamide;
N¹-(1-cyanocyclopropyl)-4-fluoro-N²-[(1S)-2,2,2-trifluoro-1-(4-quinolin-6-ylphenyl)ethyl]-L-leucinamide;
N¹-(1-cyanocyclopropyl)-4-fluoro-N²-{(1S)-2,2,2-trifluoro-1-[4'-(methylsulfinyl)-1,1'-biphenyl-4-yl]ethyl}-L-leucinamide;
N¹-(1-cyanocyclopropyl)-N²-{(1S)-2,2,2-trifluoro-1-[4'-(1-hydroxyethyl)-1,1'-biphenyl-4-yl]ethyl}-L-leucinamide;
N²-[(1S)-1-(4'-acetyl-1,1'-biphenyl-4-yl)-2,2,2-trifluoroethyl]-N¹-(1-cyanocyclopropyl)-L-leucinamide;
N¹-(1-cyanocyclopropyl)-N²-[(1S)-2,2,2-trifluoro-1-(4-quinolin-6-ylphenyl)ethyl]-L-leucinamide;
N²-[(1S)-1-(4-bromophenyl)-2,2,2-trifluoroethyl]-N¹-(1-cyanocyclopropyl)-4,4-difluoro-L-norvalinamide;
N¹-(1-cyanocyclopropyl)-4,4-difluoro-N²-{(1S)-2,2,2-trifluoro-1-[4'-(methylthio)-1,1'-biphenyl-4-yl]ethyl}-L-norvalinamide;
N¹-(1-cyanocyclopropyl)-4,4-difluoro-N²-{(1S)-2,2,2-trifluoro-1-[4'-(methylsulfonyl)-1,1'-biphenyl-4-yl]ethyl}-L-norvalinamide;
N¹-(1-cyanocyclopropyl)-4-fluoro-N²-((1S)-2,2,2-trifluoro-1-{4-[5-methyl-6-(methylsulfonyl)pyridin-3-yl]phenyl}ethyl)-L-leucinamide;
N¹-(1-cyanocyclopropyl)-4-fluoro-N²-((1S)-2,2,2-trifluoro-1-{4-[6-(1-hydroxy-1-methylethyl)-5-methylpyridin-3-yl]phenyl}ethyl)-L-leucinamide;
N¹-(1-cyanocyclopropyl)-4-fluoro-N²-[(1S)-2,2,2-trifluoro-1-(4'-fluoro-1,1'-biphenyl-4-yl)ethyl]-L-leucinamide;
N¹-(1-cyanocyclopropyl)-4-fluoro-N²-{(1S)-2,2,2-trifluoro-1-[3'-methyl-4'-(methylsulfonyl)-1,1'-biphenyl-4yl]ethyl}-L-leucinamide;
N¹-(1-cyanocyclopropyl)-4-fluoro-N²-{(1S)-2,2,2-trifluoro-1-[4-(6-methylpyridin-3-yl)phenyl]ethyl}-L-leucinamide;
N¹-(1-cyanocyclopropyl)-4-fluoro-N²-{(1S)-2,2,2-trifluoro-1-[4'-(methylthio)-1,1'-biphenyl-4-yl]ethyl}-L-leucinamide;
N¹-(1-cyanocyclopropyl)-4-fluoro-N²-{(1S)-2,2,2-trifluoro-1-[4'-(1-hydroxy-1-methylethyl)-1,1'-biphenyl-4-yl]ethyl}-L-leucinamide;

$N^1$-(1-cyanocyclopropyl)-4-fluoro-$N^2$-{(1S)-2,2,2-trifluoro-1-[4-(2-methylquinolin-7-yl)phenyl]ethyl}-L-leucinamide;

$N^2$-[(1S)-1-(4-bromophenyl)-2,2,2-trifluoroethyl]-$N^1$-(cyanomethyl)-4,4-difluoro-L-norvalinamide;

$N^1$-(1-cyanocyclopropyl)-4-fluoro-$N^2$-((1S)-2,2,2-trifluoro-1-{4'-[(1S)-1-hydroxyethyl]-1,1'-biphenyl-4-yl}ethyl)-L-leucinamide;

$N^1$-(1-cyanocyclopropyl)-4-fluoro-$N^2$-((1S)-2,2,2-trifluoro-1-{4'-[(1R)-1-hydroxyethyl]-1,1'-biphenyl-4-yl}ethyl)-L-leucinamide;

$N^1$-(1-cyanocyclopropyl)-$N^2$-{(1S)-2,2,2-trifluoro-1-[4'-(trifluoroacetyl)-1,1'-biphenyl-4-yl]ethyl}-L-leucinamide;

$N^1$-(1-cyanocyclopropyl)-$N^2$-{(1S)-2,2,2-trifluoro-1-[5-(2-naphthyl)pyridin-2-yl]ethyl}-L-leucinamide;

$N^1$-(cyanomethyl)-4,4-difluoro-$N^2$-{(1S)-2,2,2-trifluoro-1-[4'-(methylthio)-1,1'-biphenyl-4-yl]ethyl}-L-norvalinamide;

$N^1$-(cyanomethyl)-4,4-difluoro-$N^2$-{(1S)-2,2,2-trifluoro-1-[4'-(methylsulfonyl)-1,1'-biphenyl-4-yl]ethyl}-L-norvalinamide;

$N^1$-(1-cyanocyclopropyl)-4-fluoro-$N^2$-{(1S)-2,2,2-trifluoro-1-[4-(5-methyl-1,3-thiazol-2-yl)phenyl]ethyl}-L-leucinamide;

$N^1$-(1-cyanocyclopropyl)-$N^2$-{(1S)-1-[4-(1,1-dioxido-3-oxo-2,3-dihydro-1,2-benzisothiazol-5-yl)phenyl]-2,2,2-trifluoroethyl}-4-fluoro-L-leucinamide;

$N^2$-[(4-bromophenyl)(phenyl)methyl]-$N^1$-(1-cyanocyclopropyl)-L-leucinamide;

$N^1$-(1-cyanocyclopropyl)-4-fluoro-$N^2$-[(1S)-2,2,2-trifluoro-1-(4'-methyl-1,1'-biphenyl-4-yl)ethyl]-L-leucinamide;

$N^2$-[(1S)-1-(1,1'-biphenyl-4-yl)-2,2,2-trifluoroethyl]-$N^1$-(1-cyanocyclopropyl)-4-fluoro-L-leucinamide;

$N^2$-{(1S)-1-[4-(5-chloropyridin-2-yl)phenyl]-2,2,2-trifluoroethyl}-$N^1$-(1-cyanocyclopropyl)-4-fluoro-L-leucinamide;

$N^1$-(1-cyanocyclopropyl)-4-fluoro-$N^2$-[(1S)-2,2,2-trifluoro-1-(4-pyridin-4-ylphenyl)ethyl]-L-leucinamide;

$N^1$-(1-cyanocyclopropyl)-4-fluoro-$N^2$-((1S)-2,2,2-trifluoro-1-{4'-[(methylsulfonyl)amino]-1,1'-biphenyl-4-yl}ethyl)-L-leucinamide;

$N^2$-[(1S)-1-(4-bromophenyl)-2,2-difluoroethyl]-$N^1$-(1-cyanocyclopropyl)-L-leucinamide;

$N^1$-(1-cyanocyclopropyl)-$N^2$-{(1S)-2,2-difluoro-1-[4'-(methylthio)-1,1'-biphenyl-4-yl]ethyl}-L-leucinamide;

$N^1$-(1-cyanocyclopropyl)-4-fluoro-$N^2$-[(1S)-2,2,2-trifluoro-1-(4-pyrimidin-5-ylphenyl)ethyl]-L-leucinamide;

$N^2$-[(1S)-1-(4'-acetyl-1,1'-biphenyl-4-yl)-2,2,2-trifluoroethyl]-$N^1$-(1-cyanocyclopropyl)-4-fluoro-L-leucinamide;

$N^1$-(1-cyanocyclopropyl)-4-fluoro-$N^2$-{(1S)-2,2,2-trifluoro-1-[3'-(1-hydroxyethyl)-1,1'-biphenyl-4-yl]ethyl}-L-leucinamide;

$N^2$-[(1S)-1-(4'-acetyl-1,1'-biphenyl-4-yl)-2,2-difluoroethyl]-$N^1$-(1-cyanocyclopropyl)-L-leucinamide;

$N^1$-(1-cyanocyclopropyl)-$N^2$-{(1S)-1-[4-(3,5-dimethylisoxazol-4-yl)phenyl]-2,2,2-trifluoroethyl}-4-fluoro-L-leucinamide;

and the pharmaceutically acceptable salts, stereoisomers and N-oxide derivatives thereof.

Also included within the scope of the present invention is a pharmaceutical composition which is comprised of a compound of Formula I as described above and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

Utilities

The compounds of the present invention are inhibitors of cathepsins and are therefore useful to treat or prevent cathepsin dependent diseases or conditions in mammals, preferably humans. Specifically, the compounds of the present invention are inhibitors of Cathepsin K and are therefore useful to treat or prevent Cathepsin K dependent diseases or conditions in mammals, preferably humans.

"Cathepsin dependent diseases or conditions" refers to pathologic conditions that depend on the activity of one or more cathepsins. "Cathepsin K dependent diseases or conditions" refers to pathologic conditions that depend on the activity of Cathepsin K. Diseases associated with Cathepsin K activities include osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, metastatic bone disease, hypercalcemia of malignancy, and multiple myeloma. In treating such conditions with the instantly claimed compounds, the required therapeutic amount will vary according to the specific disease and is readily ascertainable by those skilled in the art. Although both treatment and prevention are contemplated by the scope of the invention, the treatment of these conditions is the preferred use.

An embodiment of the invention is a method of inhibiting cathepsin activity in a mammal in need thereof, comprising administering to the mammal a therapeutically effective amount of any of the compounds or any of the pharmaceutical compositions described above.

A class of the embodiment is the method wherein the cathepsin activity is cathepsin K activity.

Another embodiment of the invention is a method of treating or preventing cathepsin dependent conditions in a mammal in need thereof, comprising administering to the mammal a therapeutically effective amount of any of the compounds or any of the pharmaceutical compositions described above.

A class of the embodiment is the method wherein the cathepsin activity is cathepsin K activity.

Another embodiment of the invention is a method of inhibiting bone loss in a mammal in need thereof, comprising administering to the mammal a therapeutically effective amount of any of the compounds or any of the pharmaceutical compositions described above. Another embodiment of the invention is a method of reducing bone loss in a mammal in need thereof, comprising administering to the mammal a therapeutically effective amount of any of the compounds or any of the pharmaceutical compositions described above. The utility of cathepsin K inhibitors in the inhibition of bone resorption is known in the literature, see Stroup, G. B., Lark, M. W., Veber, D F., Bhattacharrya, A., Blake, S., Dare, L. C., Erhard, K. F., Hoffman, S. J., James, I. E., Marquis, R. w., Ru, Y., Vasko-Moser, J. A., Smith, B. R., Tomaszek, T. and Gowen, M. Potent and selective inhibition of human cathepsin K leads to inhibition of bone resorption in vivo in a nonhuman primate. J. Bone Miner. Res., 16:1739-1746; 2001; and Votta, B. J., Levy, M. A., Badger, A., Dodds, R. A., James, I. E., Thompson, S., Bossard, M. J., Carr, T., Connor, J. R., Tomaszek, T. A., Szewczuk, L., Drake, F. H., Veber, D., and Gowen, M. Peptide aldehyde inhibitors of cathepsin K inhibit bone resorption both in vivo and in vitro. J. Bone Miner. Res. 12:1396-1406; 1997.

Another embodiment of the invention is a method of treating or preventing osteoporosis in a mammal in need thereof, comprising administering to the mammal a therapeutically effective amount of any of the compounds or any of the above pharmaceutical compositions described above. The utility of cathepsin K inhibitors in the treatment or prevention of osteoporosis is known in the literature, see Saftig, P., Hunziker, E., Wehmeyer, O., Jones, S., Boyde, A., Rommerskirch, W., Moritz, J. D., Schu, P., and Vonfigura, K. Impaired osteoclast bone resorption leads to osteoporosis in cathepsin K-deficient mice. Proc. Natl. acad. Sci. USA 95:13453-13458; 1998.

Another embodiment of the invention is a method of treating or preventing rheumatoid arthritic condition in a mammal in need thereof, comprising administering to the mammal a therapeutically effective amount of any of the compounds or any of the pharmaceutical compositions described above. It is known in the literature that progressive destruction of the periarticular bone is a major cause of joint dysfunction and disability in patients with rheumatoid arthritis (RA), see Goldring S R, "Pathogenesis of bone erosions in rheumatoid arthritis". Curr. Opin. Rheumatol. 2002; 14: 406-10. Analysis of joint tissues from patients with RA have provided evidence that cathepsin K positive osteoclasts are the cell types that mediate the focal bone resorption associated with rheumatoid synovial lesion, see Hou, W-S, Li, W, Keyszer, G, Weber, E, Levy, R, Klein, M J, Gravallese, E M, Goldring, S R, Bromme, D, "Comparision of Cathepsin K and S expression within the Rheumatoid and Osteoarthritic Synovium", Arthritis Rheumatism 2002; 46: 663-74. In addition, generalized bone loss is a major cause of morbidity associated with severe RA. The frequency of hip and spinal fractures is substantially increased in patients with chronic RA, see Gould A, Sambrook, P, Devlin J et al, "Osteoclastic activation is the principal mechanism leading to secondary osteoporosis in rheumatoid arthritis". J. Rheumatol. 1998; 25: 1282-9. The utility of cathepsin K inhibitors in the treatment or prevention of resorption in subarticular bone and of generalized bone loss represent a rational approach for pharmacological intervention on the progression of rheumatoid arthritis.

Another embodiment of the invention is a method of treating or preventing the progression of osteoarthritis in a mammal in need thereof, comprising administering to the mammal a therapeutically effective amount of any of the compounds or any of the pharmaceutical compositions described above. It is known in the literature that osteoarthritis (OA) is accompanied with a well-defined changes in the joints, including erosion of the articular cartilage surface, peri-articular endochondral ossification/osteophytosis, and subchondral bony sclerosis and cyst formation, see Oettmeier R, Abendroth, K, "Osteoarthritis and bone: osteologic types of osteoarthritis of the hip", Skeletal Radiol. 1989; 18: 165-74. Recently, the potential contribution of subchondral bone sclerosis to the initiation and progression of OA have been suggested. Stiffened subchondral bone as the joint responding to repetitive impulsive loading, is less able to attenuate and distribute forces through the joint, subjecting it to greater mechanical stress across the articular cartilage surface. This in turn accelerates cartilage wear and fibrillate, see Radin, E L and Rose R M, "Role of subchondral bone in the initiation and progression of cartilage damage", Clin. Orthop. 1986; 213: 34-40. Inhibition of excessive subarticular bone resorption by an anti-resorptive agent such as a cathepsin K inhibitor, will lead to inhibition of subchondral bone turnover, thus may have a favorable impact on OA progression. In addition to the above hypothesis, cathepsin K protein expression was recently identified in synovial fibroblasts, macrophage-like cells, and chondrocytes from synovium and articular cartilage specimens derived from OA patients, see Hou, W-S, Li, W, Keyszer, G, Weber, E, Levy, R, Klein, M J, Gravallese, E M, Goldring, S R, Bromme, D, "Comparison of Cathepsin K and S expression within the Rheumatoid and Osteoarthritic Synovium", Arthritis Rheumatism 2002; 46: 663-74;and Dodd, R A, Connor, J R, Drake, F H, Gowen, M, "Expression of Cathepsin K messenger RNA in giant cells and their precursors in human osteoarthritic synovial tissues". Arthritis Rheumatism 1999; 42: 1588-93; and Konttinen, Y T, Mandelin, J, Li, T-F, Salo, J, Lassus, J et al. "Acidic cysteine endoproteinase cathepsin K in the degeneration of the superficial articular hyaline cartilage in osteoarthritis", Arthritis Rheumatism 2002; 46: 953-60. These recent studies thus implicated the role of cathepsin K in the destruction of collagen type II in the articular cartilage associated with the progression of osteoarthritis. The utility of cathepsin K inhibitors in the treatment or prevention of osteoarthritis as described in this invention thus comprise of two different mechanisms, one is on the inhibition of osteoclast-driven subchondral bone turnover, and two is on the direct inhibition of collagen type II degeneration in the synovium and cartilage of patients with OA.

Another embodiment of the invention is a method treating cancer in a mammal in need thereof, comprising administering to the mammal a therapeutically effective amount of any of the compounds or any of the pharmaceutical compositions described above. It is known in the literature that cathepsin K is expressed in human breast carcinoma, see Littlewood-Evans A J, Bilbe G, Bowler W B, Farley D, Wlodarski B, Kokubo T, Inaoka T, Sloane J, Evans D B, Gallagher J A, "The osteoclast-associated protease cathepsin K is expressed in human breast carcinoma." Cancer Res 1997 Dec. 1;57(23):5386-90.

Exemplifying the invention is the use of any of the compounds described above in the preparation of a medicament for the treatment and/or prevention of osteoporosis in a mammal in need thereof. Still further exemplifying the invention is the use of any of the compounds described above in the preparation of a medicament for the treatment and/or prevention of: bone loss, bone resorption, bone fractures, metastatic bone disease and/or disorders related to cathepsin functioning.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

In the case of tablets for oral use, carriers which are commonly used include lactose and corn starch, and lubricating agents, such as magnesium stearate, are commonly added. For oral administration in capsule form, useful diluents include lactose and dried corn starch. For oral use of a therapeutic compound according to this invention, the selected compound may be administered, for example, in the form of tablets or capsules, or as an aqueous solution or suspension. For oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polyactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

The instant compounds are also useful in combination with known agents useful for treating or preventing osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, metastatic bone disease, hypercalcemia of malignancy, and multiple myeloma. Combinations of the presently disclosed compounds with other agents useful in treating or preventing osteoporosis or other bone disorders are within the scope of the invention. A person of ordinary skill in the art would be able to discern which combinations of agents would be useful based on the particular characteristics of the drugs and the disease involved. Such agents include the following: an organic bisphosphonate; an estrogen receptor modulator; an androgen receptor modulator; an inhibitor of osteoclast proton ATPase; an inhibitor of HMG-CoA reductase; an integrin receptor antagonist; an osteoblast anabolic agent, such as PIM; and the pharmaceutically acceptable salts and mixtures thereof. A preferred combination is a compound of the present invention and an organic bisphosphonate. Another preferred combination is a compound of the present invention and an estrogen receptor modulator. Another preferred combination is a compound of the present invention and an androgen receptor modulator. Another preferred combination is a compound of the present invention and an osteoblast anabolic agent.

"Organic bisphosphonate" includes, but is not limited to, compounds of the chemical formula

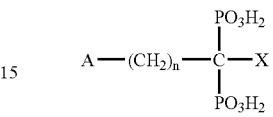

wherein n is an integer from 0 to 7 and wherein A and X are independently selected from the group consisting of H, OH, halogen, $NH_2$, SH, phenyl, C1-C30 alkyl, C3-C30 branched or cycloalkyl, bicyclic ring structure containing two or three N, C1-C30 substituted alkyl, C1-C10 alkyl substituted $NH_2$, C3-C10 branched or cycloalkyl substituted $NH_2$, C1-C10 dialkyl substituted $NH_2$, C1-C10 alkoxy, C1-C10 alkyl substituted thio, thiophenyl, halophenylthio, C1-C10 alkyl substituted phenyl, pyridyl, furanyl, pyrrolidinyl, imidazolyl, imidazopyridinyl, and benzyl, such that both A and X are not selected from H or OH when n is 0; or A and X are taken together with the carbon atom or atoms to which they are attached to form a C3-C10 ring.

In the foregoing chemical formula, the alkyl groups can be straight, branched, or cyclic, provided sufficient atoms are selected for the chemical formula. The C1-C30 substituted alkyl can include a wide variety of substituents, nonlimiting examples which include those selected from the group consisting of phenyl, pyridyl, furanyl, pyrrolidinyl, imidazonyl, $NH_2$, C1-C10 alkyl or dialkyl substituted $NH_2$, OH, SH, and C1-C10 alkoxy.

The foregoing chemical formula is also intended to encompass complex carbocyclic, aromatic and hetero atom structures for the A and/or X substituents, nonlimiting examples of which include naphthyl, quinolyl, isoquinolyl, adamantyl, and chlorophenylthio.

Pharmaceutically acceptable salts and derivatives of the bisphosphonates are also useful herein. Non-limiting examples of salts include those selected from the group consisting alkali metal, alkaline metal, ammonium, and mono-, di-, tri-, or tetra-C1-C30-alkyl-substituted ammonium. Preferred salts are those selected from the group consisting of sodium, potassium, calcium, magnesium, and ammonium salts. More preferred are sodium salts. Non-limiting examples of derivatives include those selected from the group consisting of esters, hydrates, and amides.

It should be noted that the terms "bisphosphonate" and "bisphosphonates", as used herein in referring to the therapeutic agents of the present invention are meant to also encompass diphosphonates, biphosphonic acids, and diphosphonic acids, as well as salts and derivatives of these materials. The use of a specific nomenclature in referring to the bisphosphonate or bisphosphonates is not meant to limit the scope of the present invention, unless specifically indicated. Because of the mixed nomenclature currently in use by those of ordinary skill in the art, reference to a specific weight or percentage of a bisphosphonate compound in the present invention is on an acid active weight basis, unless indicated otherwise herein. For example, the phrase "about 5 mg of a bone resorption inhibiting bisphosphonate selected from the group consisting of alendronate, pharmaceutically acceptable salts thereof, and mixtures thereof, on an alendronic acid active weight basis" means that the amount of the bisphosphonate compound selected is calculated based on 5 mg of alendronic acid.

Non-limiting examples of bisphosphonates useful herein include the following:

Alendronic acid, 4-amino-1-hydroxybutylidene-1,1-bisphosphonic acid.

Alendronate (also known as alendronate sodium or alendronate monosodium trihydrate), 4-amino-1-hydroxybutylidene-1,1-bisphosphonic acid monosodium trihydrate.

Alendronic acid and alendronate are described in U.S. Pat. No. 4,922,007, to Kieczykowski et al., issued May 1, 1990; U.S. Pat. No. 5,019,651, to Kieczykowski et al., issued May 28, 1991; U.S. Pat. No. 5,510,517, to Dauer et al., issued Apr. 23, 1996; U.S. Pat. No. 5,648,491, to Dauer et al., issued Jul. 15, 1997, all of which are incorporated by reference herein in their entirety.

Cycloheptylaminomethylene-1,1-bisphosphonic acid, YM 175, Yamanouchi (incadronate, formerly known as cimadronate), as described in U.S. Pat. No. 4,970,335, to Isomura et al., issued Nov. 13, 1990, which is incorporated by reference herein in its entirety.

1,1-dichloromethylene-1,1-diphosphonic acid (clodronic acid), and the disodium salt (clodronate, Procter and Gamble), are described in Belgium Patent 672,205 (1966) and *J. Org. Chem* 32, 4111 (1967), both of which are incorporated by reference herein in their entirety.

1-hydroxy-3-(1-pyrrolidinyl)-propylidene-1,1-bisphosphonic acid (EB-1053).

1-hydroxyethane-1,1-diphosphonic acid (etidronic acid).

1-hydroxy-3-(N-methyl-N-pentylamino)propylidene-1,1-bisphosphonic acid, also known as BM-210955, Boehringer-Mannheim (ibandronate), is described in U.S. Pat. No. 4,927,814, issued May 22, 1990, which is incorporated by reference herein in its entirety.

1-hydroxy-2-imidazo-(1,2-a)pyridin-3-yethylidene (minodronate).

6-amino-1-hydroxyhexylidene-1,1-bisphosphonic acid (neridronate).

3-(dimethylamino)-1-hydroxypropylidene-1,1-bisphosphonic acid (olpadronate).

3-amino-1-hydroxypropylidene-1,1-bisphosphonic acid (pamidronate).

[2-(2-pyridinyl)ethylidene]-1,1-bisphosphonic acid (piridronate) is described in U.S. Pat. No. 4,761,406, which is incorporated by reference in its entirety.

1-hydroxy-2-(3-pyridinyl)-ethylidene-1,1-bisphosphonic acid (risedronate).

(4-chlorophenyl)thiomethane-1,1-disphosphonic acid (tiludronate) as described in U.S. Pat. No. 4,876,248, to Breliere et al., Oct. 24, 1989, which is incorporated by reference herein in its entirety.

1-hydroxy-2-(1H-imidazol-1-yl)ethylidene-1,1-bisphosphonic acid (zoledronate).

Nonlimiting examples of bisphosphonates include alendronate, cimadronate, clodronate, etidronate, ibandronate, incadronate, minodronate, neridronate, olpadronate, pamidronate, piridronate, risedronate, tiludronate, and zolendronate, and pharmaceutically acceptable salts and esters thereof. A particularly preferred bisphosphonate is alendronate, especially a sodium, potassium, calcium, magnesium or ammonium salt of alendronic acid. Exemplifying the preferred bisphosphonate is a sodium salt of alendronic acid, especially a hydrated sodium salt of alendronic acid. The salt can be hydrated with a whole number of moles of water or non whole numbers of moles of water. Further exemplifying the preferred bisphosphonate is a hydrated sodium salt of alendronic acid, especially when the hydrated salt is alendronate monosodium trihydrate.

It is recognized that mixtures of two or more of the bisphosphonate actives can be utilized.

The precise dosage of the organic bisphosphonate will vary with the dosing schedule, the particular bisphosphonate chosen, the age, size, sex and condition of the mammal or human, the nature and severity of the disorder to be treated, and other relevant medical and physical factors. Thus, a precise pharmaceutically effective amount cannot be specified in advance and can be readily determined by the caregiver or clinician. Appropriate amounts can be determined by routine experimentation from animal models and human clinical studies. Generally, an appropriate amount of bisphosphonate is chosen to obtain a bone resorption inhibiting effect, i.e. a bone resorption inhibiting amount of the bisphosphonate is administered. For humans, an effective oral dose of bisphosphonate is typically from about 1.5 to about 6000 µg/kg body weight and preferably about 10 to about 2000 µg/kg of body weight. For alendronate monosodium trihydrate, common human doses which are administered are generally in the range of about 2 mg/day to about 40 mg/day, preferably about 5 mg/day to about 40 mg/day. In the U.S. presently approved dosages for alendronate monosodium trihydrate are 5 mg/day for preventing osteoporosis, 10 mg/day for treating osteoporosis, and 40 mg/day for treating Paget's disease.

In alternative dosing regimens, the bisphosphonate can be administered at intervals other than daily, for example once-weekly dosing, twice-weekly dosing, biweekly dosing, and twice-monthly dosing. In a once weekly dosing regimen, alendronate monosodium trihydrate would be administered at dosages of 35 mg/week or 70 mg/week.

"Selective estrogen receptor modulators" refers to compounds which interfere or inhibit the binding of estrogen to the receptor, regardless of mechanism. Examples of estrogen receptor modulators include, but are not limited to, estrogen, progestogen, estradiol, droloxifene, raloxifene, lasofoxifene, TSE-424, tamoxifen, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenylhydrazone, and SH646.

An "estrogen receptor beta modulator" is a compound that selectively agonizes or antagonizes estrogen receptor beta (ERβ). Agonizing ERβ increases transcription of the tryptophan hydroxylase gene (TPH, the key enzyme in serotonin synthesis) via an ERβ mediated event. Examples of estrogen receptor beta agonists can be found in PCT International publication WO 01/82923, which published on Nov. 8, 2001, and WO 02/41835, which published on May 20, 2002, both of which are hereby incorporated by reference in their entirety.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"An inhibitor of osteoclast proton ATPase" refers to an inhibitor of the proton ATPase, which is found on the apical membrane of the osteoclast, and has been reported to play a significant role in the bone resorption process. This proton pump represents an attractive target for the design of inhibitors of bone resorption which are potentially useful for the treatment and prevention of osteoporosis and related metabolic diseases. See C. Farina et al., "Selective inhibitors of the osteoclast vacuolar proton ATPase as novel bone anti-resorptive agents," DDT, 4: 163-172 (1999)), which is hereby incorporated by reference in its entirety.

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30-33. The terms "HMG-CoA reductase inhibitor" and "inhibitor of HMG-CoA reductase" have the same meaning when used herein.

Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342,952) and cerivastatin (also known as rivastatin and BAY-CHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention. An illustration of the lactone portion and its corresponding open-acid form is shown below as structures I and II.

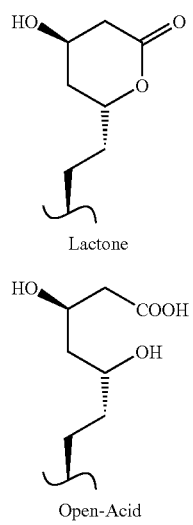

Lactone

Open-Acid

In HMG-CoA reductase inhibitors where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin. Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenzimidazole, diethylamine, piperazine, and tris(hydroxymethyl) aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

As used above, "integrin receptor antagonists" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. H. N. Lode and coworkers in PNAS USA 96: 1591-1596 (1999) have observed synergistic effects between an antiangiogenic $\alpha v$ integrin antagonist and a tumor-specific antibody-cytokine (interleukin-2) fusion protein in the eradication of spontaneous tumor metastases. Their results suggested this combination as having potential for the treatment of cancer and metastatic tumor growth. $\alpha_v\beta_3$ integrin receptor antagonists inhibit bone resorption through a new mechanism distinct from that of all currently available drugs. Integrins are heterodimeric transmembrane adhesion receptors that mediate cell-cell and cell-matrix interactions. The $\alpha$ and $\beta$ integrin subunits interact non-covalently and bind extracellular matrix ligands in a divalent cation-dependent manner. The most abundant integrin on osteoclasts is $\alpha_v\beta_3$ ($>10^7$/osteoclast), which appears to play a rate-limiting role in cytoskeletal organization important for cell migration and polarization. The $\alpha_v\beta_3$ antagonizing effect is selected from inhibition of bone resorption, inhibition of restenosis, inhibition of macular degeneration, inhibition of arthritis, and inhibition of cancer and metastatic growth.

"An osteoblast anabolic agent" refers to agents that build bone, such as PTH. The intermittent administration of parathyroid hormone (PTH) or its amino-terminal fragments and analogues have been shown to prevent, arrest, partially reverse bone loss and stimulate bone formation in animals and humans. For a discussion refer to D. W. Dempster et al., "Anabolic actions of parathyroid hormone on bone," Endocr Rev 14: 690-709 (1993). Studies have demonstrated the clinical benefits of parathyroid hormone in stimulating bone formation and thereby increasing bone mass and strength. Results were reported by R M Neer et al., in New Eng J Med 344 1434-1441 (2001).

In addition, parathyroid hormone-related protein fragments or analogues, such as PTHrP-(1-36) have demonstrated potent anticalciuric effects [see M. A. Syed et al., "Parathyroid hormone-related protein-(1-36) stimulates renal tubular calcium reabsorption in normal human volunteers: implications for the pathogenesis of humoral hypercalcemia of malignancy," JCEM 86: 1525-1531 (2001)] and may also have potential as anabolic agents for treating osteoporosis.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents. The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985, which is incorporated by reference herein in its entirety. Metabolites of these compounds include active species produced upon introduction of compounds of this invention into the biological milieu.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The terms "treating" or "treatment" of a disease as used herein includes: preventing the disease, i.e. causing the clinical symptoms of the disease not to develop in a mammal that may be exposed to or predisposed to the disease but does not yet experience or display symptoms of the disease; inhibiting the disease, i.e., arresting or reducing the development of the disease or its clinical symptoms; or relieving the disease, i.e., causing regression of the disease or its clinical symptoms.

The term "bone resorption," as used herein, refers to the process by which osteoclasts degrade bone.

The present invention also encompasses a pharmaceutical composition useful in the treatment of osteoporosis or other bone disorders, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's bloodstream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for a cathepsin dependent condition. Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

The compounds of the present invention can be used in combination with other agents useful for treating cathepsin-mediated conditions. The individual components of such combinations can be administered separately at different times during the course of therapy or concurrently in divided or single combination forms. The instant invention is therefore to be understood as embracing all such regimes of simultaneous or alternating treatment and the term "administering" is to be interpreted accordingly. It will be understood that the scope of combinations of the compounds of this invention with other agents useful for treating cathepsin-mediated conditions includes in principle any combination with any pharmaceutical composition useful for treating disorders related to estrogen functioning.

The scope of the invention therefore encompasses the use of the instantly claimed compounds in combination with a second agent selected from: an organic bisphosphonate; an estrogen receptor modulator; an androgen receptor modulator; an inhibitor of osteoclast proton ATPase; an inhibitor of HMG-CoA reductase; an integrin receptor antagonist; an osteoblast anabolic agent, such as PTH; and the pharmaceutically acceptable salts and mixtures thereof.

These and other aspects of the invention will be apparent from the teachings contained herein.

Definitions

The compounds of the present invention may have asymmetric centers, chiral axes, and chiral planes (as described in: E. L. Eliel and S. H. Wilen, *Stereochemistry of Carbon Compounds,* John Wiley & Sons, New York, 1994, pages 1119-1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure is depicted. For example, any claim to compound A below is understood to include tautomeric structure B, and vice versa, as well as mixtures thereof.

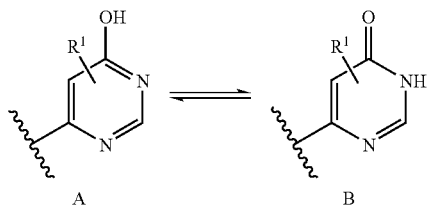

When any variable (e.g. R1, R2, Ra etc.) occurs more than one time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring carbon atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to three substituents.

As used herein, "alkyl" is intended to include both branched and straight-chain saturated aliphatic hydrocarbon groups having one to ten carbon atoms unless otherwise specified. For example, $C_1$-$C_{10}$, as in "$C_1$-$C_{10}$ alkyl" is defined to include groups having 1, 2, 3, 4, 5, 6, 7, 8, 9 or 10 carbons in a linear, branched, or cyclic arrangement. For example, "$C_1$-$C_{10}$ alkyl" specifically includes methyl, ethyl, propyl, butyl, pentyl, hexyl, heptyl, octyl, nonyl, decyl, and so on.

"Alkoxy" or "alkyloxy" represents an alkyl group as defined above, unless otherwise indicated, wherein said alkyl group is attached through an oxygen bridge.

The term "cycloalkyl" or "carbocycle" shall mean cyclic rings of alkanes of three to eight total carbon atoms, unless otherwise indicated, or any number within this range (i.e., cyclopropyl, cyclobutyl, cyclopentyl, cyclohexyl, cycloheptyl or cyclooctyl).

If no number of carbon atoms is specified, the term "alkenyl" refers to a non-aromatic hydrocarbon radical, straight or branched, containing from 2 to 10 carbon atoms and at least 1 carbon to carbon double bond. Preferably 1 carbon to carbon double bond is present, and up to 4 non-aromatic carbon-carbon double bonds may be present. Thus, "$C_2$-$C_6$ alkenyl" means an alkenyl radical having from 2 to 6 carbon atoms. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated.

The term "cycloalkenyl" shall mean cyclic rings of 3 to 10 carbon atoms, unless otherwise specified, containing at least 1 carbon to carbon double bond (i.e., cyclopropenyl, cyclobutenyl, cyclopenentyl, cyclohexenyl, cycloheptenyl or cycloocentyl).

The term "alkynyl" refers to a hydrocarbon radical straight or branched, containing from 2 to 10 carbon atoms, unless otherwise specified, containing at least 1 carbon to carbon triple bond. Up to 3 carbon-carbon triple bonds may be present. Thus, "$C_2$-$C_6$ alkynyl" means an alkynyl radical having from 2 to 6 carbon atoms. Alkynyl groups include ethynyl, propynyl and butynyl. As described above with respect to alkyl, the straight, branched or cyclic portion of the alkynyl group may contain triple bonds and may be substituted if a substituted alkynyl group is indicated.

In certain instances, substituents may be defined with a range of carbons that includes zero, such as ($C_0$-$C_6$)alkylene-aryl. If aryl is taken to be phenyl, this definition would include phenyl itself as well as —$CH_2$Ph, —$CH_2CH_2$Ph, $CH(CH_3)$ $CH_2CH(CH_3)$Ph, and so on.

As used herein, "aryl" is intended to mean any stable monocyclic or bicyclic carbon ring of up to 12 atoms in each ring, wherein at least one ring is aromatic. Examples of such aryl elements include phenyl, naphthyl, tetrahydronaphthyl, indanyl, biphenyl, phenanthryl, anthryl or acenaphthyl. In cases where the aryl substituent is bicyclic and one ring is non-aromatic, it is understood that attachment is via the aromatic ring.

The term "heteroaryl", as used herein, represents a stable monocyclic, bicyclic or tricyclic ring of up to 10 atoms in each ring, wherein at least one ring is aromatic and contains from 1 to 4 heteroatoms selected from the group consisting of O, N and S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, methylenedioxybenzene, benzothiazolyl, benzothienyl, quinolinyl, isoquinolinyl, oxazolyl, and tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

As appreciated by those of skill in the art, "halo" or "halogen" as used herein is intended to include chloro, fluoro, bromo and iodo. The term "keto" means carbonyl (C=O). The term "alkoxy" as used herein means an alkyl portion, where alkyl is as defined above, connected to the remainder of the molecule via an oxygen atom. Examples of alkoxy include methoxy, ethoxy and the like.

The term "haloalkyl" means an alkyl radical as defined above, unless otherwise specified, that is substituted with one to five, preferably one to three halogen. Representative examples include, but are not limited to trifluoromethyl, dichloroethyl, and the like.

The term "haloalkoxy" represents a radical —OR where R is alkyl as defined above that is substituted with one to five, preferably one to three halogen. Representative examples include, but are not limited to trifluoromethyloxy, dichloroethyloxy, and the like.

The term "arylalkyl" includes an alkyl portion where alkyl is as defined above and to include an aryl portion where aryl is as defined above. Examples of arylalkyl include, but are not limited to, benzyl, fluorobenzyl, chlorobenzyl, phenylethyl, phenylpropyl, fluorophenylethyl, and chlorophenylethyl. Examples of alkylaryl include, but are not limited to, toluyl, ethylphenyl, and propylphenyl.

The term "heteroarylalkyl" as used herein, shall refer to a system that includes a heteroaryl portion, where heteroaryl is as defined above, and contains an alkyl portion. Examples of heteroarylalkyl include, but are not limited to, thienylmethyl, thienylethyl, thienylpropyl, pyridylmethyl, pyridylethyl and imidazoylmethyl.

The term "cycloalkylalkyl" includes an alkyl portion where alkyl is as defined above and also includes an cycloalkyl portion where cycloalkyl is as defined above. Examples of cycloalkylalkyl include, but are not limited to, cyclopropylmethyl, cyclopentylmethyl, cyclohexylmethyl, cyclopropylethyl, and the like.

The term "hydroxyalkyl" means a linear monovalent hydrocarbon raidcal of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxyethyl, 2-hydroxypropyl, 3-hydroxypropyl, and the like.

The term "heterocycle" or "heterocyclyl" as used herein is intended to mean a 5- to 10-membered nonaromatic ring, unless otherwise specified, containing from 1 to 4 heteroatoms selected from the group consisting of O, N, S, SO, or $SO_2$ and includes bicyclic groups. "Heterocyclyl" therefore includes, but is not limited to the following: piperazinyl, piperidinyl, pyrrolidinyl, morpholinyl, thiomorpholinyl, tetrahydropyranyl, dihydropiperidinyl, tetrahydrothiophenyl and the like. If the heterocycle contains a nitrogen, it is understood that the corresponding N-oxides thereof are also emcompassed by this definition.

The present invention also includes N-oxide derivatives and protected derivatives of compounds of Formula I. For example, when compounds of Formula I contain an oxidizable nitrogen atom, the nitrogen atom can be converted to an N-oxide by methods well known in the art. Also when compounds of Formula I contain groups such as hydroxy, carboxy, thiol or any group containing a nitrogen atom(s), these groups can be protected with a suitable protecting groups. A comprehensive list of suitable protective groups can be found in T. W. Greene, Protective Groups in Organic Synthesis, John Wiley & Sons, Inc. 1981, the disclosure of which is incorporated herein by reference in its entirety. The protected derivatives of compounds of Formula I can be prepared by methods well known in the art.

Whenever the term "alkyl" or "aryl" or either of their prefix roots appear in a name of a substituent (e.g., aryl $C_{0-8}$ alkyl) it shall be interpreted as including those limitations given above for "alkyl" and "aryl." Designated numbers of carbon atoms (e.g., $C_{1-10}$) shall refer independently to the number of carbon atoms in an alkyl or cyclic alkyl moiety or to the alkyl portion of a larger substituent in which alkyl appears as its prefix root.

The pharmaceutically acceptable salts of the compounds of this invention include the conventional non-toxic salts of the compounds of this invention as formed inorganic or organic acids. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like. The preparation of the pharmaceutically acceptable salts described above and other typical pharmaceutically acceptable salts is more fully described by Berg et al., "Pharmaceutical Salts," *J. Pharm. Sci.*, 1977:66:1-19, hereby incorporated by reference. The pharmaceutically acceptable salts of the compounds of this invention can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

For purposes of this specification, the following abbreviations have the indicated meanings:

| | |
|---|---|
| AcOH = | acetic acid |
| $BF_3$ = | boron trifluoride |
| Boc = | t-butyloxycarbonyl |
| $Boc_2O$ = | di-tert-butyl dicarbonate |
| BuLi = | butyl lithium |
| $CCl_4$ = | carbon tetrachloride |
| $CH_2Cl_2$ = | methylene chloride |
| $CH_3CN$ = | acetonitrile |
| $CHCl_3$ = | chloroform |

| | |
|---|---|
| Cs₂CO₃ = | cesium carbonate |
| CuI = | copper iodide |
| DAST = | diethylaminosulfur trifluoride |
| DIPEA = | diisopropylethylamine |
| DMA = | N,N-dimethyl acetamide |
| DMAP = | 4-(dimethylamino)pyridine |
| DMF = | N,N-dimethylformamide |
| DMSO = | dimethylsulfoxide |
| DPPA = | diphenylphosphoryl azide |
| EDCI = | 1-(3-dimethylaminopropyl)-3-ethylcarbodiimide hydrochloride |
| Et₂O = | diethyl ether |
| Et₃N = | triethylamine |
| EtOAc = | ethyl acetate |
| EtOH = | ethanol |
| HATU = | o-(7-azabenzotriazol-1-yl)-N,N,N',N'-tetramethyluronium hexafluorophosphate |
| HOAc = | acetic acid |
| K₂CO₃ = | potassium carbonate |
| KHMDS = | potassium hexamethyldisilazane |
| KOBuᵗ = | potassium tert-butoxide |
| LDA = | lithium diisopropylamide |
| LiOH = | lithium hydroxide |
| mCPBA = | metachloroperbenzoic acid |
| MeOH = | methanol |
| MeSO₃H = | methane sulfonic acid |
| MgSO₄ = | magnesium sulfate |
| Ms = | methanesulfonyl = mesyl |
| MsCl = | methanesulfonyl chloride |
| NaBH₄ = | sodium borohydride |
| NaH = | sodium hydride |
| NaI = | sodium iodide |
| NaCNBH₃ = | sodium cyanoborohydride |
| Na₂CO₃ = | sodium carbonate |
| NaHCO₃ = | sodium hydrogencarbonate |
| NaOH = | sodium hydroxide |
| Na₂SO₄ = | sodium sulfate |
| NBS = | N-bromosuccinimide |
| NH₃ = | ammonia |
| NH₄Cl = | ammonium chloride |
| Pd/C = | palladium on carbon |
| PdCl₂ = | dichloropalladium(II) |
| PdCl₂(dppf) = | [1,1'-bis(diphenylphosphino)ferrocene]dichloropalladium(II) |
| Pd₂(dba)₃ = | tris(dibenzylideneacetone)dipalladium(0) |
| PG = | protecting group |
| PPh₃ = | triphenylphosphine |
| (PhO)₃PMeI = | methyltriphenoxyphosphonium iodide |
| PPTS = | pyridinium p-toluenesulfonate |
| iPr₂Nli = | lithium diisopropyl amide |
| PyBOP = | benzotriazol-1-yloxytris(pyrrolidino)phosphonium-hexafluorophosphate |
| rt = | room temperature |
| sat. aq. = | saturated aqueous |
| TFA = | trifluoroacetic acid |
| THF = | tetrahydrofuran |
| TiCl₄ = | titanium(IV) chloride |
| tlc = | thin layer chromatography |
| TMSCl = | chlorotrimethylsilane |
| Me = | methyl |
| Et = | ethyl |
| n-Pr = | normal propyl |
| i-Pr = | isopropyl |
| n-Bu = | normal butyl |
| i-Bu = | isobutyl |
| s-Bu = | secondary butyl |
| t-Bu = | tertiary butyl |

The novel compounds of the present invention can be prepared according to the following general procedures using appropriate materials and are further exemplified by the following specific examples. The compounds illustrated in the examples are not, however, to be construed as forming the only genus that is considered as the invention. The following examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted.

Schemes

Compounds of the present invention can be prepared according to Scheme 1, as indicated below. Thus an α-amino ester may be added to a haloalkyl ketone to form an aminal which may be dehydrated to an imine in the presence of a dehydrating agent such as TiCl₄, MgSO₄ or isopropyl trifluoroacetate. Reduction of the imine with a reducing agent such as sodium cyanoborohydride or sodium borohydride provides the amine. Ester hydrolysis and amide formation with an appropriately substituted aminoacetonitrile provides compounds of the current invention. If the substituent on D system is a halogen, a palladium-catalyzed Suzuki coupling with an appropriate boronic acid provides additional compounds of the current invention.

SCHEME 1

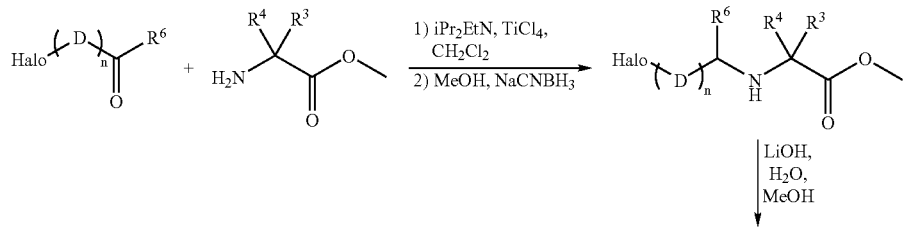

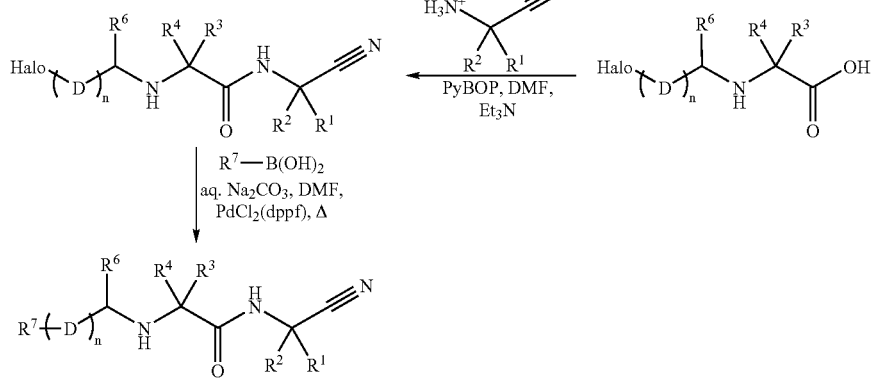

Compounds of the present invention may also be prepared according to Scheme 2, as indicated below. A ketone or aldehyde may be condensed with an amino alcohol to give a cyclic aminal. Treatment with 3 equivalents of a Grignard reagent or organolithium reagent will provide the appropriate alkylated amino alcohol. Oxidation of the alcohol with a chromium system such as a Jones oxidation or $H_5IO_6/CrO_3$, or alternatively by a two-step oxidation (eg oxalyl chloride/DMSO/Et$_3$N followed by NaClO) will provide the corresponding carboxylic acid. Peptide coupling and Suzuki reaction as described in Scheme 1 will provide compounds of the current invention.

SCHEME 2

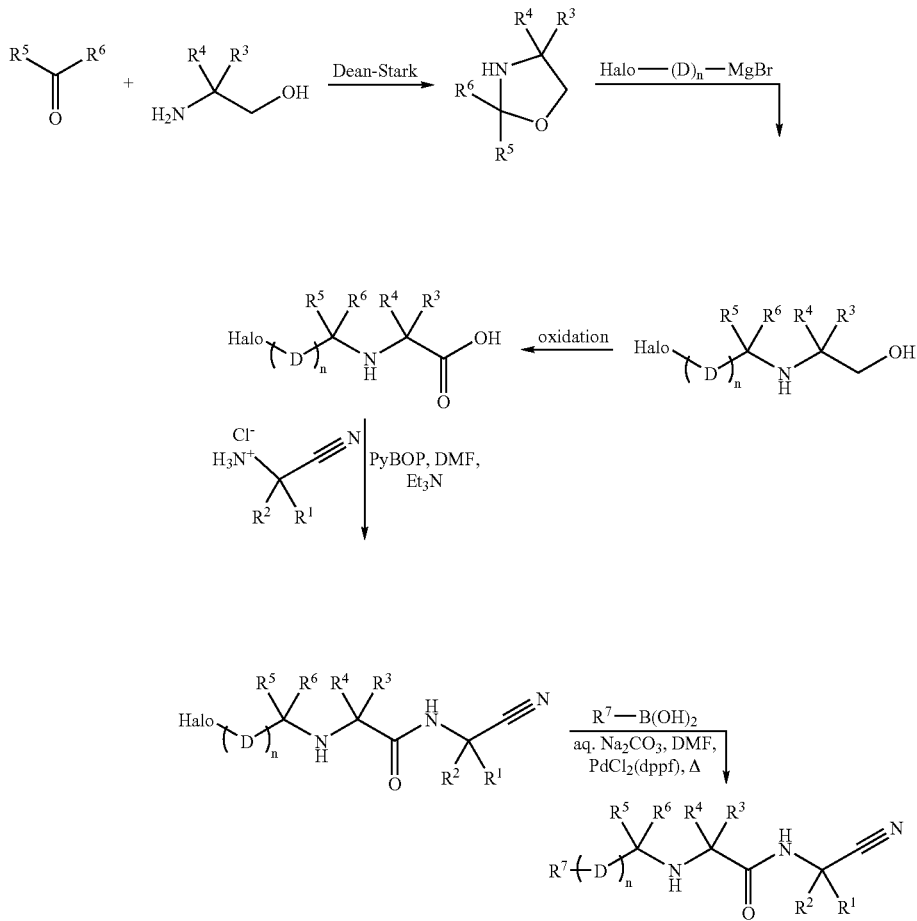

Compounds of the present invention may also be prepared according to Scheme 3, as indicated below. A ketone or aldehyde may be condensed with an amino alcohol to give an acyclic aminal. Treatment with multiple equivalents of a Grignard reagent or organolithium reagent will provide the appropriate alkylated amino alcohol. This alcohol can be converted into compounds of the current invention by the method described in Scheme 2.

SCHEME 3

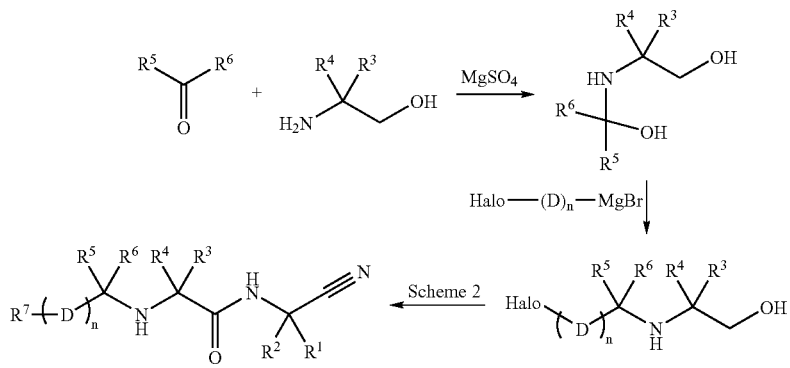

Compounds of the current invention may also be prepared according to Scheme 4. An appropriately substituted acetate may be enolized with a suitable base (including, but not limited to LDA, KHMDS, NaH or nBuLi) and treated with paraformaldehyde to generate the diol. This diol may be converted to the difluoride using a fluorinating reagent such as DAST. Hydrolysis of the ester followed by Curtius rearrangement will then provide the amine. This amine can displace an appropriately substituted alpha-bromo ester to provide the alpha-amino ester. This may be converted into compounds of the current invention by the method described in Scheme 1.

SCHEME 4

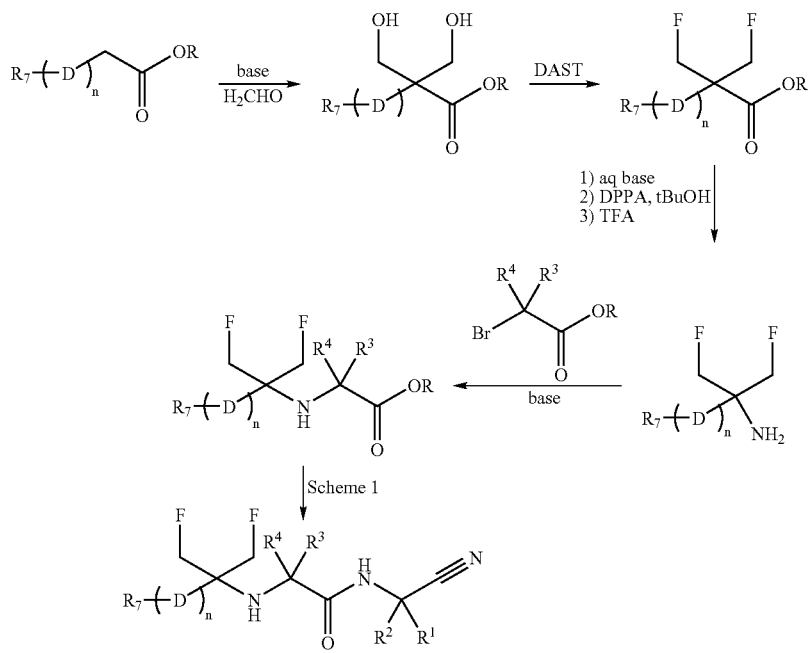

Compounds of the current invention may also be prepared according to Scheme 5, as indicated below. A hemiacetal may be condensed with an amino alcohol in which the alcohol moiety is protected with a suitable protecting group. Treatment of the resulting imine with a Grignard reagent or organolithium reagent will provide the appropriate alkylated amino alcohol. The alcohol protecting group can then be removed and the alcohol can be converted into compounds of the current invention either by the method described in Scheme 2 or by first conducting the Suzuki reaction, followed by oxidizing the alcohol with $H_5IO_6/CrO_3$ and then peptide coupling.

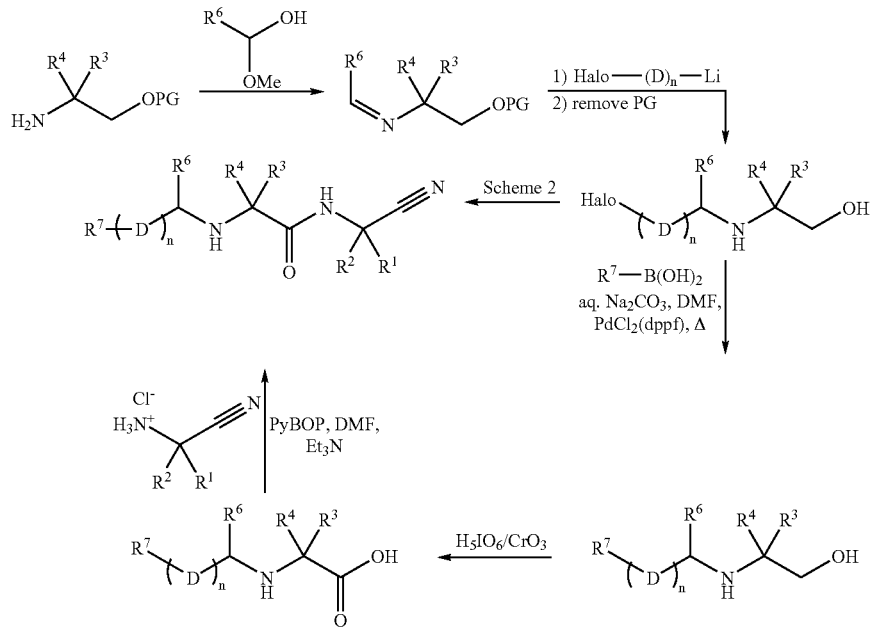

SCHEME 5

Compounds of the current invention may also be prepared according to Scheme 6, as indicated below. The peptide coupling of an alpha-amino acid described in Schemes 1, 2, or 5, with an alpha-amino amide followed by dehydration of the resulting primary amide (Voegel, J. J.; Benner, S. A. *Helv. Chem. Acta* 1996, 79, 1863) will provide compounds of the current invention.

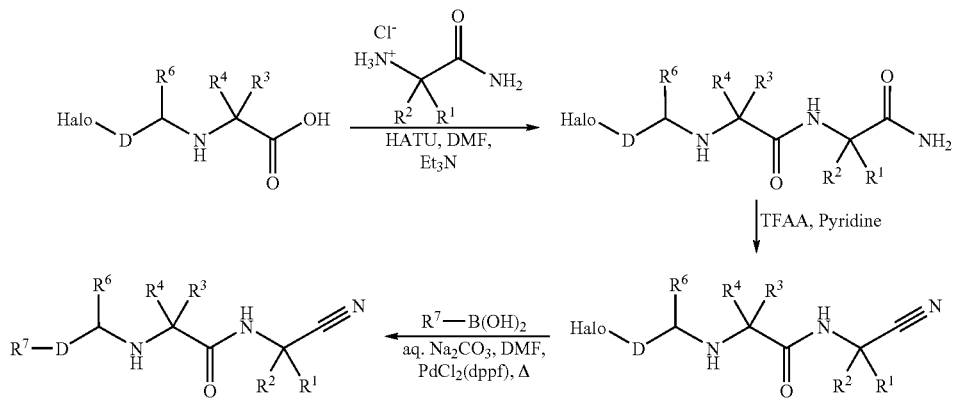

SCHEME 6

The synthesis of some of the amino alcohols used at the beginning of Schemes 2, 3 and 5 are described in Schemes 7-11. For example, the synthesis of (2S)-2-amino-4-fluoro-4-methylpentan-1-ol where R=Me is described in Scheme 7 below. Starting with a suitable diprotected aspartic acid, the carboxy group can be reduced to an alcohol using standard literature procedures (i.e. mixed anyhdride formation followed by NaBH₄ reduction). A protected version of 2-amino-4-methylpentane-1,4-diol (R=Me) can then be generated by an appropriate Grignard or organolithiation reaction. Finally, the hydroxy moiety can be converted to the desired fluoro using a fluorinating agent such as DAST. The protected or unprotected version of this amino alcohol can then be converted to compounds of the current invention according to Schemes 1, 2, 3 and 5.

-continued

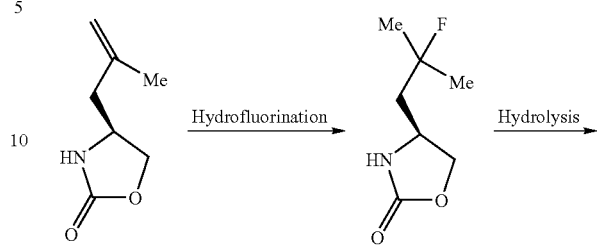

SCHEME 7

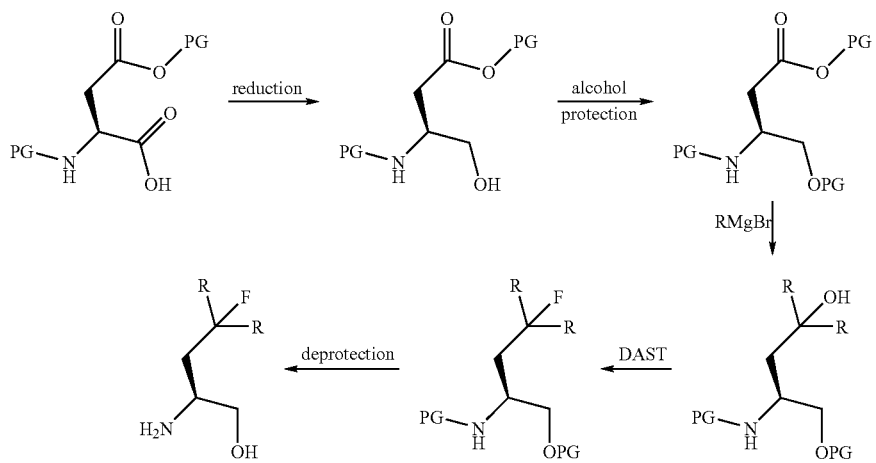

The 4-fluoroleucinol can also be synthesized according to Scheme 8. 4,5-Dehydroleucine is converted to (4S)-4-(2-methylprop-2-enyl)-1,3-oxazolidin-2-one as described in the scheme below. This intermediate is then treated with a hydrofluorination reagent such as HF-pyridine to give (4S)-4-(2-fluoro-2-methylpropyl)-1,3-oxazolidin-2-one. Basic hydrolysis (i.e. Ba(OH)₂ or NaOH) then affords (2S)-2-amino-4-fluoro-4-methylpentan-1-ol.

SCHEME 8

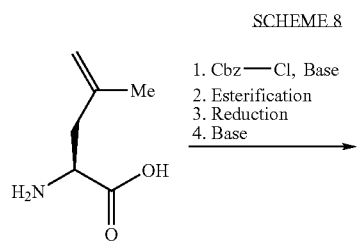

1. Cbz—Cl, Base
2. Esterification
3. Reduction
4. Base

The synthesis of 4,4-difluoro-L-norvaline where R=Me is described in Scheme 9 below. Starting with a suitable diprotected serine, iodination can be carried out using a reagent such as $(PhO)_3P^+MeI^-$. Zincation of the resultant iodide may proceed using Zn.Cu couple and TMSCI. The resultant zincate can then undergo a palladium catalyzed coupling reaction with alkanoyl chloride to generate the ketone. Finally, the ketone moiety can be converted to the desired difluoro derivative using a fluorinating agent such as DAST. The protected or unprotected version of this amino acid or amino alcohol can then be converted to compounds of the current invention according to Schemes 1, 2, 3 and 5.

SCHEME 9

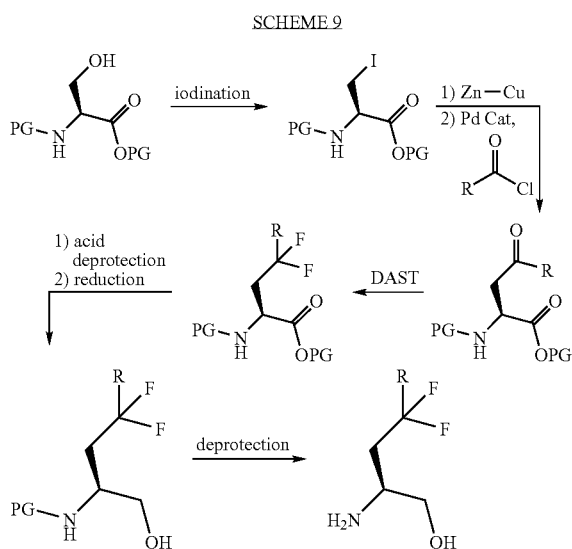

The amino alcohols used for the present invention can also be synthesized according to Scheme 10. A protected amino acid is reduced with a reducing agent such as NaBH₄ with or without an additive such as LiCl, in a solvent such as EtOH or a mixed solvent system such as EtOH and THF. The amino protecting group is then removed with the appropriate method according to the nature of the protecting group.

SCHEME 10

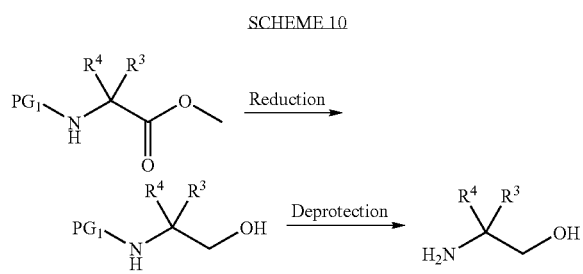

Synthesis of (2S,4S)-2-amino-5,5,5-trifluoro-4-methylpentan-1-ol used in the present invention is described in Scheme 11. The N-benzoyl-5,5,5-trifluoroleucine (Ojiima, et. al. J. Org. Chem., 1989, 54, 4511-4522) can be hydrolysed with an aqueous acid such as 6M HCl under refluxing conditions. The amino acid HCl salt intermediate is then converted to the N-acetyl-5,5,5-trifluoroleucine and the amino group chiral centre is resolved by an enzymatic method (Synthetic Communications, 1996, 26, 1109-1115.). The isolated 5,5,5-trifluoro-L-leucine is then protected with a protecting group such as benzyl carbamate and the carboxylic acid group is esterified. The two diastereomers at the 4-position are then separated by flash column chromatography. One of the enantiomers, the (2S,4S) protected amino acid is then converted to the amino alcohol as described in scheme 10.

SCHEME 11

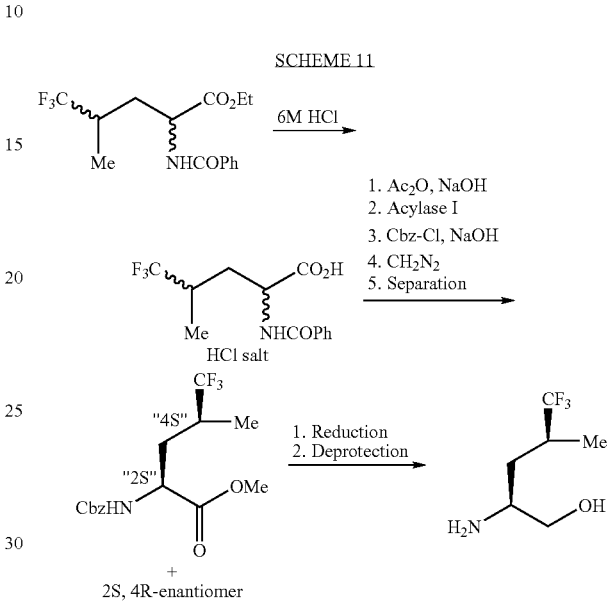

Compounds of the current invention where $R^5$ is hydrogen and $R^6$ is aryl or heteroaryl may also be prepared according to Scheme 12 as shown below. Condensation of an aryl or heteroaryl aldehyde with an amino alcohol in which the alcohol moiety is protected with a suitable protecting group, followed by treatment of the resulting imine with a Grignard or organolithium reagent of formula halo-(D)$_n$-Li or halo-(D)$_n$-MgX (where D is as defined in the Summary of the Invention), followed by removal of the oxygen protecting group provides the alkylated aminoalcohol. The alkylated aminoalcohol is then converted into compounds of the current invention either by the method described in Scheme 2 or by first conducting the Suzuki reaction with the boronic ester of the formula $R^7$—B(OH)$_2$, then oxidizing the alcohol with a suitable oxidizing agent such as H$_5$IO$_6$/CrO$_3$ to give the acid and finally treating the acid with an aminoacetonitrile under peptide coupling conditions as described previously.

SCHEME 12

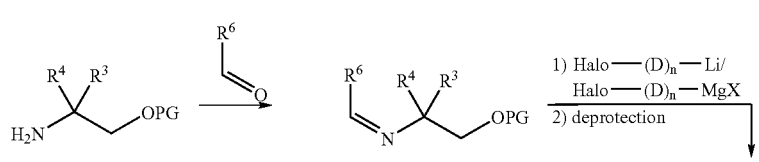

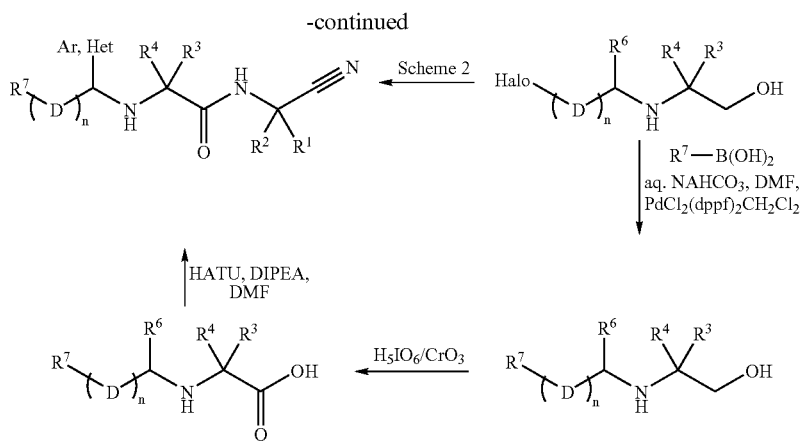

Compounds of the current invention may also be prepared according to Scheme 13, as shown below. Reaction of a suitably N-protected amino acid derivative with oxetane tosylate in the presence of sodium iodide in a suitable organic solvent such as dimethylformamide provides the corresponding oxetane ester which upon treatment with diborane provides the ortho ester. Removal of the amino protecting group affords an amine which upon condensation with an aldehyde of formula $R^6CHO$ (where $R^6$ is aryl or heteroaryl) or a hemiacetal of formula $R^6C(OH)(OR)$ (where R is an alkyl group) under the reaction conditions described above provides an imine. Treatment of the imine with a Grignard or organolithium reagent under the reaction conditions described above provides an N-alkylated derivative. Removal of the ortho ester provides the corresponding carboxylic acid which is then converted into compounds of the current invention by condensation with an aminoacetonitrile under peptide coupling conditions, followed by Suzuki reaction as described above.

SCHEME 13

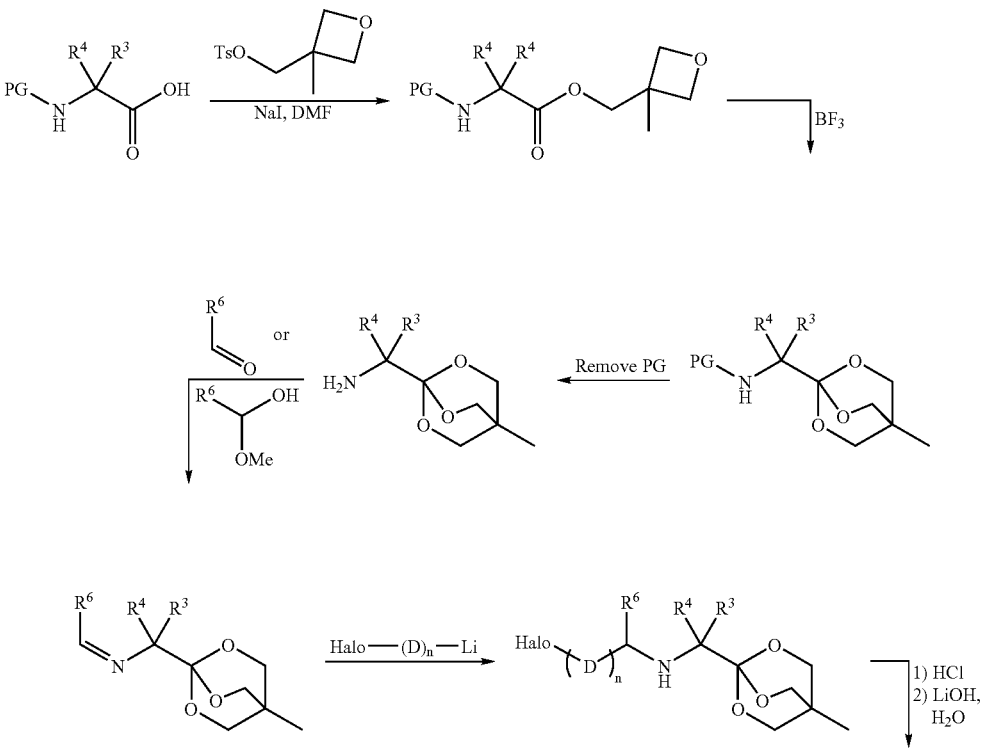

-continued

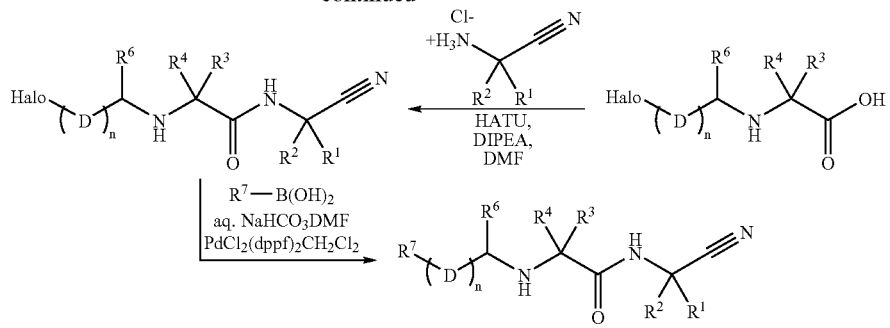

The following examples describe the synthesis of selected compounds of the present invention.

EXAMPLE 1

Synthesis of $N^1$-(cyanomethyl)-$N^2$-(2,2,2-trifluoro-1-phenylethyl)-L-leucinamide

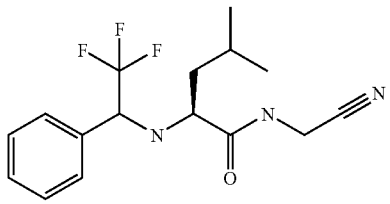

To a solution of L-leucine methyl ester hydrochloride (975 mg, 5.37 mmol) in dichloromethane (30 mL) was added 2,2,2-trifluoroacetophenone (0.75 mL, 5.34 mmol) and diisopropylethylamine (3.5 mL, 20 mmol). TiCl$_4$ (0.55 mL, 5.0 mmol) in 0.45 mL dichloromethane was added dropwise, and the mixture was stirred overnight. Additional TiCl$_4$ (0.4 mL, 3.6 mmol) was then added and the mixture was stirred 3 h. A solution of NaCNBH$_3$ (1050 mg, 16.7 mmol) in MeOH (20 mL) was added and the mixture was stirred 2 h. Poured into 1N NaOH and extracted with ethyl acetate (2×). The organic phase was washed with 1N NaOH and brine, then dried over MgSO$_4$ and evaporated. Purification by ISCO column chromatography (gradient 30% to 90% ethyl acetate/hexanes) provided methyl N-(2,2,2-trifluoro-1-phenylethyl)-L-leucinate.

To a room temperature solution of methyl N-(2,2,2-trifluoro-1-phenylethyl)-L-leucinate (150 mg, 0.50 mmol) in 2:1 THF/MeOH was added 1M LiOH. The mixture was stirred overnight and concentrated. The residue was partitioned between ethyl acetate and pH 3.5 phosphate buffer. The organic phase was washed with brine, dried over MgSO$_4$ and concentrated to give N-(2,2,2-trifluoro-1-phenylethyl)-L-leucine.

A mixture of N-(2,2,2-trifluoro-1-phenylethyl)-L-leucine (149 mg, 0.50 mmol), aminoacetonitrile hydrochloride (102 mg, 1.1 mmol) and PyBOP (260 mg, 0.50 mmol) was dissolved in DMF (5 mL). Triethylamine (0.3 mL, 2.1 mmol) was added and the mixture was stirred overnight, then poured into pH 3 phosphate buffer and extracted with 3:1 ether/ethyl acetate. The organic phase was washed with saturated aqueous NaHCO$_3$ and brine, dried over MgSO$_4$ and evaporated. Purification by ISCO column chromatography (gradient 20% to 50% ethyl acetate/hexanes) provided $N^1$-(cyanomethyl)-$N^2$-(2,2,2-trifluoro-1-phenylethyl)-L-leucinamide as a 1:1 mixture of diastereomers. MS (+APCI): 313.9 [M+1].

EXAMPLE 2

Synthesis of $N^2$-[1-(4-bromophenyl)-2,2,2-trifluoroethyl]-$N^1$-(cyanomethyl)-L-leucinamide

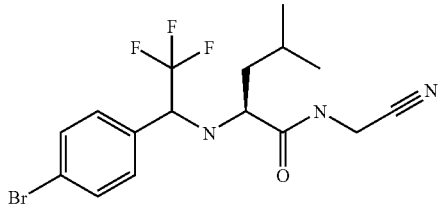

Using the method of Example 1, $N^2$-[1-(4-bromophenyl)-2,2,2-trifluoroethyl]-$N^1$-(cyanomethyl)-L-leucinamide was prepared. MS (−ESI): 403.9, 405.9 [M−1]$^-$

EXAMPLE 3

Synthesis of $N^1$-(cyanomethyl)-$N^2$-[2,2,2-trifluoro-1-(4'-piperazin-1-yl-1,1'-biphenyl-4-yl)ethyl]-L-leucinamide

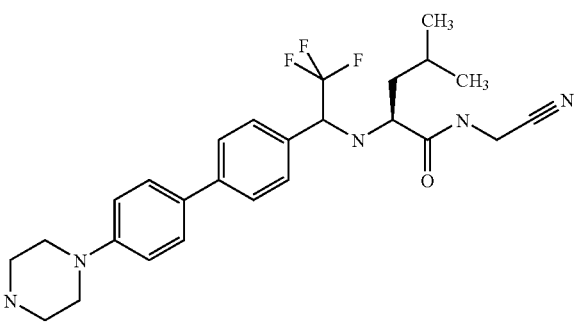

To $N^2$-[1-(4-bromophenyl)-2,2,2-trifluoroethyl]-$N^1$-(cyanomethyl)-L-leucinamide (242 mg, 0.60 mmol), and 4-[4-

(tert-butoxycarbonyl)-1-piperazinyl]phenylboronic acid (220 mg, 0.72 mmol) in DME (3 mL) under dry nitrogen was added 2M aqueous sodium carbonate (0.9 mL, 1.8 mmol) followed by the catalyst PdCl$_2$(dppf) (63 mg, 0.077 mmol). The reaction was heated to 85° C. for 18 hours. Water was added and the product was extracted with EtOAc, the organic layer was dried over Na$_2$SO$_4$ and concentrated in vacuo. The crude product was purified by chromatography using EtOAc in hexane to afford tert-butyl (4'-{1-[((1S)-1-{[(cyanomethyl)amino]carbonyl}-3-methylbutyl)amino]-2,2,2-trifluroethyl}-1,1'-biphenyl-4-yl)-1-piperazinecarboxylate.

To tert-butyl (4'-{1-[((1S)-1-{[(cyanomethyl)amino]carbonyl}-3-methylbutyl)amino]-2,2,2-trifluoroethyl}-1,1'-biphenyl-4-yl)-1-piperazinecarboxylate (275 mg, 0.47 mmol) in dry THF (1 mL) under dry nitrogen was added dropwise MeSO$_3$H (125 μL, 1.9 mmol) over 15 min. and the reaction was allowed to proceed for 18 hours. The reaction mixture was partitioned between EtOAc and water+saturated NaHCO$_3$ to adjust the pH at 7.5. The organic layer was dried over Na$_2$SO$_4$ and concentrated in vacuo. The crude product was purified by chromatography using silica gel eluted with NH$_4$OH conc./MeOH/CH$_2$Cl$_2$, (Jan. 10, 1989) to afford N$^1$-(cyanomethyl)-N$^2$-[2,2,2-trifluoro-1-(4'-piperazin-1-yl-1,1'-biphenyl-4-yl)ethyl]-L-leucinamide as a light yellow foam. MS (+ESI): 488.3 [M+1]$^+$.

EXAMPLE 4

Synthesis of N$^1$-(Cyanomethyl)-N$^2$-{[4'-(methylsulfonyl)-1,1'-biphenyl-4-yl][4-(methylsulfonyl)phenyl]methyl}-L-Leucinamide

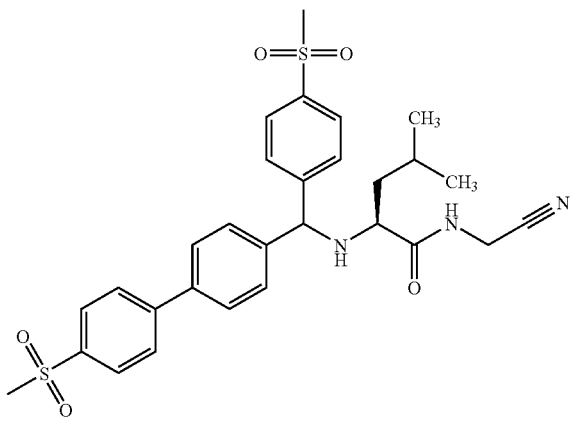

Step 1: Methyl N-{(4-bromophenyl)[4-(methylsulfonyl)phenyl]methylene}-L-leucinate A solution of (4-bromophenyl)[4-(methylsulfonyl)phenyl]methanone (202 mg, 0.59 mmol), L-leucine methyl ester hydrochloride (328 mg, 2.0 mmol) and camphor sulfonic acid (52 mg, 0.22 mmol) in toluene was refluxed for 18 hours using a Dean-Stark trap. The solvent was removed in vacuo and the resulting residue was purified by chromatography using EtOAc and hexane as eluant to give a 1:1 mixture of the title compound and the starting (4-bromophenyl)[4-(methylsulfonyl)phenyl]methanone.

Step 2: Methyl N-{(4-bromophenyl)[4-(methylsulfonyl)phenyl]methyl}-L-leucinate

To a solution of a 1:1 mixture of methyl N-{(4-bromophenyl)[4-(methylsulfonyl)phenyl]methylene}leucinate and (4-bromophenyl)[4-(methylsulfonyl)phenyl]methanone from step 1 (185 mg, ~0.2 mmol) in acetic acid/methanol (1:3, 4 mL) was added sodium borohydride (~400 mg) by portions every 30 min over 2 days (addition was stopped during the night) using a solid addition funnel. The reaction mixture was partitioned between EtOAc and water, the organic layer was dried over Na$_2$SO$_4$ and concentrated. The resulting mixture was purified by chromatography using EtOAc and hexane as eluant. Methyl N-{(4-bromophenyl)[4-(methylsulfonyl)phenyl]methyl}-L-leucinate was obtained as a colorless gum and (4-bromophenyl)[4-(methylsulfonyl)phenyl]methanol was obtained as a white solid.

Step 3: N-{(4-bromophenyl)[4-(methylsulfonyl)phenyl]methyl}-L-leucine

To a solution of methyl N-{(4-bromophenyl)[4-(methylsulfonyl)phenyl]methyl}-L-leucinate from step 2 (81 mg, 0.17 mmol) in THF (1 mL) and MeOH (0.5 mL) was added 1N LiOH (0.3 mL, 0.3 mmol). The resulting mixture was stirred at room temperature for 18 hours and then partitioned between EtOAc and water+1N HCl (0.5 mL). The organic layer was dried over Na$_2$SO$_4$, filtered and concentrated in vacuo to give the title compound as a colorless gum.

Step 4: N$^2$-{(4-bromophenyl)[4-(methylsulfonyl)phenyl]methyl}-N$^1$-(cyanomethyl)-L-leucinamide To a solution of N-{(4-bromophenyl)[4-(methylsulfonyl)phenyl]methyl}-L-leucine from step 3 (76 mg, 0.17 mmol), HATU (146 mg, 0.38 mmol), aminoacetonitrile hydrochloride (52 mg, 0.56 mmol) in DMF (1.1 mL) cooled to −10° C., was added N,N-diisopropylethylamine (0.13 mL, 0.75 mmol). The reaction was allowed to proceed at room temperature for 18 h and it was partitioned between EtOAc and water. The organic layer was dried over Na$_2$SO$_4$, filtered and concentrated in vacuo. The crude product was purified by chromatography using EtOAc and hexane as eluant to give the title compound as a colorless gum.

Step 5: N$^1$-(cyanomethyl)-N$^2$-{[4-(methylsulfonyl)phenyl][4'-(methylthio)-1,1'-biphenyl-4-yl]methyl}-L-leucinamide A heterogeneous mixture of N$^2$-{(4-bromophenyl)[4-(methylsulfonyl)phenyl]methyl}-N$^1$-(cyanomethyl)-L-leucinamide from step 4 (72 mg, 0.15 mmol), 4-(methylthio)phenylboronic acid (37 mg, 0.22 mmol) in ethylene glycol dimethyl ether (1 mL) and 2M aqueous sodium carbonate was degassed under vacuum and purged with nitrogen. To this mixture was added [1,1'-bis(diphenylphosphino)ferrocene]dichloropalladium(II), dichloromethane complex (19 mg, 0.023 mmol), followed by degassing and purging with nitrogen. The reaction mixture was heated at 85° C. for 16 hours with efficient stirring. The reaction mixture was partitioned between EtOAc and aqueous NH$_4$OAc 25% w/v. The organic layer was dried over Na$_2$SO$_4$, filtered and concentrated in vacuo. The crude product was purified by chromatography using EtOAc and hexane as eluant to give the title compound as a colorless gum.

Step 6: N$^1$-(Cyanomethyl)-N$^2$-{[4'-(methylsulfo-nyl)-1,1'-biphenyl-4-yl][4-(methylsulfonyl)phenyl]methyl}-L-leucinamide To a solution of N$^1$-(cyanomethyl)-N$^2$-{[4-(methylsulfonyl)phenyl][4'-(methylthio)-1,1'-biphenyl-4-yl]methyl}-L-leucinamide (63 mg, 0.12 mmol), sodium tungstate dihydrate (2 mg, 0.006 mmol), tetrabutylammonium hydrogensulfate (4 mg, 0.01 mmol) was added a solution of 30% w/v aqueous hydrogen peroxide (100 µL, 0.9 mmol) and the resulting mixture was stirred at room temperature for 10 min. The reaction mixture was partitioned between EtOAc and water+1M NaHSO$_3$ (~3:1). The organic layer was dried over Na$_2$SO$_4$, filtered and concentrated in vacuo. The crude product was purified by chromatography using EtOAc and hexane as eluant to give the title compound as a colorless gum.

MS (+ESI): 568.2 [M+1]$^+$.

EXAMPLE 5

Synthesis of N$^1$-(cyanomethyl)-N$^2$-{2,2,2-trifluoro-1-[4'-(methylsulfonyl)-1,1'-biphenyl-3-yl]ethyl}-L-leucinamide

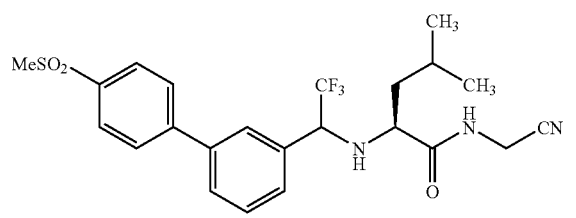

Using the procedure described for example 8, where N$^2$-[1-(4-bromophenyl)-2,2,2-trifluoroethyl]-N$^1$-(cyanomethyl)-L-leucinamide was substituted for N$^2$-[1-(3-bromophenyl)-2,2,2-trifluoroethyl]-N$^1$-(cyanomethyl)-L-leucinamide, the title compound was obtained as a colorless gum.
MS (+ESI): 482.2 [M+1]$^+$.

EXAMPLE 6

Synthesis of N$^1$-(cyanomethyl)-N$^2$-[2,2,2-trifluoro-1-(3-pyridin-4-ylphenyl)ethyl]-L-leucinamide

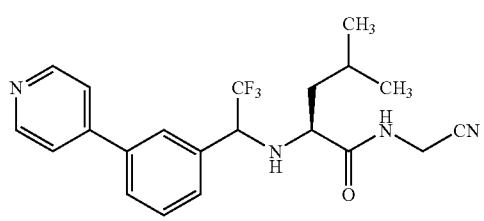

Using the procedure described for example 8, where N$^2$-[1-(4-bromophenyl)-2,2,2-trifluoroethyl]-N$^1$-(cyanomethyl)-L-leucinamide was substituted for N$^2$-[1-(3-bromophenyl)-2,2,2-trifluoroethyl]-N$^1$-(cyanomethyl)-L-leucinamide, the title compound was obtained as a colorless gum.
MS (+ESI): 405.1 [M+1]$^+$.

EXAMPLE 7

Synthesis of N$^1$-(cyanomethyl)-N$^2$-[2,2,2-trifluoro-1-(4'-piperazin-1-yl-1,1'-biphenyl-3-yl)ethyl]-L-leucinamide

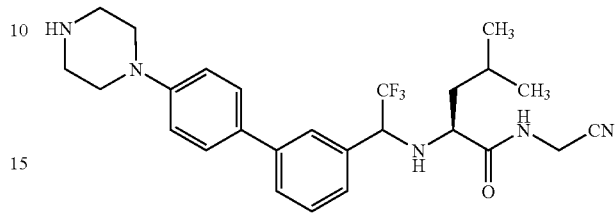

Using the procedure described for example 3, where N$^2$-[1-(4-bromophenyl)-2,2,2-trifluoroethyl]-N$^1$-(cyanomethyl)-L-leucinamide was substituted for N$^2$-[1-(3-bromophenyl)-2,2,2-trifluoroethyl]-N$^1$-(cyanomethyl)-L-leucinamide, the title compound was obtained as a colorless gum.
MS (+ESI): 488.3 [M+1]$^+$.

EXAMPLE 8

Synthesis of N$^1$(cyanomethyl)-N$^2${(1S)-2,2,2-trifluoro-1-[4'-(methylsulfonyl)-1,1'-biphenyl-4-yl]ethyl}-L-leucinamide

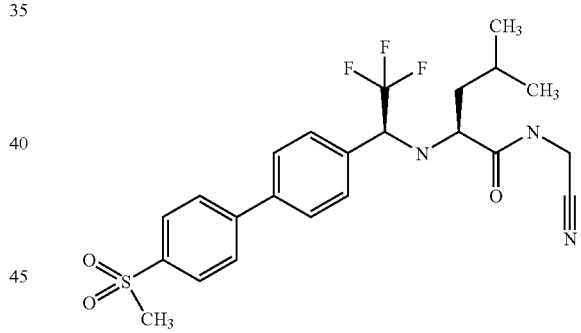

Step 1: Preparation of (2S)-1-{[tert-butyl(dimethyl)silyl]oxy}-4-methylpentan-2-amine To a room temperature dichloromethane (100 mL) solution of L-leucinol (6.0 g) was added triethylamine (11 mL), DMAP (0.1 g) and t-butyldimethylsilyl chloride (8.5 g). The mixture was stirred at room temperature for 2 hours and then water was added. The organic layer was separated and the aqueous further extracted with dichloromethane. The combined organic layers were washed with brine, dried with magnesium sulfate and the solvent was removed in vacuo to yield the title compound, a residue which was used as such in the next reaction. $^1$H NMR (CD$_3$COCD$_3$) δ 3.48 (m, 2H), 3.32 (m, 1H), 2.76 (m, 1H), 1.78 (m, 1H), 1.22-1.02 (m, 2H), 0.88 (m, 15H), 0.06 (s, 6H).

Step 2: Preparation of (2S)-1-{[tert-butyl(dimethyl) silyl]oxy}-4-methyl-N-[(1E)-2,2,2-trifluoroethylidene]pentan-2-amine A toluene (300 mL) solution of (2S)-1-{[tert-butyl(dimethyl)silyl]oxy}-4-methylpentan-2-amine from Step 1 (50 g) and tifluoroacetaldehyde methyl hemiacetal (35 mL) was heated to reflux for 16 hours during which time water was collected in a Dean-Stark trap. The solvent was evaporated in vacuum and the residue was purified on $SiO_2$ using hexanes and ethyl acetate (9:1) as eluant to yield the title compound.

$^1$H NMR ($CD_3COCD_3$) δ 7.88 (m, 1H), 3.76-3.45 (m, 3H), 1.60-1.25 (m, 3H), 0.88 (m, 15H), 0.06 (s, 3H), 0.04 (s, 3H).

Step 3: Preparation of (2S)-2-{[(1S)-1-(4-bromophenyl)-2,2,2-trifluoroethyl]amino}-4-methylpentan-1-ol n-BuLi (2.5 M in hexanes, 42 mL) was added to a −70° C. THF (400 mL) solution of 1,4-dibromobenzene (25.8 g) and the mixture was stirred for 25 minutes. A THF (30 mL) solution of (2S)-1-{[tert-butyl(dimethyl)silyl]oxy}-4-methyl-N-[(1E)-2,2,2-trifluoroethylidene]pentan-2-amine (31 g) was then added dropwise and the mixture was stirred for 1.5 hour. It was then poured slowly into a mixture of ethyl acetate (500 mL), water (2 L), ice (300 g) and ammonium chloride (100 g) under vigorous stirring. The organic layer was separated and the aqueous further extracted with ethyl acetate (2×500 mL). The combined organic layers were washed with brine, dried with magnesium sulfate and the solvent was removed in vacuo to yield a residue, which was used as such. The residue from above was dissolved in THF (250 mL) and the solution was cooled to 0° C. A 1 M THF solution of t-butylammonium fluoride (110 mL) was added dropwise and the mixture was reacted for 4 hours. It was poured into ethyl acetate (300 mL), water (2 L) and ammonium chloride (100 g) under vigorous stirring. The organic layer was separated and the aqueous further extracted with ethyl acetate (2×100 mL). The combined organic layers were washed with brine, dried with magnesium sulfate and the solvent was removed in vacuo to yield a residue which was purified purified on $SiO_2$ using a gradient of ethyl acetate and hexanes (1:5 to 1:4) as eluant to yield the title compound.

$^1$H NMR ($CD_3COCD_3$) δ 7.6 (2H, d), 7.45 (2H, d), 4.55 (1H, m), 3.65-3.7 (1H, m) 3.5-3.55 (1H, m), 3.25-3.35 (1H, m), 2.6-2.7 (1H, m), 2.25-2.35 (1H, m), 1.65-1.75 (1H, m), 1.3-1.4 (1H, m), 1.2-1.3 (1H, m), 0.75-0.9 (6H, dd).

Step 4: Preparation of (2S)-4-methyl-2-({(1S)-2,2,2-trifluoro-1-[4'-(methylthio)-1,1'-biphenyl-4-yl]ethyl}amino)pentan-1-ol A stream of nitrogen was passed through a suspension made of the bromide from Step 3 (27.7 g), 4-(methylthio)phenylboronic acid (15.7 g), 2 M $Na_2CO_3$ (100 mL) and n-propanol (500 mL) for 15 minutes. A 1:3 mixture (3.5 g) of $Pd(OAc)_2$ and $PPh_3$ was then added and the reaction was warmed to 70° C. and stirred under nitrogen for 8 hours. The mixture was cooled to room temperature, diluted with ethylacetate (500 mL) and poured over water (2 L) and ice (500 g). The ethyl acetate layer was separated and the aqueous further extracted with ethyl acetate (200 mL). The combined ethyl acetate extracts were washed with 0.5 N NaOH (2×200 mL), with aqueous $NH_4Cl$, brine and dried with magnesium sulfate. Removal of the solvent left a residue that was purified by chromatography on $SiO_2$ using a gradient of ethyl acetate and hexanes (1:4 to 1:3) and again with acetone and toluene (1:10). The residue was dissolve in hot hexanes (200 mL) and the solution was allowed to cool to 0° C. under stirring. The obtained solid was filtered and dried to yield the title compound.

$^1$H NMR ($CD_3COCD_3$) δ 7.7 (2H, d), 7.65 (2H, d), 7.6 (2H, d), 7.35 (2H, d), 4.5-4.6 (1H, m), 3.7 (1H(OH), m), 3.5-3.6 (1H, m), 3.3-3.4 (1H, m), 2.7 (1H, m), 2.5 (3H, s), 2.3-2.4 (1H(NH), m), 1.65-1.75 (1H, m), 1.2-1.4 (3H, m), 0.8-0.9 (6H, dd).

Step 5: Preparation of (2S)-4-methyl-2-({(1S)-2,2,2-trifluoro-1-[4'-(methylsulfonyl)-1,1'-biphenyl-4-yl]ethyl}amino)pentan-1-ol To a 0° C. solution of the sulfide (19 g) from Step 4 in toluene (400 mL) was added $Na_2WO_4.2H_2O$ (0.16 g) and $Bu_4NHSO_4$ (0.81 g). Then 30% hydrogen peroxide (12.2 mL) was slowly added and the mixture was stirred at room temperature for 4.5 hours. The mixture was poured slowly on a mixture of ice, dilute aqueous sodium thiosulfate, and ethyl acetate. The organic layer was separated and the aqueous further extracted with ethyl acetate (2×100 mL). The combined organic layers were washed with brine, dried with magnesium sulfate and the solvent were removed in vacuo to yield a residue which was purified purified on $SiO_2$ using ethyl acetate and hexanes (1:1) as eluant to yield the product.

$^1$H NMR ($CD_3COCD_3$) δ 8.05 (2H, d), 8.0 (2H, d), 7.85 (2H, d), 7.7 (2H, d), 4.6-4.7 (1H, m), 3.75 (1H, m), 3.6 (1H, m), 3.35-3.45 (1H, m), 3.2 (3H, s), 2.7-2.8 (1H, m), 2.35-2.45 (1H, m), 1.7-1.8 (1H, m), 1.2-1.5 (2H, m), 0.8-0.95 (6H, dd).

Step 6: Preparation of N-{(1S)-2,2,2-trifluoro-1-[4'-(methylsulfonyl)-1,1'-bipheny-4-yl]ethyl}-L-leucine A suspension of $H_5IO_6/CrO_3$ (529 mL of 0.44 M in CH3CN; see Note below) was cooled to 0° C. and a solution of the alcohol from Step 5 (20 g) in $CH_3CN$ (230 mL) was added dropwise. The mixture was stirred at 0-5° C. for 3.5 hours. It was poured into pH 4 $Na_2HPO_4$ (1.5 L) under vigorous stirring and the mixture was extracted with diethyl ether (3×250 mL). The combined ether extracts were washed with water and brine (1:1), with dilute aqueous $NaHSO_3$ and brine. The organic extract was dried with sodium sulfate, filtered and the solvents were evaporated to dryness to yield a residue that was split into two batches for the following purification.

The crude acid from above (10 g) was dissolved in isopropyl acetate (250 mL) and extracted into cold 0.1 N NaOH (3×250 mL). The combined extracts were washed with diethyl ether (250 mL) and then slowly acidified with 6 N HCl to pH 4. The carboxylic acid was extracted with isopropyl acetate (2×250 mL) and the isopropyl acetate layer dried and concentrated to yield the product essentially pure and used as such in the next step.

Note: The oxidizing reagent ($H_5IO_6/CrO_3$) was prepared as described in Tetrahedron Letters 39 (1998) 5323-5326 but using HPLC grade $CH_3CN$ (contains 0.5% water); no water was added.

$^1$H NMR ($CD_3COCD_3$) δ 8.05 (2H, d), 7.95 (2H, d), 7.8 (2H, d), 7.65 (2H, d), 4.45-4.55 (1H, m), 3.55-3.6 (1H, m), 3.2 (3H, s), 2.8-3.0 (broad m, NH/OH)1.95-2.05 (1H, m), 1.55-1.6 (2H, m), 0.9-1.0 (6H, m).

Step 7: Preparation of $N^1$(cyanomethyl)-$N^2$ {(1S)-2,2,2-trifluoro-1-[4'-(methylsulfonyl)-1,1'-biphenyl-4-yl]ethyl}-L-leucinamide To a DMF (200 mL) solution of the acid from Step 7 (9 g) was added benzotriazol-1-yloxytris(dimethylamino)phosphonium hexafluorophosphate (11.6 g), aminoacetonitrile hydrochloride (3.94 g) and the mixture was cooled to 0° C. Triethylamine (9.9 mL) was added dropwise and the mixture warmed to room temperature and stirred for 16 hours. It was poured into ice and saturated aqueous sodium bicarbonate and extracted with diethyl ether (3×100 mL). The combined extracts were washed with brine, dried with magnesium sulfate and the solvent removed in vacuo. The residue was purified by chromatography on $SiO_2$ using ethyl acetate and hexanes (1:1). The title compound was then stirred in diethyl ether for 16 hours, filtered and dried (mp 140.5° C.).

$^1$H NMR ($CD_3COCD_3$) δ 8.0 (2H, d), 7.95 (2H, d), 7.8 (2H, d), 7.65 (2H, d), 4.35-4.45 (1H, m), 4.1-4.2 (2H, m), 3.45-3.55 (1H, m), 3.15 (3H, s), 2.65-2.7 (1H, m), 1.85-1.95 (1H, m), 1.4-1.6 (2H, m), 0.85-0.95 (6H, m).

EXAMPLE 9

Synthesis of $N^2$ {(1S)-1-[4'-(aminosulfonyl)-1,1'-biphenyl-4-yl]-2,2,2-trifluoroethyl}-$N^1$(cyanomethyl)-L-leucinamide

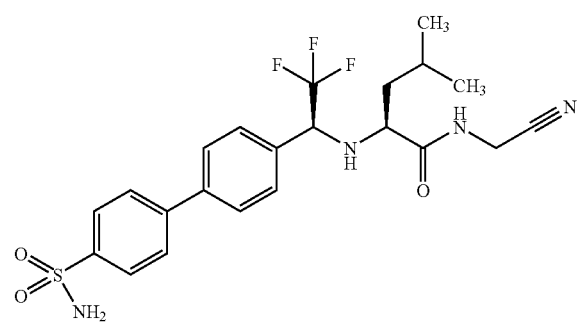

Step 1: Preparation of $N^2$[(1S)-1-(4-bromophenyl)-2,2,2-trifluoroethyl]-$N^1$(cyanomethyl)-L-leucinamide A suspension of $H_5IO_6/CrO_3$ (1925 mL of 0.44 M in $CH_3CN$; see Note in step 6, example 8) was cooled to 0° C. and a solution of (2S)-2-{[(1S)-1-(4-bromophenyl)-2,2,2-trifluoroethyl]amino}-4-methylpentan-1-ol from Step 4, Example 8 (60 g) in $CH_3CN$ (1500 mL) was added dropwise. The mixture was stirred at 0-5° C. for 3.5 hours. It was poured into pH 4 $Na_2HPO_4$ (2.5 L) under vigorous stirring and the mixture was extracted with diethyl ether (3×500 mL). The combined ether extracts were washed with water and brine (1:1), with dilute aqueous $NaHSO_3$ and brine. The organic extract was dried with sodium sulfate, filtered and concentrated in vacuo to yield N-[(1S)-1-(4-bromophenyl)-2,2,2-trifluoroethyl]-L-leucine used as such in the following coupling with aminoacetonitrile.

To a DMF (1500 mL) solution of the crude acid (46 g) was added benzotriazol-1-yloxytris(dimethylamino)phosphonium hexafluorophosphate (71.5 g), aminoacetonitrile hydrochloride (25.4 g) and the mixture was cooled to 0° C. Triethyl amine (60.8 mL) was added dropwise and the mixture warmed to room temperature and stirred for 16 hours. It was poured into ice and saturated aqueous sodium bicarbonate and extracted with diethyl ether (3×300 mL). The combined extracts were washed with brine, dried with magnesium sulfate and the solvent removed in vacuo. The residue was purified by chromatography on $SiO_2$ using a gradient of ethyl acetate and hexanes (1:3 to 1:2) to yield the title compound pure enough for use in the next step.

$^1$H NMR ($CD_3COCD_3$) δ 7.95-8.05 (bs, NH), 7.6 (2H, d), 7.45 (2H, d), 4.4 (1H, m), 4.1-4.2 (2H, m), 3.4-3.5 (1H, m), 2.6-2.7 (1H, m), 1.8-1.95 (1H, m), 1.4-1.6 (2H, m), 0.85-0.95 (6H, m).

Step 2: Preparation of $N^1$-(cyanomethyl)-$N^2$ {(1S)-2,2,2-trifluoro-1-[4-(4,4,5,5-tetramethyl-1,3,2-dioxaborolan-2-yl)phenyl]ethyl}-L-leucinamide A stream of nitrogen was passed through a DMF (700 mL) suspension of $N^2$[(1S)-1-(4-bromophenyl)-2,2,2-trifluoroethyl]-$N^1$(cyanomethyl)-L-leucinamide from Step 1 (28.5 g), bis(pinacolato)diboron (23 g) and potassium acetate (24 g) for 15 minutes followed by the addition of [1,1'-bis(diphenylphosphino)-ferrocene]dichloropalladium(II), complex (1:1) with dichloromethane (2.9 g). The mixture was warmed to 65° C. and stirred under nitrogen for 2.5 hours. The mixture was cooled to room temperature, diluted with ethylacetate and hexanes (1:1, 300 mL) and poured over water (2 L) and ice (500 g). The organic layer was separated and the aqueous layer further extracted with ethyl acetate and hexanes (1:1, 3×200 mL). The combined extracts were washed with brine and dried with magnesium sulfate. Removal of the solvent left a residue that was purified by chromatography on $SiO_2$ using ethyl acetate and hexanes (1:2) to yield the boronate.

1H NMR ($CD_3COCD_3$) δ 7.95-8.05 (bs, NH), 7.7-7.8 (2H, d), 7.45-7.55 (2H, d), 4.3-4.4 (1H, m), 4.05-4.15 (2H, m), 3.4-3.5 (1H, m), 2.55-2.65 (1H, m), 1.85-1.95 (1H, m), 1.45-1.55 (2H, m), 1.15-1.4 (12H, m; some pinacol also present as a contaminant), 0.85-0.95 (6H, m).

Step 3: Preparation of $N^2$ {(1S)-1-[4'-(aminosulfonyl)-1,1'-biphenyl-4-yl]-2,2,2-trifluoroethyl}-$N^1$(cyanomethyl)-L-leucinamide A stream of nitrogen was passed through a suspension made of the boronate from Step 2 (4 g), 4-bromobenzenesulfonamide (3.3 g), 2 M $Na_2CO_3$ (20 mL) and n-propanol (100 mL) for 15 minutes. A 1:3 mixture (0.25 g) of Pd(OAc)$_2$ and $PPh_3$ was then added and the reaction was warmed to 85° C. and stirred under nitrogen for 3 hours. The mixture was cooled to room temperature, diluted with ethylacetate (100 mL) and poured over water (500 mL) and ice (100 g). The ethyl acetate layer was separated and the aqueous further extracted with ethyl acetate (100 mL). The combined ethyl acetate extracts were washed with dilute aqueous $NaHCO_3$, brine and dried with magnesium sulfate. Removal of the solvent left a residue that was purified by chromatography on $SiO_2$ using a gradient of ethyl acetate, hexanes and dichloromethane (2:3:0.1 to 1:1:0.1). The product was then stirred in diethyl ether for 16 hours, filtered and dried to yield the title compound.

$^1$H NMR ($CD_3COCD_3$) δ 8-8.1 (3H, m), 7.9 (2H, d), 7.8 (2H, d), 7.65 (2H, d), 6.6-6.7 (2H, m), 4.4 (1H, m), 4.1-4.2 (2H, m), 3.5 (1H, m), 2.6-2.7 (1H, m), 1.9 (1H, m), 1.45-1.6 (2H, m), 1.4-1.6 (4H, m), 0.9-1.0 (6H, m).

EXAMPLE 10

Synthesis of $N^1$(1-cyanocyclopropyl)-$N^2${(1S)-2,2,2-trifluoro-1-[4'-(methylsulfonyl)-1,1'-biphenyl-4-yl]ethyl}-L-leucinamide

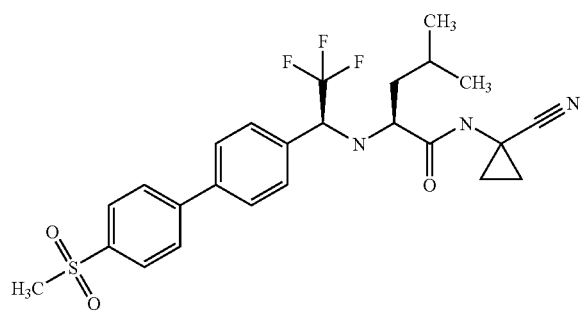

To a mixture of N-{(1S)-2,2,2-trifluoro-1-[4'-(methylsulfonyl)-1,1'-biphenyl-4-yl]ethyl}-L-leucine from Example 8 (0.83 g), O-(7-azabenzotriazol-1-yl)-N,N,N',N'-tetramethyluronium hexafluorophosphate (0.78 g), cyclopropylamine hydrochloride (0.466 g) in DMF (18 mL) at 0° C. was added triethylamine (0.9 mL). The mixture was kept at room temperature for 48 hours and then poured into dilute aqueous ammonium chloride and diethyl ether. The ether layer was separated and the aqueous further extracted with diethylether. The combined ether extracts were washed with brine, dried with magnesium sulfate and the solvent was removed in vacuo. The residue was purified in $SiO_2$ using ethyl acetate and hexanes (1:1) as eluant, followed by a swish in diethyl ether to yield the title compound.

$^1$H NMR (CD$_3$COCD$_3$) δ 8.15 (1H, bs), 8.05 (2H, d), 8.0 (2H, d), 7.8 (2H, d), 7.65 (2H, d), 4.35-4.45 (1H, m), 3.35-3.45 (1H, m), 3.2 (3H, s), 2.65-2.7 (1H, m), 1.85-1.95 (1H, m), 1.3-1.6 (5H, m), 1.05-1.15 (1H, m), 0.85-0.95 (6H, m).

EXAMPLE 11

Synthesis of $N^1$-(cyanomethyl)-$N^2$-[(1S)-2,2,3,3,3-pentafluoro-1-(4-pyridin-4-ylphenyl)propyl]-L-leucinamide

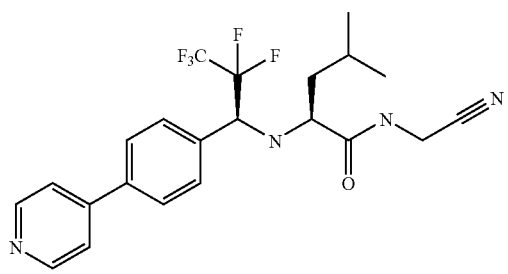

Step 1: Preparation of (4S)-4-isobutyl-2-(pentafluoroethyl)-1,3-oxazolidine

Pentafluoropropanal methyl hemiacetal (14.9 g, 82.8 mmol) and L-leucinol (9.7 g, 82.8 mmol) were dissolved in 100 mL of benzene and heated to reflux overnight in a flask equipped with a Dean-Stark tube. The resulting solution was cooled and concentrated to provide the title compound as an oil which was used directly in the following step.

Step 2: Preparation of (2S)-2-{[(1S)-1-(4-bromophenyl)-2,2,3,3,3-pentafluoropropyl]amino}-4-methylpentan-1-ol To a −78° C. solution of dibromobenzene (9.85 g, 41.8 mmol) in 100 mL of THF was added nBuLi (16.5 mL of 2.5M hexanes solution, 41.2 mmol) giving a thick suspension. After stirring 10 min, a solution of (4S)-4-isobutyl-2-(pentafluoroethyl)-1,3-oxazolidine (3.3 g, 13 mmol) in 3 mL THF was added giving a dark brown solution. The solution was allowed to warm to room temperature, then was poured into saturated aqueous ammonium chloride and extracted with ether. Purification by silica gel chromatography (10% to 40% ethyl acetate/hexanes gradient) gave the title compound as a single diastereomer.

Step 3: Preparation of $N^2$-[(1S)-1-(4-bromophenyl)-2,2,3,3,3-pentafluoropropyl]-$N^1$-(cyanomethyl)-L-leucinamide The total sample of (2S)-2-{[(1S)-1-(4-bromophenyl)-2,2,3,3,3-pentafluoropropyl]amino}-4-methylpentan-1-ol (1.6 g, 4.0 mmol) was converted to the title compound using the method of Example 8, Steps 6 and 7. Purification by silica gel chromatography (15% to 80% ethyl acetate/hexanes gradient) provided the title compound as a solid.

$^1$H NMR (CD$_3$COCD$_3$, 500 MHz) δ 7.8 (1H, br), 7.55 (2H, m), 7.40 (2H, m), 4.4-4.5 (1H, m), 3.95 (2H, m), 3.33 (1H, m), 2.75 (1H, m), 1.82 (1H, m), 1.5 (1H, m), 1.38 (1H, m), 0.88 (6H, dd).

Step 4: Preparation of $N^1$-(cyanomethyl)-$N^2$-[(1S)-2,2,3,3,3-pentafluoro-1-(4-pyridin-4-ylphenyl)propyl]-L-leucinamide To a solution of $N^2$-[(1S)-1-(4-bromophenyl)-2,2,3,3,3-pentafluoropropyl]-$N^1$-(cyanomethyl)-L-leucinamide (82 mg, 0.18 mmol), 4-pyridylboronic acid (30 mg, 0.24 mmol) and PdCl$_2$(dppf) (14 mg, 0.02 mmol) in 2.5 mL DMF was added 2M Na$_2$CO$_3$ (0.25 mL). The mixture was heated to 95° C. for 2.5 h, then cooled and partitioned between aq. Na$_2$CO$_3$ and ether. The aqueous phase was washed with brine and dried over MgSO$_4$. Purification by silica gel chromatography (65% to 95% ethyl acetate/hexanes gradient) provided the title compound.

1H NMR (CD$_3$COCD$_3$, 500 MHz) δ 8.66 (2H, m), 7.85 (1H, br), 7.81 (2H, m), 7.70 (2H, m), 7.62 (2H, m), 4.5-4.6 (1H, m), 3.95 (2H, m), 3.4 (1H, m), 2.81 (1H, m), 1.88 (1H, m), 1.55 (1H, m), 1.42 (1H, m), 0.92 (6H, dd).

EXAMPLE 12

Synthesis of N¹-(1-cyanocyclopropyl)-N²-{(1S)-2,2-difluoro-1-[4'-(methylsulfonyl)-1,1'-biphenyl-4-yl]ethyl}-L-leucinamide

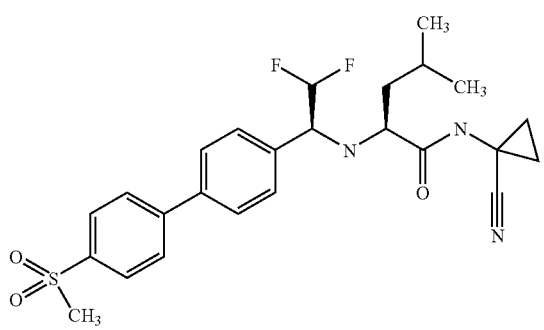

Step 1: Preparation of (2S)-1-{[tert-butyl(dimethyl)silyl]oxy}-4-methylpentan-2-amine Prepared as in Step 1 of Example 8.

Step 2: Preparation of (2S)-1-{[tert-butyl(dimethyl)silyl]oxy}-N-[(1E)-2,2-difluoroethylidene]-4-methylpentan-2-amine A mixture of (2S)-1-{[tert-butyl(dimethyl)silyl]oxy}-4-methylpentan-2-amine (8.5 g, 36.8 mmol) and difluoroacetaldehyde ethyl hemiacetal (5.0 g, 39.7 mmol) in benzene was refluxed with a Dean-stark trap overnight. Solvent was removed in vacuo. The residue was passed through a short silica column and eluted with hexanes:EtOAc (10:1) to give the title compound as a pale yellow oil.

$^1$H NMR (CD$_3$COCD$_3$) δ 7.72 (m, 1H), 6.12 (dt, 1H), 3.70 (dd, 1H), 3.54 (dd, 1H), 3.36 (m, 1H), 1.48 (m, 2H), 1.32 (m, 1H), 0.95-0.78 (m, 15H), 0.06 (s, 3H), 0.02 (s, 3H).

Step 3: Preparation of (2S)-2-{[(1S)-1-(4-bromophenyl)-2,2-difluoroethyl]amino}-4-methylpentan-1-ol n-BuLi (2.5 M in hexanes, 1.43 mL) was added to a −70° C. THF (8.5 mL) solution of 1,4-dibromobenzene (884 mg) and the mixture was stirred for 15 minutes. A THF (8.5 mL) solution of (2S)-1-{[tert-butyl(dimethyl)silyl]oxy}-4-methyl-N-[(1E)-2,2-difluoroethylidene]pentan-2-amine (1.0 g) was then added dropwise and the mixture was stirred for 1.5 hours. The mixture was then poured slowly into an icy saturated aqueous solution of ammonium chloride under vigorous stirring and was extracted with 3 portions of ethyl acetate. The combined organic layers were washed with brine, dried with magnesium sulfate and the solvent was removed in vacuo to yield a residue, which was purified on SiO$_2$ using a gradient of hexanes and ethyl acetate (90:10 to 75:25) as eluent to yield (2S)-N-[(1S)-1-(4-bromophenyl)-2,2-difluoroethyl]-1-{[tert-butyl(dimethyl)silyl]oxy}-4-methylpentan-2-amine. (2S)-N-[(1S)-1-(4-Bromophenyl)-2,2-difluoroethyl]-1-{[tert-butyl(dimethyl)silyl]oxy}-4-methylpentan-2-amine (200 mg) was dissolved in CH$_3$CN (4 mL) and the solution was cooled to 0° C. HF-pyridine (40 μL) was added dropwise and the mixture was reacted for 16 hours. The mixture was poured into a saturated solution of sodium bicarbonate, ethyl acetate was added and the resultant mixture was vigorously shaken. The organic layer was separated and the aqueous further extracted with ethyl acetate (2×50 mL). The combined organic layers were washed with brine, dried with magnesium sulfate and the solvent was removed in vacuo to yield a residue which was purified on SiO$_2$ using a gradient of hexanes and ethyl acetate (80:20 to 60:40) as eluent to yield the title compound.

$^1$H NMR (CD$_3$COCD$_3$) δ 7.6 (2H, d), 7.45 (2H, d), 6.0 (1H, dt), 4.25 (1H, m), 3.65 (1H, t), 3.5-3.55 (1H, m), 3.3-3.35 (1H, m), 2.55-2.65 (1H, m), 2.15-2.25 (1H, m), 1.6-1.7 (1H, m), 1.3-1.4 (1H, m), 1.2-1.3 (1H, m), 0.9 (3H, d), 0.8 (3H, d).

Step 4: Preparation of N-[(1S)-1-(4-bromophenyl)-2,2-difluoroethyl]-L-leucine A suspension of H$_5$IO$_6$/CrO$_3$ (5.5 mL of 0.40 M in CH3CN; see Note below) was cooled to 0° C. and a solution of the alcohol from Step 3 (250 mg) in CH$_3$CN (3.7 mL) was added dropwise. The mixture was stirred at 0-5° C. for 3.5 hours. After this period, 2.0 mL of the oxidant was added. After 1.5 hours the mixture was poured into Na$_2$HPO$_4$ buffer (0.4 g in 10 mL) under vigorous stirring and the mixture was extracted with diethyl ether (3×20 mL). The combined ether extracts were washed with water and brine (1:1), dilute aqueous NaHSO$_3$ and brine. The organic extract was dried with magnesium sulfate, filtered and the solvent was evaporated to dryness to yield the title compound which was used without further purification.

Note: The oxidizing reagent (H$_5$IO$_6$/CrO$_3$) was prepared as described in Tetrahedron Letters 39 (1998) 5323-5326 but using HPLC grade CH$_3$CN (contains 0.5% water); no water was added.

$^1$H NMR (CD$_3$COCD$_3$) δ 7.55 (2H, d), 7.4 (2H, d), 6.05 (1H, dt), 3.95-4.05 (1H, m), 3.45 (1H, t), 2.7-3.0 (bm, NH/OH), 1.85-1.95 (1H, m), 1.5 (2H, t), 0.95 (3H, d), 0.9 (3H, d).

Step 5: Preparation of N²-[(1S)-1-(4-bromophenyl)-2,2-difluoroethyl]-N¹-(1-cyanocyclopropyl)-L-leucinamide To a DMF (2 mL) solution of the acid from Step 4 (258 mg) was added O-(7-azabenzotriazol-1-yl)-N,N,N',N'-tetramethyluronium hexafluorophosphate (337 mg) and 1-aminocyclopropanecarbonitrile hydrochloride (175 mg). After stirring for 1 min, diisopropylethylamine (0.45 mL) was added dropwise and the mixture was stirred for 16 hours. The resultant mixture was poured into saturated aqueous sodium bicarbonate and extracted with ethyl acetate (3×15 mL). The combined extracts were washed with brine, dried with magnesium sulfate and the solvent removed in vacuo. The residue was purified by chromatography on SiO$_2$ using hexanes and ethyl acetate (80:20 to 50:50) to afford the title compound.

$^1$H NMR (CD$_3$COCD$_3$) δ 8.05 (1H, m), 7.55 (2H, d), 7.4 (2H, d), 6.05 (1H, dt), 3.95-4.05 (1H, m), 3.25-3.3 (1H, m), 2.4-2.45 (1H, m), 1.8-1.9 (1H, m), 1.4-1.55 (2H, m), 0.95-1.1 (2H, m), 0.95 (6H, t).

Step 6: Preparation of N¹-(1-cyanocyclopropyl)-N²-{(1S)-2,2-difluoro-1-[4'-(methylthio)-1,1'-biphenyl-4-yl]ethyl}-L-leucinamide A stream of nitrogen was passed through a suspension of the aryl bromide from Step 5 (65 mg), 4-(methylthio)phenylboronic acid (40 mg), 2 M Na$_2$CO$_3$ (0.22 mL) and DMF (1.0 mL) for 5 minutes. PdCl$_2$dppf was then added and the reaction was warmed to 80° C. and stirred under nitrogen for 4 hours. The mixture was cooled to room temperature, diluted with ethyl acetate (20 mL) and poured into a saturated solution of sodium bicarbonate. The ethyl acetate layer was separated and the aqueous further extracted with ethyl acetate (2×15 mL). The combined ethyl acetate extracts were washed with brine and dried with magnesium sulfate. Removal of the solvent left a residue that was purified by chromatography on SiO$_2$ using a gradient of hexanes and ethyl acetate (90:10 to 50:50) to afford the title compound.

$^1$H NMR (CD$_3$COCD$_3$) δ 8.1 (1H, m), 7.6-7.65 (4H, m), 7.45 (2H, d), 7.35 (2H, d), 6.05 (1H, dt), 3.9-4.0 (1H, m), 3.2-3.3 (1H, m), 2.5 (3H, s), 2.35-2.4 (1H, m), 1.8-1.9 (1H, m), 1.3-1.5 (4H, m), 0.85-1.0 (8H, m).

Step 7: Preparation of N¹-(1-cyanocyclopropyl)-N²-{(1S)-2,2-difluoro-1-[4'-(methylsulfonyl)-1,1'-biphenyl-4-yl]ethyl}-L-leucinamide To a solution of the sulfide (50 mg) from Step 6 in toluene (1.0 mL) and ethyl acetate (0.1 mL) was added Na$_2$WO$_4$·2H$_2$O (1 mg) and Bu$_4$NHSO$_4$ (2 mg). 30% Hydrogen peroxide (30 μL) was then slowly added and the mixture was stirred at room temperature for 1.5 hours. The mixture was poured into dilute aqueous sodium thiosulfate and ethyl acetate. The organic layer was separated and the aqueous further extracted with ethyl acetate (2×10 mL). The combined organic layers were washed with brine, dried with magnesium sulfate and the solvent was removed in vacuo to yield a residue which was purified on SiO$_2$ using hexanes and ethyl acetate (50:50 to 0:100) followed by dichloromethane and diethyl ether (90:10) as eluent to yield the title compound.

$^1$H NMR (CD$_3$COCD$_3$) δ 8.15 (1H, m), 8.0 (2H, d), 7.95 (2H, d), 7.75 (2H, d), 7.55 (2H, d), 6.1 (1H, dt), 4.0-4.1 (1H, m), 3.25-3.35 (1H, m), 3.15 (3H, s), 2.4-2.5 (1H, m), 1.8-1.9 (1H, m), 1.4-1.55 (4H, m), 0.85-1.05 (8H, m).

EXAMPLE 13

Synthesis of N²-[(1S)-1-(6-chloropyridin-3-yl)-2,2,2-trifluoroethyl]-N¹-(1-cyanocyclopropyl)-L-leucinamide

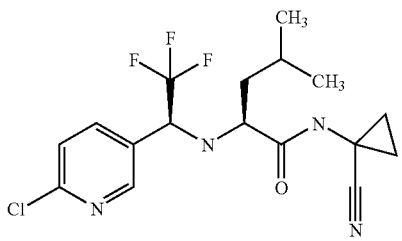

Step 1: Preparation of (2S)-2-{[(1S)-1-(6-chloropyridin-3-yl)-2,2,2-trifluoroethyl]amino}-4-methylpentan-1-ol To a solution of 5-bromo-2-chloropyridine (2.5 g, 13 mmol) in ether (30 mL) at −78° C. was added n-butyllithium (13 mmol, 2.5 M in hexane). The mixture was stirred at −78° C. for 1 h. (2S)-1-{[tert-butyl(dimethyl)silyl]oxy}-4-methyl-N-[(1E)-2,2,2-trifluoroethylidene]pentan-2-amine (3.64 g, 11.7 mmol, see Step 2, Example 8) was added. The mixture was stirred at −78° C. for 2 h. Saturated aqueous NH$_4$Cl was added to the reaction mixture and the mixture was extracted twice with EtOAc. The combined organic extracts were washed with brine, dried over anhyd. MgSO$_4$ and concentrated to an oil (5.3 g). The crude oil (2.0 g) was then treated with (Bu)$_4$NF (6 mL, 1M in THF). The mixture was stirred at rt for 1 h, saturated aqueous NH$_4$Cl was added and the mixture was extracted twice with EtOAc. The combined organic extracts were washed with brine, dried over anhyd. MgSO$_4$ and concentrated to an oil. Chromatography (20% EtOAc/hexane) afforded the title compound.

Step 2: Preparation of N-[(1S)-1-(6-chloropyridin-3-yl)-2,2,2-trifluoroethyl]-L-leucine A stock solution of H$_5$IO$_6$/CrO$_3$ was prepared by dissolving H$_5$IO$_6$ (68.4 g, 0.3 mol) and CrO$_3$ (138 mg, 1.2 mol %) in CH$_3$CN (684 mL) to give a 0.44 M solution. To a solution of H$_5$IO$_6$/CrO$_3$ (16 mmol, 36 mL, 0.44 M in THF) at −5° C. (ice and salt bath) was added a solution of (2S)-2-{[(1S)-1-(6-chloropyridin-3-yl)-2,2,2-trifluoroethyl]amino}-4-methylpentan-1-ol (1 g) in 3 mL THF dropwise. The internal temperature was monitored and reaction temperature was not allowed to rise above 0° C. The reaction was monitored by TLC until the reaction was complete (3-4 h). Na$_2$HPO4 (80 mL) was added to the reaction mixture which was then extracted with EtOAc. The organic extract was washed with brine, NaHSO$_3$ (120 mL) and brine again, dried over anhyd. MgSO$_4$ and concentrated to an oil. The oil was redissolved in EtOAc and filtered through a short pad of silica gel, eluted with EtOAc and the filtrated was concentrated to give the title compound.

Step 3: Preparation of N²-[(1S)-1-(6-chloropyridin-3-yl)-2,2,2-trifluoroethyl]-N¹-(1-cyanocyclopropyl)-L-leucinamide To a solution of the crude acid (0.73 g, 2.25 mmol) from Step 2 in DMF (12 mL) was added 1-aminocyclopropanecarbonitrile hydrochloride (0.4 g, 3.37 mmol.) and HATU (0.86 g, 2.25 mmol). Diisopropylethylamine (1.96 mL, 11.24 mmol) was added, the mixture was stirred at rt for 20 h. EtOAc and water were added. The mixture was separated after agitation and the organic extract was washed with water and brine and dried over anhyd. MgSO4. Concentration of the organic extract followed by chromatography (30-50% EtOAc/hexane) gave the title compound.

MS (+ESI): 389.3 [M+1]$^+$.

$^1$H NMR (500 MHz, CD$_3$COCD$_3$): δ 0.92 (d, 3H, J=6.6 Hz), 0.93 (d, 3H, J=6.6 Hz), 1.00 (m, 1H), 1.09 (m, 1H), 1.45 (m, 4H), 1.90 (m, 1H), 2.81 (m, 1H), 3.43 (m, 1H), 4.47 (m, 1H), 7.54 (d, 1H, J=8.3 Hz), 7.98 (d, 1H J=6.2 Hz), 8.1 (s, 1H), 8.5 (s, 1H).

EXAMPLE 14

Synthesis of N²-{(1S)-1-[6-(4-acetylphenyl)pyridin-3-yl]-2,2,2-trifluoroethyl}-N¹-(1-cyanocyclopropyl)-L-leucinamide

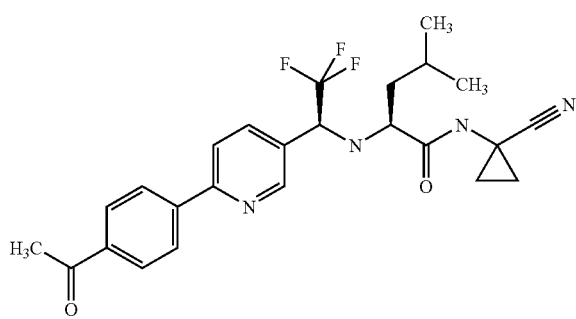

To a solution of N²-[(1S)-1-(6-chloropyridin-3-yl)-2,2,2-trifluoroethyl]-N¹-(1-cyanocyclopropyl)-L-leucinamide (100 mg, 0.26 mmol) in toluene (1.5 mL) and n-propanol (0.4 mL) was added under a stream of nitrogen, 4-(acetyl) phenylboronic acid (55 mg, 0.33 mmol ), Pd(PPh₃)₄ (15 mg, 0.013 mmol) and Na₂CO₃ (2 M, 0.5 mL). The mixture was degassed with a rapid stream of nitrogen bubbling through the mixture and the mixture was heated to 150° C. in a Smith Creator microwave reactor (Personal Chemistry AB, Uppsala, Sweden) for 800 sec. The mixture was cooled, diluted with EtOAc and washed with water. Chromatography (50% EtOAc/Hexane) gave the title compound.

MS (+ESI): 473.2 [M+1]⁺.

¹H NMR (500 MHz, CD₃COCD₃): δ 0.93 (d, 3H, J=6.6 Hz), 0.94 (d, 3H, J=6.6 Hz), 1.07 (m, 1H), 1.40 (m, 2H), 1.49 (m, 1H), 1.55 (m, 1H), 1.92 (m, 1H), 2.66 (s, 3H), 2.83 (m, 2H), 3.45 (m, 1H), 4.50 (m, 1H), 8.15 (m, 5H), 8.30 (d, 2H, J=8.5 Hz), 8.79 (s, 1H).

EXAMPLE 15

Synthesis of of N¹-(1-cyanocyclopropyl)-4-fluoro-N²-{(1S)-2,2,2-trifluoro-1-[4'-(methylsulfonyl)-1,1'-biphenyl-4-yl]ethyl}-L-leucinamide

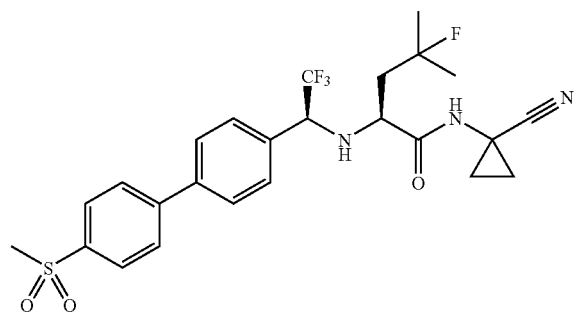

Step 1: Preparation of benzyl (3S)-3-[(tert-butoxycarbonyl)amino]-4-hydroxybutanoate N-(tert-Butoxycarbonyl)-L-aspartic acid 4-benzyl ester (30 g) was dissolved in dimethoxyethane (90 mL) and the solution was cooled to −5° C. N-Methylmorpholine (10.32 mL) was added followed by a slow addition of isobutyl chloroformate (12.66 mL) such that the reaction temperature was kept below −10° C. The mixture was aged for 0.5 hour. The solids were quickly filtered and washed with dimethoxyethane (90 mL). The filtrate was cooled to −50° C. and a solution of sodium borohydride (4.4 g) in water (45 mL) was added slowly such that the reaction temperature was maintained between −30° C. and −15° C. Water (500 mL) was then added such that the reaction mixture temperature was maintained below −15° C. The suspension was filtered, the solid washed with water (400 mL) and dried to yield benzyl (3S)-3-[(tert-butoxycarbonyl)amino]-4-hydroxybutanoate.

¹H NMR (CD₃COCD₃) δ 7.3-7.45 (5H, m), 5.85-5.95 (1H, NH), 5.15 (2H, s), 3.95-4.1 (2H, m), 3.5-3.7 (2H, m), 2.55-2.75 (2H, m), 1.4 (9H, s).

Step 2: Preparation of benzyl [(4S)-2-oxo-1,3-oxazolidin-4-yl]acetate

To a solution of the alcohol (95.7 g) from Step 1 in dichloroethane (925 mL) was added pyridine (625 mL) and the mixture was cooled to 0-5° C. Anhydrous p-toluenesulfonic anhydride (105.7 g) was added and the mixture was warmed to room temperature and stirred for 1 hour and then heated to 90° C. for 2 hours. The mixture was cooled, diluted with dichloromethane (1000 mL) and washed with 1N HCl (3×600 mL). The organic layer was washed with brine, dried with sodium sulfate and the solvents were removed in vacuo. The residue was purified by chromatography on SiO₂ using ethyl acetate and hexanes in a 1:1 ratio followed by ethyl acetate to yield benzyl [(4S)-2-oxo-1,3-oxazolidin-4-yl]acetate.

¹H NMR (CD₃SOCD₃) δ 7.8 (1H, NH), 7.3-7.45 (5H, m), 5.05-5.15 (2H, m), 4.4-4.5 (1H, m), 4.1-4.2 (1H, m), 4.0-4.05 (1H, m), 3.6-3.8 (2H, m).

Step 3: Preparation of (4S)-4-(2-hydroxy-2-methylpropyl)-1,3-oxazolidin-2-one

Methylmagnesium bromide (227 mL of 3M solution in diethyl ether) was added to a mixture of toluene (340 mL) and THF (340 mL) at −20° C. A warm THF solution (170 mL) of the ester from Step 2 (40 g) was then added dropwise maintaining the temperature below −10° C. The mixture was aged for 2 hours and was then slowly added to a mixture of water (1000 mL) and acetic acid (200 mL) and the resultant mixture was stirred for 2 hours at room temperature. The aqueous layer was separated and the organic layer was extracted with water (2×200 mL). The product was extracted from the combined aqueous layers using dichloromethane and a continuous extractor. The dichloromethane extract was evaporated to dryness using heptane as a co-solvent to azeotrope off the acetic acid. The residue was purified by chromatography on SiO₂ using ethanol and dichloromethane (1:30) to yield (4S)-4-(2-hydroxy-2-methylpropyl)-1,3-oxazolidin-2-one.

¹H NMR (CD₃COCD₃) δ 6.1-6.4 (1H, NH), 4.45-4.55 (1H, m), 4.1-4.2 (1H, m), 3.95-4.05 (1H, m), 3.7 (1H, s), 1.65-1.85 (2H, m), 1.25 (6H, m).

Step 4: Preparation of (4S)-4-(2-fluoro-2-methylpropyl)-1,3-oxazolidin-2-one

A dichloromethane solution (100 mL) of the alcohol (47.8 g) from Step 3 was added to a −70° C. solution of (diethylamino)sulfur trifluoride (48.5 g) in dichloromethane (500 mL). The mixture was warmed to room temperature and stirred for 1 hour. The mixture was then carefully added to a 0° C. mixture of saturated aqueous NaHCO$_3$ (800 mL). The organic layer was separated and washed with saturated aqueous NaHCO$_3$. The aqueous was further extracted with dichloromethane (100 mL) and the combined dichloromethane layers were dried and concentrated. The residue was purified by chromatography on SiO$_2$ using ethyl acetate and hexanes (1:5) followed by ethyl acetate to yield (4S)-4-(2-fluoro-2-methylpropyl)-1,3-oxazolidin-2-one.

$^1$H NMR (CD$_3$SOCD$_3$) δ 7.6 (1H, NH), 4.4-4.5 (1H, m), 3.95-4.05 (1H, m), 3.9-3.95 (1H, m), 1.8-1.95 (2H, m), 1.25-1.4 (6H, 2s).

Step 5: Preparation of (2S)-2-amino-4-fluoro-4-methylpentan-1-ol

To a solution of the fluoro derivative (21.0 g) from Step 4 in 90% aqueous ethyl alcohol (216 mL) was added potassium hydroxide (21.9 g). The mixture was heated at reflux for 4 hours and cooled to room temperature. The mixture was then concentrated and co-evaporated with toluene (3×300 mL). The residue was dissolved in dichloromethane (500 mL) and stirred for 0.5 hour. The suspension was filtered through celite and the celite was washed with dichloromethane (3×100 mL). The filtrate was concentrated to dryness to yield (2S)-2-amino-4-fluoro-4-methylpentan-1-ol.

$^1$H NMR (CD$_3$OD) δ 3.4-3.5 (1H, m), 3.2-3.3 (1H, m), 3.0-3.1 (1H, m), 1.5-1.7 (2H, m), 1.35 (3H, s), 1.3 (3H, s).

Step 6: Preparation of (2S)-1-{[tert-butyl(dimethyl)silyl]oxy}-4-fluoro-4-methylpentan-2-amine The amino alcohol (21.0 g) from Step 5 was dissolved in dichloromethane (300 mL) and the solution was cooled to 0° C. 4-(Dimethylamino)pyridine (0.051 g) and tert-butyldimethylsilyl chloride (21 g) were added followed by triethylamine (25 mL). The mixture was stirred at room temperature overnight. The reaction mixture was slowly poured into 0° C. saturated aqueous ammonium chloride and extracted with dichloromethane (3×300 mL). The organic layer was washed with brine, dried with sodium sulfate and the solvents were removed in vacuo to yield (2S)-1-{[tert-butyl(dimethyl)silyl]oxy}-4-fluoro-4-methylpentan-2-amine.

$^1$H NMR (CD$_3$OD) δ 3.6-3.65 (1H, m), 3.4-3.5 (1H, m), 3.1-3.2 (1H, m), 1.6-1.8 (2H, m), 1.35-1.45 (6H, m), 0.93 (9H, s), 0.1 (6H, s).

Step 7: Preparation of (2S)-1-{[tert-butyl(dimethyl)silyl]oxy}-4-fluoro-4-methyl-N-[(1E)-2,2,2-trifluoroethylidene]pentan-2-amine To a solution of the amine (31.5 g) from Step 6 in benzene (126 mL) was added trifluoroacetaldehyde methyl hemiacetal (21.6 mL.). The solution was heated at reflux overnight using a Dean-Stark trap to collect water. The reaction mixture was cooled to room temperature and concentrated to dryness. The residue was purified on SiO$_2$ using 4% of ethyl acetate in hexanes to yield (2S)-1-{[tert-butyl(dimethyl)silyl]oxy}-4-fluoro-4-methylpentan-2-amine.

$^1$H NMR (CD$_3$COCD$_3$) δ 7.9-7.95 (1H, m), 3.75-3.85 (1H, m), 3.7-3.75 (1H, m), 3.53-3.6 (1H, m), 1.9-2.0 (2H, m), 1.3-1.4 (6H, m), 0.9 (9H, s), 0.1 (3H, s), 0.05 (3H, s).

Step 8: Preparation of (2S)-2-{[(1S)-1-(4-bromophenyl)-2,2,2-trifluoroethyl]amino}-4-fluoro-4-methylpentan-1-ol To a −75° C. solution of 1,4-dibromobenzene (0.26 g) in THF (4 mL) was added n-BuLi (0.42 mL of a 2.5M hexanes solution) and the mixture was aged for 20 minutes. The imine (0.329 g) from Step 7 in THF (2 mL) was added and the mixture was aged 2 hours. The mixture was then added to a mixture of water (50 mL), NH$_4$Cl (1 g) and crushed ice. It was extracted with ethyl acetate (2×25 mL) and the combined ethyl acetate layers were dried and evaporated to dryness.

The same procedure was repeated on a larger scale using 1,4-dibromobenzene (1.2 g), n-BuLi (1.84 mL) and the imine (1.38 g) and the reaction mixture was treated as above. The combined residues from both preparations were dissolved in THF (10 mL) and cooled to 0° C. n-Tetrabutylammonium flurroride (6 mL from a 1M THF solution) was added and the mixture was stirred at +5° C. for 16 h. The mixture was poured into a mixture of water (50 mL), ammonium chloride (1 g) and crushed ice and the organic layer was separated. The aqueous was further extracted with ethyl acetate (2×15 mL) and the combined organic layers were dried and concentrated. The residue was purified on SiO$_2$ using ethyl acetate and hexanes (1:5) to yield (2S)-2-{[(1S)-1-(4-bromophenyl)-2,2,2-trifluoroethyl]amino}-4-fluoro-4-methylpentan-1-ol.

1H NMR (CD$_3$COCD$_3$) δ 7.65 (2H, m), 7.5 (2H, m), 4.5-4.6 (1H, m), 3.8 (1H, m), 3.6 (1H, m), 3.3-3.4 (1H, m), 2.85-2.0 (1H, m), 2.55 (1H, m), 1.7-1.9 (2H, s), 1.3-1.4 (6H, m).

Step 9: Preparation N$^2$-[(1S)-1-(4-bromophenyl)-2,2,2-trifluoroethyl]-N$^1$-(1-cyanocyclopropyl)-4-fluoro-L-leucinamide A suspension of H$_5$IO$_6$/CrO$_3$ (66 mL of 0.44 M in CH$_3$CN; Note) was cooled to 0° C. and a solution of the alcohol from Step 8 (1.55 g) in CH$_3$CN (5 mL) was added dropwise. The mixture was stirred at 0-5° C. for 3.5 hours. It was poured into pH 4 Na$_2$HPO$_4$ (200 mL) under vigorous stirring and the mixture was extracted with diethyl ether (3×50 mL). The combined ether extracts were washed with water and brine (1:1) followed by dilute aqueous NaHSO$_3$ and brine. The mixture was dried with sodium sulfate, filtered and the solvents were evaporated to dryness to yield of N-[(1S)-1-(4-bromophenyl)-2,2,2-trifluoroethyl]-4-fluoro-L-leucine which was used as such in the next step.

Note. The oxidizing reagent (H$_5$IO$_6$/CrO$_3$) was prepared as described in Tetrahedron Letters 39 (1998) 5323-5326 but using HPLC grade CH$_3$CN (contains 0.5% water); no water was added.

Diisopropylethylamine (4.2 mL) was added to a 0° C. suspension of the acid (1.5 g) from above, 1-amino-1-cyclopropanecarbonitrile hydrochloride (1.18 g), O-(7-azabenzotriazol-1-yl)-N,N,N',N'-tetramethyluronium hexafluorophosphate (1.94 g) and dimethylformamide (5 mL) and the mixture was reacted at room temperature for 48 h. It was then poured on ice and dilute aqueous ammonium chloride. The mixture was extracted with ethyl acetate and ether (1:1) and the combined organic layers were washed with pH 3 dilute Na$_2$HPO$_4$ and brine. The solvents were evaporated to dryness and the residue was purified by chromatography on SiO$_2$ using ethyl acetate and hexanes (1:2) to yield N$^2$-[(1S)-

1-(4-bromophenyl)-2,2,2-trifluoroethyl]-N¹-(1-cyanocyclopropyl)-4-fluoro-L-leucinamide in a sufficient purity state for the next step.

¹H NMR (CD₃COCD₃) δ 8.15 (1H, NH), 7.6 (2H, m), 7.45 (2H, m), 4.35-4.45 (1H, m), 3.45-3.55 (1H, m), 1.9-2.1 (2H, m), 1.75-1.85 (1H, NH),1.35-1.55 (8H, m), 1.1-1.15 (1H, m), 0.95-1.05 (1H, m).

Step 10: Preparation of N¹-(1-cyanocyclopropyl)-4-fluoro-N²-{(1S)-2,2,2-trifluoro-1-[4'-(methylthio)-1,1'-biphenyl-4-yl]ethyl}-L-leucinamide A stream of nitrogen was passed through a suspension of the bromide from Step 9 (0.338 g), 4-(methylthio)phenylboronic acid (0.252 g), 2M aqueous Na₂CO₃ (0.8 mL) and DMF (4 mL) for 15 minutes. PdCl₂ dppf (0.1 g) was then added and the reaction was warmed to 85° C. and stirred under nitrogen for 5 hours. The mixture was cooled to room temperature, diluted with ethyl acetate (10 mL) and poured into water (50 mL) and ice. The ethyl acetate layer was separated and the aqueous further extracted with ethyl acetate. The combined ethyl acetate extracts were dried and the solvents removed in vacuo. The residue was purified by chromatography on SiO₂ using ethyl acetate and hexanes (1:2) to yield N¹-(1-cyanocyclopropyl)-4-fluoro-N²-{(1S)-2,2,2-trifluoro-1-[4'-(methylthio)-1,1'-biphenyl-4-yl]ethyl}-L-leucinamide.

¹H NMR (CD₃COCD₃) δ 8.15 (1H, NH), 7.1-7.2 (4H, m),7.5-7.55 (2H, m), 7.35-7.4 (2H, m), 4.3-4.4 (1H, m), 3.45-3.55 (1H, m), 2.75-2.8 (1H, NH), 2.5 (3H, s), 1.9-2.05 (2H, m), 1.3-1.5 (8H, m), 1.0-1.1 (1H, m), 0.85-0.95 (1H, m).

Step 11: Preparation of N¹-(1-cyanocyclopropyl)-4-fluoro-N²-{(1S)-2,2,2-trifluoro-1-[4'-(methylsulfonyl)-1,1'-biphenyl-4-yl]ethyl}-L-leucinamide To a 0° solution of the sulfide (0.265 g) from Step 10 in toluene (5 mL) and dichloromethane (5 mL) was added Na₂WO₄.2H₂O (0.002 g) and n-Bu₄NHSO₄ (0.01 g). 30% Hydrogen peroxide (0.137 mL) was then slowly added and the mixture was stirred at room temperature for 3 hours. The mixture was poured slowly onto a mixture of ice, dilute aqueous sodium thiosulfate and ethyl acetate. The organic layer was separated and the aqueous further extracted with ethyl acetate. The combined organic layers were washed with brine, dried with magnesium sulfate and the solvent was removed in vacuo to yield a residue which was purified on SiO₂ using ethyl acetate, hexanes and dichloromethane (1:1:0.1) as eluant. The residue was triturated in diethyl ether to yield N¹-(1-cyanocyclopropyl)-4-fluoro-N²-{(1S)-2,2,2-trifluoro-1-[4'-(methylsulfonyl)-1,1'-biphenyl-4-yl]ethyl}-L-leucinamide.

¹H NMR (CD₃COCD₃) δ 8.2 (1H, NH), 8.05-8.1 (2H, m), 7.95-8.0 (2H, m), 7.8 (2H, m), 7.65 (2H, m), 4.35-4.45 (1H, m), 3.5-3.6 (1H, m), 3.2 (3H, s), 2.8-2.9 (1H, NH), 1.9-2.1 (2H, m), 1.3-1.5 (8H, m), 1.05-1.15 (1H, m), 0.9-1.0 (1H, m).

EXAMPLE 16

Synthesis of (4S)-N¹-(1-cyanocyclopropyl)-5,5,5-trifluoro-N²-{(1S)-2,2,2-trifluoro-1-[4'-(methylsulfonyl)-1,1'-biphenyl-4-yl]ethyl}-L-leucinamide

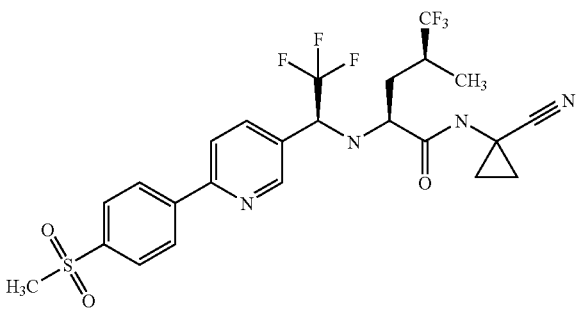

Step 1: Preparation of 5,5,5-Trifluoroleucine hydrochloride salt

A racemic diastereomeric mixture of ethyl N-benzoyl-5,5,5-trifluoroleucinate (10.0 g, 31.5 mmol), prepared according to the procedure of Ojima et. al. (J. Org. Chem., 1989, 54, 4511-4522.), was refluxed in 6M aqueous HCl (100 mL) for 16 h. After cooling, the mixture was washed with Et₂O and concentrated in vacuo to afford a racemic diastereomeric mixture of 5,5,5-trifluoroleucine HCl salt.

¹H NMR (Methanol-d₄) δ 4.10 (m, 1H), 2.65 (m, 1H), 2.35-1.80 (m, 2H), 1.25 (m, 3H).

Step 2: Methyl (4S)-N-[(benzyloxy)carbonyl]-5,5,5-trifluoro-L-leucinate and methyl (4R)-N-[(benzyloxy)carbonyl]-5,5,5-trifluoro-L-leucinate To a cold (0° C.) solution of the 5,5,5-trifluoroleucine HCl salt (from Step 1 above) in H₂O (30 mL) was added 1M aqueous NaOH (60 mL, 60 mmol) followed by acetic anhydride (3.5 mL, 36.7 mmol). The mixture was stirred at room temperature for 30 min to 1 h. After acidification with 6M aqueous HCl (6 mL), the mixture was extracted with EtOAc (6×). The combined EtOAc extracts were washed with brine, dried (MgSO₄) and concentrated. The residue was swished with hexanes:Et₂O (1:1) to afford N-acetyl-5,5,5-trifluoroleucine as a white solid.

To a suspension of N-acetyl-5,5,5-trifluoroleucine (4.2 g, 18.5 mmol) in H₂O (35 mL) was added 1 M aqueous NaOH (18.5 mL, 18.5 mmol) and the mixture was stirred for 15 to 30 min to give a homogenous solution. Acylase I (EC 3.5.1.14, from Sigma, Cat. # A 3010; 55 mg) was added and the mixture was stirred at room temperature overnight. Crude NMR of a small aliquot (evaporated under vacuum) showed a ratio of 53:47 for starting material and product. The mixture was then acidified with 6M aqueous HCl (~3.5 mL) and extracted with EtOAc (4×, each EtOAc extraction was washed with a small amount of H₂O). The combined EtOAc extracts were washed with brine, dried (MgSO₄) and concentrated to afford the crude N-acetyl-5,5,5-trifluoro-D-leucine as a pale yellow solid, $[\alpha]_D$=+27.6° (c 1.5, EtOH). The aqueous layer was concentrated under vacuum and dried under vacuum overnight to afford 5,5,5-trifluoro-L-leucine, probably contaminated with NaCl and HCl salts, $[\alpha]_D$=−4.1° (c 0.77, H₂O).

To a stirred solution of the 5,5,5-trifluoro-L-leucine (12 g) in H₂O (150 mL) at 0° C. was added benzyl chloroformate (4.8 mL, 34 mol), followed by dropwise addition of 1 M aqueous NaOH (120 mL, 120 mmol). More benzyl chloroformate (4.8 mL, 34 mmol) was added. The mixture was further stirred at 0° C. and the pH of the mixture became ~7. The mixture was washed with Et₂O (2×) and acidified with aqeous HCl. The aqueous layer was extracted with EtOAc (3×), dried (Na₂SO₄) and concentrated in vacuo to provide N-[(benzyloxy)carbonyl]-5,5,5-trifluoro-L-leucine. The crude acid was dissolved in Et₂O and treated with a solution of diazomethane in Et₂O. Chromatography over silica gel and elution with hexanes:Et₂O (7:3) gave methyl (4S)-N-[(benzyloxy)carbonyl]-5,5,5-trifluoro-L-leucinate as the less polar fraction.

1H NMR (Acetone-d₆) δ 7.45-7.25 (m, 5H), 6.86 (d, 1H), 5.10 (m, 2H), 4.38 (m, 1H), 3.70 (s, 3H), 2.45 (m, 1H), 2.05 (m, 1H), 1.85 (m, 1H), 1.16 (d, 3H).

Further elution afforded (4R)-N-[(benzyloxy)carbonyl]-5,5,5-trifluoro-L-leucinate as the more polar fraction, contaminated with small amount of benzyl alcohol.

1H NMR (Acetone-d₆) δ 7.40-7.25 (m, 5H), 6.86 (d, 1H), 5.08 (s, 2H), 4.35 (m, 1H), 3.70 (s, 3H), 2.54 (m, 1H), 2.20 (m, 1H), 1.75 (m, 1H), 1.16 (d, 3H).

Step 3: (2S,4S)-2-amino-5,5,5-trifluoro-4-methylpentan-1-ol

To a solution of methyl (4S)-N-[(benzyloxy)carbonyl]-5,5,5-trifluoro-L-leucinate (5.4 g, 16.2 mmol) in EtOH (150 mL) at room temperature was added LiCl (2.8 g, 66 mol) and the mixture was stirred for 10 to 15 min, followed by the addition of NaBH₄ (2.5 g, 66 mmol). The mixture was stirred at room temperature for 6 h. After dilution with H₂O (60 mL), the mixture was quenched with 6M aqueous HCl (18 mL). More H₂O was added and the mixture was extracted with EtOAc (2×). The combined EtOAc extracts were washed with brine, dried (Na₂SO₄) and concentrated to give the crude benzyl (1S,3S)-4,4,4-trifluoro-1-(hydroxymethyl)-3-methylbutylcarbamate.

The above alcohol was dissolved in EtOH (150 mL) and 10% Pd/C (~500 mg) was added. The mixture was stirred under a H₂ atmosphere (ballon) overnight. The catalyst was filtered off through celite and the filtrate was concentrated to give the title compound as a colorless oil.

1H NMR (Methanol-d₄) δ 3.48 (dd, 1H), 3.38 (dd, 1H), 2.85 (m, 1H), 2.50 (m, 1H), 1.62-1.40 (m, 2H), 1.12 (d, 3H).

Step 4: (2S,4S)-1-{[tert-butyl(dimethyl)silyl]oxy}-5,5,5-trifluoro-4-methyl-N-[(1E)-2,2,2-trifluoroethylidene]pentan-2-amine (2S,4S)-2-Amino-5,5,5-trifluoro-4-methylpentan-1-ol (2.6 g, 15.2 mmol) was converted to the title compound as described in Steps 1 and 2, Example 8.

¹H NMR (Acetone-d₆) δ 7.98 (m, 1H), 3.80 (m, 1H), 3.60 (m, 2H), 2.18 (m, 1H), 1.98 (m, 1H), 1.65 (m, 1H), 1.12 (d, 3H), 0.88 (s, 9H), 0.06 (s, 3H), 0.02 (s, 3H).

Step 5: (2S,4S)-2-{[(1S)-1-(4-bromophenyl)-2,2,2-trifluoroethyl]amino}-5,5,5-trifluoro-4-methylpentan-1-ol To a cold (−78° C.) solution of 1,4-dibromobenzene (7.0 g, 29.7 mmol) in Et₂O (75 mL) at was added dropwise a solution of 2.5 M n-BuLi in hexanes (7.0 mL, 17.5 mmol) and the mixture was stirred for 2 h at −78° C. A solution of (2S,4S)-1-{[tert-butyl(dimethyl)silyl]oxy}-5,5,5-trifluoro-4-methyl-N-[(1E)-2,2,2-trifluoroethylidene]pentan-2-amine (3.7 g, 10.1 mmol) in a small amount of Et₂O was added and the mixture was further stirred at −78° C. for an additional 1 h. The mixture was then quenched with H₂O, extracted with EtOAc, dried (MgSO₄) and concentrated.

The crude product from above was dissolved in THF (20 mL) and HOAc (0.3 mL) was added. After addition of a solution of 1M of tetrabutylammonium fluoride in THF (20 mL, 20 mmol), the mixture was stirred at room temperature overnight. Solvent was removed in vacuo, the residue was diluted with H₂O and extracted with EtOAc. The EtOAc extract was washed with brine, dried (MgSO₄) and concentrated. Chromatography over silica gel and elution with hexanes:EtOAc (4:1) afforded the title compound as a pale yellow oil.

¹H NMR (Acetone-d₆) δ 7.60 (d, 2H), 7.48 (d, 2H), 4.58 (m, 1H), 3.80 (t, 1H), 3.45 (m, 2H), 2.90 (m, 1H), 2.70 (m, 1H), 2.25 (m, 1H), 1.75 (m, 1H), 1.45 (m, 1H), 1.14 (d, 3H).

Step 6: (4S)-N-[(1S)-1-(4-bromophenyl)-2,2,2-trifluoroethyl]-5,5,5-trifluoro-L-leucine The title compound was prepared as described in Step 9, Example 15 from (2S,4S)-2-{[(1S)-1-(4-bromophenyl)-2,2,2-trifluoroethyl]amino}-5,5,5-trifluoro-4-methylpentan-1-ol.

¹H NMR (Acetone-d₆) δ 7.58 (d, 2H), 7.46 (d, 2H), 4.46 (m, 1H), 3.58 (dd, 1H), 2.80 (m, 1H), 1.92 (m, 1H), 1.72 (m, 1H), 1.20 (d, 3H).

Step 7: (4S)-N²-[(1S)-1-(4-bromophenyl)-2,2,2-trifluoroethyl]-N¹-(1-cyanocyclopropyl)-5,5,5-trifluoro-L-leucinamide The title compound was prepared as described in Step 9, Example 15 from (4S)-N-[(1S)-1-(4-bromophenyl)-2,2,2-trifluoroethyl]-5,5,5-trifluoro-L-leucine.

¹H NMR (Acetone-d₆) δ 8.20 (br s, 1H), 7.59 (d, 2H), 7.43 (d, 2H), 4.34 (m, 1H), 3.48 (m, 1H), 2.78 (m, 1H), 1.85 (m, 1H), 1.55 (m, 1H), 1.39 (m, 2H), 1.14 (d, 3H), 1.15-0.90 (m, 2H).

MS (+ESI): 486, 488 [M+1]⁺.

Step 8: (4S)-N¹-(1-cyanocyclopropyl)-5,5,5-trifluoro-N²-{(1S)-2,2,2-trifluoro-1-[4'-(methylsulfonyl)-1,1'-biphenyl-4-yl]ethyl}-L-leucinamide The title compound was prepared as described in Steps 10 and 11, Example 15 from (4S)-N²-[(1S)-1-(4-bromophenyl)-2,2,2-trifluoroethyl]-N¹-(1-cyanocyclopropyl)-5,5,5-trifluoro-L-leucinamide.

[α]_D=+66° (c 0.5, acetone).

¹H NMR (Acetone-d₆) δ 8.20 (br s, 1H), 8.03 (d, 2H), 7.94 (d, 2H), 7.78 (d, 2H), 7.62 (d, 2H), 4.41 (m, 1H), 3.52 (m, 1H), 3.17 (s, 3H), 2.88 (m, 1H), 1.98 (m, 1H), 1.58 (m, 1H), 1.35 (m, 2H), 1.16 (d, 3H), 1.15-0.85 (m, 2H).

MS (+ESI): 562 [M+1]⁺.

EXAMPLE 17

Synthesis of N-benzyl-1-(benzyloxy)-4-fluoro-4-methylpentan-2-amine

Step 1: Preparation of N-(tert-butoxycarbonyl)-4-methylenenorvaline

To a solution of dehydro-L-leucine (2.00 g, 15.48 mmol) and di-tert-butyldicarbonate (10.14 g, 46.4 mmol) in THF (ca 100 mL) and water (ca 50 mL) was added triethylamine (12.94 mL, 92.8 mmol). The reaction mixture was stirred at ambient temperature overnight. Citric acid (ca 100 mL of a 1M aqueous solution) was added and the product was extracted into ca. 400 mL of methylene chloride. The organic phase was dried with sodium sulfate, filtered and concentrated by rotary evaporation. Purification by silica gel chromatography using 0-10% methanol in dichloromethane as eluant yielded the title compound.

Step 2: Preparation of tert-butyl 1-(hydroxymethyl)-3-methylbut-3-enylcarbamate To a solution of Boc-dehydro-L-leucine (2.84 g, 12.4 mmol) and 4-methylmorpholine (1.36 mL, 12.4 mmol) in dry THF (40 mL), equilibrated to −10° C., was added dropwise isobutylchloroformate (1.61 mL, 12.4 mmol). The reaction was allowed to stir for 30 minutes and the precipitate was removed by filtration. The filtrate was equilibrated at 0° C. and with stirring a solution of sodium borohydride (0.938 g, 24.8 mmol) in about 10 mL of water was added dropwise. The reaction was allowed to return to ambient temperature and stirred for an additional hour. The reaction was quenched with saturated aqueous sodium bicarbonate and the product was extracted into ethyl acetate. The organic layer was dried with magnesium sulfate, filtered, and concentrated by rotary evaporation to yield the title compound. MS (+ESI): 216.1 [M-boc-+1]$^+$

Step 3: Preparation of tert-butyl benzyl{1-[(benzyloxy)methyl]-3-methylbut-3-enyl}carbamate To a solution of Boc-dehydro-L-leucinol (2.56 g, 11.91 mmol) and benzyl bromide (3.54 mL, 29.8 mmol) in DMF (50 mL) was added sodium hydride (1.19 g of a 60% dispersion in mineral oil, 29.8 mmol) and the reaction was allowed to stir for 3 hours. Additional benzyl bromide (3.54 mL) and sodium hydride dispersion (1.19 g) were added and the reaction was allowed to stir an additional 16 hours. Water (ca 100 mL) was added and the product was extracted twice into dichloromethane (100 mL). The organic phases were combined and washed twice with about 100 mL of water. The organic phase was dried with magnesium sulfate, filtered, and concentrated by rotary evaporation. Purification by silica gel chromatography using a gradient of 0-5% ethyl acetate in hexanes yielded the title compound.

Step 4: Preparation of N-benzyl-1-(benzyloxy)-4-fluoro-4-methylpentan-2-amine A solution of 70% hydrogen fluoride in pyridine (3.75 mL) was equilibrated to 0° C. in a polypropylene vessel. A solution of N-benzyl-boc-(L)-leucinol benzyl either (1.52 g, 3.85 mmol) was added and the reaction mixture was allowed to stir for 6 hours. The reaction vessel was then equilibrated in an ice bath and allowed to react for 5 days. The reaction was quenched by addition of ice water and the product was extracted into methylene chloride. Purification of silica gel chromatography using a gradient of 0-10% methanol in dichloromethane yielded the title compound.

MS (+ESI): 316.0 [M+1]$^+$

EXAMPLE 18

Synthesis of (2S)-5,5,5-trifluoro-2-({(1S)-2,2,2-trifluoro-1-[4'-(methylsulfonyl)-1,1'-biphenyl-4-yl]ethyl}amino)pentanoic acid cyanomethyl amide

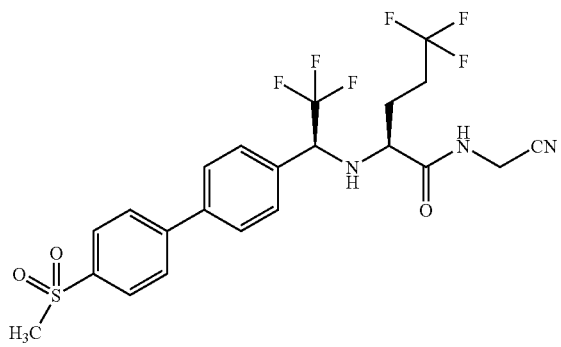

Step 1: Preparation of 2-benzyloxycarbonylamino-5,5,5-trifluoro-pent-2-enoic acid methyl ester N-(Benzyloxycarbonyl)-α-phosphonoglycine trimethyl ester and DBU were dissolved in dry methylene chloride (50 mL) and the reaction mixture was chilled to −30° C. 3,3,3-Trifluoropropanal (1 eq) was added dropwise to the chilled and stirred solution and the reaction was allowed to stir for an additional hour at −30° C., and then overnight at ambient temperature. Methylene chloride (ca. 100 mL) was added and the organic phase was washed with 1N HCl (ca. 100 mL), then saturated brine (ca. 100 mL). The organic phase was dried over MgSO$_4$, filtered, and concentrated by rotary evaporation. This crude product was purified by silica gel chromatography with a gradient of 10-30% ethyl acetate in hexanes to yield 2-benzyloxycarbonylamino-5,5,5-trifluoro-pent-2-enoic acid methyl ester as a white, crystalline solid.

MS (+ESI): 318.0 [M+1]$^+$

Step 2: Preparation of (S)-2-benzyloxycarbonylamino-5,5,5-trifluoropentanoic acid methyl ester 2-Benzyloxycarbonylamino-5,5,5-trifluoropent-2-enoic acid methylester (15.37 g, 48.5 mmol) was dissolved in absolute ethanol (100 mL) in a Parr hydrogenation vessel. The solution was sparged with a stream of nitrogen and then (+)Duphos (350 mg) was added. The reaction mixture was placed on a Parr hydrogenation apparatus and the headspace was evacuated and then pressurized with 50 psi of hydrogen. This process was repeated seven times and the vessel was then pressurized with 50 psi of hydrogen and agitated on the Parr apparatus overnight. The reaction mixture was then concentrated by rotary evaporation, dissolved in 1:1 ethyl acetate:hexanes, and filtered through a bed of silica to remove catalyst. The filtrate was concentrated by rotary evaporation yielding crude (S)-2-benzyloxycarbonylamino-5,5,5-trifluoropentanoic acid methyl ester that was carried forward without further purification.

Step 3: Preparation of (S)-(4,4,4-trifluoro-1-hydroxymethyl-butyl)-carbamic acid benzyl ester (2S)-2-Benzyloxycarbonylamino-5,5,5-trifluoropentanoic acid methyl ester from Step 2 was dissolved in dry THF (400 mL). A solution of LiBH$_4$ (2.11 g in 100 mL of dry THF) was added dropwise with stirring and the solution was allowed to stir at ambient temperature overnight. The reaction mixture was concentrated by rotary evaporation and 400 mL of water was added. The pH was then adjusted to pH 2 by addition of concentrated HCl and then the product was extracted into ethyl acetate. The organic phase was washed two times with water, dried with MgSO$_4$, filtered, and concentrated by rotary evaporation to yield crude (S)-(4,4,4-trifluoro-1-hydroxymethyl-butyl)-carbamic acid benzyl ester.

MS (−ESI): 290.2 [M−1]$^−$

Step 4: Preparation of [1-(tert-butyl-dimethyl-silanyloxymethyl)-4,4,4-trifluoro-butyl]-carbamic acid benzyl ester To a solution of (S)-(4,4,4-trifluoro-1-hydroxymethyl-butyl)-carbamic acid benzyl ester (13.89 g, 47.7 mmol) and triethylamine (7.32 mL, 52.5 mmol) in DMF (60 mL) was added dropwise, with stirring, a solution of t-butyldimethylsilyl chloride (7.91 g in 40 mL of DMF) at ambient temperature. The solution was allowed to stir overnight at ambient temperature. The reaction mixture was then concentrated by rotary evaporation and ethyl acetate was added. The organic phase was washed twice with water, dried with MgSO$_4$, filtered, and concentrated by rotary evaporation. The crude product was purified by silica gel chromatography using 10% ethyl acetate in hexanes as eluant to yield [1-(tert-butyl-dimethyl-silanyloxymethyl)-4,4,4-trifluoro-butyl]-carbamic acid benzyl ester as a white crystalline solid.

MS (+ESI): 406.2 [M+1]$^+$

Step 5: Preparation of (2S)-1-{[tert-butyl(dimethyl)silyl]-oxy}-5,5,5-trifluoro-pentan-2-amine

[1-(tert-Butyldimethyl-silanyloxymethyl)-4,4,4-trifluorobutyl]carbamic acid benzyl ester was dissolved in absolute ethanol (100 mL) in a Parr hydrogenation vessel and the solution was sparged with nitrogen. 10% Pd on carbon (1.8 g) was added and the vessel was placed on a Parr hydrogenation apparatus. The head space of the vessel was evacuated and then pressurized with 50 psi of hydrogen. This process was repeated seven times and the vessel was pressurized with 50 psi of hydrogen and then agitated on the apparatus overnight. The catalyst was removed by filtering through Celite® and then the reaction mixture was concentrated by rotary evaporation to yield (2S)-1-{[tert-butyl(dimethyl)silyl]-oxy}-5,5,5-trifluoro-pentan-2-amine.

MS (+ESI): 272.1 [M+1]$^+$

Step 6: Preparation of (2S)-1-{[tert-butyl(dimethyl)silyl]oxy}-5,5,5-trifluoro-N-[(1E)-2,2,2-trifluoroethylidene]pentan-2-amine A solution of (2S)-1-{[tert-butyl(dimethyl)silyl]oxy}-5,5,5-trifluoro-pentan-2-amine (3.00 g, 11.06 mmol) and trifluoroacetaldehyde ethyl hemiacetal (1.6 g, 11.1 mmol) in benzene (20 mL) was refluxed for 2 hours during which time water was collected in a Dean-Stark trap. The solvent was removed in vacuo yielding crude (2S)-1-{[tert-butyl(dimethyl)silyl]oxy}-5,5,5-trifluoro-N-[(1E)-2,2,2-trifluoroethylidene]pentan-2-amine.

MS (+ESI): 352.2 [M+1]$^+$

Step 7: Preparation of (2S)-2-{[(1S)-1-(4-bromophenyl)-2,2,2-trifluoroethyl]amino}-5,5,5-trifluoropentan-1-ol n-BuLi (2.5 M in hexanes, 21.4 mL) was added dropwise to a stirred solution of 1,4-dibromobenzene (12.6 g) in dry diethyl ether (80 mL) at −30° C. and the reaction mixture was stirred for 30 minutes. A solution of (2S)-1-{[tert-butyl(dimethyl)silyl]oxy}-5,5,5-trifluoro-N-[(1E)-2,2,2-trifluoroethylidene]pentan-2-amine (3.75 g, 10.7 mmol) in dry diethyl ether (30 mL) was then added dropwise and the reaction mixture was allowed to warm to ambient temperature and stirred for 16 hours. The reaction mixture was then quenched with 100 mL of water. The organic phase was washed with brine, dried with magnesium sulfate, and filtered. The filtrate was concentrated by rotary evaporation to yield crude product which was purified by silica gel chromatography using 1% ethyl acetate in hexanes as eluant to yield (S)-[1-(4-bromophenyl)-2,2,2-trifluoro-ethyl]-[1-(tert-butyl-dimethyl-silanyloxymethyl)-4,4,4-trifluoro-butyl]-amine (1.8 g). (S)-[1-(4-Bromophenyl)-2,2,2-trifluoro-ethyl]-[1-(tert-butyl-dimethyl-silanyloxymethyl)-4,4,4-trifluoro-butyl]-amine was dissolved in THF (50 mL) and chilled to 0° C. and tert-butylammonium fluoride (10.6 mL, 1 M THF solution) was added dropwise. The reaction mixture was allowed to warm to ambient temperature and stirred for 4 hours. The reaction mixture was quenched with a saturated aqueous solution of ammonium chloride and then ethyl acetate was added and the mixture vigorously shaken. The organic layer was separated and washed two times with brine, dried with magnesium sulfate and filtered. The solvent was removed by rotary evaporation to yield a residue which was purified on SiO$_2$ using a gradient of 20-25% ethyl acetate in hexanes as eluant to yield (2S)-2-{[(1S)-1-(4-bromophenyl)-2,2,2-trifluoroethyl]amino}-5,5,5-trifluoropentan-1-ol.

MS (+ESI): 393.9, 395.8 [M+1]$^+$

Step 8: Preparation of (2S)-5,5,5-trifluoro-2-({(1S)-2,2,2-trifluoro-1-[4'-(methylsulfonyl)-1,1'-biphenyl-4-yl]ethyl}amino)pentan-1-ol A stream of nitrogen was passed through a suspension of (2S)-2-{[(1S)-1-(4-bromophenyl)-2,2,2-trifluoroethyl]amino}-5,5,5-trifluoropentan-1-ol (0.55 g), 2-(4-methanesulfonyl-phenyl)-4,4,5,5-tetramethyl-[1,3,2]dioxaborolane (0.59 g) 2.5 M K$_2$CO$_3$ (2.75 mL) and DMF (0.91 mL) for 20 minutes. [1,1'-Bis(diphenyl-phosphino)ferrocene]-palladium (II) chloride (1:1 complex with dichloromethane, 34 mg) was then added, the vessel sealed, and the reaction was warmed to 85° C. and stirred under nitrogen for 5 hours. The reaction mixture was cooled to room temperature, diluted with ethyl acetate (50 mL) and water (50 mL) and shaken vigorously. The ethyl acetate layer was separated and washed 3 times with water, dried with magnesium sulfate, and filtered. Removal of the solvent left a residue that was purified by chromatography on SiO$_2$ using a gradient of 10-30% ethyl acetate in hexanes. Rotary evaporation of appropriate fractions yielded (2S)-5,5,5-trifluoro-2-({(1S)-2,2,2-trifluoro-1-[4'-(methylsulfonyl)-1,1'-biphenyl-4-yl]ethyl}amino)pentan-1-ol.

Step 9: Preparation of (2S)-5,5,5-trifluoro-2-({(1S)-2,2,2-trifluoro-1-[4'-(methylsulfonyl)-1,1'-biphenyl-4-yl]ethyl}amino)pentanoic acid A stock oxidant suspension was prepared by stirring periodic acid (2.28 g) and chromium trioxide (4.6 mg) in wet acetonitrile (0.75% water) to create a suspension of total volume of 22.8 mL. The oxidant suspension (4.22 mL) was then added to a stirred solution of (2S)-5,5,5-trifluoro-2-({(1S)-2,2,2-trifluoro-1-[4'-(methylsulfonyl)-1,1'-biphenyl-4-yl]ethyl}amino)pentan-1-ol (0.35 g, 0.74 mmol) in wet acetonitrile (3.7 mL) dropwise while maintaining the temperature at 0-5° C. The reaction mixture was allowed to warm to ambient temperature after one hour and then stirred for an additional 4 hours. The reaction was quenched with aqueous sodium hydrogen phosphate (6 g/100 mL) and toluene was added and the mixture shaken vigorously. The organic phase was wased with 1:1 brine:water, then with aqueous sodium bisulfite (2.2 g/50 mL), then brine. The organic layer was then dried with sodium sulfate, filtered, and concentrated by rotary evaporation. The crude product was purified by silica gel chromatography using 5-10% methanol in methylene chloride as eluant to yield (2S)-5,5,5-trifluoro-2-({(1S)-2,2,2-trifluoro-1-[4'-(methylsulfonyl)-1,1'-biphenyl-4-yl]ethyl}amino)pentanoic acid.

MS (−ESI): 482.0 [M−1]⁻

Step 10: Preparation of (2S)-5,5,5-trifluoro-2-({(1S)-2,2,2-trifluoro-1-[4'-(methylsulfonyl)-1,1'-biphenyl-4-yl]ethyl}amino)pentanoic acid cyanomethyl amide (2S)-5,5,5-Trifluoro-2-({(1S)-2,2,2-trifluoro-1-[4'-(methylsulfonyl)-1,1'-biphenyl-4-yl]ethyl}amino)pentanoic acid (0.55 g, 0.114 mmol), aminoacetonitrile hydrochloride (21 mg, 0.228 mmol) and HATU (43 mg, 0.114 mmol) were dissolved in DMF (2 mL) and the reaction mixture was cooled to −20° C. Diisopropylethylamine (0.10 mL, 0.57 mmol) was added and the reaction mixture was stirred at −20° C. for three hours and then at ambient temperature for 16 hours. Ethyl acetate (ca.30 mL) and water (ca.30 mL) were added and the mixture was shaken vigorously. The organic layer was washed with water, dried with magnesium sulfate, and filtered. The filtrate was concentrated by rotary evaporation and the residue was purified by silica gel chromatography using 30% ethyl acetate in hexanes as eluant to yield (2S)-5,5,5-trifluoro-2-({(1S)-2,2,2-trifluoro-1-[4'-(methylsulfonyl)-1,1'-biphenyl-4-yl]ethyl}amino)pentanoic acid cyanomethyl amide as a white solid.

MS (+ESI): 522.3 [M+1]⁺

¹H NMR (CDCl₃) δ 8.0-8.053 (2H, d), 7.74-7.78 (2H, d), 7.63-7.66 (2H, d), 7.48-7.51 (2H, d), 6.94-7.00 (1H, bt, NH), 4.06-4.22 (3H, m), 3.36-3.43(1H, m), 2.21-2.37 (3H, m), 1.88-2.03 (2H, m). ¹⁹F NMR (CDCl₃) δ −66.74−−66.83 (3F, t),−74.14−−74.17 (3F, d).

EXAMPLE 19

Synthesis of N¹-(cyanomethyl)-N²-{(S)-(4-fluorophenyl)[4'-(methylsulfonyl)-1,1'-biphenyl-4-yl]methyl}-L-leucinamide

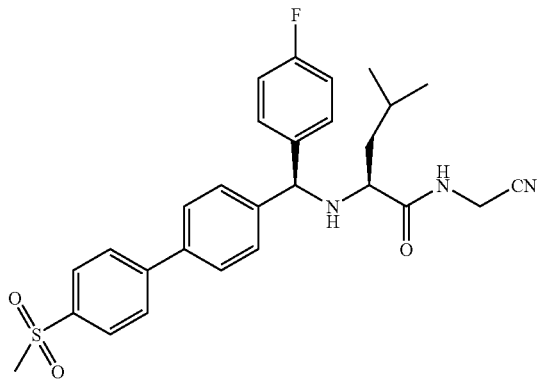

Step 1: Preparation of (S)-2-[(4-fluorobenzylidene)-amino]-4-methylpentan-1-ol A mixture of (L)-leucinol (1.13 g, 9.67 mmol) and 4-fluorobenzaldehyde (1.20 g, 9.67 mmol) was dissolved in benzene (30 mL) and heated at reflux for 1 hour, using a Dean-Stark apparatus to remove water. (S)-2-[(4-Fluorobenzylidene)-amino]-4-methylpentan-1-ol was isolated by concentration in vacuo, and was used immediately without further purification.

Step 2: Preparation of (2S)-2-{(R)-[(4-bromophenyl)-(4-fluorophenyl)-methyl]-amino}-4-methylpentan-1-ol To a solution of 1,4-dibromobenzene (11.4 g, 48.35 mmol) in ether (120 mL) at −30° C. was added n-butyllithium (24.2 mL, 2.0M cyclohexane solution) over 10 minutes. The reaction mixture was stirred for 45 minutes, whereupon a solution of (S) 2-[(4-fluorobenzylidene)-amino]-4-methylpentan-1-ol (maximum 2.16 g, 9.67 mmol from the previous step) in ether (30 mL) was added dropwise. After 2 hours, during which the reaction mixture was allowed to warm to 0° C., water (200 mL) was added. The product was extracted with ethyl acetate (150 mL), washed with brine (100 mL), dried over MgSO₄, filtered, concentrated in vacuo, and purified on a short plug of silica gel (20% ethyl acetate/hexane elution) to give (2S)-2-{(R)-[(4-bromophenyl)-(4-fluorophenyl)-methyl]-amino}-4-methylpentan-1-ol.

MS (+APCI): 380, 382 [M+1]⁺

¹H NMR (CDCl₃): δ 0.91 (d, 6H), 1.22 (m, 1H), 1.43 (m, 1H), 1.61 (m, 1H), 2.62 (m, 1H), 3.28 (m, 1H), 3.63 (m, 1H), 4.95 (s, 1H); 7.00 (m, 2H), 7.22 (d, 2H), 7.2 (m, 2H), 7.44 (d, 2H).

Step 3: Preparation of (2S)-2-{(R)-[(4-bromophenyl)-(4-fluorophenyl)-methyl]-amino}-4-methylpentanoic acid To a solution of (2S)-2-{(R)-[(4-bromophenyl)-(4-fluorophenyl)-methyl]-amino}-4-methylpentan-1-ol (3.28 g, 8.65 mmol) in acetonitrile (50 mL) containing water (0.375 mL) at 0-5° C. was added, over 20 minutes, a solution of periodic acid and chromium [VI] oxide in acetonitrile (50 mL: prepared by dissolving 11.4 grams of $H_5IO_6$ and 23 mg of $CrO_3$ in 100 mL of $CH_3CN$ and stirring for 2 hours at room temperature according to the procedure described in Tetrahedron Letters, 1998, vol. 39, p. 5323-5326). The reaction mixture was stirred overnight while warming to room temperature. Disodium phosphate (1.8 g/100 mL water) was added. The reaction mixture was extracted with toluene (150 mL), washed with 1:1 brine/water (50 mL), freshly prepared sodium bisulfite solution (2 g/50 mL water), brine (50 mL), dried over $MgSO_4$, filtered, concentrated in vacuo, and purified on a short plug of silica gel (30% ethyl acetate/hexane elution to remove non-polar impurities, then 50% ethyl acetate/dichloromethane elution) to give (2S)-2-{(R)-[(4-bromophenyl)-(4-fluorophenyl)-methyl]-amino}-4-methylpentanoic acid.

Step 4: Preparation of (2S)-2-{(R)-[(4-bromophenyl)-(4-fluorophenyl)-methyl]-amino}-4-methylpentanoic acid cyanomethylamide To a solution of (2S)-2-{(R)-[(4-bromophenyl)-(4-fluorophenyl)-methyl]-amino}-4-methylpentanoic acid (1.17 g, 2.86 mmol) in THF (20 mL) at −10° C. were added 4-methylmorpholine (0.315 mL, 2.86 mmol) and isobutyl chloroformate (0.371 mL, 2.86 mmol). The reaction mixture was stirred for 10 minutes, whereupon aminoacetonitrile hydrochloride (0.318 g, 3.43 mmol) was added, followed by 4-methylmorpholine (0.315 mL, 2.86 mmol). The solution was stirred for 90 minutes. Ethyl acetate (30 mL) and aqueous disodium phosphate (30 mL) were added. The organic phase was separated, washed with brine, dried over $MgSO_4$, and evaporated to dryness. The product was purified on a short plug of silica gel (10-50% ethyl acetate/hexane gradient elution) to give (2S)-2-{(R)-[(4-bromophenyl)-(4-fluorophenyl)-methyl]-amino}-4-methylpentanoic acid cyanomethylamide.

Step 5: Preparation of $N^1$-(cyanomethyl)-$N^2$-{(S)-(4-fluorophenyl)[4'-(methylsulfonyl)-1,1'-biphenyl-4-yl]methyl}-L-leucinamide A mixture of (2S)-2-{(R)-[(4-bromophenyl)-(4-fluorophenyl)-methyl]-amino}-4-methylpentanoic acid cyanomethylamide (0.27 g, 0.636 mmol), 2-(4-methanesulfonylphenyl)-4,4,5,5-tetramethyl-[1,3,2]dioxaborolane (0.177 g, 0.626 mmol) and potassium carbonate (0.703 mL of a 2.0 M solution) in DMF (5 mL) was degassed. [1,1'-Bis(diphenylphosphino)ferrocene]dichloropalladium(II), dichloromethane complex (27 mg, 0.038 mmol) was added. The reaction mixture was heated in a sealed tube at 80-85° C. for 3 hours and cooled to room temperature. Ethyl acetate (15 mL) was added. The reaction mixture was washed with brine (10 mL), saturated aqueous $NaHCO_3$ (10 mL), brine (10 mL), filtered through a plug of $MgSO_4$/DARCO activated charcoal/silica gel, concentrated in vacuo, and purified by preparative TLC (Chromatotron® using 5% ethyl acetate/dichloromethane to elute to give $N^1$-(cyanomethyl)-$N^2$-{(S)-(4-fluorophenyl)[4'-(methylsulfonyl)-1,1'-biphenyl-4-yl]methyl}-L-leucinamide.

$^1$H NMR δ ($CDCl_3$): 0.77 (d, 3H), 0.9 (d, 3H); 1.38 (m, 1H), 1.57 (m, 1H), 1.71 (m, 1H), 2.01 (br s, 1H), 3.09 (s, 3H), 3.09 (m, 1H), 4.07 (m, 2H), 4.89 (1H, s), 7.03 (m, 2H), 7.21 (m, 1H), 7.33 (m, 2H), 7.42 (d, 2H), 7.53 (m, 2H), 7.68 (d, 2H), 7.97 (d, 2H).

EXAMPLE 20

Synthesis of (2S)-2-{(S)-[(2,4-difluoro-phenyl)-(4'-methanesulfonylbiphenyl-4-yl)-methyl]-amino}-4-methylpentanoic acid cyanomethylamide

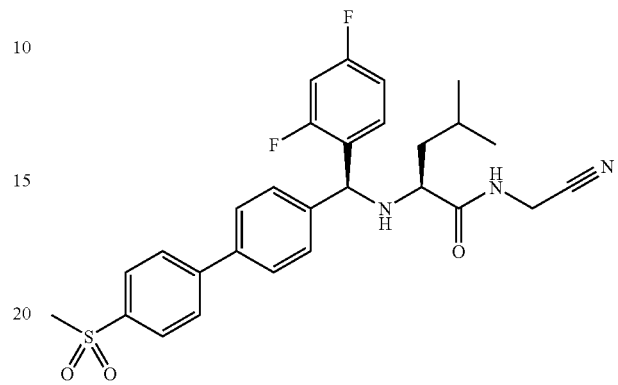

Step 1: Preparation of (2S)-2-[(2,4-difluorobenzylidene)-amino]-4-methylpentan-1-ol A solution of (S)-(+)-leucinol (2.47 g, 21 mmol) and 2,4-difluorobenzaldehyde (3 g, 21 mmol) in benzene (50 mL) was heated to reflux for 4 hours during which time water was collected in a Dean-Stark trap. The solvent was evaporated in vacuum to give (2S)-2-[(2,4-difluorobenzylidene)-amino]-4-methylpentan-1-ol.

$^1$H NMR ($CD_3SOCD_3$) δ 8.18 (s, 1H), 7.51 (d, 1H), 6.81 (d, 2H), 4.6 (br s, 1H), 3.8-3.2 (m, 3H), 1.6-1.2 (m, 3H), 0.9-0.8 (m, 6H).

Step 2: Preparation of (2S)-2-{(S)-[(4-bromophenyl)-(2,4-difluorophenyl)-methyl]-amino}-4-methylpentan-1-ol To a solution of 1,4-dibromobenzene (24.5 g, 100 mmol, 5eq) in dry ether (200 mL) under nitrogen atmosphere at −30° C., nBuLi (64.75 mL, 1.6 M solution in hexanes, 5 eq) was added and the reaction mixture was stirred for 1 h. A solution of 2-[(2,4-difluorobenzylidene)-amino]-4-methylpentan-1-ol (5 g, 20 mmol) in dry ether was added slowly at −30° C. After stirring for 4 h, the reaction was quenched with water. The ether layer was washed with saturated solution of NaCl, and dried over $MgSO_4$. The solvent was removed under reduced pressure and the crude was flash chromatographed on 500 cm$^3$ of silica gel using 8:2 hexanes:EtOAc as an eluant to yield (2S)-2-{(S)-[(4-bromophenyl)-(2,4-difluorophenyl)-methyl]-amino}-4-methylpentan-1-ol.

$^1$H NMR ($CD_3SOCD_3$) δ 7.31 (dd, 2H), 7.05 (d, 1H), 6.94 (dd, 2H), 6.63 (d, 1H), 6.54 (d, 1H), 5.02 (s, 1H), 4.45 (t, 1H), 3.5-3.3 (m, 2H), 2.3 (s, 1H), 2.15 (s, 1H), 1.85 (m, 1H), 1.18-1.4 (m, 2H), 0.9-0.8 (m, 6H).

Step 3: Preparation of (2S)-2-{(S)-[(4-bromophenyl)-(2,4-difluoro-phenyl)-methyl]-amino}-4-methylpentanoic acid Using the procedure mentioned in Step 3 of Example 19, 2-{[(4-bromophenyl)-(2,4-difluorophenyl)-methyl]-amino}-4-methylpentan-1-ol was oxidized to get (2S)-2-{

(S)-[(4-bromophenyl)-(2,4-difluoro-phenyl)-methyl]-amino}-4-methylpentanoic acid as a cream-colored solid.

Step 4: Preparation of (2S)-2-{(S)-[(4-bromophenyl)-(2,4-difluorophenyl)-methyl]-amino}-4-methyl-pentanoic acid cyanomethylamide Using the procedure mentioned in the Step 4 of Example 19, (2S)-2-{(S)-[(4-bromophenyl)-(2,4-difluorophenyl)-methyl]-amino}-4-methyl-pentanoic acid was coupled with amino acetonitrile to give (2S)-2-{(S)-[(4-bromophenyl)-(2,4-difluorophenyl)-methyl]-amino}-4-methylpentanoic acid cyanomethylamide as a white solid.
$^1$H NMR (CD$_3$SOCD$_3$) δ 7.31 (dd, 2H), 7.05 (d, 1H), 6.94 (dd, 2H), 6.63 (d, 1H), 6.54 (d, 1H), 4.92 (s, 1H), 4.14 (t, 2H), 3.32 (m, 1H), 3.19 (m, 1H), 2.98 (m, 1H), 1.85 (m, 1H), 1.46 (m, 1H), 0.9-0.8 (m, 6H).

Step 5: Preparation of (2S)-2-{(S)-[(2,4-difluorophenyl)-(4'-methanesulfonyl-biphenyl-4-yl)-methyl]-amino}-4-methylpentanoic acid cyanomethylamide Using the procedure mentioned in the Step 5 of Example 19, Suzuki coupling was done with (2S)-2-{(S)-[(4-bromophenyl)-(2,4-difluorophenyl)-methyl]-amino}-4-methylpentanoic acid cyanomethylamide to give (2S)-2-{(S)-[(2,4-difluorophenyl)-(4'-methanesulfonyl-biphenyl-4-yl)-methyl]-amino}-4-methylpentanoic acid cyanomethylamide as a white solid.
$^1$H NMR (CD$_3$SOCD$_3$) δ 8.01 (dd, 2H), 7.8 (dd, 2H), 7.35 (dd, 2H), 7.11 (dd, 2H), 7.03 (d, 1H), 6.93 (d, 2H), 6.62 (d, 1H), 6.55 (d, 1H), 5.0 (s, 1H), 4.13 (t, 2H), 3.35 (m, 1H), 3.0 (m, 1H), 2.99 (m, 1H), 2.85 (s, 3H), 1.84 (m, 1H), 1.45 (m, 1H), 0.9-0.8 (m, 6H).

EXAMPLE 21

Synthesis of N$^2$-[(1S)-1-(4-bromophenyl)-2,2,2-trifluoroethyl]-N$^1$-(1-cyanocyclopropyl)-L-norvalinamide

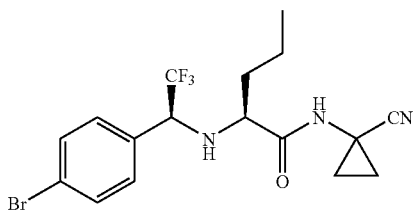

Step 1: Preparation of (S)-[1-(tert-butyldimethylsilanyloxymethyl)-butyl]-(2,2,2-trifluoroethylidene)-amine A mixture of (S)-1-(tert-butyldimethylsilanyloxymethyl)-butylamine (27 g, 126 mmol) and trifluoroacetaldehyde methyl hemiacetal (17.2 g, 132 mmol) in benzene (250 mL) was heated at reflux, using a Dean-Stark trap to remove water. After 2 hours, no more water was collected. The reaction mixture was cooled and concentrated to give (S)-[1-(tert-butyldimethylsilanyloxymethyl)-butyl]-(2,2,2-trifluoroethylidene)-amine which was used in the next step without further purification or extended drying due to its volatility.

Step 2: Preparation of (2S)-(S)-[1-(4-bromophenyl)-2,2,2-trifluoroethyl]-[1-(tert-butyldimethylsilanyloxymethyl)-butyl]-amine To a solution of dibromobenzene (63.7 g, 270 mmol) in ether (600 mL) at –30° C. was added n-BuLi (108 mL of a 2.5 M hexane solution) over 15 minutes via addition funnel. The solution was allowed to warm to –10° C. over 35 minutes, and was cooled back to –30° C. (S)-[1-(tert-Butyldimethylsilanyloxymethyl)-butyl]-(2,2,2-trifluoroethylidene)-amine (35.12 g, 108 mmol) was added in ether (200 mL) over 20 minutes. The reaction mixture was stirred for 1 hour while warming to 0° C. Water (200 mL) was added. The organic phase was separated, washed with brine (200 mL), dried over MgSO$_4$, filtered, and evaporated to dryness to give (2S)-(S)-[1-(4-bromophenyl)-2,2,2-trifluoroethyl]-[1-(tert-butyldimethylsilanyloxymethyl)-butyl]-amine which was used directly in the following step without further purification.

Step 3 Preparation of (2S)-2-[(S)-1-(4-bromophenyl)-2,2,2-trifluoroethylamino]-pentan-1-ol To a solution of (2S)-(S)-[1-(4-bromophenyl)-2,2,2-trifluoro-ethyl]-[1-(tert-butyldimethylsilanyloxymethyl)-butyl]-amine (49.58 g, 109 mmol) in THF (200 mL) was added tetrabutylammonium fluoride (110 mL of a 1.0 M solution). The reaction mixture was stirred overnight at room temperature. After concentration of the reaction mixture, ether (300 mL) was added. The reaction mixture was washed with water (2×100 mL), brine (100 mL), evaporated to dryness, and then purified by flash chromatography (3% ethyl acetate/hexane elution of highly non-polar materials then 40% ethyl acetate/hexanes to elute the product). The fractions containing product were combined, concentrated to a volume of 300 mL, washed with 0.25 M citric acid (200 mL), brine (100 mL), dried over MgSO$_4$, filtered, and evaporated to give (2S)-2-[(S)-1-(4-bromophenyl)-2,2,2-trifluoroethylamino]-pentan-1-ol. This material was used directly in the next step without further purification. TLC (30% ethyl acetate/hexanes) R$_f$=0.28.

Step 4: Preparation of (2S)-2-[(S)-1-(4-bromophenyl)-2,2,2-trifluoroethylamino]-pentanoic acid To a solution of crude (2S)-2-[(S)-1-(4-bromophenyl)-2,2,2-trifluoroethylamino]-pentan-1-ol (37.1 g, 109 mmol in dry acetonitrile (500 mL) at –78° C. was added a solution of periodic acid (71.7 g) and chromium trioxide (144 mg) in dry acetonitrile (630 mL) over 1 hour. The reaction mixture was allowed to warm to room temperature while stirring overnight. The reaction mixture was concentrated under reduced pressure to a total volume of approximately 500 mL. A solution of citric acid (22 g in 250 mL H$_2$O) was added and the mixture was extracted with ethyl acetate (800 mL). The solution was washed with freshly prepared NaHSO$_3$ (2×200 mL, 25 g solid dissolved to 200 mL with water) brine (300 mL), dried over MgSO$_4$, filtered, and evaporated to give a pale orange solid, which was triturated with 5% ethyl acetate/hexanes to give (2S)-2-[(S)-1-(4-bromophenyl)-2,2,2-trifluoroethylamino]-pentanoic acid. Additional acid was obtained by concentrating the mother liquors, partitioning the residue between ether and aqueous NaHCO$_3$, acidifying the aqueous layer with citric acid, extracting with ethyl acetate, drying over MgSO$_4$, filtering, and evaporating the solvent.

Step 5: Preparation of N²-[(1S)-1-(4-bromophenyl)-2,2,2-trifluoroethyl]-N¹-(1-cyanocyclopropyl)-L-norvalinamide A mixture of (2S)-2-[(S)-1-(4-bromophenyl)-2,2,2-trifluoroethylamino]-pentanoic acid (19.0 g, 53.6 mmol), 1-aminocyclopropanecarbonitrile hydrochloride (12.71 g, 107 mmol, synthesized according to O'Donnell, M. J. et al., *Synthesis*, 1984, 127-128), and HATU (22.42 g, 59.0 mmol) was dissolved in DMF (200 mL) and cooled to −78° C. Diisopropylethylamine (37.35 mL, 214 mmol) was added and after stirring for 1 hour, the cooling bath was removed. The reaction mixture was allowed to stir for an additional 1 hour, whereupon saturated NaHCO₃ (300 mL) was added. The product was extracted with ethyl acetate (500 mL), washed with brine (100 mL), 0.25 M citric acid (200 mL), saturated NaHCO₃ (200 mL), brine (200 mL), dried over MgSO₄/DARCO, filtered through silica, and evaporated to dryness. After eluting the residue through another short plug of silica with 10% ethyl acetate/dichloromethane as mobile phase, the product was concentrated and recrystallized from ether/hexanes to yield N²-[(1S)-1-(4-bromophenyl)-2,2,2-trifluoroethyl]-N¹-(1-cyanocyclopropyl)-L-norvalinamide.

MS (−ESI): 416, 418 [M−1]⁻

¹H NMR (CDCl₃): δ 0.97 (3H, t), 0.98 (m, 1H), 1.07 (m, 1H), 1.41 (m, 2H), 1.49 (m, 2H), 1.62 (m, 1H), 1.72 (m, 1H), 3.27 (1H, m), 1.04 (m, 1H), 7.1 (br s, 1H), 1.24 (d, 2H), 7.75 (d, 2H).

EXAMPLE 22

Synthesis of N¹-(1-cyanocyclopropyl)-N²-{(1S)-2,2,2-trifluoro-1-[4'-(methylsulfonyl)-1,1'-biphenyl-4-yl]ethyl}-L-norvalinamide

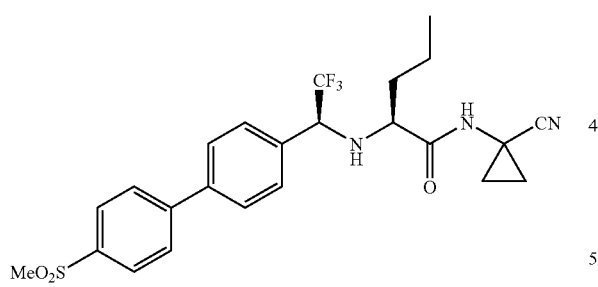

A mixture of N²-[(1S)-1-(4-bromophenyl)-2,2,2-trifluoroethyl]-N¹-(1-cyanocyclopropyl)-L-norvalinamide (6.46 g, 15.44 mmol), 4-methanesulfonylphenyl-boronic acid (3.40 g, 16.98 mmol), and 2M K₂CO₃ (19.3 mL) was dissolved in DMF (75 mL) in a thick-walled flask. The reaction mixture was degassed, and [1,1'-bis(diphenyl-phosphino)ferrocene]dichloropalladium(II), dichloromethane complex (0.678 g, 0.926 mmol) was added. The flask was sealed, heated at 80-85° C. for 3 hours, cooled, and diluted with ethyl acetate (300 mL). The solution was washed with 1:1 water/brine (200 mL), brine (200 mL), filtered through a three-layered plug of silica (bottom) DARCO, and MgSO₄ (top), concentrated in vacuo, and purified on a plug of silica gel (50-70% ethyl acetate/hexane elution). The product was then further purified by recrystallization from ethyl acetate/hexanes to yield the title compound.

MS (+ESI): 494 [M+1]⁺

¹H NMR (CDCl₃): δ 0.97 (t, 3H), 0.98 (m, 1H), 1.1 (m, 1H), 1.42 (m, 2H), 1.29 (m, 2H), 1.63 (m, 1H), 1.77 (m, 1H), 3.13 (s, 3H), 3.28 (dd, 1H), 4.17 (q, 1H), 7.21 (br s, 1H), 7.47 (d, 2H), 7.63 (d, 2H), 7.78 (d, 2H), 8.02 (d, 2H).

EXAMPLE 23

Synthesis of N²-[1-(4-bromophenyl)-2,2,2-trifluoroethyl]-N¹-(cyanomethyl)-L-norvalinamide

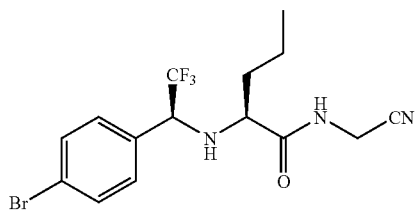

N²-[1-(4-Bromophenyl)-2,2,2-trifluoroethyl]-N¹-(cyanomethyl)-L-norvalinamide was prepared in similar manner to N¹-(1-cyanocyclopropyl)-N²-{(1S)-2,2,2-trifluoro-1-[4'-(methylsulfonyl)-1,1'-biphenyl-4-yl]ethyl}-L-norvalinamide using aminoacetonitrile in the coupling step with (2S)-2-[(S)-1-(4-bromophenyl)-2,2,2-trifluoroethylamino]-pentanoic acid.

MS (+ESI): 392, 394 [M+1]⁺

EXAMPLE 24

Synthesis of N¹-(cyanomethyl)-N²-{(1S)-2,2,2-trifluoro-1-[4'-(methylsulfonyl)-1,1'-biphenyl-4-yl]ethyl}-L-norvalinamide

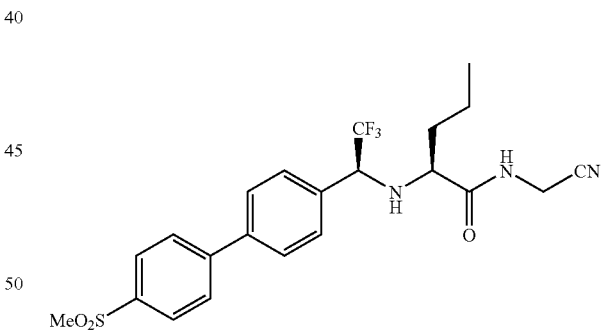

N¹-(Cyanomethyl)-N²-{(1S)-2,2,2-trifluoro-1-[4'-(methylsulfonyl)-1,1'-biphenyl-4-yl]ethyl}-L-norvalinamide was prepared in similar manner to N¹-(1-cyanocyclopropyl)-N²-{(1S)-2,2,2-trifluoro-1-[4'-(methylsulfonyl)-1,1'-biphenyl-4-yl]ethyl}-L-norvalinamide using N²-[1-(4-bromophenyl)-2,2,2-trifluoroethyl]-N¹-(cyanomethyl)-L-norvalinamide described above, in the Suzuki coupling with 4-methanesulfonylphenylboronic acid or pinacolboronate. Alternatively, the compound could be prepared from Suzuki coupling between (2S)-(S)-[1-(4-bromophenyl)-2,2,2-trifluoroethyl]-[1-(tert-butyldimethylsilanyloxymethyl)-butyl]-amine and 4-methanesulfonylphenylboronic acid, in the presence of [1,1'-bis(diphenylphosphino)ferrocene]dichloropalladium(II), dichloromethane complex according to the procedure described above, followed by cleavage of the silyl ether with tetrabutylammonium fluoride, oxidation using $H_5IO_6/CrO_3$ (vide supra) to afford (2S)-2-[(S)-2,2,2-trifluoro-1-(4'-methanesulfonylbiphenyl-4-yl)-ethylamino]-pentanoic acid, and coupling of this material with aminoacetonitrile hydrochloride in the presence of HATU/diisopropylethylamine/DMF afforded the title compound.

MS (+ESI): 468 [M+1]⁺

EXAMPLE 25

Synthesis of $N^1$-(cyanomethyl)-$N^2$-{(1R)-2,2,2-trifluoro-1-[4'-(methylsulfonyl)-1,1'-biphenyl-4-yl]ethyl}-L-norvalinamide

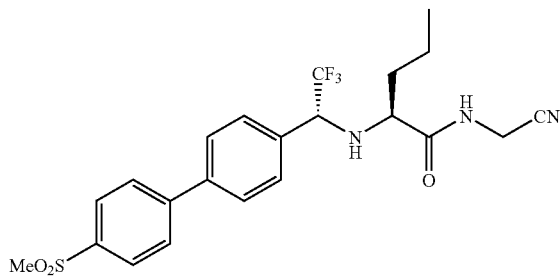

Step 1: Preparation of (4S)-4-propyl-2-trifluoromethyloxazolidine (L)-Norvalinol hydrochloride (5.25 g, 37.60 mmol) and trifluoroacetaldehyde methyl hemiacetal (5 mL, 37.6 mmol) were heated in benzene (100 mL) in the presence of triethylamine (5.26 mL, 37.6 mmol) at reflux, using a Dean-Stark apparatus to trap water. After 3 hours, the reaction mixture was cooled, diluted with ether (100 mL), filtered, and evaporated to dryness, giving (4S)-4-propyl-2-trifluoromethyloxazolidine, which was used without further purification.

Step 2: Preparation of (2S)-2-[1-(4-bromophenyl)-2,2,2-trifluoroethylamino]-pentan-1-ol Butyllithium (41 mL of a 2.0M cyclohexane solution) was added at −30° C. to a solution of 1,4-dibromobenzene (19.3 g, 81.89 mmol) in ether (250 mL) over 10 minutes. After 1 hour, a solution of (4S)-4-propyl-2-trifluoromethyloxazolidine (3.00 g, 16.38 mmol) was added in ether (50 mL) over 30 minutes via an addition funnel. After 90 minutes of stirring, water (100 mL) was added. The organic phase was washed with brine (100 mL), dried over MgSO₄, filtered, and evaporated to dryness. The residue was purified on a plug of silica gel (10-30% ethyl acetateihexane elution). An approximately 2:1 mixture of diastomers of (2S)-2-[1-(4-bromophenyl)-2,2,2-trifluoroethylamino]-pentan-1-ol at the $CF_3$ residue was observed based on the norvaline methyl triplet at 0.98 ppm (¹H NMR).

Step 3: Preparation of $N^1$-(cyanomethyl)-$N^2$-{(1S)-2,2,2-trifluoro-1-[4'-(methylsulfonyl)-1,1'-biphenyl-4-yl]ethyl}-L-norvalinamide and $N^1$-(cyanomethyl)-$N^2$-{(1R)-2,2,2-trifluoro-1-[4'-(methylsulfonyl)-1,1'-biphenyl-4-yl]ethyl}-L-norvalinamide Synthesis of (2S)-2-[1-(4-bromophenyl)-2,2,2-trifluoroethylamino]-pentanoic acid and elaboration to the aminoacetonitrile adduct was accomplished in identical manner to that described above for $N^2$-[1-(4-bromophenyl)-2,2,2-trifluoroethyl]-$N^1$-(cyanomethyl)-L-norvalinamide. Suzuki coupling of the product, in identical manner to that described for $N^1$-(cyanomethyl)-$N^2$-{(1S)-2,2,2-trifluoro-1-[4'-(methylsulfonyl)-1,1'-biphenyl-4-yl]ethyl}-L-norvalinamide yielded a 2:1 mixture of $N^1$-(cyanomethyl)-$N^2$-{(1S)-2,2,2-trifluoro-1-[4'-(methylsulfonyl)-1,1'-biphenyl-4-yl]ethyl}-L-norvalinamide and $N^1$-(cyanomethyl)-$N^2$-{(1R)-2,2,2-trifluoro-1-[4'-(methylsulfonyl)-1,1'-biphenyl-4-yl]ethyl}-L-norvalinamide, which was isolated by means of preparative TLC (Chromatotron®).

MS (+ESI): 468 [M+1]⁺

EXAMPLE 26

Synthesis of $N^1$-(cyanomethyl)-$N^2$-{1-[4'-(4-cyclopropylpiperazin-1-yl)-1,1'-biphenyl-4-yl]-2,2,2-trifluoroethyl}-L-norvalinamide

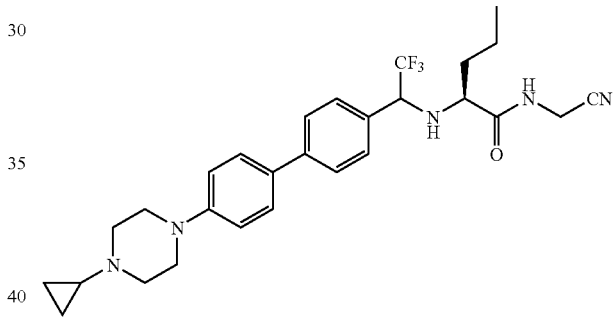

The title compound was prepared by the Suzuki cross-coupling of 4-cyclopropylpiperazinephenyl bromide with (2S)-2-{2,2,2-Trifluoro-1-[4-(4,4,5,5-tetramethyl-[1,3,2]dioxaborolan-2-yl)-phenyl]-ethylamino}-pentanoic acid cyanomethylamide in the presence of [1,1'-bis(diphenylphosphino)ferrocene]-dichloropalladium(II), dichloromethane complex as described above, followed by purification by preparative TLC (Chromatotron®).

MS (+ESI): 514 [M+1]⁺

EXAMPLE 27

Synthesis of $N^2$-{(1S)-1-[4'-(aminosulfonyl)-1,1'-biphenyl-4-yl]-2,2,2-trifluoroethyl}-$N^1$-(1-cyanocyclopropyl)-L-norvalinamide

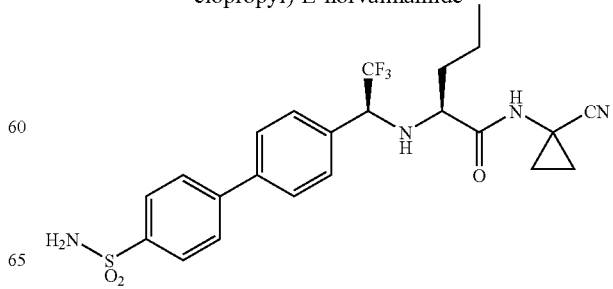

The title compound was prepared in similar manner to that described for N¹-(cyanocyclopropyl)-N²-{(1S)-2,2,2-trifluoro-1-[4'-(methylsulfonyl)-1,1'-biphenyl-4-yl]ethyl}-L-norvalinamide (Example 24).

MS (+ESI): 495 [M+1]$^+$ $^1$H NMR (CDCl$_3$): δ 0.97 (3H, t) 0.98 (m*, 1H); 1.08 (m, 1H), 1.42 (m, 2H), 1.44 (m, 2H), 1.57-1.8 (m, 4H), 3.28 (m, 1H), 4.16 (q, 1H), 4.9 (br s*, 1H), 7.2 (s, 1H), 7.43 (d, 2H), 7.6 (d, 2H), 7.72 (d, 2H), 7.99 (d, 2H).

EXAMPLE 28

Synthesis of (2S)-2-[(1S)-1-(4'-acetylbiphenyl-4-yl)-2,2,2-trifluoroethylamino]-pentanoic acid (1-cyano-cyclopropyl)-amide

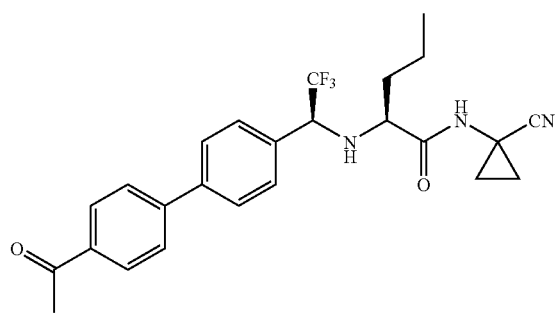

The title compound was prepared in similar manner to that described for N¹-(1-cyanocyclopropyl)-N²-{(1S)-2,2,2-trifluoro-1-[4'-(methylsulfonyl)-1,1'-biphenyl-4-yl]ethyl}-L-norvalinamide via Suzuki cross-coupling between 4-acetylphenylboronic acid and N²-[(1S)-1-(4-bromophenyl)-2,2,2-trifluoroethyl]-N¹-(1-cyanocyclopropyl)-L-norvalinamide in the presence of [1,1'-bis(diphenylphosphino)ferrocene]-dichloropalladium(II), dichloromethane complex.

MS (+ESI): 458 [M+1]$^+$, 480 [M+1+Na]$^+$ $^1$H NMR (CDCl$_3$): δ 0.97 (t, 3H), 0.98 (m, 1H), 1.-7 (m, 1H), 1.42 (m, 2H), 1.57 (s, 2H), 1.63 (m, 1H), 1.78 (m, 1H), 2.33 (s, 3H), 3.33 (dd, 1H), 4.17 (q, 1H), 7.21 (br s, 1H), 7.43 (d, 2H), 7.65-7.69 (2xd, 4H), 8.03 (d, 2H).

EXAMPLE 29

Preparation of (2S)-2-[(1S)-1-(2',4'-difluorobiphenyl-4-yl)-2,2,2-trifluoroethylamino]-pentanoic acid (1-cyanocyclopropyl)-amide

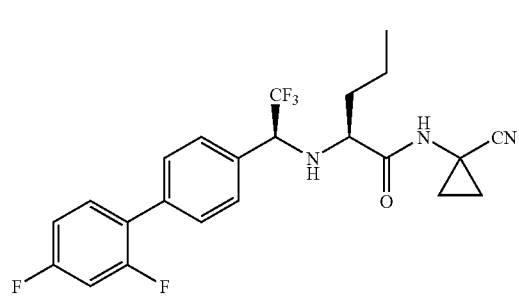

The title compound was synthesized in similar manner to that described for N¹-(1-cyanocyclopropyl)-N²-{(1S)-2,2,2-trifluoro-1-[4'-(methylsulfonyl)-1,1'-biphenyl-4-yl]ethyl}-L-norvalinamide via Suzuki cross-coupling between 2,4-difluorophenylboronic acid and N²-[(1S)-1-(4-bromophenyl)-2,2,2-trifluoroethyl]-N¹-(1-cyanocyclopropyl)-L-norvalinamide in the presence of [1,1'-bis(diphenylphosphino)ferrocene]-dichloropalladium(II), dichloromethane complex.

MS (+ESI): 452 [M+1]$^+$, 474 [M+1+Na]$^+$ $^1$H NMR (CDCl$_3$): δ 0.90 (m, 1H), 0.97 (t, 3H), 1.04 (m, 1H), 1.41-1.5 (m, 4H), 1.62 (m, 1H), 1.78 (m, 1H), 2.19 (br s, 1H), 3.32 (dd, 1H), 4.13 (dd, 1H), 6.95 (m, 2H), 7.19 (br s, 1H), 7.41 (m, 3H), 7.53 (d, 2H).

EXAMPLE 30

Synthesis of (2S)-2-[(1S)-1-(3',4'-difluorobiphenyl-4-yl)-2,2,2-trifluoroethylamino]-pentanoic acid (1-cyanocyclopropyl)-amide

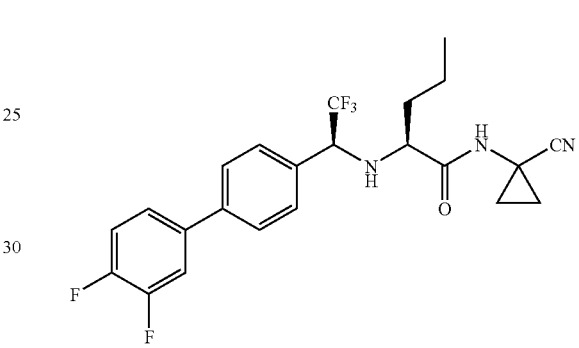

The title compound was prepared in similar manner to that described for N¹-(1-cyanocyclopropyl)-N²-{(1S)-2,2,2-trifluoro-1-[4'-(methylsulfonyl)-1,1'-biphenyl-4-yl]ethyl}-L-norvalinamide via Suzuki cross-coupling between 3,4-difluorophenylboronic acid and N²-[(1)-1-(4-bromophenyl)-2,2,2-trifluoroethyl]-N¹-(1-cyanocyclopropyl)-L-norvalinamide in the presence of 1,1'-bis(diphenylphosphino)ferrocene]-dichloropalladium(II), dichloromethane complex.

MS (+ESI): 452 [M+1]$^+$, 474 [M+1+Na]$^+$ $^1$H NMR (CDCl$_3$): δ 0.97 (t, 3H), 0.98 (m, 1H), 1.07 (m, 1H), 1.42 (m, 2H), 1.5 (m, 2H), 1.62 (m, 1H), 1.77 (m, 1H), 2.18 (br s, 1H), 3.29 (dd, 1H), 4.17 (q, 1H), 7.21 (br s, 1H), 7.13-7.3 (m, 2H), 7.38 (m, 1H), 7.42 (d, 2H), 7.57 (d, 2H).

EXAMPLE 31

Preparation of (2S)-2-[(1S)-1-(3'-chloro-4'-fluorobiphenyl-4-yl)-2,2,2-trifluoroethylamino]-pentanoic acid (1-cyano-cyclopropyl)-amide

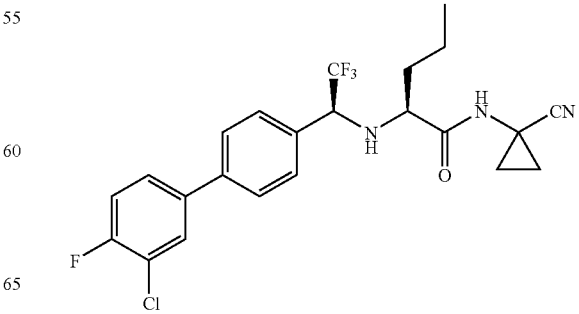

The title compound was prepared in similar manner to that described for N¹-(1-cyanocyclopropyl)-N²-{(1S)-2,2,2-trifluoro-1-[4'-(methylsulfonyl)-1,1'-biphenyl-4-yl]ethyl}-L-norvalinamide via Suzuki cross-coupling between 3-chloro-4-fluorophenylboronic acid and N²-[(1S)-1-(4-bromophenyl)-2,2,2-trifluoroethyl]-N¹-(1-cyanocyclopropyl)-L-norvalinamide in the presence of [1,1'-bis(diphenylphosphino)-ferrocene]dichloropalladium(II), dichloromethane complex.

MS (+ESI): 468 [M+1]⁺

¹H NMR (CDCl₃): δ 0.99 (t, 3H), 1.00 (m, 1H), 1.08 (m, 1H), 1.42 (m, 2H), 1.51 (m, 2H), 1.62 (m, 1H), 1.79 (m, 1H), 2.19 (br s, 1H), 3.33 (dd, 1H), 4.17 (q, 1H), 7.21 (m, 2H), 7.42 (m, 3H), 7.57 (d, 2H), 7.62 (m, 1H).

EXAMPLE 32

Synthesis of (2S)-2-[(1S)-2,2,2-trifluoro-1-(4'-methylbiphenyl-4-yl)-ethylamino]-pentanoic acid (1-cyanocyclopropyl)-amide

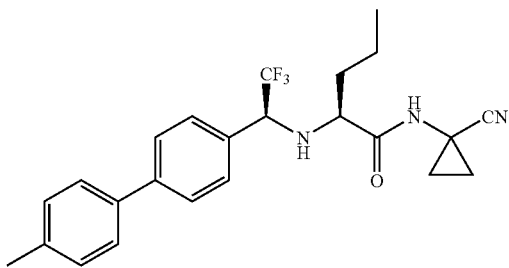

The title compound was synthesized in similar manner to that described for N¹-(1-cyanocyclopropyl)-N²-{(1S)-2,2,2-trifluoro-1-[4'-(methylsulfonyl)-1,1'-biphenyl-4-yl]ethyl}-L-norvalinamide via Suzuki cross-coupling between p-tolylboronic acid and N²-[(1S)-1-(4-bromophenyl)-2,2,2-trifluoroethyl]-N¹-(1-cyanocyclopropyl)-L-norvalinamide in the presence of [1,1'-bis(diphenylphosphino)ferrocene]-dichloropalladium(II), dichloromethane complex. MS (+ESI): 430 [M+1]⁺

¹H NMR (CDCl₃) δ 0.90 (m, 1H), 0.98 (t, 3h), 1.02 (m, 1H) 1.4-1.5 (m, 4H), 1.62 (m, 1H), 1.69 (m, 1H), 2.19 (br s, 1H), 2.41 (s, 3H), 3.35 (dd, 1H), 4.1 (q, 1H), 7.21 (s, 1H) 7.24 (d, 2H), 7.38 (d, 2H), 7.46 (d, 2H), 7.60 (d, 2H).

EXAMPLE 33

Synthesis of (2S)-2-[(1S)-1-(4'-cyanobiphenyl-4-yl)-2,2,2-trifluoroethylamino]-pentanoic acid (1-cyanocyclopropyl)-amide

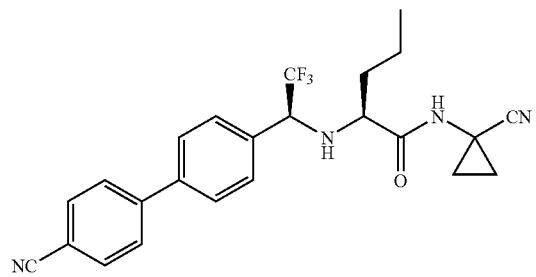

The title compound was synthesized in similar manner to that described for N¹-(1-cyanocyclopropyl)-N²-{(1S)-2,2,2-trifluoro-1-[4'-(methylsulfonyl)-1,1'-biphenyl-4-yl]ethyl}-L-norvalinamide via Suzuki cross-coupling between 4-cyanophenylboronic acid and N²-[(1S)-1-(4-bromophenyl)-2,2,2-trifluoroethyl]-N¹-(1-cyanocyclopropyl)-L-norvalinamide in the presence of [1,1'-bis(diphenylphosphino)ferrocene]-dichloropalladium(II), dichloromethane complex.

MS (+ESI): 441 [M+1]⁺

EXAMPLE 34

Synthesis of (2S)-2-{(S)-[(4-bromophenyl)-thiazol-2-yl-methyl]-amino}-4-methylpentanoic acid cyanomethylamide

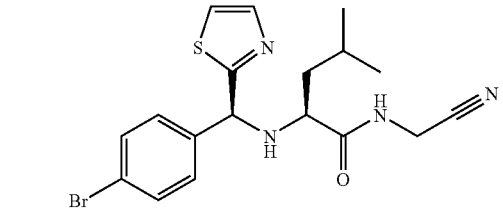

Step 1: Preparation of 3-methyl-3-(toluenesulfonyl-oxymethyl)oxetane p-Toluenesulfonyl chloride (57.2 g, 300 mmol) was dissolved in dry pyridine (400 mL) under nitrogen atmosphere. 3-methyl-3-(hydroxymethyl)oxetane (20.4 g, 200 mmol) was added slowly, and the solution was stirred for 1.5 h. Crushed ice (400 g) was then added to vigorously stirring mixture, which was allowed to stir for an additional 0.5 h. The white precipitate was then collected on Whatman filter paper #1 and washed with cold water. The product was dried under high vacuum to obtain 3-methyl-3-(toluenesulfonyl-oxymethyl)oxetane (oxetane tosylate) as a white powder of oxetane tosylate.

¹H NMR (CDCl₃) δ 7.81 (d, 2H), 7.37 (d, 2H), 4.37 (m, 4H), 4.11 (s, 2H), 2.46 (s, 3H), 1.31 (s, 3H).

Step 2: Preparation of (2S)-2-benzyloxycarbonylamino-4-methyl-pentanoic acid 3-methyloxetan-3-ylmethyl ester Cbz-L-leucine (2 g, 7.5 mmol) and Cs₂CO₃ (1.46 g, 4.5 mmol, 0.6 eq) were dissolved in water (20 mL). Water was then removed in vacuo, and the resulting oil was lyophilized for 12 h to give a white solid. To this solid were added 3-methyl-3-(toluenesulfonyl-oxymethyl)oxetane (oxetane tosylate) (1.8 g, 4.5 mmol), and NaI (224 mg,1.5 mmol, 0.2 eq.) which were taken up in DMF (35 mL) and allowed to stir under nitrogen for 48 h. The DMF was then removed in vacuo, and the resulting solid was dissolved in EtOAc (60 mL) and washed with 10% NaHCO$_3$ (20 mL) and saturated NaCl (10 mL) and dried over MgSO$_4$. The solvent was removed under reduced pressure to yield yellow oil which was flash column chromatographed on 200 cm$^3$ of silica gel using 3:1 hexanes:EtOAc as an eluant to give (2S)-2-benzyloxycarbonylamino-4-methyl-pentanoic acid 3-methyloxetan-3-ylmethyl ester (Cbz-Leu oxetane ester) as a yellow thick oil.

$^1$H NMR (CD$_3$SOCD$_3$) 7.75 (d, 1H), 7.26-7.38 (m, 5H), 5.05 (s, 2H), 4.0-4.4 (m, 8H), 1.45-1.7 (m, 3H), 1.25 (s, 3H), 0.85-0.9 (m, 6H).

Step 3: Preparation of [3-methyl-1-(4-methyl-2,6,7-trioxa-bicyclo[2.2.2]oct-1-yl)-butyl]-carbamic acid benzyl ester (2S)-2-Benzyloxycarbonylamino-4-methyl-pentanoic acid 3-methyloxetan-3-ylmethyl ester (Cbz-Leu oxetane ester) (2 g, 5.7 mmol) was dissolved in dry CH$_2$Cl$_2$ (10 mL) under nitrogen. BF$_3$.Et$_2$O (40 µl, 0.3 mmol, 0.054 eq.) was diluted in dry CH$_2$Cl$_2$ (1 mL) and added to the reaction flask. The reaction was allowed to warm up to room temperature and stirred for 12 h. Triethylamine (335 µl, 3.3 mmol, 0.58 eq) was added and the reaction was stirred for an additional 30 min., before being concentrated to thick oil. The crude product was redissolved on EtOAc (15 mL), washed with 3% NH$_4$Cl (10 mL), and saturated NaCl (10 mL), dried (MgSO$_4$), and evaporated to dryness. The reaction yielded a colorless thick oil, which crystallized on standing to give [3-methyl-1-(4-methyl-2,6,7-trioxa-bicyclo[2.2.2]oct-1-yl)-butyl]-carbamic acid benzyl ester, (Cbz-Leu-OBO ester).

$^1$H NMR (CD$_3$SOCD$_3$) 7.25-7.35 (br m, 5H), 6.88 (d, 1H), 5.05 (s, 2H), 3.80 (s, 6H), 3.7 (m, 1H) 1.2-1.6 (m, 3H), 0.75-0.85 (m, 6H), 0.70 (s, 3H).

Step 4: Preparation of 3-methyl-1-(4-methyl-2,6,7-trioxa-bicyclo[2.2.2]oct-1-yl)-butylamine To [3-methyl-1-(4-methyl-2,6,7-trioxa-bicyclo[2.2.2]oct-1-yl)-butyl]-carbamic acid benzyl ester (3.2 g, 9.2 mmol) in absolute EtOH (30 mL) was added 10% Pd in activated carbon (320 mg, 10%) under nitrogen. The reaction mixture was hydrogenated at 50 psi for 6 h. The reaction was monitored by TLC and the reaction mixture was filtered through Celite. The solvent was removed to get 3-methyl-1-(4-methyl-2,6,7-trioxa-bicyclo[2.2.2]oct-1-yl)-butylamine as a white solid.

$^1$H NMR (CD$_3$SOCD$_3$) 3.80 (s, 6H), 3.2-3.4 (br s, 3H), 1.75 (m, 1H), 1.0-1.4 (m, 2H), 0.75-0.90 (m, 6H), 0.75 (s, 3H).

Step 5: Preparation of [3-methyl-1-(4-methyl-2,6,7-trioxa-bicyclo[2.2.2]oct-1-yl)-butyl]-thiazol-2-ylmethyleneamine A solution of 3-methyl-1-(4-methyl-2,6,7-trioxa-bicyclo [2.2.2]oct-1-yl)-butylamine (1.9 g, 8.8 mmol) and thiazole-2-carboxaldehyde (998 mg, 8.8 mmol) in benzene was refluxed for 3 h using a Dean-Stark trap, during which time water was collected and the remaining residue was evaporated under reduced pressure to get [3-methyl-1-(4-methyl-2,6,7-trioxa-bicyclo[2.2.2]oct-1-yl)-butyl]-thiazol-2-ylmethyleneamine as an orange solid.

$^1$H NMR (CD$_3$SOCD$_3$) 8.4 (s, 1H), 7.97 (d, 1H), 7.84 (d, 1H), 3.82 (s, 6H), 3.4 (m, 1H), 1.7 (m, 1H), 1.5 (m, 1H), 1.3 (m, 1H), 0.9 (m, 6H), 0.75 (s, 3H).

Step 6: Preparation of [(4-bromo-phenyl)-thiazol-2-yl-methyl]-[3-methyl-1-(4-methyl-2,6,7-trioxa-bicyclo[2,2,2]oct-1-yl)-butyl]-amine To a solution of dibromobenzene (760 mg, 3.2 mmol) in dry ether was added 2.5 M solution of nBuLi in hexanes (1.3 mL, 3.2 mmol) at −30° C. After stirring for 1 h, a solution of [3-methyl-1-(4-methyl-2,6,7-trioxa-bicyclo[2.2.2]oct-1-yl)-butyl]-thiazol-2-ylmethylene-amine (500mg, 1.6 mmol) in 5 mL of dry ether was added slowly. The reaction mixture was allowed to stir at the same temperature for 2 h and then the reaction was quenched with water and extracted with ethyl acetate. The organic layer was washed with saturated NaCl and dried over MgSO$_4$. The solvent was evaporated in vacuo. The crude was flash column chromatographed using 2:1 hexanes:EtOAc as an eluant to get [(4-bromo-phenyl)-thiazol-2-yl-methyl]-[3-methyl-1-(4-methyl-2,6,7-trioxa-bicyclo[2.2.2]oct-1-yl)-butyl]-amine as a pale yellow solid.

$^1$H NMR (CD$_3$SOCD$_3$) 7.64 (d, 1H), 7.59 (d, 1H), 7.5 (d, 2H), 7.28 (d, 2H), 5.68 (s, 1H), 3.82 (s, 6H), 3.3 (m, 1H), 2.65 (m, 1H), 1.95 (m, 1H),1.4 (m, 1H), 1.2 (m, 1H), 0.9 (d, 3H), 0.75 (s, 3H), 0.7 (d, 3H).

Step 7: Preparation of (2S)-2-{(S)-[(4-bromophenyl)-thiazol-2-yl-methyl]-amino}-4-methylpentanoic acid To a solution of [(4-bromo-phenyl)-thiazol-2-yl-methyl]-[3-methyl-1-(4-methyl-2,6,7-trioxa-bicyclo[2.2.2]oct-1-yl)-butyl]-amine (500 mg, 1.06 mmol) in THF (20 mL) and water (18 mL), was added 1N HCl (3.5 mL). The reaction mixture was stirred for 2 h. After checking the TLC for the disapperance of the starting material, Li(OH).H$_2$O (280.2 mg, 6.3 eq.) was added and stirred at room temperature for 2 h. Then 1N HCl was added to adjust the pH 4-6, and the product was extracted with EtOAC and the organic layer dried over MgSO4. The solvent was evaporated to yield (2S)-2-{(S)-[(4-bromophenyl)-thiazol-2-yl-methyl]-amino}-4-methylpentanoic acid as a yellow solid.

Step 8: Preparation of (2S)-2-{(S)-[(4-bromophenyl)-thiazol-2-yl-methyl]-amino}-4-methylyentanoic acid cyanomethylamide In the presence of HATU (1 eq.) and diisopropylethylamine (4 eq.), (2S)-2-{(S)-[(4-bromophenyl)-thiazol-2-yl-methyl]-amino}-4-methylpentanoic acid was coupled with aminoacetonitrile (2 eq., 1 eq. excess) to give (2S)-2-{(S)-[(4-bromophenyl)-thiazol-2-yl-methyl]-amino}-4-methylpentanoic acid cyanomethylamide as a cream solid.

$^1$H NMR (CD$_3$SOCD$_3$) 8.73 (t, 1H), 7.66 (d, 1H), 7.64 (d, 1H), 7.5 (dd, 2H), 7.25 (dd, 2H) 4.92(d, 1H), 4.14 (t, 2H), 3.32 (s, 1H), 3.19 (m, 1H), 2.98 (m, 1H), 1.85 (m, 1H), 1.46 (m, 1H), 0.9-0.85 (m, 6H).

EXAMPLE 35

Synthesis of (2S) 2-{(S)-[(4-bromophenyl)-thiazol-2-yl-methyl]-amino}-4-methylpentanoic acid (1-cyanocyclopropyl)-amide

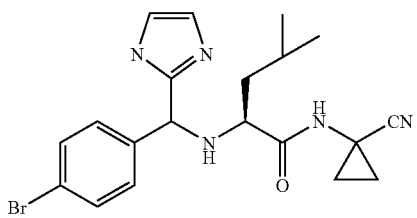

The title compound was prepared by the coupling of (2S)-2-{(S)-[(4-bromophenyl)-thiazol-2-yl-methyl]-amino}-4-methylpentanoic acid with 1-aminocyclopropanecarbonitrile in the presence of HATU and diisopropylamine, in similar manner to that described for the preparation of Example 34. The synthesis of (2S)-2-{(S)-[(4-bromophenyl)thiazol-2-yl-methyl]-amino}-4-methylpentanoic acid was accomplished via addition of bromophenyllithium (generated in situ from 1,4-dibromobenzene and n-butyllithium) to the imine condensation product between thiazole 2-carboxayldehyde and 3-methyl-1-(4-methyl-2,6,7-trioxa-bicyclo[2.2.2]oct-1-yl)-butylamine (L-leucine OBO ester, prepared according to the method described for Example 34), followed by ortho ester deprotection.

$^1$H NMR (CDCl$_3$): δ 0.82 (d, 3H), 0.95 (d, 3H), 1.04 (m, 2H), 1.46-1.62 (m, 4H), 1.80 (m, 1H), 3.12 (dd, 1H), 4.95 (s, 1H), 7.22 (s, 1H), 7.23-7.25 (d, 2H), 7.31 (m, 2H), 7.47 (d, 2H), 7.74 (m, 1H).

EXAMPLE 36

Synthesis of (2S)-2-{(S)-[(2',4'-difluorobiphenyl-4-yl)-thiazol-2-yl-methyl]-amino}-4-methylpentanoic acid (1-cyanocyloropyl)-amide

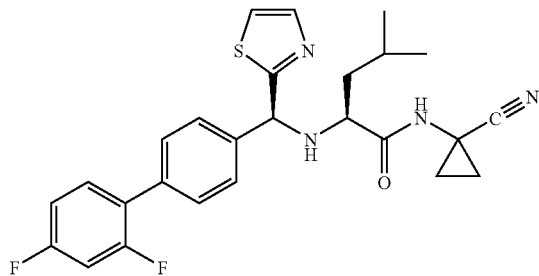

The title compound was prepared via the Suzuki cross-coupling of (2S)-2-{(S)-[(4-bromophenyl)-thiazol-2-yl-methyl]-amino}-4-methylpentanoic acid (1-cyanocyclopropyl)-amide with 2,4-difluorobenzeneboronic acid, in the presence of [1,1'-bis(diphenylphosphino)ferrocene]dichloropalladium(II), dichloromethane complex. MS (–ESI): 479 [M–1]$^-$ $^1$H NMR (CDCl$_3$): δ 0.84 (d, 3H), 0.97 (d, 3H), 1.03 (m, 2H), 1.47 (m, 2H), 1.57-1.62 (m, 4H), 1.95 (m, 1H), 3.27 (dd, 1H), 5.02 (s, 1H), 6.93 (m, 2H), 7.32 (m, 1H), 7.39 (m, 1H), 7.42 (m, 3H), 7.48 (d, 2H), 7.77 (d, 1H).

EXAMPLE 37

Synthesis of (2S)-2-{(S)-[(4'-methanesulfonylbiphenyl-4-yl)-thiazol-2-yl-methyl]-amino}-4-methylpentanoic acid (1-cyanocyclopropyl)-amide

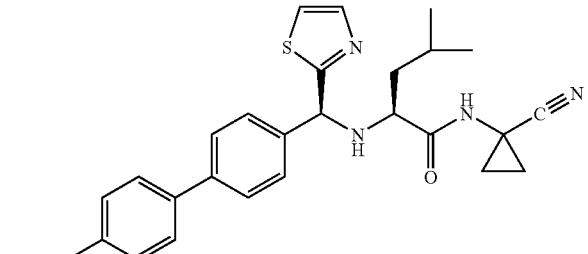

The title compound was prepared in similar manner to that described for (2S)-2-{(S)-[(2',4'-difluorobiphenyl-4-yl)-thiazol-2-yl-methyl]-amino}-4-methylpentanoic acid (1-cyanocyclopropyl)-amide, via Suzuki cross-coupling of (2S)-2-{(S)-[(4-bromophenyl)-thiazol-2-yl-methyl]-amino}-4-methylpentanoic acid (1-cyanocyclopropyl)-amide with 4-methanesulfonylphenylboronic acid, in the presence of [1,1'-bis(diphenylphosphino)-ferrocene]dichloropalladium (II), dichloromethane complex.

MS (–ESI): 521 [M–1]$^-$

EXAMPLE 38

Synthesis of N$^1$-(1-cyanocyclopropyl)-4,4-difluoro-N$^2$-{(1S)-2,2,2-trifluoro-1-[4'-(methylsulfonyl)-1,1'-biphenyl-4-yl]ethyl}-L-norvalinamide

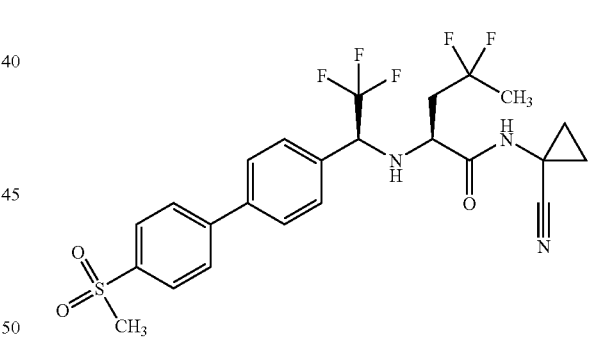

Step 1: Preparation of methyl N-((benzyloxy)carbonyl)-3-iodo-L-alaninate

To a solution of carbobenzyloxy-L-serine (25 g, 104 mmol) in ethyl acetate (200 mL) was added a solution of diazomethane in ether until a slight yellow color persisted. The solvent was evaporated under vacuum. To the residue was added N,N-dimethylformamide (400 mL) and methyltriphenoxyphosphonium iodide (50 g, 110 mmol). The mixture was stirred for 15 minutes, then methanol (15 mL) was added and the mixture was then poured over 20% sodium thiosulfate and extracted with a 1:1 mixture of ethyl acetate: hexanes (2 L). The organic layer was washed with water, brine (3×), dried over magnesium sulfate, filtered and the solvent evaporated under vacuum. The residue was purified by silica gel chromatography using ethyl acetate and hexanes. The compound obtained was triturated in diethyl ether/hexanes, filtered and air dried to afford methyl N-((benzyloxy)carbonyl)-3-iodo-L-alaninate.

Step 2: Preparation of methyl N-((benzyloxy)carbonyl)-4-oxo-L-norvalinate

A mixture of methyl N-((benzyloxy)carbonyl)-3-iodo-L-alaninate (10 g, 27.5 mmol), from Step 1, zinc-copper couple (3.3 g) in benzene (110 mL) and N,N-dimethylacetamide (7.4 mL) was sonicated in an ultra-sound bath for 2 hours. Over this period, 3 portions of 1,2-dibromoethane (0.24 mL) and chlorotrimethylsilane (0.17 mL) were added. To this mixture was then added bis(triphenylphosphine) palladium chloride (0.958 g, 1.4 mmol) and acetyl chloride (2.5 mL, 35.2 mmol) and the mixture was heated at 70° C. for 2 hours. After cooling to room temperature, the mixture was filtered on celite with ethyl acetate, the organic layer was then washed with a saturated solution of ammonium chloride, brine (2×), dried over magnesium sulfate, filtered and the solvent evaporated under vacuum. The residue was purified by silica gel chromatography using ethyl acetate and hexanes to afford methyl N-((benzyloxy)carbonyl)-4-oxo-L-norvalinate.

Step 3: Preparation of methyl N-((benzyloxy)carbonyl)-4,4-difluoro-L-norvalinate To a solution of methyl N-((benzyloxy)carbonyl)-4-oxo-L-norvalinate (1.3 g, 4.65 mmol) in dichloromethane (20 mL) and methanol (0.019 mL) at 0° C. was added DAST (2.46 mL) slowly. The ice bath was removed and replaced with a hot water (57° C.) bath. The hot water bath was replaced 3 times, then the mixture was stirred overnight at room temperature. The mixture was slowly poured over cold saturated NaHCO$_3$, extracted with ethyl acetate, washed with brine, dried over magnesium sulfate, filtered and the solvent evaporated under vacuum. The residue was purified by silica gel chromatography using ethyl acetate and hexanes to afford methyl N-((benzyloxy)carbonyl)-4,4-difluoro-L-norvalinate.

Step 4: Preparation of benzyl (1S)-3,3-difluoro-1-(hydroxymethyl)butylcarbamate To a solution of methyl N-((benzyloxy)carbonyl)-4,4-difluoro-L-norvalinate (1.59 g, 5.29 mmol) in ethanol (50 mL) was added lithium chloride (919 mg) and the mixture was stirred for 10 minutes. Sodium borohydride (820 mg) was added slowly, the mixture stirred for 2 hours. Then, another portion of sodium borohydride (100 mg) was added and stirring continued for 30 minutes. The mixture was diluted with water (20 mL) and neutralized slowly with 1N HCl followed by the addition of another aliquot of water. The mixture was extracted with ethyl acetate (2×), washed with brine, dried over magnesium sulfate, filtered and the solvent evaporated under vacuum to afford benzyl (1S)-3,3-difluoro-1-(hydroxymethyl)butylcarbamate.

Step 5: Preparation of (2S)-1-((tert-butyl(dimethyl) silyl)oxy)-4,4-difluoropentan-2-amine To a solution of benzyl (1S)-3,3-difluoro-1-(hydroxymethyl)butylcarbamate (from Step 4) in ethanol (25 mL) was added palladium on charcoal (10%, 150 mg) and the mixture was stirred under a H$_2$ atmosphere (ballon) for 2 h. Dichloromethane was added and the mixture was filtered on celite. The solvent was evaporated under vacuum. The residue was dissolved in dichloromethane (15 mL) and triethylamine (1 mL), N,N-dimethylaminopyridine (10 mg) and chloro-t-butyldimethylsilane (844 mg) were added. The mixture was stirred overnight, then water and brine were added. The mixture was extracted with ethyl acetate (2×), washed with brine, dried over magnesium sulfate, filtered and the solvent evaporated under vacuum to afford (2S)-1-((tert-butyl(dimethyl)silyl)oxy)-4,4-difluoropentan-2-amine.

Step 6: Preparation of (2S)-1-((tert-butyl(dimethyl) silyl)oxy)-4,4-difluoro-N-((1E)-2,2,2-trifluoroethylidene)pentan-2-amine A solution of (2S)-1-((tert-butyl(dimethyl)silyl)oxy)-4,4-difluoropentan-2-amine, from Step 5, and trifluoroacetaldehyde methyl hemiacetal (80%, 0.9 mL) in benzene (20 mL) was refluxed over night with a Dean-Stark apparatus. The solvent was evaporated under vacuum and the residue purified by silica gel chromatography using ethyl acetate and hexanes to afford (2S)-1-((tert-butyl(dimethyl)silyl)oxy)-4,4-difluoro-N-((1E)-2,2,2-trifluoroethylidene)pentan-2-amine.

Step 7: Preparation of (2S)-2-(((1S)-1-(4-bromophenyl)-2,2,2-trifluoroethyl)amino)-4,4-difluoropentan-1-ol To a −78° C. solution of 1,4-dibromobenzene (330 mg) in THF (5.2 mL) was added 2.5M n-BuLi in hexanes (0.52 mL) and the solution was aged for 30 minutes. Then, a solution of (2S)-1-((tert-butyl(dimethyl)silyl)oxy)-4,4-difluoro-N-((1E)-2,2,2-trifluoroethylidene)pentan-2-amine (333 mg) in THF (5.2 mL) was added. The mixture was stirred at −78° C. for 45 minutes, then poured over cold saturated ammonium chloride, extracted with ethyl acetate (2×), washed with brine, dried over magnesium sulfate, filtered and the solvent evaporated under vacuum. The residue was dissolved in THF (10 mL) cooled in an ice/water bath and n-tetrabutylammonium fluoride (1M in THF, 1.5 mL) was added. The mixture was stirred at 0° C. for 1 h, poured over cold water, extracted with ethyl acetate (2×), washed with brine, dried over magnesium sulfate, filtered and the solvent evaporated under vacuum to afford (2S)-2-(((1S)-1-(4-bromophenyl)-2,2,2-trifluoroethyl)amino)-4,4-difluoropentan-1-ol.

Step 8: Preparation of N$^2$-[(1S)-1-(4-bromophenyl)-2,2,2-trifluoroethyl]-N$^1$-(1-cyanocyclopropyl)-4,4-difluoro-L-norvalinamide (2S)-2-(((1S)-1-(4-Bromophenyl)-2,2,2-trifluoroethyl) amino)-4,4-difluoropentan-1-ol was converted to the title compound using the method described in Step 9 of Example 15.

Step 9: Preparation of N$^1$-(1-cyanocyclopropyl)-4,4-difluoro-N$^2$-{(1S)-2,2,2-trifluoro-1-[4'-(methylthio)-1,1'-biphenyl-4-yl]ethyl}-L-norvalinamide N$^2$-[(1S)-1-(4-Bromophenyl)-2,2,2-trifluoroethyl]-N$^1$-(1-cyanocyclopropyl)-4,4-difluoro-L-norvalinamide was converted to the title compound using the method described in Step 10 of Example 15.

Step 10: Preparation of N$^1$-(1-cyanocyclopropyl)-4,4-difluoro-N$^2$-{(1S)-2,2,2-trifluoro-1-[4'-(methylsulfonyl)-1,1'-biphenyl-4-yl]ethyl}-L-norvalinamide N$^1$-(1-Cyanocyclopropyl)-4,4-fluoro-N$^2$-{(1S)-2,2,2-trifluoro-1-[4'-(methylthio)-1,1'-biphenyl-4-yl]ethyl}-L-norvalinamide was converted to the title compound using the method described in Step 11 of Example 15.

Using similar experimental procedures as those listed above, the following compounds were synthesized.

| NAME | CHARACTERIZATION |
|---|---|
| $N^1$-(cyanomethyl)-$N^2$-(2,2,2-trifluoro-1-phenylethyl)-L-leucinamide | MS(+ESI): 328.3[M+1]$^+$ |
| $N^1$-(cyanomethyl)-$N^2$-[2,2,2-trifluoro-1-(4-fluoro-3-methylphenyl)ethyl]-L-leucinamide | MS(+ESI): 360.2[M+1]$^+$ |
| $N^1$-(cyanomethyl)-$N^2$-[(1R)-2,2,2-trifluoro-1-(4-pyridin-3-ylphenyl)ethyl]-L-leucinamide | MS(+ESI): 405.1[M+1]$^+$ |
| $N^1$-(cyanomethyl)-$N^2$-[(1S)-2,2,2-trifluoro-1-(4-pyridin-3-ylphenyl)ethyl]-L-leucinamide | MS(+ESI): 405.1[M+1]$^+$ |
| $N^1$-(cyanomethyl)-$N^2$-[(1R)-2,2,2-trifluoro-1-(4-pyridin-4-ylphenyl)ethyl]-L-leucinamide | MS(+ESI): 405.1[M+1]$^+$ |
| $N^1$-(cyanomethyl)-$N^2$-[(1S)-2,2,2-trifluoro-1-(4-pyridin-4-ylphenyl)ethyl]-L-leucinamide | MS(+ESI): 405.1[M+1]$^+$ |
| $N^1$-(cyanomethyl)-$N^2$-[(1R)-2,2,2-trifluoro-1-(4-{[4-(2-fluoroethyl)piperazin-1-yl]carbonyl}phenyl)ethyl]-L-leucinamide | MS(+ESI): 486.3[M+1]$^+$ |
| $N^1$-(cyanomethyl)-$N^2$-[2,2,2-trifluoro-1-(4-{[4-(2-fluoroethyl)piperazin-1-yl]carbonyl}phenyl)ethyl]-L-leucinamide | MS(+ESI): 486.2[M+1]$^+$ |
| $N^2$-[1-(1,1'-biphenyl-4-yl)-2,2,2-trifluoroethyl]-$N^1$-(cyanomethyl)-L-leucinamide | MS(+ESI): 404.2[M+1]$^+$ |
| $N^1$-(cyanomethyl)-$N^2$-{2,2,2-trifluoro-1-[4-(3-hydroxy-3-methylbut-1-ynyl)phenyl]ethyl}-L-leucinamide | MS(+ESI): 410.2[M+1]$^+$ |
| $N^1$-(cyanomethyl)-$N^2$-{(1S)-2,2,2-trifluoro-1-[4-(3-hydroxy-3-methylbutyl)phenyl]ethyl}-L-leucinamide | MS(+ESI): 436.2[M+Na]$^+$, 414.2[M+1]$^+$ |
| $N^2$-[(1S)-1-(4-bromophenyl)-2,2,3,3,3-pentafluoropropyl]-$N^1$-(cyanomethyl)-L-leucinamide | MS(+ESI): 458.1, 456.1[M+1]$^+$ |
| $N^1$-(cyanomethyl)-$N^2$-[(1S)-2,2,3,3,3-pentafluoro-1-(4-pyridin-4-ylphenyl)propyl]-L-leucinamide | MS(+ESI): 455.2[M+1]$^+$ |
| $N^1$-(cyanomethyl)-$N^2$-[(1S)-2,2,2-trifluoro-1-(4'-fluoro-1,1'-biphenyl-4-yl)ethyl]-L-leucinamide | MS(+ESI): 422.2[M+1]$^+$ |
| $N^1$-(cyanomethyl)-$N^2$-((1S)-2,2,2-trifluoro-1-{4-[(1E)-3-hydroxy-3-methylbut-1-enyl]phenyl}ethyl)-L-leucinamide | MS(+ESI): 434.1[M+Na]$^+$ |
| $N^1$-(cyanomethyl)-$N^2$-{(1S)-2,2,3,3,3-pentafluoro-1-[4'-(methylthio)-1,1'-biphenyl-4-yl]propyl}-L-leucinamide | MS(+ESI): 500.1[M+Na]$^+$ |
| $N^1$-(cyanomethyl)-$N^2$-{(1S)-2,2,3,3,3-pentafluoro-1-[4'-(methylsulfonyl)-1,1'-biphenyl-4-yl]propyl}-L-leucinamide | MS(+ESI): 532.1[M+Na]$^+$ |
| $N^1$-(cyanomethyl)-$N^2$-{(1S)-2,2,2-trifluoro-1-[4-(1-oxidopyridin-3-yl)phenyl]ethyl}-L-leucinamide | MS(+ESI): 421.2[M+Na]$^+$ |
| $N^1$-(cyanomethyl)-$N^2$-{(1S)-2,2,2-trifluoro-1-[4-(morpholin-4-ylcarbonyl)phenyl]ethyl}-L-leucinamide | MS(+ESI): 441.3[M+1]$^+$ |
| $N^1$-(cyanomethyl)-$N^2$-[(1S)-2,2,2-trifluoro-1-(4-{[methoxy(methyl)amino]carbonyl}phenyl)ethyl]-L-leucinamide | MS(+ESI): 415.1[M+1]$^+$ |
| $N^1$-(cyanomethyl)-$N^2$-[(1S)-2,2,2-trifluoro-1-(4-thien-3-ylphenyl)ethyl]-L-leucinamide | MS(−ESI): 388.3[M−21]$^-$ |
| $N^1$-(cyanomethyl)-$N^2$-{(1S)-2,2,2-trifluoro-1-[4-(4-methylpyridin-2-yl)phenyl]ethyl}-L-leucinamide | MS(−ESI): 397.2[M−21]$^-$ |
| $N^1$-(cyanomethyl)-$N^2$-{(1S)-2,2,2-trifluoro-1-[4-(5-methylpyridin-2-yl)phenyl]ethyl}-L-leucinamide | MS(−ESI): 397.4[M−21]$^-$ |
| $N^1$-(cyanomethyl)-$N^2$-{(1S)-1-[4-(3,5-dimethylisoxazol-4-yl)phenyl]-2,2,2-trifluoroethyl}-L-leucinamide | MS(−ESI): 401.4[M−21]$^-$ |

| NAME | CHARACTERIZATION |
|---|---|
| $N^2$-[(1S)-1-(4'-cyano-1,1'-biphenyl-4-yl)-2,2,2-trifluoroethyl]-$N^1$-(cyanomethyl)-L-leucinamide | MS(−ESI): 407.4[M−21]$^-$ |
| $N^1$-(cyanomethyl)-$N^2$-[(1S)-1-(3',4'-difluoro-1,1'-biphenyl-4-yl)-2,2,2-trifluoroethyl]-L-leucinamide | MS(−ESI): 418.4[M−21]$^-$ |
| 4'-{1-[1-(Cyanomethyl-carbamoyl)-3-methyl-butylamino]-2,2,2-trifluoro-ethyl}-biphenyl-2-carboxylic acid methyl ester | MS(−ESI): 440.5[M−21]$^-$ |
| 4'-{1-[1-(Cyanomethyl-carbamoyl)-3-methyl-butylamino]-2,2,2-trifluoro-ethyl}-biphenyl-3-carboxylic acid methyl ester | MS(−ESI): 440.4[M−21]$^-$ |
| $N^1$-(cyanomethyl)-$N^2$-[(1S)-1-(3',4'-dimethoxy-1,1'-biphenyl-4-yl)-2,2,2-trifluoroethyl]-L-leucinamide | MS(−ESI): 442.5[M−21]$^-$ |
| $N^1$-(cyanomethyl)-$N^2$-{(1S)-2,2,2-trifluoro-1-[2'-(trifluoromethyl)-1,1'-biphenyl-4-yl]ethyl}-L-leucinamide | MS(−ESI): 450.4[M−21]$^-$ |
| $N^1$-(cyanomethyl)-$N^2$-[(1S)-1-(3',4'-dichloro-1,1'-biphenyl-4-yl)-2,2,2-trifluoroethyl]-L-leucinamide | MS(−ESI): 450.4[M−21]$^-$ |
| $N^1$-(cyanomethyl)-$N^2$-[(1S)-2,2,2-trifluoro-1-(3'-formyl-1,1'-biphenyl-4-yl)ethyl]-L-leucinamide | MS(−ESI): 410.2[M−21]$^-$ |
| $N^2$-{(1S)-1-[4-(5-bromopyridin-3-yl)phenyl]-2,2,2-trifluoroethyl}-$N^1$-(cyanomethyl)-L-leucinamide | MS(−ESI): 461.4[M−21]$^-$ |
| $N^1$-(cyanomethyl)-$N^2$-{(1S)-2,2,2-trifluoro-1-[4'-(trifluoromethoxy)-1,1'-biphenyl-4-yl]ethyl}-L-leucinamide | MS(−ESI): 466.4[M−21]$^-$ |
| $N^1$-(cyanomethyl)-$N^2$-{(1S)-2,2,2-trifluoro-1-[4-(1H-indol-4-yl)phenyl]ethyl}-L-leucinamide | MS(−ESI): 421.5[M−21]$^-$ |
| $N^1$-(cyanomethyl)-$N^2$-[(1S)-2,2,2-trifluoro-1-(4-pyrimidin-5-ylphenyl)ethyl]-L-leucinamide | MS(−ESI): 384.4[M−21]$^-$ |
| $N^1$-(cyanomethyl)-$N^2$-[(1S)-2,2,2-trifluoro-1-(4-quinolin-3-ylphenyl)ethyl]-L-leucinamide | MS(−ESI): 433.5[M−21]$^-$ |
| 4'-{1-[1-(Cyanomethyl-carbamoyl)-3-methyl-butylamino]-2,2,2-trifluoro-ethyl}-biphenyl-4-carboxylic acid methyl ester | MS(−ESI): 440.4[M−21]$^-$ |
| $N^1$-(cyanomethyl)-$N^2$-[(1S)-2,2,2-trifluoro-1-(4-pyrimidin-2-ylphenyl)ethyl]-L-leucinamide | MS(−ESI): 384.4[M−21]$^-$ |
| $N^1$-(cyanomethyl)-$N^2$-{(1S)-2,2,2-trifluoro-1-[4-(3-furyl)phenyl]ethyl}-L-leucinamide | MS(−ESI): 372.4[M−21]$^-$ |
| $N^1$-(cyanomethyl)-$N^2$-((1S)-2,2,2-trifluoro-1-{4-[3-(trifluoromethyl)pyridin-2-yl]phenyl}ethyl)-L-leucinamide | MS(−ESI): 451.4[M−21]$^-$ |
| $N^1$-(cyanomethyl)-$N^2$-((1S)-2,2,2-trifluoro-1-{4-[4-(trifluoromethyl)pyridin-2-yl]phenyl}ethyl)-L-leucinamide | MS(−ESI): 451.4[M−21]$^-$ |
| $N^1$-(cyanomethyl)-$N^2$-((1S)-2,2,2-trifluoro-1-{4-[5-(trifluoromethyl)pyridin-2-yl]phenyl}ethyl)-L-leucinamide | MS(−ESI): 451.4[M−21]$^-$ |
| $N^1$-(cyanomethyl)-$N^2$-[(1S)-2,2,2-trifluoro-1-(3'-methoxy-1,1'-biphenyl-4-yl)ethyl]-L-leucinamide | MS(−ESI): 412.4[M−21]$^-$ |
| $N^2$-{(1S)-1-[4'-(acetylamino)-3'-fluoro-1,1'-biphenyl-4-yl]-2,2,2-trifluoroethyl}-$N^1$-(cyanomethyl)-L-leucinamide | MS(−ESI): 457.4[M−21]$^-$ |
| $N^1$-(cyanomethyl)-$N^2$-{(1S)-2,2,2-trifluoro-1-[4-(3-methylthien-2-yl)phenyl]ethyl}-L-leucinamide | MS(−ESI): 402.4[M−21]$^-$ |
| $N^1$-(cyanomethyl)-$N^2$-[(1S)-2,2,2-trifluoro-1-(3'-fluoro-1,1'-biphenyl-4-yl)ethyl]-L-leucinamide | MS(−ESI): 400.4[M−21]$^-$ |
| $N^2$-{(1S)-1-[4-(5-acetylthien-2-yl)phenyl]-2,2,2-trifluoroethyl}-$N^1$-(cyanomethyl)-L-leucinamide | MS(−ESI): 430.4[M−21]$^-$ |
| $N^2$-[(1S)-1-(3'-acetyl-1,1'-biphenyl-4-yl)-2,2,2-trifluoroethyl]-$N^1$-(cyanomethyl)-L-leucinamide | MS(−ESI): 424.4[M−21]$^-$ |
| $N^1$-(cyanomethyl)-$N^2$-{(1S)-2,2,2-trifluoro-1-[3'-(trifluoromethyl)-1,1'-biphenyl-4-yl]ethyl}-L-leucinamide | MS(−ESI): 450.4[M−21]$^-$ |

| NAME | CHARACTERIZATION |
|---|---|
| $N^1$-(cyanomethyl)-$N^2$-[(1S)-2,2,2-trifluoro-1-(5'-fluoro-2'-methoxy-1,1'-biphenyl-4-yl)ethyl]-L-leucinamide | MS(−ESI): 430.4[M−21]⁻ |
| $N^1$-(cyanomethyl)-$N^2$-[(1S)-1-(3',5'-difluoro-1,1'-biphenyl-4-yl)-2,2,2-trifluoroethyl]-L-leucinamide | MS(−ESI): 418.4[M−21]⁻ |
| $N^1$-(cyanomethyl)-$N^2$-[(1S)-2,2,2-trifluoro-1-(2',3',5'-trifluoro-1,1'-biphenyl-4-yl)ethyl]-L-leucinamide | MS(−ESI): 436.4[M−21]⁻ |
| 3-(4'-{1-[1-(Cyanomethyl-carbamoyl)-3-methyl-butylamino]-2,2,2-trifluoro-ethyl}-biphenyl-3-yl)-acrylic acid | MS(−ESI): 452.5[M−21]⁻ |
| $N^2$-{(1S)-1-[4-(9-anthryl)phenyl]-2,2,2-trifluoroethyl}-$N^1$-(cyanomethyl)-L-leucinamide | MS(−ESI): 482.5[M−21]⁻ |
| $N^2$-[(1S)-1-(4'-benzoyl-1,1'-biphenyl-4-yl)-2,2,2-trifluoroethyl]-$N^1$-(cyanomethyl)-L-leucinamide | MS(−ESI): 486.5[M−21]⁻ |
| $N^2$-[(1S)-1-(3'-acetyl-4'-hydroxy-1,1'-biphenyl-4-yl)-2,2,2-trifluoroethyl]-$N^1$-(cyanomethyl)-L-leucinamide | MS(−ESI): 440.5[M−21]⁻ |
| $N^1$-(cyanomethyl)-$N^2$-{(1S)-1-[2'-(cyanomethyl)-1,1'-biphenyl-4-yl]-2,2,2-trifluoroethyl}-L-leucinamide | MS(−ESI): 421.4[M−21]⁻ |
| $N^1$-(cyanomethyl)-$N^2$-{2,2,2-trifluoro-1-[4'-(methylsulfonyl)-1,1'-biphenyl-4-yl]ethyl}-L-leucinamide | MS(+APCI): 482.2[M+1]⁺ |
| $N^1$-(cyanomethyl)-$N^2$-{2,2,2-trifluoro-1-[4'-(methylsulfinyl)-1,1'-biphenyl-4-yl]ethyl}-L-leucinamide | MS(+APCI): 466.1[M+1]⁺ |
| $N^1$-(cyanomethyl)-$N^2$-[2,2,2-trifluoro-1-(4-morpholin-4-ylphenyl)ethyl]-L-leucinamide | MS(+ESI): 413.2[M+1]⁺ |
| $N^1$-(cyanomethyl)-$N^2$-{(1R)-2,2,2-trifluoro-1-[4-(6-methylpyridin-3-yl)phenyl]ethyl}-L-leucinamide | MS(+APCI): 419.2[M+1]⁺ |
| $N^1$-(cyanomethyl)-$N^2$-{(1S)-2,2,2-trifluoro-1-[4-(6-methylpyridin-3-yl)phenyl]ethyl}-L-leucinamide | MS(+APCI): 419.0[M+1]⁺ |
| $N^1$-(cyanomethyl)-$N^2$-[2,2,2-trifluoro-1-(5-phenylthien-2-yl)ethyl]-L-leucinamide | MS(+ESI): 409.4[M+1]⁺ |
| $N^1$-(cyanomethyl)-$N^2$-[2,2,2-trifluoro-1-(4-quinolin-8-ylphenyl)ethyl]-L-leucinamide | MS(+ESI): 419.0[M+1]⁺ |
| $N^1$-(cyanomethyl)-$N^2$-[(1S)-2,2,2-trifluoro-1-(4-pyridin-2-ylphenyl)ethyl]-L-leucinamide | MS(+ESI): 455.2[M+1]⁺ |
| $N^2$-{1-[4'-(aminosulfonyl)-1,1'-biphenyl-4-yl]-2,2,2-trifluoroethyl}-$N^1$-(cyanomethyl)-L-leucinamide | MS(+ESI): 483.2[M+1]⁺ |
| $N^2$-{(1S)-1-[4'-(aminosulfonyl)-1,1'-biphenyl-4-yl]-2,2,2-trifluoroethyl}-$N^1$-(cyanomethyl)-L-leucinamide | MS(+ESI): 483.2[M+1]⁺ |
| $N^1$-(cyanomethyl)-$N^2$-{(1S)-2,2,2-trifluoro-1-[4'-(methylsulfonyl)-1,1'-biphenyl-4-yl]ethyl}-L-leucinamide | MS(+ESI): 482.3[M+1]⁺ |
| $N^1$-(cyanomethyl)-$N^2$-{(1S)-2,2,2-trifluoro-1-[4'-(methylthio)-1,1'-biphenyl-4-yl]ethyl}-L-leucinamide | MS(+ESI): 450.2[M+1]⁺ |
| $N^2$-[(1S)-1-(4-bromophenyl)-2,2,2-trifluoroethyl]-$N^1$-(cyanomethyl)-L-leucinamide | MS(+ESI): 407.2/408.2[M+1]⁺/[M+2]⁺ |
| $N^1$-(cyanomethyl)-$N^2$-{(1S)-2,2,2-trifluoro-1-[4'-(morpholin-4-ylsulfonyl)-1,1'-biphenyl-4-yl]ethyl}-L-leucinamide | MS(+ESI): 553.2[M+1]⁺ |
| $N^1$-(cyanomethyl)-$N^2$-{(1S)-2,2,2-trifluoro-1-[4'-(isopropylsulfonyl)-1,1'-biphenyl-4-yl]ethyl}-L-leucinamide | MS(+APCI): 510.3[M+1]⁺ |
| $N^2$-{(1S)-1-[4'-(aminosulfonyl)-1,1'-biphenyl-4-yl]-2,2,2-trifluoroethyl}-$N^1$-(cyanomethyl)-L-leucinamide | MS(+ESI): 483.2[M+1]⁺ |
| $N^2$-((1S)-1-{4'-[(acetylamino)sulfonyl]-1,1'-biphenyl-4-yl}-2,2,2-trifluoroethyl)-$N^1$-(cyanomethyl)-L-leucinamide | MS(+APCI): 525.4[M+1]⁺ |
| $N^1$-(cyanomethyl)-$N^2$-{(1S)-2,2,2-trifluoro-1-[2'-methyl-4'-(methylsulfonyl)-1,1'-biphenyl-4-yl]ethyl}-L-leucinamide | MS(+ESI): 496.2[M+1]⁺ |

| NAME | CHARACTERIZATION |
|---|---|
| $N^2$-[1-(5-bromothien-2-yl)-2,2,2-trifluoroethyl]-$N^1$-(cyanomethyl)-L-leucinamide | MS(+ESI): 413.2[M+1]$^+$ |
| $N^2$-[1-(4-bromophenyl)-2,2,2-trifluoroethyl]-$N^1$-(cyanomethyl)-L-leucinamide | MS(−ESI): 403.9, 405.9[M+1]$^−$ |
| 4-(4'-{1-[1-(Cyanomethyl-carbamoyl)-3-methyl-butylamino]-2,2,2-trifluoro-ethyl}-biphenyl-4-yl)-piperazine-1-carboxylic acid tert-butyl ester | MS(+ESI): 588.2[M+1]$^+$ |
| $N^1$-(cyanomethyl)-$N^2$-[2,2,2-trifluoro-1-(4'-piperazin-1-yl-1,1'-biphenyl-4-yl)ethyl]-L-leucinamide | MS(+ESI): 488.3[M+1]$^+$ |
| $N^1$-(cyanomethyl)-$N^2$-(2,2,2-trifluoro-1-{4'-[4-(2-hydroxyethyl)piperazin-1-yl]-1,1'-biphenyl-4-yl}ethyl)-L-leucinamide | MS(+APC1): 532.3[M+1]$^+$ |
| $N^1$-(cyanomethyl)-$N^2$-(2,2,2-trifluoro-1-{4'-[4-(2-hydroxy-2-methylpropyl)piperazin-1-yl]-1,1'-biphenyl-4-yl}ethyl)-L-leucinamide | MS(+APCI): 559.9[M+1]$^+$ |
| $N^1$-(cyanomethyl)-$N^2$-(1-{4-[(dimethylamino)carbonyl]phenyl}-2,2,2-trifluoroethyl)-L-leucinamide | MS(+ESI): 399.2[M+1]$^+$ |
| $N^1$-(cyanomethyl)-$N^2$-(1-{4-[(cyclopropylamino)carbonyl]phenyl}-2,2,2-trifluoroethyl)-L-leucinamide | MS(+ESI): 411.2[M+1]$^+$ |
| 4-{1-[1-(Cyanomethyl-carbamoyl)-3-methyl-butylamino]-2,2,2-trifluoro-ethyl}-benzoic acid | MS(−ESI): 370.2[M−1]$^−$ |
| $N^1$-(cyanomethyl)-$N^2$-(2,2,2-trifluoro-1-{4'-[4-(2-fluoroethyl)piperazin-1-yl]-1,1'-biphenyl-4-yl}ethyl)-L-leucinamide | MS(+ESI): 534.3[M+1]$^+$ |
| $N^1$-(cyanomethyl)-$N^2$-(2,2,2-trifluoro-1-{4-[(4-methylpiperazin-1-yl)carbonyl]phenyl}ethyl)-L-leucinamide | MS(+ESI): 454.3[M+1]$^+$ |
| $N^1$-(cyanomethyl)-$N^2$-[2,2,2-trifluoro-1-(4-{[4-(2-hydroxy-2-methylpropyl)piperazin-1-yl]carbonyl}phenyl)ethyl]-L-leucinamide | MS(+ESI): 512.3[M+1]$^+$ |
| $N^1$-(cyanomethyl)-$N^2$-{(1S)-2,2,2-trifluoro-1-[4-(2-methyl-1,3-thiazol-4-yl)phenyl]ethyl}-L-leucinamide | MS(+ESI): 425.1[M+1]$^+$ |
| $N^2$-{1-[4-(3-tert-butyl-1,2,4-triazin-5-yl)phenyl]-2,2,2-trifluoroethyl}-$N^1$-(cyanomethyl)-L-leucinamide | MS(+ESI): 463.2[M+1]$^+$ |
| $N^1$-(cyanomethyl)-$N^2$-[2,2,2-trifluoro-1-(4-{2-[3-(methylsulfonyl)phenyl]-1,3-thiazol-4-yl}phenyl)ethyl]-L-leucinamide | MS(+ESI): 565.1[M+1]$^+$ |
| $N^1$-(cyanomethyl)-$N^2$-((1S)-2,2,2-trifluoro-1-{4-[2-(1H-pyrazol-4-yl)-1,3-thiazol-4-yl]phenyl}ethyl)-L-leucinamide | MS(+ESI): 477.1[M+1]$^+$ |
| $N^1$-(cyanomethyl)-$N^2$-(2,2,2-trifluoro-1-{4'-[4-(methylsulfonyl)piperazin-1-yl]-1,1'-biphenyl-4-yl}ethyl)-L-leucinamide | MS(+ESI): 566.3[M+1]$^+$ |
| $N^2$-[1-(3-bromophenyl)-2,2,2-trifluoroethyl]-$N^1$-(cyanomethyl)-L-leucinamide | MS(+ESI): 406.0, 408.1[M+1]$^+$ |
| $N^1$-(cyanomethyl)-$N^2$-{2,2,2-trifluoro-1-[4'-(methylthio)-1,1'-biphenyl-3-yl]ethyl}-L-leucinamide | MS(+ESI): 450.1[M+1]$^+$ |
| $N^1$-(cyanomethyl)-$N^2$-[2,2,2-trifluoro-1-(3-pyridin-4-ylphenyl)ethyl]-L-leucinanmide | MS(+ESI): 405.1[M+1]$^+$ |
| $N^1$-(cyanomethyl)-$N^2$-[2,2,2-trifluoro-1-(4'-piperazin-1-yl-1,1'-biphenyl-3-yl)ethyl]-L-leucinamide | MS(+ESI): 488.3[M+1]$^+$ |
| $N^1$-(cyanomethyl)-$N^2$-{2,2,2-trifluoro-1-[4'-(methylsulfonyl)-1,1'-biphenyl-3-yl]ethyl}-L-leucinamide | MS(+ESI): 482.2[M+1]$^+$ |
| N-(cyanomethyl)-1-[(2,2,2-trifluoro-1-phenylethyl)amino]cyclohexanecarboxamide | MS(−ESI: 337[M−1]$^−$ |
| 1-{[1-(4-bromophenyl)-2,2,2-trifluoroethyl]amino}-N-(cyanomethyl)cyclohexanecarboxamide | MS(+ESI): 418, 420[M+1]$^+$ |
| N-(cyanomethyl)-1-{[2,2,2-trifluoro-1-(4'-piperazin-1-yl-1,1'-biphenyl-4-yl)ethyl]amino}cyclohexanecarboxamide | MS(+ESI): 500[M+1]$^+$ |
| $N^1$-(cyanomethyl)-$N^2$-[2,2,2-trifluoro-1-(4-piperidin-4-ylphenyl)ethyl]-L-leucinamide | MS(+ESI): 411[M+1]$^+$ |

-continued

| NAME | CHARACTERIZATION |
|---|---|
| $N^1$-(cyanomethyl)-$N^2$-{2,2,2-trifluoro-1-[4-(4-pyridin-2-ylpiperazin-1-yl)phenyl]ethyl}-L-leucinamide | MS(+ESI): 489[M+1]$^+$ |
| $N^2$-[1-(4-bromophenyl)-2,2,2-trifluoroethyl]-$N^1$-(cyanomethyl)-3-cyclopropylalaninamide | MS(+ESI): 404, 406[M+1]$^+$ |
| $N^1$-(cyanomethyl)-3-cyclopropyl-$N^2$-[2,2,2-trifluoro-1-(4-pyridin-4-ylphenyl)ethyl]alaninamide | MS(+ESI): 403[M+1]$^+$ |
| $N^1$-(cyanomethyl)-$N^2$-[2,2,2-trifluoro-1-(4'-pyridin-4-yl-1,1'-biphenyl-4-yl)ethyl]-L-leucinamide | MS(+ESI): 481[M+1]$^+$ |
| $N^1$-(cyanomethyl)-$N^2$-[(1R)-2,2,2-trifluoro-1-(1,3-thiazol-2-yl)ethyl]-L-leucinamide | MS(+ESI): 335[M+1]$^+$ |
| $N^1$-(cyanomethyl)-$N^2$-[(1S)-2,2,2-trifluoro-1-(4'-methoxy-1,1'-biphenyl-4-yl)ethyl]-L-leucinamide | MS(+ESI): 434[M+1]$^+$ |
| $N^1$-(cyanomethyl)-$N^2$-[(1S)-2,2,2-trifluoro-1-(4-methoxyphenyl)ethyl]-L-leucinamide | MS(+ESI): 358[M+1]$^+$ |
| $N^1$-(cyanomethyl)-$N^2$-[(1S)-2,2,2-trifluoro-1-(4'-pyridin-4-yl-1,1'-biphenyl-4-yl)ethyl]-L-leucinamide | MS(+ESI): 481[M+1]$^+$ |
| $N^1$-(cyanomethyl)-$N^2$-[(1S)-2,2,2-trifluoro-1-(4-phenoxyphenyl)ethyl]-L-leucinamide | MS(+ESI): 420[M+1]$^+$ |
| $N^2$-[(1S)-1-(4'-bromo-1,1'-biphenyl-4-yl)-2,2,2-trifluoroethyl]-$N^1$-(cyanomethyl)-L-leucinamide | MS(+ESI): 482, 484[M+1]$^+$ |
| $N^2$-{(1S)-1-[4-(4-chloropyridin-3-yl)phenyl]-2,2,2-trifluoroethyl}-$N^1$-(cyanomethyl)-L-leucinamide | MS(+ESI): 439[M+1]$^+$ |
| $N^2$-{(1S)-1-[4'-(acetylamino)-2'-methyl-1,1'-biphenyl-4-yl]-2,2,2-trifluoroethyl)}-$N^1$-(cyanomethyl)-L-leucinamide | MS(+ESI): 475[M+1]$^+$ |
| $N^2$-[(1S)-1-(1,1'-biphenyl-4-yl)-2,2,2-trifluoroethyl]-$N^1$-(cyanomethyl)-L-leucinamide | MS(+ESI): 404[M+1]$^+$ |
| $N^1$-(cyanomethyl)-$N^2$-{(1S)-2,2,2-trifluoro-1-[4-(6-methoxypyridin-3-yl)phenyl]ethyl}-L-leucinamide | MS(+ESI): 435[M+1]$^+$ |
| $N^1$-(cyanomethyl)-$N^2$-{(1S)-2,2,2-trifluoro-1-[4-(6-methoxypyridin-2-yl)phenyl]ethyl}-L-leucinamide | MS(+ESI): 435[M+1]$^+$ |
| $N^1$-(cyanomethyl)-$N^2$-{(1S)-2,2,2-trifluoro-1-[4''-(methylsulfonyl)-1,1':4',1''-terphenyl-4-yl]ethyl}-L-leucinamide | MS(+ESI): 558[M+1]$^+$ |
| $N^2$-[1-(4-bromophenyl)-2,2,2-trifluoroethyl]-$N^1$-(cyanomethyl)-3-(1-methylcyclopropyl)alaninamide | MS(+ESI): 418, 420[M+1]$^+$ |
| $N^1$-(cyanomethyl)-3-(1-methylcyclopropyl)-$N^2$-{2,2,2-trifluoro-1-[4'-(methylsulfonyl)-1,1'-biphenyl-4-yl]ethyl}alaninamide | MS(+ESI): 494[M+1]$^+$ |
| $N^1$-(cyanomethyl)-3-(1-methylcyclopropyl)-$N^2$-{2,2,2-trifluoro-1-[4'-(methylthio)-1,1'-biphenyl-4-yl]ethyl}alaninamide | MS(+ESI): 462[M+1]$^+$ |
| $N^1$-(cyanomethyl)-$N^2$-[(1S)-2,2,2-trifluoro-1-(4'-methyl-1,1'-biphenyl-4-yl)ethyl]-L-leucinamide | MS(+ESI): 418[M+1]$^+$ |
| $N^2$-[(1S)-1-(4'-acetyl-1,1'-biphenyl-4-yl)-2,2,2-trifluoroethyl]-$N^1$-(cyanomethyl)-L-leucinamide | MS(+ESI): 446[M+1]$^+$ |
| $N^1$-(cyanomethyl)-$N^2$-{(1S)-2,2,2-trifluoro-1-[4'-(hydroxymethyl)-1,1'-biphenyl-4-yl]ethyl}-L-leucinamide | MS(+ESI): 434[M+1]$^+$ |
| $N^1$-(cyanomethyl)-$N^2$-{(1R)-2,2,2-trifluoro-1-[4-(1-oxidopyridin-4-yl)phenyl]ethyl}-L-leucinamide | MS(+ESI): 421.4[M+1]$^+$ |
| $N^1$-(cyanomethyl)-$N^2$-{2,2,2-trifluoro-1-[4-(1-oxidopyridin-4-yl)phenyl]ethyl}-L-leucinamide | MS(+ESI): 421.4[M+1]$^+$ |
| $N^1$-(cyanomethyl)-$N^2$-(2,2,2-trifluoro-1-{4-[6-(1-hydroxy-1-methylethyl)-1-oxidopyridin-3-yl]phenyl}ethyl)-L-leucinamide | MS(+ESI): 479.3[M+1]$^+$ |
| $N^1$-(cyanomethyl)-$N^2$-(2,2,2-trifluoro-1-{4-[6-(methylsulfonyl)pyridin-3-yl]phenyl}ethyl)-L-leucinamide | MS(+ESI): 483.2[M+1]$^+$ |

| NAME | CHARACTERIZATION |
|---|---|
| $N^1$-(cyanomethyl)-$N^2$-(2,2,2-trifluoro-1-{4-[2-(4-methylpiperazin-1-yl)-1,3-thiazol-4-yl]phenyl}ethyl)-L-leucinamide | MS(+ESI): 509.2[M+1]$^+$ |
| $N^2$-[1-(4-bromophenyl)-2,2,2-trifluoroethyl]-$N^1$-(1-cyanocyclopropyl)-L-leucinamide | MS(+ESI): 434.2[M+1]$^+$, MS(+ESI): 432.0[M+1]$^+$ |
| $N^1$-(cyanomethyl)-$N^2$-[2,2,2-trifluoro-1-(4-piperazin-1-ylphenyl)ethyl]-L-leucinanude | MS(+ESI): 412.2[M+1]$^+$ |
| $N^2$-{1-[3'-(acetylamino)-1,1'-biphenyl-4-yl]-2,2,2-trifluoroethyl}-$N^1$-(cyanomethyl)-L-leucinamide | MS(+ESI): 461.2[M+1]$^+$ |
| $N^1$-(cyanomethyl)-$N^2$-{2,2,2-trifluoro-1-[4-(4-propylpiperazin-1-yl)phenyl]ethyl}-L-leucinamide | MS(+ESI): 454.3[M+1]$^+$ |
| $N^1$-(cyanomethyl)-$N^2$-{2,2,2-trifluoro-1-[4-(piperazin-1-ylcarbonyl)phenyl]ethyl}-L-leucinamide | MS(+ESI): 440.2[M+1]$^+$ |
| $N^1$-(cyanomethyl)-$N^2$-[2,2,2-trifluoro-1-(4-{[4-(2-hydroxyethyl)piperazin-1-yl]carbonyl}phenyl)ethyl]-L-leucinamide | MS(+ESI): 484.3[M+1]$^+$ |
| $N^1$-(cyanomethyl)-$N^2$-[(1S)-2,2,2-trifluoro-1-(4-{3-[3-(trifluoromethyl)phenyl]-1,2,4-oxadiazol-5-yl}phenyl)ethyl]-L-leucinamide | MS(+ESI): 540.1[M+1]$^+$ |
| 4-{1-[1-(Cyanomethyl-carbamoyl)-3-methyl-butylamino]-2,2,2-trifluoro-ethyl}-benzoic acid methyl ester | MS(+ESI): 386.2[M+1]$^+$ |
| $N^1$-(cyanomethyl)-$N^2$-((1S)-2,2,2-trifluoro-1-{4-[(E)-2-quinolin-2-ylethenyl]phenyl}ethyl)-L-leucinamide | MS(+ESI): 481.3[M+1]$^+$ |
| $N^1$-(cyanomethyl)-$N^2$-{(1S)-2,2,2-trifluoro-1-[4-(3-methyl-1,2,4-oxadiazol-5-yl)phenyl]ethyl}-L-leucinamide | MS(+ESI): 553.3[M+1]$^+$ |
| $N^2$-((1S)-1-{4-[3-(5-bromopyridin-3-yl)-1,2,4-oxadiazol-5-yl]phenyl}-2,2,2-trifluoroethyl)-$N^1$-(cyanomethyl)-L-leucinamide | MS(+ESI): 553.3[M+1]$^+$, MS(+ESI): 551.1[M+1]$^+$ |
| $N^2$-[(1S)-1-(4-benzoylphenyl)-2,2,2-trifluoroethyl]-$N^1$-(cyanomethyl)-L-leucinamide | MS(+ESI): 432.3[M+1]$^+$ |
| $N^1$-(cyanomethyl)-$N^2$-{(1S)-2,2,2-trifluoro-1-[4-(thien-2-ylcarbonyl)phenyl]ethyl}-L-leucinamide | MS(+ESI): 438.3[M+1]$^+$ |
| $N^1$-(cyanomethyl)-$N^2$-{(1S)-2,2,2-trifluoro-1-[4-(1,3-thiazol-2-ylcarbonyl)phenyl]ethyl}-L-leucinamide | MS(+ESI): 439.2[M+1]$^+$ |
| $N^1$-(cyanomethyl)-$N^2$-[(1S)-2,2,2-trifluoro-1-(4-{(Z)-2-[4-(methylsulfonyl)phenyl]ethenyl}phenyl)ethyl]-L-leucinamide | MS(+ESI): 508.2[M+1]$^+$ |
| $N^1$-(cyanomethyl)-$N^2$-[(1S)-2,2,2-trifluoro-1-(4-{(E)-2-[4-(methylsulfonyl)phenyl]ethenyl}phenyl)ethyl]-L-leucinamide | MS(+ESI): 508.2[M+1]$^+$ |
| $N^1$-(cyanomethyl)-$N^2$-[(1S)-2,2,2-trifluoro-1-(4-isobutyrylphenyl)ethyl]-L-leucinamide | MS(+ESI): 398.2[M+1]$^+$ |
| $N^2$-{(1S)-1-[4-(4-bromo-1,3-thiazol-2-yl)phenyl]-2,2,2-trifluoroethyl}-$N^1$-(cyanomethyl)-L-leucinamide | MS(+ESI): 491.1[M+1]$^+$, MS(+ESI): 489.0[M+1]$^+$ |
| $N^1$-(cyanomethyl)-$N^2$-[(1S)-1-(4-cyanophenyl)-2,2,2-trifluoroethyl]-L-leucinamide | MS(+ESI): 353.2[M+1]$^+$ |
| $N^1$-(cyanomethyl)-$N^2$-[(1S)-1-(4-ethynylphenyl)-2,2,2-trifluoroethyl]-L-leucinamide | MS(+ESI): 352.1[M+1]$^+$ |
| $N^1$-(cyanomethyl)-$N^2$-[(1S)-2,2,2-trifluoro-1-(2'-fluoro-1,1'-biphenyl-4-yl)ethyl]-L-leucinamide | MS(+ESI): 422.3[M+1]$^+$ |
| $N^1$-(cyanomethyl)-$N^2$-{(1S)-2,2,2-trifluoro-1-[4-(1,3-thiazol-2-yl)phenyl]ethyl}-L-leucinamide | MS(+ESI): 411.1[M+1]$^+$ |
| $N^1$-(cyanomethyl)-$N^2$-{2,2,2-trifluoro-1-[4'-(methylthio)-1,1'-biphenyl-4-yl]ethyl}-L-leucinamide | MS(+ESI): 450.2[M+1]$^+$ |
| $N^1$-(cyanomethyl)-$N^2$-{2,2,2-trifluoro-1-[4-(2-methylquinolin-7-yl)phenyl]ethyl}-L-leucinamide | MS(+ESI): 469.2[M+1]$^+$ |

| NAME | CHARACTERIZATION |
|---|---|
| $N^1$-(cyanomethyl)-$N^2$-{2,2,2-trifluoro-1-[4-(1H-indol-5-yl)phenyl]ethyl}-L-leucinamide | MS(+ESI): 443.2[M+1]$^+$ |
| $N^1$-(cyanomethyl)-$N^2$-{1-[4'-(dimethylamino)-1,1'-biphenyl-4-yl]-2,2,2-trifluoroethyl}-L-leucinamide | MS(+ESI): 447.2[M+1]$^+$ |
| $N^1$-(cyanomethyl)-$N^2$-[(1S)-1-(4-{[(cyanomethyl)amino]carbonyl}phenyl)-2,2,2-trifluoroethyl]-L-leucinamide | MS(+APCI): 410.2[M+1]$^+$ |
| $N^1$-(cyanomethyl)-$N^2$-[(1R)-1-(4-{[(cyanomethyl)amino]carbonyl}phenyl)-2,2,2-trifluoroethyl]-L-leucinamide | MS(+APCI): 410.2[M+1]$^+$ |
| $N^1$-(cyanomethyl)-$N^2$-{2,2,2-trifluoro-1-[3'-(methylsulfonyl)-1,1'-biphenyl-4-yl]ethyl}-L-leucinamide | MS(+APCI): 482.1[M+1]$^+$ |
| 4'-{1-[1-(Cyanomethyl-carbamoyl)-3-methyl-butylamino]-2,2,2-trifluoro-ethyl}-biphenyl-4-carboxylic acid | MS(+APCI): 448.0[M+1]$^+$ |
| 4'-{1-[1-(Cyanomethyl-carbamoyl)-3-methyl-butylamino]-2,2,2-trifluoro-ethyl}-biphenyl-4-carboxylic acid methoxy-methyl-amide | MS(+APCI): 491.2[M+1]$^+$ |
| $N^1$-(cyanomethyl)-$N^2$-{(1S)-2,2,2-trifluoro-1-[4-({[4-(methylsulfonyl)benzyl]thio}methyl)phenyl]ethyl}-L-leucinamide | MS(+APCI): 542.3[M+1]$^+$ |
| $N^2$-{(1S)-1-[4-(5-chloropyridin-2-yl)phenyl]-2,2,2-trifluoroethyl}-$N^1$-(cyanomethyl)-L-leucinamide | MS(+APCI): 439.1[M+1]$^+$ |
| $N^2$-{(1S)-1-[3'-(aminosulfonyl)-4'-bromo-1,1'-biphenyl-4-yl]-2,2,2-trifluoroethyl}-$N^1$-(cyanomethyl)-L-leucinamide | MS(+APCI): 561.1 and 563.1[M+1]$^+$ |
| $N^2$-{(1S)-1-[4'-bromo-3'-(methylsulfonyl)-1,1'-biphenyl-4-yl]-2,2,2-trifluoroethyl}-$N^1$-(cyanomethyl)-L-leucinamide | MS(+APCI): 560.1 and 562.1[M+1]$^+$ |
| $N^1$-(cyanomethyl)-$N^2$-((1S)-2,2,2-trifluoro-1-{4-[5-methyl-6-(methylsulfonyl)pyridin-3-yl]phenyl}ethyl)-L-leucinamide | MS(+ESII): 497.2[M+1]$^+$ |
| $N^2$-[(1S)-1-(4-{5-chloro-3-[4-(methylsulfonyl)phenyl]pyridin-2-yl}phenyl)-2,2,2-trifluoroethyl]-$N^1$-(cyanomethyl)-L-leucinamide | MS(+ESI): 593.2[M+1]$^+$ |
| $N^1$-(cyanomethyl)-$N^2$-((1S)-2,2,2-trifluoro-1-{4-[(phenylthio)methyl]phenyl}ethyl)-L-leucinamide | MS(+APCI): 450.0[M+1]$^+$ |
| $N^1$-(cyanomethyl)-$N^2$-((1S)-2,2,2-trifluoro-1-{4'-[(trifluoromethyl)sulfonyl]-1,1'-biphenyl-4-yl}ethyl)-L-leucinamide | MS(+APCI): 536.1[M+1]$^+$ |
| N'-(cyanomethyl)-$N^2$-[(1S)-2,2,2-trifluoro-1-(4-{[(4-fluorobenzoyl)amino]methyl}phenyl)ethyl]-L-leucinamide | MS(+APCI): 479.1[M+1]$^+$ |
| $N^1$-(cyanomethyl)-$N^2$-{(1S)-2,2,2-trifluoro-1-[4-(methylsulfonyl)phenyl]ethyl}-L-leucinamide | MS(+APCI): 406.1[M+1]$^+$ |
| $N^1$-(1-cyanocyclopropyl)-$N^2$-{(1S)-2,2,2-trifluoro-1-[4'-(methylsulfonyl)-1,1'-biphenyl-4-yl]ethyl}-L-leucinamide | MS(+APCI): 508.2[M+1]$^+$ |
| $N^1$-(cyanomethyl)-$N^2$-{(1S)-1-[4'-(ethylsulfonyl)-1,1'-biphenyl-4-yl]-2,2,2-trifluoroethyl}-L-leucinamide | MS(+APCI): 496.1[M+1]$^+$ |
| $N^2$-((1S)-1-{4-[({[3-(2-chloro-6-fluorophenyl)-5-methylisoxazol-4-yl]carbonyl}amino)methyl]phenyl}-2,2,2-trifluoroethyl)-$N^1$-(cyanomethyl)-L-leucinamide | MS(+APCI): 594.4[M+1]$^+$ |
| $N^2$-((1S)-1-{4-[(9-chloro-3-methyl-4-oxoisoxazolo[4,3-c]quinolin-5(4H)-yl)methyl]phenyl}-2,2,2-trifluoroethyl)-$N^1$-(cyanomethyl)-L-leucinamide | MS(+APCI): 574.3[M+1]$^+$ |
| $N^1$-(cyanomethyl)-$N^2$-{(1S)-2,2,2-trifluoro-1-[4'-methoxy-3'-(methylsulfonyl)-1,1'-biphenyl-4-yl]ethyl}-L-leucinamide | MS(+APCI): 512.2[M+1]$^+$ |
| $N^2$-{(1S)-1-[4''-chloro-4'-(methylsulfonyl)-1,1':2',1''-terphenyl-4-yl]-2,2,2-trifluoroethyl}-$N^1$-(cyanomethyl)-L-leucinamide | MS(+APCI): 592.2[M+1]$^+$ |

| NAME | CHARACTERIZATION |
|---|---|
| $N^1$-(cyanomethyl)-$N^2$-{(1S)-2,2,2-trifluoro-1-[2'-methoxy-4'-(methylsulfonyl)-1,1'-biphenyl-4-yl]ethyl}-L-leucinamide | MS(+APCI): 512.2[M+1]$^+$ |
| $N^2$-{(1S)-1-[2'-chloro-4'-(methylsulfonyl)-1,1'-biphenyl-4-yl]-2,2,2-trifluoroethyl}-$N^1$-(cyanomethyl)-L-leucinamide | MS(+APCI): 516.3 and 518.2[M+1]$^+$ |
| $N^1$-(cyanomethyl)-$N^2$-((1S)-2,2,2-trifluoro-1-{4'-[(2-hydroxyethyl)thio]-1,1'-biphenyl-4-yl}ethyl)-L-leucinamide | MS(−ESI): 478.1[M−1]$^+$ |
| $N^1$-(cyanomethyl)-$N^2$-{(1S)-2,2,2-trifluoro-1-[3'-fluoro-4'-(methylsulfonyl)-1,1'-biphenyl-4-yl]ethyl}-L-leucinamide | MS(+APCI): 500.1[M+1]$^+$ |
| $N^1$-(cyanomethyl)-$N^2$-((1S)-2,2,2-trifluoro-1-{4'-[(2-hydroxyethyl)sulfonyl]-1,1'-biphenyl-4-yl}ethyl)-L-leucinamide | MS(+APCI): 512.3[M+1]$^+$ |
| $N^1$-(cyanomethyl)-$N^2$-{(1S)-2,2,2-trifluoro-1-[3'-(methylsulfonyl)-1,1'-biphenyl-4-yl]ethyl}-L-leucinamide | MS(+APCI): 482.1[M+1]$^+$ |
| $N^1$(cyanomethyl)-$N^2$-{(1S)-2,2,2-trifluoro-1-[4'-({2-[methoxy(methyl)amino]-2-oxoethyl}sulfonyl)-1,1'-biphenyl-4-yl]ethyl}-L-leucinamide | MS(+APCI): 569.3[M+1]$^+$ |
| $N^1$-(cyanomethyl)-$N^2$-((1S)-2,2,2-trifluoro-1-{4'-[(2-hydroxy-2-methylpropyl)sulfonyl]-1,1'-biphenyl-4-yl}ethyl)-L-leucinamide | MS(+APCI): 540.2[M+1]$^+$ |
| $N^2$-{(1S)-1-[4'-(aminosulfonyl)-1,1'-biphenyl-4-yl]-2,2,2-trifluoroethyl}-$N^1$-(1-cyanocyclopropyl)-L-leucinamide | MS(+APCI): 506.2[M+1]$^+$ |
| $N^2$-{(4-bromophenyl)[4-(methylsulfonyl)phenyl]methyl}-$N^1$-(cyanomethyl)-L-leucinamide | MS(+ESI): 492.0, 494.0[M+1]$^+$ |
| $N^1$-(cyanomethyl)-$N^2$-{[4-(methylsulfonyl)phenyl][4'-(methylthio)-1,1'-biphenyl-4-yl]methyl}-L-leucinamide | MS(−ESI): 534.2[M−1]$^-$ |
| $N^1$-(cyanomethyl)-$N^2$-{[4'-(methylsulfonyl)-1,1'-biphenyl-4-yl][4-(methylsulfonyl)phenyl]methyl}-L-leucinamide | MS(+ESI): 568.2[M+1]$^+$ |
| $N^1$-(1-cyanocyclopropyl)-$N^2$-[(1S)-2,2,2-trifluoro-1-(4-methylphenyl)ethyl]-L-leucinamide | MS(+ESI): 368.4[M+1]$^+$ |
| $N^1$-(1-cyanocyclopropyl)-$N^2$-{(1S)-2,2,2-trifluoro-1-[4-(1H-pyrazol-3-yl)phenyl]ethyl}-L-leucinamide | MS(+APCI): 420.1[M+1]$^+$ |
| $N^1$-(1-cyanocyclopropyl)-$N^2$-{(1S)-2,2,2-trifluoro-1-[4-(2-methyl-1,3-oxazol-4-yl)phenyl]ethyl}-L-leucinamide | MS(+ESI): 435.4[M+1]$^+$ |
| $N^1$(cyanomethyl)-$N^2$-[(1S)-2,2,2-trifluoro-1-(4-pyrazin-2-ylphenyl)ethyl]-L-leucinamide | MS(+ESI): 406.2[M+1]$^+$ |
| $N^1$-(cyanomethyl)-$N^2$-{(1S)-2,2,2-trifluoro-1-[4-(2-methylpyridin-4-yl)phenyl]ethyl}-L-leucinamide | MS(+ESI): 419.2[M+1]$^+$ |
| $N^1$-(cyanomethyl)-$N^2$-{(1S)-2,2,2-trifluoro-1-[4-(4-methylpyridin-3-yl)phenyl]ethyl}-L-leucinamide | MS(+ESI): 419.2[M+1]$^+$ |
| $N^1$-(1-cyanocyclopropyl)-$N^2$-{(1S)-2,2,2-trifluoro-1-[4-(1H-pyrazol-4-yl)phenyl]ethyl}-L-leucinamide | MS(+APCI): 420.1[M+1]$^+$ |
| $N^1$-(1-cyanocyclopropyl)-$N^2$-[(1S)-2,2,2-trifluoro-1-(4-pyridin-4-ylphenyl)ethyl]-L-leucinamide | MS(+ESI): 431.1[M+1]$^+$ |
| $N^2$-[(1S)-1-(3'-acetyl-1,1'-biphenyl-4-yl)-2,2,2-trifluoroethyl]-$N^1$-(1-cyanocyclopropyl)-L-leucinamide | MS(+ESI): 472.2[M+1]$^+$ |
| $N^1$-(1-cyanocyclopropyl)-$N^2$-[(1S)-2,2,2-trifluoro-1-(3'-fluoro-4'-methyl-1,1'-biphenyl-4-yl)ethyl]-L-leucinamide | MS(+ESI): 462.1[M+1]$^+$ |
| $N^1$-(1-cyanocyclopropyl)-$N^2$-((1S)-2,2,2-trifluoro-1-{5-[4-(1-hydroxy-1-methylethyl)phenyl]pyridin-2-yl}ethyl)-L-leucinamide | MS(+ESI): 489.6[M+1]$^+$ |
| $N^1$-(cyanomethyl)-$N^2$-{(1S)-2,2,3,3,3-pentafluoro-1-[4'-(1-hydroxy-1-methylethyl)-1,1'-biphenyl-4-yl]propyl}-L-leucinamide | MS(+ESI): 512.2[M+1]$^+$ |

| NAME | CHARACTERIZATION |
| --- | --- |
| N¹-(1-cyanocyclopropyl)-N²-[(1S)-2,2,3,3,3-pentafluoro-1-(4'-methyl-1,1'-biphenyl-4-yl)propyl]-L-leucinamide | MS(+ESI): 494.1[M+1]⁺ |
| N¹-(cyanomethyl)-N²-{(1S)-2,2,3,3,3-pentafluoro-1-[4-(6-methoxypyridin-3-yl)phenyl]propyl}-L-leucinamide | MS(+ESI): 485.2[M+1]⁺ |
| N¹-(cyanomethyl)-N²-[(1S)-2,2,3,3,3-pentafluoro-1-(2'-fluoro-1,1'-biphenyl-4-yl)propyl]-L-leucinamide | MS(+ESI): 472.2[M+1]⁺ |
| N¹-(1-cyanocyclopropyl)-N²-{(1S)-2,2,2-trifluoro-1-[4'-methoxy-3'-(methylsulfonyl)-1,1'-biphenyl-4-yl]ethyl}-L-leucinamide | MS(+ESI): 538.1[M+1]⁺ |
| N²-{(1S)-1-[3'-(aminosulfonyl)-4'-methoxy-1,1'-biphenyl-4-yl]-2,2,2-trifluoroethyl}-N¹-(1-cyanocyclopropyl)-L-leucinamide | MS(+ESI): 539.1[M+1]⁺ |
| N¹-(1-cyanocyclopropyl)-N²-{(1S)-2,2,2-trifluoro-1-[4-(6-methoxypyridin-3-yl)phenyl]ethyl}-L-leucinamide | MS(+APCI): 461.3[M+1]⁺ |
| N¹-(cyanomethyl)-N²-{(1S)-2,2,3,3,3-pentafluoro-1-[4-(5-methylpyridin-2-yl)phenyl]propyl}-L-leucinamide | MS(+ESI): 469.2[M+1]⁺ |
| N¹-(1-cyanocyclopropyl)-N²-((1S)-2,2,2-trifluoro-1-{4-[5-(methylsulfonyl)pyridin-2-yl]phenyl}ethyl)-L-leucinamide | MS(+APCI): 509.2[M+1]⁺ |
| N¹-(1-cyanocyclopropyl)-N²-{(1S)-2,2,2-trifluoro-1-[4-(5-methylpyridin-2-yl)phenyl]ethyl}-L-leucinamide | MS(+APCI): 446.1[M+1]⁺ |
| N¹-(cyanomethyl)4-fluoro-N²-{(1S)-2,2,2-trifluoro-1-[4'-(methylsulfonyl)-1,1'-biphenyl-4-yl]ethyl}-L-leucinamide | MS(+ESI): 500.1[M+1]⁺ |
| N¹-(1-cyanocyclopropyl)-4-fluoro-N²-{(1S)-2,2,2-trifluoro-1-[4'-(methylsulfonyl)-1,1'-biphenyl-4-yl]ethyl}-L-leucinamide | MS(+ESI): 526.1[M+1]⁺ |
| N¹-(1-cyanocyclopropyl)-4-fluoro-N²-{(1S)-2,2,2-trifluoro-1-[2'-methyl-4'-(methylsulfonyl)-1,1'-biphenyl-4-yl]ethyl}-L-leucinamide | MS(+ESI): 540.1[M+1]⁺ |
| N¹-(1-cyanocyclopropyl)-N²-{(1S)-2,2,2-trifluoro-1-[5-(1H-pyrazol-3-yl)pyridin-2-yl]ethyl}-L-leucinamide | MS(+APCI): 421.0[M+1]⁺ |
| N¹-(1-cyanocyclopropyl)-N²-[(1S)-2,2,2-trifluoro-1-(5-quinolin-5-ylpyridin-2-yl)ethyl]-L-leucinamide | MS(+APCI): 482.3[M+1]⁺ |
| N¹-(1-cyanocyclopropyl)-N²-[(1S)-2,2,2-trifluoro-1-(5-quinolin-6-ylpyridin-2-yl)ethyl]-L-leucinamide | MS(+APCI): 482.3[M+1]⁺ |
| N¹-(1-cyanocyclopropyl)-N²-{(1S)-2,2-difluoro-1-[4'-(methylsulfonyl)-1,1'-biphenyl-4-yl]ethyl}-L-leucinamide | 1H NMR(CD3COCD3) δ 8.15(1H, m), 8.0(2H, d), 7.95(2H, d), 7.75(2H, d), 7.55(2H, d), 6.1(1H, dt), 4.0-4.1(1H, m), 3.25-3.35(1H, m), 3.15(3H, s), 2.4-2.5(1H, m), 1.8-1.9(1H, m), 1.4-1.55(4H, m), 0.85-1.05(8H, m). |
| N²-[(1S)-1-(4'-acetyl-1,1'-biphenyl-4-yl)-2,2,3,3,3-pentafluoropropyl]-N¹-(1-cyanocyclopropyl)-L-leucinamide | MS(+ESI): 522.3[M+1]⁺ |
| N²-[(1S)-1-(1,1'-biphenyl-4-yl)-2,2,2-trifluoroethyl]-N¹-(1-cyanocyclopropyl)-L-leucinamide | MS(+ESI): 430.2[M+1]⁺ |
| N²-{(1S)-1-[4'-(aminosulfonyl)-1,1'-biphenyl-4-yl]-2,2,3,3,3-pentafluoropropyl}-N¹-(1-cyanocyclopropyl)-L-leucinamide | MS(−ESI): 557.2[M−1]⁻ |
| N¹-(1-cyanocyclopropyl)-N²-{(1S)-1-[4-(1-ethoxyvinyl)phenyl]-2,2,2-trifluoroethyl}-L-leucinamide | MS(−ESI): 422.2[M−1]⁻ |
| N²-[(1S)-1-(4-acetylphenyl)-2,2,2-trifluoroethyl]-N¹-(1-cyanocyclopropyl)-L-leucinamide | MS(+ESI): 396.0[M+1]⁺ |
| N¹-(1-cyanocyclopropyl)-N²-[(1S)-2,2,2-trifluoro-1-(4-isopropylphenyl)ethyl]-L-leucinamide | MS(+ESI): 396.2[M+1]⁺ |
| N¹-(1-cyanocyclopropyl)-N²-[(1S)-2,2,2-trifluoro-1-phenylethyl]-L-leucinamide | MS(+ESI): 354.0[M+1]⁺ |
| N¹-(1-cyanocyclopropyl)-N²-{(1S)-2,2,2-trifluoro-1-[4-(1-hydroxy-1-methylethyl)phenyl]ethyl}-L-leucinamide | MS(+ESI): 434.3[M+Na]⁺ |

| NAME | CHARACTERIZATION |
|---|---|
| $N^1$-(1-cyanocyclopropyl)-$N^2$-{(1S)-2,2,2-trifluoro-1-[4-(1-methylcyclopropyl)phenyl]ethyl}-L-leucinamide | MS(+ESI): 408.2[M+1]$^+$ |
| $N^1$-(1-cyanocyclopropyl)-$N^2$-[(1S)-2,2,2-trifluoro-1-(2',4',6'-trimethyl-1,1'-biphenyl-4-yl)ethyl]-L-leucinamide | MS(+ESI): 472.2[M+1]$^+$ |
| $N^2$-[(1S)-1-(6-chloropyridin-3-yl)-2,2,2-trifluoroethyl]-$N^1$-(1-cyanocyclopropyl)-L-leucinamide | MS(+ESI): 389.3[M+1]$^+$ |
| $N^2$-{(1S)-1-[5-(4-acetylphenyl)pyridin-2-yl]-2,2,2-trifluoroethyl}-$N^1$-(1-cyanocyclopropyl)-L-leucinamide | MS(+ESI): 473.2[M+1]$^+$ |
| $N^2$-{(1S)-1-[6-(4-acetylphenyl)pyridin-3-yl]-2,2,2-trifluoroethyl}-$N^1$-(1-cyanocyclopropyl)-L-leucinamide | MS(+ESI): 473.2[M+1]$^+$ |
| $N^2$-{(1S)-1-[5-(3-acetylphenyl)pyridin-2-yl]-2,2,2-trifluoroethyl}-$N^1$-(1-cyanocyclopropyl)-L-leucinamide | MS(+ESI): 473.4[M+1]$^+$ |
| $N^1$-(1-cyanocyclopropyl)-$N^2$-((1S)-2,2,2-trifluoro-1-{5-[4-(1-hydroxyethyl)phenyl]pyridin-2-yl}ethyl)-L-leucinamide | MS(+ESI): 475.5[M+1]$^+$ |
| $N^2$-[(1S)-1-(1,1'-biphenyl-4-yl)-2,2,3,3,3-pentafluoropropyl]-$N^1$-(cyanomethyl)-L-leucinamide | MS(−ESI): 452.2[M−1]$^-$ |
| $N^2$-[(1S)-1-(4'-acetyl-1,1'-biphenyl-4-yl)-2,2,3,3,3-pentafluoropropyl]-$N^1$-(cyanomethyl)-L-leucinamide | MS(+ESI): 495.83[M+1]$^+$ |
| $N^2$-[(1S)-1-(1,1'-biphenyl-4-yl)-2,2,3,3,3-pentafluoropropyl]-$N^1$-(1-cyanocyclopropyl)-L-leucinamide | MS(+ESI): 479.8[M+1]$^+$ |
| $N^2$-(1-benzyl-2,2,2-trifluoroethyl)-$N^1$-(1-cyanocyclopropyl)-L-leucinamide | MS(−APCI): 366.1[M−1]− |
| $N^2$-[(1S)-1-(4-tert-butylphenyl)-2,2,2-trifluoroethyl]-$N^1$-(1-cyanocyclopropyl)-L-leucinamide | MS(+APCI): 410.2[M+1]$^+$ |
| $N^2$-[(1S)-1-(4-bromophenyl)-2,2,2-trifluoroethyl]-$N^1$-(cyanomethyl)-4-methyl-L-leucinamide | MS(+APCI): 420.2[M+1]$^+$ |
| $N^2$-[(1S)-1-(4-bromophenyl)-2,2,2-trifluoroethyl]-$N^1$-(1-cyanocyclopropyl)-4-methyl-L-leucinamide | MS(+APCI): 446.1[M+1]$^+$ |
| $N^1$-(1-cyanocyclopropyl)-$N^2$-((1S)-2,2,2-trifluoro-1-{4-[2-(1H-pyrazol-4-yl)-1,3-thiazol-4-yl]phenyl}ethyl)-L-leucinamide | MS(+APCI): 503.2[M+1]$^+$ |
| $N^1$-(1-cyanocyclopropyl)-$N^2$-{(1S)-2,2,2-trifluoro-1-[4-(2-methyl-1,3-thiazol-4-yl)phenyl]ethyl}-L-leucinamide | MS(+ESI): 451.2[M+1]$^+$ |
| $N^1$-(1-cyanocyclopropyl)-$N^2$-{(1S)-2,2,2-trifluoro-1-[4-(2-methylpyridin-4-yl)phenyl]ethyl}-L-leucinamide | MS(+ESI): 445.2[M+1]$^+$ |
| $N^1$-(1-cyanocyclopropyl)-$N^2$-{(1S)-2,2,2-trifluoro-1-[4-(2-methylpyridin-3-yl)phenyl]ethyl}-L-leucinamide | MS(+ESI): 445.1[M+1]$^+$ |
| $N^1$-(1-cyanocyclopropyl)-$N^2$-{(1S)-2,2,2-trifluoro-1-[4-(6-methylpyridin-2-yl)phenyl]ethyl}-L-leucinamide | MS(+ESI): 445.2[M+1]$^+$ |
| $N^2$-[(1S)-1-(3'-acetyl-1,1'-biphenyl-4-yl)-2,2,2-trifluoroethyl]-$N^1$-(1-cyanocyclopropyl)-4-fluoro-L-leucinamide | MS(+ESI): 490.3[M+1]$^+$ |
| $N^1$-(1-cyanocyclopropyl)-4-fluoro-$N^2$-{(1S)-2,2,2-trifluoro-1-[4-(1H-pyrazol-3-yl)phenyl]ethyl}-L-leucinamide | MS(+ESI): 438.3[M+1]$^+$ |
| $N^1$-[(1S)-1-cyanoethyl]-$N^2$-{(1S)-2,2,2-trifluoro-1-[4'-(methylsulfonyl)-1,1'-biphenyl-4-yl]ethyl}-L-leucinamide | MS(+ESI): 496.3[M+1]$^+$ |
| $N^1$-[(1S)-1-cyano-3-(methylthio)propyl]-$N^2$-{(1S)-2,2,2-trifluoro-1-[4'-(methylsulfonyl)-1,1'-biphenyl-4-yl]ethyl}-L-leucinamide | MS(+ESI): 556.3[M+1]$^+$ |
| $N^1$-[(1S)-1-cyano-3-(methylsulfonyl)propyl]-$N^2$-{(1S)-2,2,2-trifluoro-1-[4'-(methylsulfonyl)-1,1'-biphenyl-4-yl]ethyl}-L-leucinamide | MS(+ESI): 588.2[M+1]$^+$ |
| $N^2$-[(1S)-1-(4-bromophenyl)-2,2,3,3,3-pentafluoropropyl]-$N^1$-(1-cyanocyclopropyl)-L-leucinamide | MS(+ESI): 482, 484[M+1]$^+$ |

| NAME | CHARACTERIZATION |
|---|---|
| $N^1$-(cyanomethyl)-$N^2$-{(1S)-2,2,3,3,3-pentafluoro-1-[4-(6-methoxypyridin-2-yl)phenyl]propyl}-L-leucinamide | MS(+ESI): 485[M+1]$^+$ |
| $N^2$-[(1S)-1-(5-bromopyridin-2-yl)-2,2,2-trifluoroethyl]-$N^1$-(cyanomethyl)-L-leucinamide | MS(+ESI): 407, 409[M+1]$^+$ |
| $N^1$-(cyanomethyl)-$N^2$-((1S)-2,2,2-trifluoro-1-{5-[4-(methylsulfonyl)phenyl]pyridin-2-yl}ethyl)-L-leucinamide | MS(+ESI): 483[M+1]$^+$ |
| $N^1$-(1-cyanocyclopropyl)-$N^2$-{(1S)-2,2,2-trifluoro-1-[4'-(1-hydroxy-1-methylethyl)-1,1'-biphenyl-4-yl]ethyl}-L-leucinamide | MS(+ESI): 488[M+1]$^+$ |
| $N^1$-(cyanomethyl)-$N^2$-[(1S)-2,2,2-trifluoro-1-(6'-methyl-3,3'-bipyridin-6-yl)ethyl]-L-leucinamide | MS(+ESI): 420[M+1]$^+$ |
| $N^1$-(1-cyanocyclopropyl)-$N^2$-{(1S)-2,2,2-trifluoro-1-[4-(6-methoxypyridin-2-yl)phenyl]ethyl}-L-leucinamide | MS(+ESI): 461[M+1]$^+$ |
| $N^1$-(cyanomethyl)-$N^2$-{(1S)-2,2,2-trifluoro-1-[4-(6-oxo-1,6-dihydropyridin-2-yl)phenyl]ethyl}-L-leucinamide | MS(+ESI): 421[M+1]$^+$ |
| (4S)-$N^1$-(cyanomethyl)-5,5,5-trifluoro-$N^2$-{(1S)-2,2,2-trifluoro-1-[4'-(methylsulfonyl)-1,1'-biphenyl-4-yl]ethyl}-L-leucinamide | MS(+ESI): 536[M+1]$^+$ |
| (4S)-$N^1$-(1-cyanocyclopropyl)-5,5,5-trifluoro-$N^2$-{(1S)-2,2,2-trifluoro-1-[4'-(methylsulfonyl)-1,1'-biphenyl-4-yl]ethyl}-L-leucinamide | MS(+ESI): 562[M+1]$^+$ |
| (4S)-$N^1$-(cyanomethyl)-5,5,5-trifluoro-$N^2$-{(1S)-2,2,2-trifluoro-1-[4'-(methylthio)-1,1'-biphenyl-4-yl]ethyl}-L-leucinamide | MS(+ESI): 504[M+1]$^+$ |
| (4S)-$N^1$-(1-cyanocyclopropyl)-5,5,5-trifluoro-$N^2$-{(1S)-2,2,2-trifluoro-1-[4'-(methylthio)-1,1'-biphenyl-4-yl]ethyl}-L-leucinamide | MS(+ESI): 530[M+1]$^+$ |
| (4S)-$N^2$-[(1S)-1-(4-bromophenyl)-2,2,2-trifluoroethyl]-$N^1$-(cyanomethyl)-5,5,5-trifluoro-L-leucinamide | MS(+ESI): 460, 462[M+1]$^+$ |
| (4S)-$N^2$-[(1S)-1-(4-bromophenyl)-2,2,2-trifluoroethyl]-$N^1$-(1-cyanocyclopropyl)-5,5,5-trifluoro-L-leucinamide | MS(+ESI): 486, 488[M+1]$^+$ |
| $N^2$-{(1S)-1-[4-(6-aminopyridin-3-yl)phenyl]-2,2,2-trifluoroethyl}-$N^1$-(cyanomethyl)-L-leucinamide | MS(+ESI): 420[M+1]$^+$ |
| $N^2$-[(1S)-1-(4-bromophenyl)-2,2,2-trifluoroethyl]-$N^1$-(1-cyanocyclopropyl)-4-fluoro-L-leucinamide | MS(+ESI): 450, 452[M+1]$^+$ |
| $N^1$-(cyanomethyl)-$N^2$-{(1S)-2,2,3,3,3-pentafluoro-1-[4-(6-methylpyridin-3-yl)phenyl]propyl}-L-leucinamide | MS(+ESI): 468.8[M+1]$^+$ |
| $N^1$-(1-cyanocyclopropyl)-$N^2$-{(1S)-2,2,3,3,3-pentafluoro-1-[4-(6-methylpyridin-3-yl)phenyl]propyl}-L-leucinamide | MS(+ESI): 494.8[M+1]$^+$ |
| $N^1$-(1-cyanocyclopropyl)-$N^2$-{(1S)-2,2,2-trifluoro-1-[4-(6-methylpyridin-3-yl)phenyl]ethyl}-L-leucinamide | MS(+ESI): 445.0[M+1]$^+$ |
| $N^1$-(cyanomethyl)-$N^2$-{(1S)-2,2,2-trifluoro-1-[4'-(1-hydroxyethyl)-1,1'-biphenyl-4-yl]ethyl}-L-leucinamide | MS(+ESI): 447.8[M+1]$^+$ |
| $N^1$-(cyanomethyl)-$N^2$-{(1S)-2,2,2-trifluoro-1-[4'-(2,2,2-trifluoro-1-hydroxyethyl)-1,1'-biphenyl-4-yl]ethyl}-L-leucinamide | MS(+ESI): 501.8[M+1]$^+$ |
| $N^1$-(1-cyanocyclopropyl)-$N^2$-{(1S)-2,2,3,3,3-pentafluoro-1-[4'-(methylthio)-1,1'-biphenyl-4-yl]propyl}-L-leucinamide | MS(+ESI): 526.1[M+1]$^+$ |
| $N^1$-(1-cyanocyclopropyl)-$N^2$-{(1S)-2,2,3,3,3-pentafluoro-1-[4'-(1-hydroxy-1-methylethyl)-1,1'-biphenyl-4-yl]propyl}-L-leucinamide | MS(+ESI): 538.3[M+1]$^+$ |
| $N^1$-(1-cyanocyclopropyl)-$N^2$-{(1S)-2,2,3,3,3-pentafluoro-1-[4'-(methylsulfonyl)-1,1'-biphenyl-4-yl]propyl}-L-leucinamide | MS(+ESI): 558.2[M+1]$^+$ |
| (4R)-$N^1$-(cyanomethyl)-5,5,5-trifluoro-$N^2$-{(1S)-2,2,2-trifluoro-1-[4'-(methylsulfonyl)-1,1'-biphenyl-4-yl]ethyl}-L-leucinamide | MS(+ESI): 536.1[M+1]$^+$ |

-continued

| NAME | CHARACTERIZATION |
|---|---|
| (4R)-$N^1$-(1-cyanocyclopropyl)-5,5,5-trifluoro-$N^2$-{(1S)-2,2,2-trifluoro-1-[4'-(methylsulfonyl)-1,1'-biphenyl-4-yl]ethyl}-L-leucinamide | MS(+ESI): 562.1[M+1]$^+$ |
| $N^1$-(cyanomethyl)-$N^2$-[(1S)-2,2,3,3,3-pentafluoro-1-(4'-methyl-1,1'-biphenyl-4-yl)propyl]-L-leucinamide | MS(+ESI): 468.2[M+1]$^+$ |
| $N^1$-(cyanomethyl)-$N^2$-{(1S)-2,2,3,3,3-pentafluoro-1-[4-(1,3-thiazol-2-yl)phenyl]propyl}-L-leucinamide | MS(+ESI): 461.0[M+1]$^+$ |
| $N^1$-(1-cyanocyclopropyl)-$N^2$-[(1S)-1-(4-ethynylphenyl)-2,2,3,3,3-pentafluoropropyl]-L-leucinamide | MS(+ESI): 428.1[M+1]$^+$ |
| $N^1$-(cyanomethyl)-$N^2$-{(1S)-1-[4-(cyclopropylethynyl)phenyl]-2,2,2-trifluoroethyl}-L-leucinamide | MS(+ESI): 392.3[M+1]$^+$ |
| $N^1$-(1-cyanocyclopropyl)-$N^2$-{(1S)-1-[4-(cyclopropylethynyl)phenyl]-2,2,2-trifluoroethyl}-L-leucinamide | MS(+ESI): 418.3[M+1]$^+$ |
| $N^1$-(cyanomethyl)-$N^2$-{(1S)-2,2,2-trifluoro-1-[4-(5-methyl-1,3-thiazol-2-yl)phenyl]ethyl}-L-leucinamide | MS(+ESI): 425.3[M+1]$^+$ |
| $N^1$-(1-cyanocyclopropyl)-$N^2$-{(1S)-2,2,2-trifluoro-1-[4-(1,3-thiazol-2-yl)phenyl]ethyl}-L-leucinamide | MS(+ESI): 437.1[M+1]$^+$ |
| $N^1$-(1-cyanocyclopropy-$N^2$-{(1S)-2,2,2-trifluoro-1-[4-(5-methyl-1,3-thiazol-2-yl)phenyl]ethyl}-L-leucinamide | MS(+ESI): 451.2[M+1]$^+$ |
| $N^1$-(1-cyanocyclopropyl)-$N^2$-{(1S)-1-[4-(cyclopropylethynyl)phenyl]-2,2,3,3,3-pentafluoropropyl}-L-leucinamide | MS(+ESI): 468.2[M+1]$^+$ |
| $N^1$-(1-cyanocyclopropyl)-$N^2$-{(1S)-2,2,2-trifluoro-1-[4-(4-methyl-1,3-thiazol-2-yl)phenyl]ethyl}-L-leucinamide | MS(+ESI): 451.2[M+1]$^+$ |
| $N^1$-(cyanomethyl)-$N^2$-{(1S)-2,2,2-trifluoro-1-[4-(4-methyl-1,3-thiazol-2-yl)phenyl]ethyl}-L-leucinamide | MS(+ESI): 425.3[M+1]$^+$ |
| $N^1$-(cyanomethyl)-$N^2$-{(1S)-1-[4-(4,5-dimethyl-1,3-thiazol-2-yl)phenyl]-2,2,2-trifluoroethyl}-L-leucinamide | MS(+ESI): 439.3[M+1]$^+$ |
| $N^1$-(1-cyanocyclopropyl)-$N^2$-{(1S)-1-[4'-(ethylsulfonyl)-1,1'-biphenyl-4-yl]-2,2,2-trifluoroethyl}-4-fluoro-L-leucinamide | MS(+ESI): 540.1[M+1]$^+$ |
| $N^1$-(1-cyanocyclopropyl)-4-fluoro-$N^2$-[(1S)-2,2,2-trifluoro-1-(4-pyridin-3-ylphenyl)ethyl]-L-leucinamide | MS(+ESI): 449.2[M+1]$^+$ |
| $N^1$-(1-cyanocyclopropyl)-4-fluoro-$N^2$-{(1S)-2,2,2-trifluoro-1-[4'-methoxy-3'-(methylsulfonyl)-1,1'-biphenyl-4-yl]ethyl}-L-leucinamide | MS(+ESI): 556.3[M+1]$^+$ |
| $N^2$[(1S)-1-(4-bromophenyl)-2,2,2-trifluoroethyl]-$N^1$-(cyanomethyl)-L-alaninamide | MS(+APCI): 363.8, 365.8[M+1]$^+$ |
| $N^2$-{(1S)-1-[4'-(aminosulfonyl)-1,1'-biphenyl-4-yl]-2,2,3,3,3-pentafluoropropyl}-$N^1$-(cyanomethyl)-L-leucinamide | MS(+APCI): 533.2[M+1]$^+$ |
| $N^1$-(cyanomethyl)-$N^2$-((1S)-2,2,3,3,3-pentafluoro-1-{4'-[(2-hydroxy-2-methylpropyl)sulfonyl]-1,1'-biphenyl-4-yl}propyl)-L-leucinamide | MS(+APCI): 590.4[M+1]$^+$ |
| $N^1$-(cyanomethyl)-$N^2$-{(1S)-2,2,2-trifluoro-1-[4'-(methylsulfonyl)-1,1'-biphenyl-4-yl]ethyl}-L-alaninamide | MS(+APCI): 440.1[M+1]$^+$ |
| $N^1$-(cyanomethyl)-$N^2$-{(1S)-2,2,3,3,3-pentafluoro-1-[4'-(isopropylsulfonyl)-1,1'-biphenyl-4-yl]propyl}-L-leucinamide | MS(+APCI): 560.2[M+1]$^+$ |
| $N^1$-(1-cyano-1-methylethyl)-$N^2$-{(1S)-2,2,2-trifluoro-1-[4'-(methylsulfonyl)-1,1'-biphenyl-4-yl]ethyl}-L-leucinamide | MS(+APCI): 510.2[M+1]$^+$ |
| $N^1$-(1-cyanocyclopropyl)-$N^2$-((1S)-2,2,2-trifluoro-1-{4'-[(2-hydroxy-2-methylpropyl)sulfonyl]-1,1'-biphenyl-4-yl}ethyl)-L-leucinamide | MS(+APCI): 566.4[M+1]$^+$ |
| $N^1$-(1-cyanocyclopropyl)-$N^2$-{(1S)-2,2,2-trifluoro-1-[2'-methyl-4'-(methylsulfonyl)-1,1'-biphenyl-4-yl]ethyl}-L-leucinamide | MS(+APCI): 522.3[M+1]$^+$ |

-continued

| NAME | CHARACTERIZATION |
|---|---|
| $N^1$-(1-cyanocyclopropyl)-$N^2$-{(1S)-1-[4'-(ethylsulfonyl)-1,1'-biphenyl-4-yl]-2,2,2-trifluoroethyl}-L-leucinamide | MS(+APCI): 522.3[M+1]$^+$ |
| $N^2$-{(1S)-1-[4'-(aminosulfonyl)-1,1'-biphenyl-4-yl]-2,2,2-trifluoroethyl}-$N^1$-(1-cyanocyclopropyl)-4-fluoro-L-leucinamide | MS(+APCI): 527.3[M+1]$^+$ |
| $N^1$-(cyanomethyl)-$N^2$-{(S)-[4'-(methylsulfonyl)-1,1'-biphenyl-4-yl][4-(trifluoromethoxy)phenyl]methyl}-L-leucinamide | MS(−ESI): 572.2[M−1]$^-$ and 573.3 |
| $N^1$-(cyanomethyl)-$N^2$-[(S)-[4'-(methylsulfonyl)-1,1'-biphenyl-4-yl](thien-2-yl)methyl]-L-leucinamide | $^1$HNMR(d$_6$-dmso): δ 8.7(m, 2H), 7.52(d, 2H), 7.50(d, 2H), 7.39(d, 2H), 7.38(m, 1H), 7.03(2H, d), 6.98(d, 1H), 6.92(dd, 1H), 4.90(1H, s), 4.15(m, 2H), 3.30(8H, m), 3.23(1H, m), 2.65(1H, d), 1.80(1H, m), 1.45(1H, m), 1.25(1H, m), 0.86(3H, d), 0.81(3H, d). LC/MS, M+1: 502.4. |
| $N^1$-(cyanomethyl)-$N^2$-[(S)-(4'-piperazin-4-ium-1-yl-1,1'-biphenyl-4-yl)(thien-2-yl)methyl]-L-leucinamide methanesulfonate | 1HNMR(d6-dmso): δ 8.7(m, 2H), 7.52(d, 2H), 7.50(d, 2H), 7.39(d, 2H), 7.38(m, 1H), 7.03(2H, d), 6.98(d, 1H), 6.92(dd, 1H), 4.90(1H, s), 4.15(m, 2H), 3.30(8H, m), 3.23(1H, m), 2.65(1H, d), 1.80(1H, m), 1.45(1H, m), 1.25(1H, m), 0.86(3H, d), 0.81(3H, d). LC/MS, M+1: 502.4. |
| $N^1$-(cyanomethyl)-$N^2$-{(S)-(4-fluorophenyl)[4'-(methylsulfonyl)-1,1'-biphenyl-4-yl]methyl}-L-leucinamide | $^1$H NMR(H NMR δ (CDCl$_3$): 0.77(d, 3H), 0.9(d, 3H); 1.38(m, 1H), 1.57(m, 1H), 1.71(m, 1H), 2.01(br s, 1H), 3.09(s, 3H), 3.09(m, 1H), 4.07(m, 2H), 4.89(1H, s), 7.03(m, 2H), 7.21(m, 1H), 7.33(m, 2H), 7.42(d, 2H), 7.53(m, 2H), 7.68(d, 2H), 7.97(d, 2H). |
| $N^1$-(cyanomethyl)-$N^2$-{(S)-[4'-(methylsulfonyl)-1,1'-biphenyl-4-yl][4-(trifluoromethyl)phenyl]methyl}-L-leucinamide | MS(+APCI): 556.5 and 558.5[M+1]$^+$ |
| $N^2$-{(S)-(4-chlorophenyl)[4'-(methylsulfonyl)-1,1'-biphenyl-4-yl]methyl}-$N^1$-(cyanomethyl)-L-leucinamide | MS(+APCI): 524.3 and 525.5[M+1]$^+$ |
| $N^1$-(cyanometbyl)-$N^2$-{(1S)-2,2,2-trifluoro-1-[4'-(methylsulfonyl)-1,1'-biphenyl-4-yl]ethyl}-L-norvalinamide | MS(+ESI): 468[M+1]$^+$ |
| $N^2$-[(S)-(4-bromophenyl)(thien-2-yl)methyl]-$N^1$-(cyanomethyl)-L-leucinamide | $^1$HNMR(d$_6$-dmso): δ 8.64(1H, t), 7.48(2H, d), 7.39(dd, 1H), 7.31(2H, d), 6.96(1H, m), 6.91(1H, dd)), 4.90(1H, s), 4.13(2H, m), 3.15(1H, m), 2.70(1H, m), 1.85(1H, m), 1.40(1H, m), 1.25(1H, m), 0.85(3H, d), 0.80(3H, d). LC/MS, M−1: 3.81 |
| $N^1$-(cyanomethyl)-$N^2$-[(S)-[4-(4,4,5,5-tetramethyl-1,3,2-dioxaborolan-2-yl)phenyl](thien-2-yl)methyl]-L-leucinamide | LC/MS, M−1: 466.1. |
| $N^2$-{(R)-(4-bromophenyl)[4-(trifluoromethoxy)phenyl]methyl}-$N^1$-(cyanomethyl)-L-leucinamide | MS(−ESI): 496.1[M−1]$^-$ |
| $N^1$-(cyanonmthyl)-$N^2$-{(S)-[4-(4,4,5,5-tetramethyl-1,3,2-dioxaborolan-2-yl)phenyl][4-(trifluoromethoxy)phenyl]methyl}-L-leucinamide | MS(+APCI): 545.2 and 546.3[M+1]$^+$ |
| $N^2$-[(S)-(4-bromophenyl)(2-furyl)methyl]-$N^1$-(cyanomethyl)-L-leucinamide | MS(+APCI): 404.1 and 405.3[M+1]$^+$ |
| $N^1$-(cyanomethyl)-$N^2$-{(S)-2-furyl[4'-(methylsulfonyl)-1,1'-biphenyl-4-yl]methyl}-L-leucinamide | MS(+APCI): 479.2[M+1]$^+$ |
| $N^2$-[1-(4-bromophenyl)-2,2,2-trifluoroethyl]-$N^1$-(cyanomethyl)-L-norvalinamide | MS(+ESI): 392, 394[M+1]$^+$ |
| $N^2$-{(R)-(4-bromophenyl)[4-(trifluoromethyl)phenyl]methyl}-$N^1$-(cyanomethyl)-L-leucinamide | MS(+APCI): 482.1 and 481.2[M+1]$^+$ |
| $N^1$-(cyanomethyl)-$N^2$-{1-[4'-(4-cyclopropylpiperazin-1-yl)-1,1'-biphenyl-4-yl]-2,2,2-trifluoroethyl}-L-norvalinamide | MS(+ESI): 514[M+1]$^+$ |
| $N^2$-[(R)-(4-bromophenyl)(4-chlorophenyl)methyl]-$N^1$-(cyanomethyl)-L-leucinamide | MS(+APCI): 482.1 and 481.2[M+1]$^+$ |

-continued

| NAME | CHARACTERIZATION |
|---|---|
| $N^1$-(cyanomethyl)-$N^2$-{2,2,2-trifluoro-1-[4'-(methylsulfonyl)-1,1'-biphenyl-4-yl]ethyl}-L-norvalinamide | MS(+ESI): 468[M+1]$^+$ |
| $N^2$-[(S)-(4-bromophenyl)(3-methylthien-2-yl)methyl]-$N^1$-(cyanomethyl)-L-leucinamide | LC/MS, M−1: 432.0. |
| $N^2$-[(S)-(4-bromophenyl)(thien-3-yl)methyl]-$N^1$-(cyanomethyl)-L-leucinamide | LC/MS, M−1: 418.2. |
| $N^1$-(cyanomethyl)-$N^2$-{(S)-(2,4-difluorophenyl)[4'-(methylsulfonyl)-1,1'-biphenyl-4-yl]methyl}-L-leucinamide | MS(+APCI) 525.3, 524.3[M−1] and 526.4[M+1]$^+$. 1H NMR(CD$_3$SOCD$_3$) δ 8.01(dd, 2H), 7.8(dd, 2H), 7.35(dd, 2H), 7.11(dd, 2H), 7.03(d, 1H), 6.93(d, 2H), 6.62(d, 1H), 6.55(d, 1H), 5.0(s, 1H), 4.13(t, 2H), 3.35(m, 1H), 3.0(m, 1H), 2.99(m, 1H), 2.85(s, 3H), 1.84(m, 1H), 1.45(m, 1H), 0.9-0.8(m, 6H). |
| $N^1$-(cyanomethyl)-$N^2$-[(S)-[4'-(methylsulfonyl)-1,1'-biphenyl-4-yl](thien-3-yl)methyl]-L-leucinamide | $^1$HNMR(d$_6$-dmso): δ 8.62(1H, t), 7.95(2H, d), 7.85(2H, m), 7.65(2H, d), 7.49(2H, d), 7.47(2H, m), 7.10(1H, dd), 4.80(1H, d), 4.13(2H, m), 3.24(3H, s), 3.05(1H, m), 2.65(1H, m), 1.8(1H, m), 1.45(1H, m), 1.30(1H, m), 0.84(3H, d), 0.76(3H, d). LC/MS, M−1: 493.5. |
| $N^1$-(cyanomethyl)-$N^2$-[(S)-[4'-(methylsulfonyl)-1,1'-biphenyl-4-yl](3-methylthien-2-yl)methyl]-L-leucinamide | LC/MS, M−1: 507.5 |
| $N^1$-(cyanomethyl)-$N^2$-[(S)-[4'-(4-cyclopropylpiperazin-1-yl)-1,1'-biphenyl-4-yl](3-methylthien-2-yl)methyl]-L-leucinamide | LC/MS, M+1: 556.1, M−1: 554.0 |
| $N^1$-(cyanomethyl)-$N^2$-[(S)-[4'-(4-cyclopropylpiperazin-1-yl)-1,1'-biphenyl-4-yl](thien-3-yl)methyl]-L-leucinamide | LC/MS, M−1: 540.1 |
| $N^2$-[1-(4-bromophenyl)-2,2,2-trifluoroethyl]-$N^1$-(cyanomethyl)-5,5,5-trifluoro-L-norvalinamide | MS(+ESI): 446.1, 448.1[M+1]$^+$ |
| $N^1$-(cyanomethyl)-5,5,5-trifluoro-$N^2$-{(1S)-2,2,2-trifluoro-1-[4'-(methylsulfonyl)-1,1'-biphenyl-4-yl]ethyl}-L-norvalinamide | MS(+ESI): 522.3[M+1]$^+$ |
| $N^2$-[(S)-(4-bromophenyl)(3-methylthien-2-yl)methyl]-$N^1$-(1-cyanocyclopropyl)-L-leucinamide | LC/MS, M−1: 460.1. |
| $N^1$-(1-cyanocyclopropyl)-$N^2$-[(S)-[4'-(methylsulfonyl)-1,1'-biphenyl-4-yl](3-methylthien-2-yl)methyl]-L-leucinamide | $^1$HNMR(d$_6$-dmso): δ 8.96(1H, s), 7.96(2H, d), 7.87(2H, d), 7.69(2H, d), 7.45(2H, d), 7.31(1H, d), 7.76(1H, d), 4.98(1H, s), 3.24(3H, s), 3.10(1H, m), 2.5(1H, d), 2.09(3H, s), 1.85(1H, m), 1.50(2H, m), 1.40(1H, m), 1.25(1H, m), 1.10(2H, m), 0.86(3H, d), 0.83(3H, d). LC/MS, M−1: 534.2. |
| $N^1$-(cyanomethyl)-$N^2$-{(S)-3-furyl[4'-(methylsulfonyl)-1,1'-biphenyl-4-yl]methyl}-L-leucinamide | MS(+APCI): 479.2 and 478.3[M−1]$^+$ |
| $N^1$-(1-cyanocyclopropyl)-$N^2$-{(1S)-2,2,2-trifluoro-1-[4'-(methylsulfonyl)-1,1'-biphenyl-4-yl]ethyl}-L-norvalinamide | MS(+ESI): 494[M+1]$^+$. $^1$H NMR(CDCl$_3$): δ 0.97(t, 3H), 0.98(m, 1H), 1.1(m, 1H), 1.42(m, 2H), 1.29(m, 2H), 1.63(m, 1H), 1.77(m, 1H), 3.13(s, 3H), 3.28(dd, 1H), 4.17(q, 1H), 7.21(br s, 1H), 7.47(d, 2H), 7.63(d, 2H), 7.78(d, 2H), 8.02(d, 2H). |
| $N^2$-[(1S)-1-(4-bromophenyl)-2,2,2-trifluoroethyl]-$N^1$-(1-cyanocyclopropyl)-L-norvalinamide | MS(−ESI): 416, 418[M−1]$^-$ $^1$H NMR(CDCl$_3$): δ 0.97(3H, t), 0.98(m, 1H), 1.07(m, 1H), 1.41(m, 2H), 1.49(m, 2H), 1.62(m, 1H), 1.72(m, 1H), 3.27(1H, m), 1.04(m, 1H), 7.1(br s, 1H), 1.24(d, 2H), 7.75(d, 2H). |
| $N^2$-[(S)-(4-bromophenyl)(4-bromothien-2-yl)methyl]-$N^1$-(cyanomethyl)-L-leucinamide | $^1$HNMR(d$_6$-dmso): δ 8.69(1H, t), 7.52(1H, m), 7.49(2H, d), 7.31(2H, d), 7.00(1H, d), 4.91(1H, s), 4.14(2H, m), 3.15(1H, m), 2.81(1H, dd), 1.85(1H, m), 1.45(1H, m), 1.30(1H, m), 0.86(3H, d) 0.82(3H, d). |
| $N^2$-[(S)-(4-bromophenyl)(thien-3-yl)methyl]-$N^1$-(1-cyanocyclopropyl)-L-leucinamide | LC/MS, M−1: 443.8 |
| $N^1$-(cyanomethyl)-$N^2$-((S)-[4'-(methylsulfonyl)-1,1'-biphenyl-4-yl]{4-[4- | $^1$HNMR(d$_6$-dmso): δ 8.75(1H, t), 7.90(9H, m), 7.70(2H, d), 7.57(3H, m), 5.06(1H, |

| NAME | CHARACTERIZATION |
|---|---|
| (methylsulfonyl)phenyl]thien-2-yl}methyl)-L-leucinamide | s), 4.18(2H, m), 3.23(3H, s), 3.22(1H, m), 3.19(3H, s), 2.85(1H, d), 1.90(1H, m), 1.50(1H, m), 1.35(1H, m), 0.89(3H, d), 0.85(3H, d). LC/MS, M−1: 648.1. |
| $N^1$-(1-cyanocyclopropyl)-$N^2$-[(S)-[4'-(methylsulfonyl)-1,1'-biphenyl-4-yl](thien-3-yl)methyl]-L-leucinamide | LC/MS, M+1: 522.3, M−1: 521.4. |
| $N^2$-{(1S)-1-[4'-(aminosulfonyl)-1,1'-biphenyl-4-yl]-2,2,2-trifluoroethyl}-$N^1$-(1-cyanocyclopropyl)-L-norvalinamide | MS(+ESI): 495[M+1]$^+$. $^1$H NMR(CDCl$_3$): δ 0.97(3H, t). 0.98(m*, 1H); 1.08(m, 1H), 1.42(m, 2H), 1.44(m, 2H), 1.57-1.8(m, 4H), 3.28(m, 1H), 4.16(q, 1H), 4.9(br s*, 1H), 7.2(s, 1H), 7.43(d, 2H), 7.6(d, 2H), 7.72(d, 2H), 7.99(d, 2H). |
| $N^2$-[(S)-(4-bromophenyl)(4-bromothien-2-yl)methyl]-$N^1$-(1-cyanocyclopropyl)-L-leucinamide | LC/MS, M−1: 526.2. |
| $N^2$-[(S)-[4'-(aminosulfonyl)-1,1'-biphenyl-4-yl](thien-3-yl)methyl]-$N^1$-(1-cyanocyclopropyl)-L-leucinamide | LC/MS, M−1: 521.4. |
| $N^2$-[(S)-[4'-(aminosulfonyl)-1,1'-biphenyl-4-yl](thien-3-yl)methyl]-$N^1$-(cyanomethyl)-L-leucinamide | $^1$HNMR(d$_6$-dmso): δ 8.63(1H, t), 7.84(2H, d), 7.79(2H, d), 7.63(2H, d), 7.47(2H, d), 7.40(2H, m), 7.09(1H, dd), 4.81(1H, d), 4.13(2H, m), 3.05(1H, m), 2.65(1H, dd), 1.80(1H, m), 1.45(1H, m), 0.85(3H, d), 0.76(3H, d). LC/MS, M−1: 495.4. |
| $N^1$-(1-cyanocyclopropyl)-$N^2$-{(1S)-2,2,2-trifluoro-1-[4'-methoxy-3'-(methylsulfonyl)-1,1'-biphenyl-4-yl]ethyl}-L-norvalinamide | MS(+ESI): 524.2[M+1]$^+$ |
| $N^1$-(1-cyanocyclopropyl)-$N^2$-{(1S)-2,2,2-trifluoro-1-[4-(2-methylpyridin-4-yl)phenyl]ethyl}-L-norvalinamide | MS(+ESI): 431.0[M+1]$^+$ |
| $N^1$-(1-cyanocyclopropyl)-5,5,5-trifluoro-$N^2$-{(1S)-2,2,2-trifluoro-1-[4'-(methylsulfonyl)-1,1'-biphenyl-4-yl]ethyl}-L-norvalinamide | MS(+ESI): 548.3[M+1]$^+$ |
| $N^1$-(1-cyanocyclopropyl)-$N^2$-{(1S)-2,2,2-trifluoro-1-[4-(1H-pyrazol-3-yl)phenyl]ethyl}-L-norvalinamide | MS(+ESI): 406.3[M+1]$^+$ |
| $N^1$-(1-cyanocyclopropyl)-$N^2${(1S)-2,2,2-trifluoro-1-[4'-(1-hydroxy-1-methylethyl)-1,1'-biphenyl-4-yl]ethyl}-L-norvalinamide | MS(+ESI): 474.2[M+1]$^+$(100%). $^1$H NMR(400 MHz, DMSO-d6): δ 7.6(m, 8H) 7.4(m, 1H) 7.25(s, 1H) 5.2(s, 1H) 4.1(m, 2H) 3.3(m, 1H) 2.05(s, 1H) 1.75(m, 1H) 1.6(s, 6H) 1.4(m, 2H) 1.25(t, 2H) 1.0(m, 4H). |
| $N^1$-(1-cyanocyclopropyl)-$N^2$-{(1S)-2,2,2-trifluoro-1-[4-(5-methylpyridin-2-yl)phenyl]ethyl}-L-norvalinamide | $^1$HNMR(d$_6$-dmso): δ 8.72(1H, s), 8.48(1H, m), 8.02(2H, d), 7.84(1H, d), 7.67(1H, dd), 7.46(2H, d), 4.30(1H, m), 3.13(1H, m), 2.85(1H, dd), 2.33(3H, s), 1.46(2H, m), 1.32(4H, m), 0.88(1H, m), 0.86(3H, t), 0.73(1H, m). LC/MS, M+1: 431.2. |
| 2-{[(4-Bromo-phenyl)-pyridin-4-yl-methyl]-amino}-pentanoic acid cyanomethyl-amide | MS(+APCI): 400.9 and 401.2[M+1]$^+$ |
| 2-{[(4-Bromo-phenyl)-thiazol-2-yl-methyl]-amino+}-pentanoic acid cyanomethyl-amide | MS(+APCI): 407.1 and 406[M+1]$^+$ |
| (2S)-2-[(S)-1-(4'-Acetylbiphenyl-4-yl)-2,2,2-trifluoroethylamino]-pentanoic acid (1-cycanocyclopropyl)-amide | MS(+ESI): 458[M+1]$^+$, 480[M+1+Na]$^+$. $^1$H NMR(CDCl$_3$): δ 0.97(t, 3H), 0.98(m, 1H), 1.-7(m, 1H), 1.42(m, 2H), 1.57(s, 2H), 1.63(m, 1H), 1.78(m, 1H), 2.33(s, 3H), 3.33(dd, 1H), 4.17(q, 1H), 7.21(br s, 1H), 7.43(d, 2H), 7.65-7.69(2xd, 4H), 8.03(d,2H). |
| (2S)-2-[(S)-1-(2',4'-Difluorobiphenyl-4-yl)-2,2,2-trifluoroethylamino]-pentanoic acid (1-cycanocyclopropyl)-amide | MS(+ESI): 452[M+1]$^+$, 474[M+1+Na]$^+$. $^1$H NMR(CDCl$_3$): δ 0.90(t, 3H), 0.97(m, 3H), 1.04(m, 1H), 1.41-1.5(m, 4H), 1.62(m, 1H), 1.78(m, 1H), 2.19(br s, 1H), 3.32(dd, 1H), 4.13(dd, 1H), 6.95(m, 2H), 7.19(br s, 1H), 7.41(m, 3H), 7.53(d, 2H). |
| (2S)-2-[(S)-1-(3',4'-Difluorobiphenyl-4-yl)-2,2,2-trifluoroethylamino]-pentanoic acid (1-cyanocyclopropyl)-amide | MS(+ESI): 452[M+1]$^+$, 474[M+1+Na]$^+$ $^1$H NMR(CDCl$_3$): δ 0.97(t, 3H), 0.98(m, 1H), 1.07(m, 1H), 1.42(m, 2H), 1.5(m, 2H), 1.62(m, 1H), 1.77(m, 1H), 2.18(br s, 1H), 3.29(dd, 1H), 4.17(q, 1H), 7.21(br s, 1H), 7.13-7.3(m, 2H), 7.38(m, 1H), 7.42(d, 2H), 7.57(d, 2H). |
| (2S)-2-[(S)-1-(3'-Chloro-4'-fluorobiphenyl-4-yl)-2,2,2-trifluoroethylamino]-pentanoic acid(1-cyano-cyclopropyl)-amide | MS(+ESI): 468[M+1]$^+$. $^1$H NMR(CDCl$_3$): δ 0.99(t, 3H), 1.00(m, 1H), 1.08(m, 1H), 1.42(m, 2H), 1.51(m, 2H), 1.62(m, 1H), 1.79(m, 1H), 2.19(br s, 1H), 3.33(dd, |

-continued

| NAME | CHARACTERIZATION |
| --- | --- |
| | 1H), 4.17(q, 1H), 7.21(m, 2H), 7.42(m, 3H), 7.57(d, 2H), 7.62(m, 1H). |
| (2S)-2-[(S)-2,2,2-Trifluoro-1-(4'-methanesulfonylamino-biphenyl-4-yl)-ethylamino]-pentanoic acid(1-cyano-cyclopropyl)-amide | MS(−ESI): 507.0[M−1]$^-$ |
| (2S)-2-{(S)-[(4-Bromo-phenyl)-thiazol-2-yl-methyl]amino}-4-methylpentanoic acid cyanomethyl-amide | MS(+APCI): 479.2 and 478.3[M−1]$^-$ |
| $N^1$-(1-cyanocyclopropyl)-$N^2$-{(1S)-2,2,2-trifluoro-1-[4'-chloro-1,1'-biphenyl-4-yl]ethyl}-L-norvalinamide | MS(+ESI): 450.1[M+1]$^+$ |
| $N^1$-(1-cyanocyclopropyl)-$N^2$-{(1S)-2,2,2-trifluoro-1-[4'-chloro-3'-methyl-1,1'-biphenyl-4-yl]ethyl}-L-norvalinamide | MS(+ESI): 464.2[M+1]$^+$ |
| N'-(1-cyanocyclopropyl)-$N^2$-{(1S)-2,2,2-trifluoro-1-[4'-chloro-2'-methyl-1,1'-biphenyl-4-yl]ethyl}-L-norvalinamide | MS(+ESI): 464.3[M+1]$^+$ |
| (2S)-2-{(S)-2,2,2-Trifluoro-1-[4-(1H-indol-5-yl)-phenyl]-ethylamino}-pentanoic acid (1-cyano-cyclopropyl)-amide | MS(+ESI): 455.1[M+1]$^+$ |
| (2S)-2-[(S)-2,2,2-Trifluoro-1-(3'-methanesulfonylaznino-biphenyl-4-yl)-ethylamino]-pentanoic acid(1-cyano-cyclopropyl)-amide | MS(+ESI): 509.2[M+1]$^+$ |
| N'-(1-cyanocyclopropyl)-$N^2$-{(1S)-2,2,2-trifluoro-1-[4'-fluoro-1,1'-biphenyl-4-yl]ethyl}-L-norvalinamide | MS(+ESI): 434.4[M+1]$^+$ |
| $N^1$-(1-cyanocyclopropyl)-$N^2$-{(1S)-2,2,2-trifluoro-1-[4'-fluoro-3'-methyl-1,1'-biphenyl-4-yl]ethyl}-L-norvalinamide | MS(+ESI): 448.2[M+1]$^+$ |
| $N^1$-(1-cyanocyclopropyl)-$N^2$-{(1S)-2,2,2-trifluoro-1-[3'-fluoro-4'-methyl-1,1'-biphenyl-4-yl]ethyl}-L-norvalinamide | MS(+ESI): 448.3[M+1]$^+$ |
| $N^1$-(1-cyanocyclopropyl)-$N^2$-{(1S)-2,2,2-trifluoro-1-[4'-trifluoromethoxy-1,1'-biphenyl-4-yl]ethyl}-L-norvalinamide | MS(+ESI): 500.1[M+1]$^+$ |
| (2S)-2-[(S)-2,2,2-Trifluoro-1-(4'-methylbiphenyl-4-yl)-ethylamino]-pentanoic acid(1-cyanocyclopropyl)-amide | MS(+ESI): 430[M+1]$^+$. $^1$H NMR(CDCl$_3$) δ 0.90(m, 1H), 0.98(t, 3h), 1.02(m, 1H) 1.4-1.5(m, 4H), 1.62(m, 1H), 1.69(m, 1H), 2.19(br s, 1H), 2.41(s, 3H), 3.35(dd, 1H), 4.1(q, 1H), 7.21(s, 1H) 7.24(d, 2H), 7.38(d, 2H), 7.46(d, 2H), 7.60(d, 2H). |
| (2S)-2-[(S)-1-(4'-Cyanobiphenyl-4-yl)-2,2,2-trifluoroethylamino]-pentanoic acid(1-cyanocyclopropyl)-amide | MS(+ESI): 441[M+1]$^+$ |
| $N^1$-(1-cyanocyclopropyl)-$N^2$-{(1S)-2,2,2-trifluoro-1-[4'-methoxy-1,1'-biphenyl-4-yl]ethyl}-L-norvalinamide | MS(+ESI): 446.3[M+1]$^+$ |
| $N^1$-(1-cyanocyclopropyl)-$N^2$-{(1S)-2,2,2-trifluoro-1-[4-(benzo[1,3]dioxol-5-yl)phenyl]ethyl}-L-norvalinamide | MS(+ESI): 460.1[M+1]$^+$ |
| $N^1$-(1-cyanocyclopropyl)-$N^2$-{(1S)-2,2,2-trifluoro-1-[4'-(methoxycarbonyl)-1,1'-biphenyl-4-yl]ethyl}-L-norvalinamide | MS(+ESI): 474.3[M+1]$^+$ |
| (2S)-2-{(S)-[(4-Bromophenyl)-thiazol-2-yl-methyl]-amino}-4-methylpentanoic acid(1-cyanocyclopropyl)-amide | MS(−ESI): 445, 447[M−1]$^-$. NMR(CDCl$_3$): δ 0.82(d, 3H), 0.95(d, 3H), 1.04(m, 2H), 1.46-1.62(m, 4H), 1.80(m, 1H), 3.12(dd, 1H), 4.95(s, 1H), 7.22(s, 1H), 7.23-7.25(d, 2H), 7.31(m, 2H), 7.47(d, 2H), 7.74(m, 1H). |
| (2S)-2-{(S)-[(4'-Methanesulfonyl-biphenyl-4-yl)-thiazol-2-yl-methyl]-amino}-4-methyl-pentanoic acid cyanomethyl-amide | MS(+APCI): 418.9, 420.9[M−1]$^+$ |
| (2S)-2-[(S)-2,2,2-Trifluoro-1-(4'-trifluoromethyl-biphenyl-4-yl)-ethylamino]-pentanoic acid(1-cyano-cyclopropyl)-amide | MS(+APCI): 483.3[M+1]$^+$ |
| (2S)-2-[(S)-2,2,2-Trifluoro-1-(2'-trifluoromethyl-biphenyl-4-yl)-ethylamino]-pentanoic acid(1-cyano-cyclopropyl)-amide | MS(+APCI): 483.3[M+1]$^+$ |
| (2S)-2-{(S)-[(2',4'-Difluorobiphenyl-4-yl)-thiazol-2-yl-methyl]-amino}-4-methylpentanoic acid(1-cyanocyclopropyl)-amide | MS(−ESI): 479[M−1]$^-$. $^1$H NMR(CDCl$_3$): δ 0.84(d, 3H), 0.97(d, 3H), 1.03(m, 2H), 1.47(m, 2H), 1.57-1.62(m, 4H), 1.95(m, 1H), 3.27(dd, 1H), 5.02(s, 1H), 6.93(m, 2H), 7.32(m, 1H), 7.39(m, 1H), 7.42(m, 3H), 7.48(d, 2H), 7.77(d, 1H). |

-continued

| NAME | CHARACTERIZATION |
|---|---|
| (2S)-2-{(S)-[(4'-Methanesulfonylbiphenyl-4-yl)-thiazol-2-yl-methyl]-amino}-4-methylpentanoic acid(1-cyanocyclopropyl)-amide | MS(−ESI): 521[M−1]−. |
| N1-(1-cyanocyclopropyl)-4-fluoro-N2-[(1S)-2,2,2-trifluoro-1-(4-quinolin-6-ylphenyl)ethyl]-L-leucinamide | MS(+APCI): 499.4[M+1]+ |
| N1-(1-cyanocyclopropyl)-4-fluoro-N2-{(1S)-2,2,2-trifluoro-1-[4'-(methylsulfinyl)-1,1'-biphenyl-4-yl]ethyl}-L-leucinamide | MS(+APCI): 510.1[M+1]+ |
| N2-[(1S)-1-(4'-acetyl-1,1'-biphenyl-4-yl)-2,2,2-trifluoroethyl]-N1-(1-cyanocyclopropyl)-L-leucinamide | MS(+ESI): 472.1[M+1]+ |
| N1-(1-cyanocyclopropyl)-N2-[(1S)-2,2,2-trifluoro-1-(4-quinolin-6-ylphenyl)ethyl]-L-leucinamide | MS(+ESI): 482[M+1]+ |
| N2-[(1S)-1-(4-bromophenyl)-2,2,2-trifluoroethyl]-N1-(1-cyanocyclopropyl)-4,4-difluoro-L-norvalinamide | MS(+ESI): 454.1, 456.2[M+1]+ |
| N1-(1-cyanocyclopropyl)-4,4-difluoro-N2-{(1S)-2,2,2-trifluoro-1-[4'-(methylthio)-1,1'-biphenyl-4-yl]ethyl}-L-norvalinamide | MS(+ESI): 498.3[M+1]+ |
| N1-(1-cyanocyclopropyl)-4,4-difluoro-N2-{(1S)-2,2,2-trifluoro-1-[4'-(methylsulfonyl)-1,1'-biphenyl-4-yl]ethyl}-L-norvalinamide | MS(+ESI): 530.3[M+1]+ |

Pharmaceutical Composition

As a specific embodiment of this invention, 100 mg of $N^1$-(cyanomethyl)-$N^2$-[2,2,2-trifluoro-1-(4'-piperazin-1-yl-1,1'-biphenyl-4-yl)ethyl]-L-leucinamide, is formulated with sufficient finely divided lactose to provide a total amount of 580 to 590 mg to fill a size 0, hard-gelatin capsule.

The compounds disclosed in the present application exhibited activity in the following assays. In addition, the compounds disclosed in the present application have an enhanced pharmacological profile relative to previously disclosed compounds.

Cathepsin K Assay

Serial dilutions (1/3) from 500 µM down to 0.0085 µM of test compounds were prepared in dimethyl sulfoxide (DMSO). Then 2 µL of DMSO from each dilution were added to 50 µL of assay buffer (MES, 50 mM (pH 5.5); EDTA, 2.5 mM; DTT, 2.5 mM and 10% DMSO) and 25 µL of human cathepsin K (0.4 nM) in assay buffer solution. The assay solutions were mixed for 5-10 seconds on a shaker plate and incubated for 15 minutes at room temperature. Z-Leu-Arg-AMC (8 µM) in 25 µL of assay buffer was added to the assay solutions. Hydrolysis of the coumarin leaving group (AMC) was followed by spectrofluorometry (Exλ=355 nm; Emλ=460 nm) for 10 minutes. Percent of inhibition were calculated by fitting experimental values to standard mathematical model for dose response curve.

Cathepsin L Assay

Serial dilutions (1/3) from 500 µM down to 0.0085 µM of test compounds were prepared in dimethyl sulfoxide (DMSO). Then 2 µL of DMSO from each dilution were added to 50 µL of assay buffer (MES, 50 mM (pH 5.5); EDTA, 2.5 mM; DTT, 2.5 mM and 10% DMSO) and 25 µL of human cathepsin L (0.5 nM) in assay buffer solution. The assay solutions were mixed for 5-10 seconds on a shaker plate and incubated for 15 minutes at room temperature. Z-Leu-Arg-AMC (8 µM) in 25 µL of assay buffer was added to the assay solutions. Hydrolysis of the coumarin leaving group (AMC) was followed by spectrofluorometry (Exλ=355 nm; Emλ=460 nm) for 10 minutes. Percent of inhibition were calculated by fitting experimental values to standard mathematical model for dose response curve.

Cathepsin B Assay

Serial dilutions (1/3) from 500 µM down to 0.0085 µM of test compounds were prepared in dimethyl sulfoxide (DMSO). Then 2 µL of DMSO from each dilution were added to 50 µL of assay buffer (MES, 50 mM (pH 5.5); EDTA, 2.5 mM; DTT, 2.5 mM and 10% DMSO) and 25 µL of human cathepsin B (4.0 nM) in assay buffer solution. The assay solutions were mixed for 5-10 seconds on a shaker plate and incubated for 15 minutes at room temperature. Z-Leu-Arg-AMC (8 µM) in 25 µL of assay buffer was added to the assay solutions. Hydrolysis of the coumarin leaving group (AMC) was followed by spectrofluorometry (Exλ=355 nm; Emλ=460 nm) for 10 minutes. Percent of inhibition were calculated by fitting experimental values to standard mathematical model for dose response curve.

Cathepsin S Assay

Serial dilutions (1/3) from 500 µM down to 0.0085 µM of test compounds were prepared in dimethyl sulfoxide (DMSO). Then 2 µL of DMSO from each dilution were added to 50 µL of assay buffer (MES, 50 mM (pH 5.5); EDTA, 2.5 mM; DTT, 2.5 mM and 10% DMSO) and 25 µL of human cathepsin S (20 nM) in assay buffer solution. The assay solutions were mixed for 5-10 seconds on a shaker plate and incubated for 15 minutes at room temperature. Z-Leu-Arg-AMC (8 µM) in 25 µL of assay buffer was added to the assay solutions. Hydrolysis of the coumarin leaving group (AMC) was followed by spectrofluorometry (Exλ=355 nm; Emλ=460 nm) for 10 minutes. Percent of inhibition were calculated by fitting experimental values to standard mathematical model for dose response curve.

What is claimed is:

1. The present invention relates to compounds of the following chemical formula:

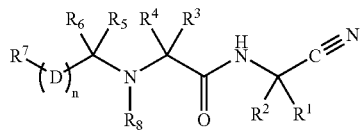

wherein R$^1$ is hydrogen, C$_{1-6}$ alkyl or C$_{2-6}$ alkenyl wherein said alkyl and alkenyl groups are optionally substituted with one to six halo, C$_{3-6}$ cycloalkyl, —SR$^9$, —SR$^{12}$, —SOR$^9$, —SOR$^{12}$, —SO$_2$R$^9$, —SO$_2$R$^{12}$, —SO$_2$CH(R$^{12}$)(R$^{11}$), —OR$^{12}$, —OR$^9$, or —N(R$^{12}$)$_2$;

R$^2$ is hydrogen, C$_{1-6}$ alkyl or C$_{2-6}$ alkenyl wherein said alkyl and alkenyl groups are optionally substituted with one to six halo, C$_{3-6}$ cycloalkyl, —SR$^9$, —SR$^{12}$, —SOR$^9$, —SOR$^{12}$, —SO$_2$R$^9$, —SO$_2$R$^{12}$, —SO$_2$CH (R$^{12}$)(R$^{11}$), —OR$^{12}$, —OR$^5$, or —N(R$^{12}$)$_2$;

or R$^1$ and R$^2$ can be taken together with the carbon atom to which they are attached to form a C$_{3-8}$ cycloalkyl or heterocyclyl ring wherein said ring system is optionally substituted with one or two substituents independently selected from C$_{1-6}$ alkyl, hydroxyalkyl, haloalkyl, or halo;

R$^3$ is hydrogen, C$_{1-6}$ alkyl or C$_{2-6}$ alkenyl wherein said alkyl and alkenyl groups are optionally substituted with C$_{3-6}$ cycloalkyl or one to six halo;

R$^4$ is hydrogen, C$_{1-6}$ alkyl or C$_{2-6}$ alkenyl wherein said alkyl and alkenyl groups are optionally substituted with C$_{3-6}$ cycloalkyl or one to six halo;

R$^5$ is hydrogen;

R$^6$ is C$_{1-6}$ haloalkyl;

D is biphenyl which is optionally substituted with one to five substituents independently selected from C$_{1-6}$ alkyl, halo, —SO$_2$R$^9$, or —SO$_2$R$^{10}$;

R$^7$ is hydrogen;

R$^8$ is hydrogen or C$_{1-6}$ alkyl;

R$^9$ is selected from the group consisting of hydrogen, aryl, aryl(C$_{1-4}$)alkyl, heteroaryl, heteroaryl(C$_{1-4}$)alkyl, C$_{3-8}$cycloalkyl, C$_{3-8}$cycloalkyl(C$_{1-4}$)alkyl, and heterocyclyl(C$_{1-4}$)alkyl wherein said groups can be optionally substituted with one, two, or three substituents independently selected from halo, alkoxy or —SO$_2$R$^{12}$;

R$^{10}$ is hydrogen or C$_{1-6}$ alkyl

R$^{11}$ is hydrogen or C$_{1-6}$ alkyl;

R$^{12}$ is hydrogen or C$_{1-6}$ alkyl which is optionally substituted with one, two, or three substituents independently selected from halo, alkoxy, cyano, —NR$^{10}$ or —SR$^{10}$;

n is one;

and the pharmaceutically acceptable salts, stereoisomers and N-oxide derivatives thereof.

2. The compound of claim 1 wherein R$^1$ is hydrogen and R$^2$ is hydrogen, or R$^1$ and R$^2$ can be taken together with the carbon atom to which they are attached to form a C$_{3-8}$ cycloalkyl ring wherein said ring system is optionally substituted with one or two substituents selected from C$_{1-6}$ alkyl or halo, and the pharmaceutically acceptable salts, stereoisomers and N-oxide derivatives thereof.

3. The compound of claim 2 wherein R$^3$ is C$_{1-6}$ alkyl which is optionally substituted with one to six halo and R$^4$ is hydrogen, and the pharmaceutically acceptable salts, stereoisomers and N-oxide derivatives thereof.

4. The compound of claim 3 wherein R$^3$ is n-propyl, isobutyl, 2-fluoro-2-methylpropyl, 2-trifluoromethylpropyl, 3-fluoro-2-(2-fluoromethyl)propyl, 2,2-difluoroethyl, 2,2-difluoropropyl, 3,3,3-trifluoropropyl, or 2,2-dichloroethyl and R$^4$ is hydrogen; and the pharmaceutically acceptable salts, stereoisomers and N-oxide derivatives thereof.

5. The compound of claim 4 wherein R$^5$ is hydrogen and R$^6$ is trifluoromethyl or 3,3,3,2,2-pentafluoroethyl; and the pharmaceutically acceptable salts, stereoisomers and N-oxide derivatives thereof.

6. The compound of claim 1 selected from:

N$^1$-(1-cyanocyclopropyl)-4-fluoro-N$^2$-{(1S)-2,2,2-trifluoro-1-[4'-(methylsulfonyl)-1,1'-biphenyl-4-yl]ethyl}-L-leucinamide;

N$^1$-(cyanomethyl)-N$^2$-[(1S)-2,2,2-trifluoro-1-(4'-fluoro-1,1'-biphenyl-4-yl)ethyl]-L-leucinamide;

N$^1$-(cyanomethyl)-N$^2$-{(1S)-2,2,3,3,3-pentafluoro-1-[4'-(methylsulfonyl)-1,1'-biphenyl-4-yl]propyl}-L-leucinamide;

N$^1$-(cyanomethyl)-N$^2$-[(1S)-2,2,2-trifluoro-1-(2'-fluoro-1,1'-biphenyl-4-yl)ethyl]-L-leucinamide;

N$^1$-(cyanomethyl)-N$^2$-[(1S)-1-(3',4'-difluoro-1,1'-biphenyl-4-yl)-2,2,2-trifluoroethyl]-L-leucinamide;

N$^1$-(cyanomethyl)-N$^2$-{(1S)-2,2,2-trifluoro-1-[2'-(trifluoromethyl)-1,1'-biphenyl-4-yl]ethyl}-L-leucinamide;

N$^1$-(cyanomethyl)-N$^2$-[(1S)-1-(3',4'-dichloro-1,1'-biphenyl-4-yl)-2,2,2-trifluoroethyl]-L-leucinamide;

N$^2$-{(1S)-1-[4'-(acetylamino)-3'-fluoro-1,1'-biphenyl-4-yl]-2,2,2-trifluoroethyl}-N$^1$-(cyanomethyl)-L-leucinamide;

N$^1$-(cyanomethyl)-N$^2$-[(1S)-2,2,2-trifluoro-1-(3'-fluoro-1,1'-biphenyl-4-yl)ethyl]-L-leucinamide;

N$^1$-(cyanomethyl)-N$^2$-[(1S)-1-(3',5'-difluoro-1,1'-biphenyl-4-yl)-2,2,2-trifluoroethyl]-L-leucinamide;

N$^1$-(cyanomethyl)-N$^2$-[(1S)-2,2,2-trifluoro-1-(2',3',5'-trifluoro-1,1'-biphenyl-4-yl)ethyl]-L-leucinamide;

N$^1$-(cyanomethyl)-N$^2$-{2,2,2-trifluoro-1-[4'-(methylsulfonyl)-1,1'-biphenyl-4-yl]ethyl}-L-leucinamide;

N$^1$-(cyanomethyl)-N$^2$-{(1S)-2,2,2-trifluoro-1-[4'-(methylsulfonyl)-1,1'-biphenyl-4-yl]ethyl}-L-leucinamide;

N$^1$-(cyanomethyl)-N$^2$-{(1R)-2,2,2-trifluoro-1-[4'-(methylsulfonyl)-1,1'-biphenyl-4-yl]ethyl}-L-leucinamide;

N$^1$-(cyanomethyl)-N$^2$-{(1S)-2,2,2-trifluoro-1-[4'-(isopropylsulfonyl)-1,1'-biphenyl-4-yl]ethyl}-L-leucinamide;

N$^1$-(cyanomethyl)-N$^2$-{(1S)-2,2,2-trifluoro-1-[2'-methyl-4'-(methylsulfonyl)-1,1'-biphenyl-4-yl]ethyl}-L-leucinamide;

N$^1$-(cyanomethyl)-N$^2$-{2,2,2-trifluoro-1-[4'-(methylsulfonyl)-1,1'-biphenyl-3-yl]ethyl}-L-leucinamide;

N$^2$-[(1S)-1-(4'-bromo-1,1'-biphenyl-4-yl)-2,2,2-trifluoroethyl]-N$^1$-(cyanomethyl)-L-leucinamide;

N$^2$-[(1S)-1-(1,1'-biphenyl-4-yl)-2,2,2-trifluoroethyl]-N$^1$-(cyanomethyl)-L-leucinamide;

N$^1$-(cyanomethyl)-3-(1-methylcyclopropyl)-N$^2$-{(1S)-2,2,2-trifluoro-1-[4'-(methylsulfonyl)-1,1'-biphenyl-4-yl]ethyl}-L-alaninamide;

N$^1$-(cyanomethyl)-N$^2$-[(1S)-2,2,2-trifluoro-1-(4'-methyl-1,1'-biphenyl-4-yl)ethyl]-L-leucinamide;

N$^1$-(cyanomethyl)-N$^2$-{2,2,2-trifluoro-1-[4'-(methylsulfonyl)-1,1'-biphenyl-4-yl]ethyl}-D-leucinamide;

N$^1$-(cyanomethyl)-N$^2$-[(1S)-2,2,2-trifluoro-1-(2'-fluoro-1,1'-biphenyl-4-yl)ethyl]-L-leucinamide;

N$^1$-(cyanomethyl)-N$^2$-{2,2,2-trifluoro-1-[3'-(methylsulfonyl)-1,1'-biphenyl-4-yl]ethyl}-L-leucinamide;

N$^2$-{(1S)-1-[4'-bromo-3'-(methylsulfonyl)-1,1'-biphenyl-4-yl]-2,2,2-trifluoroethyl}-N$^1$-(cyanomethyl)-L-leucinamide;

N$^1$-(cyanomethyl)-N$^2$-((1S)-2,2,2-trifluoro-1-{4'-[(trifluoromethyl)sulfonyl]-1,1'-biphenyl-4-yl}ethyl)-L-leucinamide;

$N^1$-(1-cyanocyclopropyl)-$N^2$-{(1S)-2,2,2-trifluoro-1-[4'-(methylsulfonyl)-1,1'-biphenyl-4-yl]ethyl}-L-leucinamide;

$N^1$-(cyanomethyl)-$N^2$-{(1S)-1-[4'-(ethylsulfonyl)-1,1'-biphenyl-4-yl]-2,2,2-trifluoroethyl}-L-leucinamide;

$N^2$-{(1S)-1-[2'-chloro-4'-(methylsulfonyl)-1,1'-biphenyl-4-yl]-2,2,2-trifluoroethyl}-$N^1$-(cyanomethyl)-L-leucinamide;

$N^1$-(cyanomethyl)-$N^2$-{(1S)-2,2,2-trifluoro-1-[3'-fluoro-4'-(methylsulfonyl)-1,1'-biphenyl-4-yl]ethyl}-L-leucinamide;

$N^1$-(cyanomethyl)-$N^2$-{(1S)-2,2,2-trifluoro-1-[3'-(methylsulfonyl)-1,1'-biphenyl-4-yl]ethyl}-L-leucinamide;

$N^1$-(1-cyanocyclopropyl)-$N^2$-[(1S)-2,2,2-trifluoro-1-(3'-fluoro-4'-methyl-1,1'-biphenyl-4-yl)ethyl]-L-leucinamide;

$N^1$-(1-cyanocyclopropyl)-$N^2$-[(1S)-2,2,3,3,3-pentafluoro-1-(4'-methyl-1,1'-biphenyl-4-yl)propyl]-L-leucinamide;

$N^1$-(cyanomethyl)-$N^2$-[(1S)-2,2,3,3,3-pentafluoro-1-(2'-fluoro-1,1'-biphenyl-4-yl)propyl]-L-leucinamide;

$N^1$-(cyanomethyl)-4-fluoro-$N^2$-{(1S)-2,2,2-trifluoro-1-[4'-(methylsulfonyl)-1,1'-biphenyl-4-yl]ethyl}-L-leucinamide;

$N^1$-(1-cyanocyclopropyl)-4-fluoro-$N^2$-{(1S)-2,2,2-trifluoro-1-[2'-methyl-4'-(methylsulfonyl)-1,1'-biphenyl-4-yl]ethyl}-L-leucinamide;

$N^1$-(1-cyanocyclopropyl)-$N^2$-{(1S)-2,2-difluoro-1-[4'-(methylsulfonyl)-1,1'-biphenyl-4-yl]ethyl}-L-leucinamide;

$N^2$-[(1S)-1-(1,1'-biphenyl-4-yl)-2,2,2-trifluoroethyl]-$N^1$-(1-cyanocyclopropyl)-L-leucinamide;

$N^1$-(1-cyanocyclopropyl)-$N^2$-[(1S)-2,2,2-trifluoro-1-(2',4',6'-trimethyl-1,1'-biphenyl-4-yl)ethyl]-L-leucinamide;

$N^2$-[(1S)-1-(1,1'-biphenyl-4-yl)-2,2,3,3,3-pentafluoropropyl]-$N^1$-(cyanomethyl)-L-leucinamide;

$N^2$-[(1S)-1-(1,1'-biphenyl-4-yl)-2,2,3,3,3-pentafluoropropyl]-$N^1$-(1-cyanocyclopropyl)-L-leucinamide;

$N^1$-[(1S)-1-cyanoethyl]-$N^2$-{(1S)-2,2,2-trifluoro-1-[4'-(methylsulfonyl)-1,1'-biphenyl-4-yl]ethyl}-L-leucinamide;

$N^1$-[(1S)-1-cyano-3-(methylthio)propyl]-$N^2$-{(1S)-2,2,2-trifluoro-1-[4'-(methylsulfonyl)-1,1'-biphenyl-4-yl]ethyl}-L-leucinamide;

$N^1$-[(1S)-1-cyano-3-(methylsulfonyl)propyl]-$N^2$-{(1S)-2,2,2-trifluoro-1-[4'-(methylsulfonyl)-1,1'-biphenyl-4-yl]ethyl}-L-leucinamide;

(4S)-$N^1$-(cyanomethyl)-5,5,5-trifluoro-$N^2$-{(1S)-2,2,2-trifluoro-1-[4'-(methylsulfonyl)-1,1'-biphenyl-4-yl]ethyl}-L-leucinamide;

(4S)-$N^1$-(1-cyanocyclopropyl)-5,5,5-trifluoro-$N^2$-{(1S)-2,2,2-trifluoro-1-[4'-(methylsulfonyl)-1,1'-biphenyl-4-yl]ethyl}-L-leucinamide;

$N^1$-(1-cyanocyclopropyl)-$N^2$-{(1S)-2,2,3,3,3-pentafluoro-1-[4'-(methylsulfonyl)-1,1'-biphenyl-4-yl]propyl}-L-leucinamide;

(4R)-$N^1$-(cyanomethyl)-5,5,5-trifluoro-$N^2$-{(1S)-2,2,2-trifluoro-1-[4'-(methylsulfonyl)-1,1'-biphenyl-4-yl]ethyl}-L-leucinamide;

(4R)-$N^1$-(1-cyanocyclopropyl)-5,5,5-trifluoro-$N^2$-{(1S)-2,2,2-trifluoro-1-[4'-(methylsulfonyl)-1,1'-biphenyl-4-yl]ethyl}-L-leucinamide;

$N^1$-(cyanomethyl)-$N^2$-[(1S)-2,2,3,3,3-pentafluoro-1-(4'-methyl-1,1'-biphenyl-4-yl)propyl]-L-leucinamide;

$N^1$-(1-cyanocyclopropyl)-$N^2$-{(1S)-1-[4'-(ethylsulfonyl)-1,1'-biphenyl-4-yl]-2,2,2-trifluoroethyl}-4-fluoro-L-leucinamide;

$N^1$-(cyanomethyl)-$N^2$-{(1S)-2,2,2-trifluoro-1-[4'-(methylsulfonyl)-1,1'-biphenyl-4-yl]ethyl}-L-alaninamide;

$N^1$-(cyanomethyl)-$N^2$-{(1S)-2,2,3,3,3-pentafluoro-1-[4'-(isopropylsulfonyl)-1,1'-biphenyl-4-yl]propyl}-L-leucinamide;

$N^1$-(1-cyano-1-methylethyl)-$N^2$-{(1S)-2,2,2-trifluoro-1-[4'-(methylsulfonyl)-1,1'-biphenyl-4-yl]ethyl}-L-leucinamide;

$N^1$-(1-cyanocyclopropyl)-$N^2$-{(1S)-2,2,2-trifluoro-1-[2'-methyl-4'-(methylsulfonyl)-1,1'-biphenyl-4-yl]ethyl}-L-leucinamide;

$N^1$-(1-cyanocyclopropyl)-$N^2$-{(1S)-1-[4'-(ethylsulfonyl)-1,1'-biphenyl-4-yl]-2,2,2-trifluoroethyl}-L-leucinamide;

$N^1$-(cyanomethyl)-$N^2$-{2,2,2-trifluoro-1-[4'-(methylsulfonyl)-1,1'-biphenyl-4-yl]ethyl}-L-norvalinamide;

$N^1$-(cyanomethyl)-5,5,5-trifluoro-$N^2$-{(1S)-2,2,2-trifluoro-1-[4'-(methylsulfonyl)-1,1'-biphenyl-4-yl]ethyl}-L-norvalinamide;

$N^1$-(1-cyanocyclopropyl)-$N^2$-{(1S)-2,2,2-trifluoro-1-[4'-(methylsulfonyl)-1,1'-biphenyl-4-yl]ethyl}-L-norvalinamide;

$N^1$-(1-cyanocyclopropyl)-5,5,5-trifluoro-$N^2$-{(1S)-2,2,2-trifluoro-1-[4'-(methylsulfonyl)-1,1'-biphenyl-4-yl]ethyl}-L-norvalinamide;

(2S)-2-[(S)-1-(2',4'-Difluorobiphenyl-4-yl)-2,2,2-trifluoroethylamino]-pentanoic acid (1-cyanocyclopropyl)-amide;

(2S)-2-[(S)-1-(3',4'-Difluorobiphenyl-4-yl)-2,2,2-trifluoroethylamino]-pentanoic acid (1-cyanocyclopropyl)-amide;

(2S)-2-[(S)-1-(3'-Chloro-4'-fluorobiphenyl-4-yl)-2,2,2-trifluoroethylamino]-pentanoic acid (1-cyano-cyclopropyl)-amide;

$N^1$-(1-cyanocyclopropyl)-$N^2$-{(1S)-2,2,2-trifluoro-1-[4'-chloro-1,1'-biphenyl-4-yl]ethyl}-L-norvalinamide;

$N^1$-(1-cyanocyclopropyl)-$N^2$-{(1S)-2,2,2-trifluoro-1-[4'-chloro-3'-methyl-1,1'-biphenyl-4-yl]ethyl}-L-norvalinamide;

$N^1$-(1-cyanocyclopropyl)-$N^2$-{(1S)-2,2,2-trifluoro-1-[4'-chloro-2'-methyl-1,1'-biphenyl-4-yl]ethyl}-L-norvalinamide;

$N^1$-(1-cyanocyclopropyl)-$N^2$-{(1S)-2,2,2-trifluoro-1-[4'-fluoro-1,1'-biphenyl-4-yl]ethyl}-L-norvalinamide;

$N^1$-(1-cyanocyclopropyl)-$N^2$-{(1S)-2,2,2-trifluoro-1-[4'-fluoro-3'-methyl-1,1'-biphenyl-4-yl]ethyl}-L-norvalinamide;

$N^1$-(1-cyanocyclopropyl)-$N^2$-{(1S)-2,2,2-trifluoro-1-[3'-fluoro-4'-methyl-1,1'-biphenyl-4-yl]ethyl}-L-norvalinamide;

(2S)-2-[(S)-2,2,2-Trifluoro-1-(4'-methylbiphenyl-4-yl)-ethylamino]-pentanoic acid (1-cyanocyclopropyl)-amide;

$N^1$-(1-cyanocyclopropyl)-4,4-difluoro-$N^2$-{(1S)-2,2,2-trifluoro-1-[4'-(methylsulfonyl)-1,1'-biphenyl-4-yl]ethyl}-L-norvalinamide;

$N^1$-(cyanomethyl)-4,4-difluoro-$N^2$-{(1S)-2,2,2-trifluoro-1-[4'-(methylsulfonyl)-1,1'-biphenyl-4-yl]ethyl}-L-norvalinamide;

$N^1$-(cyanomethyl)-4-fluoro-$N^2$-{(1S)-2,2,2-trichloro-1-[4'-(methylsulfonyl)-1,1'-biphenyl-4-yl]ethyl}-L-leucinamide;

$N^1$-(1-cyanocyclopropyl)-4-fluoro-$N^2$-{(1S)-2,2,2-trichloro-1-[4'-(methylsulfonyl)-1,1'-biphenyl-4-yl]ethyl}-L-leucinamide;

$N^1$-(1-cyanocyclopropyl)-4,4-difluoro-$N^2$-{(1S)-2,2,2-trichloro-1-[4'-(methylsulfonyl)-1,1'-biphenyl-4-yl]ethyl}-L-norvalinamide;

$N^1$-(cyanomethyl)-4,4-difluoro-$N^2$-{(1S)-2,2,2-trichloro-1-[4'-(methylsulfonyl)-1,1'-biphenyl-4-yl]ethyl}-L-norvalinamide;

(2S)-N-(cyanomethyl)-4,4-difluoro-2-({(1S)-2,2,2-trifluoro-1-[4'-(methylsulfonyl)-1,1'-biphenyl-4-yl]ethyl}amino)butanamide;

(2S)-N-(1-cyanocyclopropyl)-4,4-difluoro-2-({(1S)-2,2,2-trifluoro-1-[4'-(methylsulfonyl)-1,1'-biphenyl-4-yl]ethyl}amino)butanamide;

(2S)-N-(1-cyanocyclopropyl)-4,4-difluoro-2-({(1S)-2,2,2-trichloro-1-[4'-(methylsulfonyl)-1,1'-biphenyl-4-yl]ethyl}amino)butanamide;

(2S)-N-(cyanomethyl)-4,4-difluoro-2-({(1S)-2,2,2-trichloro-1-[4'-(methylsulfonyl)-1,1'-biphenyl-4-yl]ethyl}amino)butanamide;

(2S)-4,4-dichloro-N-(cyanomethyl)-2-({(1S)-2,2,2-trifluoro-1-[4'-(methylsulfonyl)-1,1'-biphenyl-4-yl]ethyl}amino)butanamide;

(2S)-4,4-dichloro-N-(1-cyanocyclopropyl)-2-({(1S)-2,2,2-trifluoro-1-[4'-(methylsulfonyl)-1,1'-biphenyl-4-yl]ethyl}amino)butanamide;

(2S)-4,4-dichloro-N-(1-cyanocyclopropyl)-2-({(1S)-2,2,2-trichloro-1-[4'-(methylsulfonyl)-1,1'-biphenyl-4-yl]ethyl}amino)butanamide;

(2S)-4,4dichloro-N-(cyanomethyl)-2-({(1S)-2,2,2-trichloro-1-[4'-(methylsulfonyl)-1,1'-biphenyl-4-yl]ethyl}amino)butanamide;

$N^2$-[(1S)-1-(1,1'-biphenyl-4-yl)-2,2,2-trifluoroethyl]-$N^1$-(1-cyanocyclopropyl)-4-fluoro-L-leucinamide;

$N^1$-(1-cyanocyclopropyl)-4-fluoro-$N^2$-[(1S)-2,2,2-trifluoro-1-(4'-methyl-1,1'-biphenyl-4-yl)ethyl]-L-leucinamide;

$N^1$-(1-cyanobutyl)-4-fluoro-$N^2$-{(1S)-2,2,2-trifluoro-1-[4'-(methylsulfonyl)-1,1'-biphenyl-4-yl]ethyl}-L-leucinamide;

$N^1$-(1-cyano-2-cyclopropylethyl)-4-fluoro-$N^2$-{(1S)-2,2,2-trifluoro-1-[4'-(methylsulfonyl)-1,1'-biphenyl-4-yl]ethyl}-L-leucinamide;

$N^1$-(1-cyano-3-hydroxy-3-methylbutyl)-4-fluoro-$N^2$-{(1S)-2,2,2-trifluoro-1-[4'-(methylsulfonyl)-1,1'-biphenyl-4-yl]ethyl}-L-leucinamide;

$N^1$-(1-cyanocyclopropyl)-4,4-difluoro-$N^2$-{(1S)-2,2,2-trifluoro-1-[4'-(methylsulfonyl)-1,1'-biphenyl-4-yl]ethyl}-L-norvalinamide;

$N^1$-[(1S)-1-cyano-3-(methylsulfonyl)propyl]-$N^2$-{(1S)-2,2,2-trifluoro-1-[4'-(methylsulfonyl)-1,1'-biphenyl-4-yl]ethyl}-L-leucinamide;

$N^1$-(1-cyanocyclopropyl)-4,4-difluoro-$N^2$-{(1S)-2,2,2-trifluoro-1-[4'-(methylsulfonyl)-1,1'-biphenyl-4-yl]ethyl}-L-norvalinamide;

$N^1$-(1-cyanocyclopropyl)-4-fluoro-$N^2$-[(1S)-2,2,2-trifluoro-1-(4'-fluoro-1,1'-biphenyl-4-yl)ethyl]-L-leucinamide;

$N^1$-(1-cyanocyclopropyl)-4-fluoro-$N^2$-{(1S)-2,2,2-trifluoro-1-[3'-methyl-4'-(methylsulfonyl)-1,1'-biphenyl-4-yl]ethyl}-L-leucinamide;

$N^1$-(cyanomethyl)-4,4-difluoro-$N^2$-{(1S)-2,2,2-trifluoro-1-[4'-(methylsulfonyl)-1,1'-biphenyl-4-yl]ethyl}-L-norvalinamide;

$N^1$-(1-cyanocyclopropyl)-4-fluoro-$N^2$-[(1S)-2,2,2-trifluoro-1-(4'-methyl-1,1'-biphenyl-4-ylethyl]-L-leucinamide;

$N^2$-[(1S)-1-(1,1'-biphenyl-4-yl)-2,2,2-trifluoroethyl]-$N^1$-(1-cyanocyclopropyl)-4-fluoro-L-leucinamide;

$N^1$-[(1S)-1-cyano-3-(methylsulfonyl)propyl]-$N^2$-{(1S)-2,2,2-trifluoro-1-[4'-(methylsulfonyl)-1,1'-biphenyl-4-yl]ethyl}-L-leucinamide;

$N^1$-(1-cyanocyclopropyl)-4,4-difluoro-$N^2$-{(1S)-2,2,2-trifluoro-1-[4'-(methylsulfonyl)-1,1'-biphenyl-4-yl]ethyl}-L-norvalinamide;

$N^1$-(1-cyanocyclopropyl)-4-fluoro-$N^2$-[(1S)-2,2,2-trifluoro-1-(4'-fluoro-1,1'-biphenyl-4-yl)ethyl]-L-leucinamide;

$N^1$-(1-cyanocyclopropyl)-4-fluoro-$N^2$-{(1S)-2,2,2-trifluoro-1-[3'-methyl-4'-(methylsulfonyl)-1,1'-biphenyl-4-yl]ethyl}-L-leucinamide;

$N^1$-(cyanomethyl)-4,4-difluoro-$N^2$-{(1S)-2,2,2-trifluoro-1-[4'-(methylsulfonyl)-1,1'-biphenyl-4-yl]ethyl}-L-norvalinamide;

$N^1$-(1-cyanocyclopropyl)-4-fluoro-$N^2$-[(1S)-2,2,2-trifluoro-1-(4'-methyl-1,1'-biphenyl-4-yl)ethyl]-L-leucinamide;

$N^2$-[(1S)-1-(1,1'-biphenyl-4-yl)-2,2,2-trifluoroethyl]-$N^1$-(1-cyanocyclopropyl)-4-fluoro-L-leucinamide;

and the pharmaceutically acceptable salts, stereoisomers and N-oxide derivatives thereof.

7. $N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide or a pharmaceutically acceptable salt thereof.

8. $N^1$(cyanomethyl)-$N^2${(1S)-2,2,2-trifluoro-1-[4'-(methylsulfonyl)-1,1'-biphenyl-4-yl]ethyl}-L-leucinamide or a pharmaceutically acceptable salt thereof.

9. A pharmaceutical composition comprising a compound according to claim 1 and a pharmaceutically acceptable carrier.

10. A pharmaceutical composition made by combining a compound according to claim 1 and a pharmaceutically acceptable carrier.

\* \* \* \* \*

UNITED STATES PATENT AND TRADEMARK OFFICE
CERTIFICATE OF CORRECTION

| | | |
|---|---|---|
| PATENT NO. | : 7,375,134 B2 | Page 1 of 1 |
| APPLICATION NO. | : 10/505796 | |
| DATED | : May 20, 2008 | |
| INVENTOR(S) | : Christopher I. Bayly et al. | |

It is certified that error appears in the above-identified patent and that said Letters Patent is hereby corrected as shown below:

On the Title page, item (75), the Inventors should read:

Inventors: Christopher I. Bayly, Beaconsfield (CA); Cameron Black, Baie d'Urfe (CA); Serge Leger, Notre-Dame-del'lle-Perrot (CA); Chun Sing Li, Dollard-Des-Ormeaux (CA); Dan McKay, Ottawa (CA); Christophe Mellon, L'ile-Bizard (CA); Jacques Yves Gauthier, Laval (CA); Vouy-Linh Truong, Pierrefonds (CA); Cheuk Lau, Ile Bizard (CA); Michel Therien, Laval (CA) --; Michael J. Green, Half Moon Bay, CA (US); Bernard L. Hirschbein, San Francisco, CA (US); James William Janc, Burlingame, CA (US); James T. Palmer, Corte Madera, CA (US); Chitra Baskaran, Foster City, CA (US)--

Signed and Sealed this

Eleventh Day of October, 2011

David J. Kappos
*Director of the United States Patent and Trademark Office*